(12) United States Patent
Davie et al.

(10) Patent No.: US 11,613,527 B2
(45) Date of Patent: Mar. 28, 2023

(54) ENZYME INHIBITORS

(71) Applicant: KalVista Pharmaceuticals Limited, Porton Down (GB)

(72) Inventors: Rebecca Louise Davie, Porton Down (GB); Hannah Joy Edwards, Porton Down (GB); David Michael Evans, Porton Down (GB); Simon Teanby Hodgson, Ampthill (GB); Alessandro Mazzacani, Porton Down (GB); Michael John Stocks, Leicestershire (GB); Thomas Matthew Baker, Nottingham (GB); Matthew Robert Conroy, Nottingham (GB); Alun John Smith, Nottingham (GB); David Edward Clark, Harlow (GB)

(73) Assignee: KalVista Pharmaceuticals Limited, Porton Down (GB)

(*) Notice: Subject to any disclaimer, the term of this patent is extended or adjusted under 35 U.S.C. 154(b) by 29 days.

(21) Appl. No.: 17/496,905

(22) Filed: Oct. 8, 2021

(65) Prior Publication Data
US 2022/0048894 A1 Feb. 17, 2022

Related U.S. Application Data

(63) Continuation of application No. PCT/GB2020/050331, filed on Feb. 13, 2020.

(30) Foreign Application Priority Data

Aug. 9, 2019 (WO) ............... PCT/GB2019/052252

(51) Int. Cl.
| | |
|---|---|
| C07D 401/14 | (2006.01) |
| C07D 487/04 | (2006.01) |
| C07D 403/14 | (2006.01) |
| C07D 405/14 | (2006.01) |
| C07D 413/14 | (2006.01) |
| C07D 417/14 | (2006.01) |
| C07D 471/04 | (2006.01) |
| C07D 487/08 | (2006.01) |
| C07D 491/107 | (2006.01) |
| C07D 491/147 | (2006.01) |
| C07D 491/20 | (2006.01) |

(52) U.S. Cl.
CPC ......... *C07D 401/14* (2013.01); *C07D 403/14* (2013.01); *C07D 405/14* (2013.01); *C07D 413/14* (2013.01); *C07D 417/14* (2013.01); *C07D 471/04* (2013.01); *C07D 487/04* (2013.01); *C07D 487/08* (2013.01); *C07D 491/107* (2013.01); *C07D 491/147* (2013.01); *C07D 491/20* (2013.01)

(58) Field of Classification Search
CPC ............... C07D 401/14; C07D 487/04
See application file for complete search history.

(56) References Cited

U.S. PATENT DOCUMENTS

| | | |
|---|---|---|
| 5,187,157 A | 2/1993 | Kettner et al. |
| 5,786,328 A | 7/1998 | Dennis et al. |
| 6,682,761 B2 | 1/2004 | Pace et al. |
| 7,101,878 B1 | 9/2006 | Anderson et al. |
| 8,207,378 B2 | 6/2012 | Steinmetzer et al. |
| 9,382,219 B2 | 7/2016 | Das et al. |
| 9,512,065 B2 | 12/2016 | Northen et al. |
| 9,533,987 B2 | 1/2017 | Davie et al. |
| 9,670,157 B2 | 6/2017 | Allan et al. |
| 9,738,641 B2 | 8/2017 | Edwards et al. |
| 9,834,513 B2 | 12/2017 | Allan et al. |
| 10,221,161 B2 | 3/2019 | Edwards et al. |
| 10,364,238 B2 | 7/2019 | Davie et al. |
| 10,611,758 B2 | 4/2020 | Davie et al. |
| 10,752,607 B2 | 8/2020 | Beaton et al. |
| 10,781,181 B2 | 9/2020 | Evans et al. |

(Continued)

FOREIGN PATENT DOCUMENTS

| | | |
|---|---|---|
| BR | 112015028879 A2 | 7/2017 |
| CA | 2730078 A1 | 1/2010 |
| CN | 101437577 A | 5/2009 |
| EA | 201200917 | 12/2012 |
| EA | 021359 B1 | 5/2015 |
| EP | 0672658 A1 | 9/1995 |
| EP | 1426364 A1 | 6/2004 |
| EP | 1568698 A1 | 8/2005 |
| EP | 2281885 A1 | 2/2011 |
| EP | 2807157 A1 | 12/2014 |

(Continued)

OTHER PUBLICATIONS

Partridge et al., "Structures of full-length plasma kallikrein bound to highly specific inhibitors describe a new mode of targeted inhibition", Journal of Structural Biology, 206, 2019, 170-182.

(Continued)

*Primary Examiner* — Brian E McDowell
(74) *Attorney, Agent, or Firm* — BakerHostetler

(57) ABSTRACT

The present invention provides compounds of formula (I):

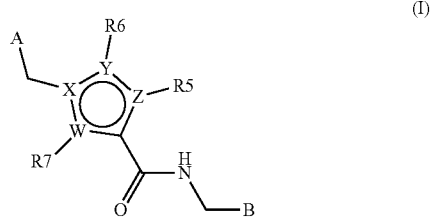

compositions comprising such compounds; the use of such compounds in therapy (for example in the treatment or prevention of a disease or condition in which plasma kallikrein activity is implicated); and methods of treating patients with such compounds; wherein R5, R6, R7, A, B, W, X, Y and Z are as defined herein.

46 Claims, 20 Drawing Sheets

(56) References Cited

U.S. PATENT DOCUMENTS

| | | |
|---|---|---|
| 2002/0012704 A1 | 1/2002 | Pace et al. |
| 2002/0058065 A1 | 5/2002 | Guivarc et al. |
| 2006/0148901 A1 | 7/2006 | Sturzebecher et al. |
| 2007/0254894 A1 | 11/2007 | Kane et al. |
| 2007/0270344 A1 | 11/2007 | Belichard |
| 2008/0038276 A1 | 2/2008 | Sinha et al. |
| 2008/0221091 A1 | 9/2008 | Gege et al. |
| 2009/0163545 A1 | 6/2009 | Goldfarb |
| 2010/0113782 A1 | 5/2010 | Bolin et al. |
| 2011/0152533 A1 | 6/2011 | Sinha et al. |
| 2012/0035168 A1 | 2/2012 | Brandl et al. |
| 2012/0190944 A1 | 7/2012 | Thaveeprungsriporn et al. |
| 2012/0298326 A1 | 11/2012 | Born |
| 2013/0058965 A1 | 3/2013 | Ferguson et al. |
| 2014/0066793 A1 | 3/2014 | Liu et al. |
| 2014/0213611 A1 | 7/2014 | Evans et al. |
| 2014/0378474 A1 | 12/2014 | Flohr et al. |
| 2015/0191421 A1 | 7/2015 | Northen et al. |
| 2015/0225450 A1 | 8/2015 | Evans et al. |
| 2015/0315198 A1 | 11/2015 | Li et al. |
| 2016/0039752 A1 | 2/2016 | Allan et al. |
| 2017/0305863 A1 | 10/2017 | Evans et al. |
| 2018/0319782 A1 | 11/2018 | Davie et al. |

FOREIGN PATENT DOCUMENTS

| | | |
|---|---|---|
| EP | 3089746 A1 | 11/2016 |
| EP | 3224256 A1 | 10/2017 |
| EP | 3469984 A1 | 4/2019 |
| GB | 1421083 A | 1/1976 |
| JP | 2009-529553 A | 8/2009 |
| JP | 2009-545611 A | 12/2009 |
| JP | 2010-520294 A | 6/2010 |
| JP | 2011-157349 A | 8/2011 |
| JP | 2013-532713 A | 8/2013 |
| RU | 2485114 C2 | 6/2013 |
| WO | 92/04371 A1 | 3/1992 |
| WO | 94/29335 A1 | 12/1994 |
| WO | 95/07921 A1 | 3/1995 |
| WO | 02/44145 A1 | 6/2002 |
| WO | 03/35076 A1 | 5/2003 |
| WO | 03/37274 A2 | 5/2003 |
| WO | 03/76458 A2 | 9/2003 |
| WO | 03/91226 A1 | 11/2003 |
| WO | 2004/062657 A1 | 7/2004 |
| WO | 2004/069792 A2 | 8/2004 |
| WO | 2005/049578 A1 | 6/2005 |
| WO | 2005/079800 A1 | 9/2005 |
| WO | 2005/123680 A1 | 12/2005 |
| WO | 2006/025714 A1 | 3/2006 |
| WO | 2006/091459 A2 | 8/2006 |
| WO | 2006/114313 A1 | 11/2006 |
| WO | 2007/001139 A1 | 1/2007 |
| WO | 2007/011626 A2 | 1/2007 |
| WO | 2007/104541 A2 | 9/2007 |
| WO | 2007/113289 A1 | 10/2007 |
| WO | 2007/130842 A2 | 11/2007 |
| WO | 2008/003697 A1 | 1/2008 |
| WO | 2008/016883 A2 | 2/2008 |
| WO | 2008/049595 A1 | 5/2008 |
| WO | 2008/091692 A2 | 7/2008 |
| WO | 2008/119825 A2 | 10/2008 |
| WO | 2008/121670 A1 | 10/2008 |
| WO | 2009/012998 A1 | 1/2009 |
| WO | 2009/026407 A1 | 2/2009 |
| WO | 2009/083553 A1 | 7/2009 |
| WO | 2009/097141 A1 | 8/2009 |
| WO | 2009/106980 A2 | 9/2009 |
| WO | 2009/114677 A1 | 9/2009 |
| WO | 2010/142801 A1 | 12/2010 |
| WO | 2011/051671 A1 | 5/2011 |
| WO | 2011/075684 A1 | 6/2011 |
| WO | 2011/080148 A2 | 7/2011 |
| WO | 2011/094496 A2 | 8/2011 |
| WO | 2011/118672 A1 | 9/2011 |
| WO | 2012/004678 A2 | 1/2012 |
| WO | 2012/009009 A2 | 1/2012 |
| WO | 2012/017020 A1 | 2/2012 |
| WO | 2012/142308 A1 | 10/2012 |
| WO | 2012/174362 A1 | 12/2012 |
| WO | 2013/001265 A2 | 1/2013 |
| WO | 2013/005045 A1 | 1/2013 |
| WO | 2013/048982 A1 | 4/2013 |
| WO | 2013/049096 A1 | 4/2013 |
| WO | 2013/111107 A1 | 8/2013 |
| WO | 2013/111108 A1 | 8/2013 |
| WO | 2013/120104 A2 | 8/2013 |
| WO | 2013/130603 A1 | 9/2013 |
| WO | 2014/006414 A1 | 1/2014 |
| WO | 2014/108406 A1 | 7/2014 |
| WO | 2014/108679 A1 | 7/2014 |
| WO | 2014/108685 A1 | 7/2014 |
| WO | 2014/113712 A1 | 7/2014 |
| WO | 2014/125355 A1 | 8/2014 |
| WO | 2014/125431 A1 | 8/2014 |
| WO | 2014/145986 A1 | 9/2014 |
| WO | 2014/188211 A1 | 11/2014 |
| WO | 2015/022546 A1 | 2/2015 |
| WO | 2015/022547 A1 | 2/2015 |
| WO | 2015/103317 A1 | 7/2015 |
| WO | 2015/134998 A1 | 9/2015 |
| WO | 2015/171526 A2 | 11/2015 |
| WO | 2015/171527 A1 | 11/2015 |
| WO | 2016/011209 A1 | 1/2016 |
| WO | 2016/029214 A1 | 2/2016 |
| WO | 2016/044662 A1 | 3/2016 |
| WO | 2016/083816 A1 | 6/2016 |
| WO | 2016/083818 A1 | 6/2016 |
| WO | 2016/083820 A1 | 6/2016 |
| WO | 2016/096919 A1 | 6/2016 |
| WO | 2016/138532 A1 | 9/2016 |
| WO | 2017/001924 A1 | 1/2017 |
| WO | 2017/001926 A2 | 1/2017 |
| WO | 2017/001936 A2 | 1/2017 |
| WO | 2017/072020 A1 | 5/2017 |
| WO | 2017/072021 A1 | 5/2017 |
| WO | 2017/140748 A2 | 8/2017 |
| WO | 2017/198981 A1 | 11/2017 |
| WO | 2017/207983 A1 | 12/2017 |
| WO | 2017/207985 A1 | 12/2017 |
| WO | 2017/207986 A1 | 12/2017 |
| WO | 2017/207989 A1 | 12/2017 |
| WO | 2017/208002 A1 | 12/2017 |
| WO | 2017/208005 A1 | 12/2017 |
| WO | 2018/011628 A1 | 1/2018 |
| WO | 2019/030540 A1 | 2/2019 |
| WO | 2019/106359 A1 | 6/2019 |
| WO | 2019/106361 A1 | 6/2019 |
| WO | 2019/106375 A1 | 6/2019 |
| WO | 2019/106377 A1 | 6/2019 |
| WO | 2020/249977 A1 | 12/2020 |
| WO | 2020/249979 A1 | 12/2020 |
| WO | 2021/028645 A1 | 2/2021 |
| WO | 2021/028649 A1 | 2/2021 |
| WO | 2021/032933 A1 | 2/2021 |
| WO | 2021/032934 A1 | 2/2021 |
| WO | 2021/032935 A1 | 2/2021 |
| WO | 2021/032936 A1 | 2/2021 |
| WO | 2021/032937 A1 | 2/2021 |
| WO | 2021/032938 A1 | 2/2021 |
| WO | 2021/116679 A1 | 6/2021 |

OTHER PUBLICATIONS

Tang et al., "Expression, Crystallization, and Three-dimensional Structure of the Catalytic Domain of Human Plasma Kallikrein", The Journal of Biological Chemistry, 280, 49, 2005, 41077-41089.
Chemical Abstracts Registry No. 955899-78-2, indexed in the Registry file on STN CAS Online on Nov. 25, 2007.
Chilcote et al., "ASP-634: An Oral Drug Candidate for Diabetic Macular Edema", ARVO May 6, 2012-May 9, 2012, Fort Lauderdale, Florida, (Presentation 2240), 1 page.

(56) References Cited

OTHER PUBLICATIONS

Cicardid et al., "DX-88 a 1-45 recombinant inhibitor of human plasma kallikrein. Efficacy and safety in hereditary and acquired angioedema", Molecular Immunology, Jan. 1, 2003, vol. 40, No. 1-2, 197-198.
Clermont et al., "Plasma Kallikrein Mediates Retinal Vascular Dysfunction and Induces Retinal Thickening in Diabetic Rats", Diabetes, May 2011, 60(5), 1590-1598.
Clermont, et al: IOVS, Plasma Kallikrein Mediates Vascular Endothelial Growth Factor-Induced Retinal Dysfunction and Thickening, May 2016, vol. 57, No. 6, 2391-2399.
Collis et al., "BCX4161, An Oral Kallikrein Inhibitor: Safety and Pharmacokinetic Results of a Phase 1 Study in Healthy Volunteers", Journal of Allergy and Clinical Immunology, vol. 133, Issue 2, Supplement, Feb. 2014, p. AB39.
Colman, "Plasma and tissue kallikrein in arthritis and inflammatory bowel disease", Immunopharmacology, 1999, 43, 103-108.
Craig et al., "Diagnosis and Treatment of Bradykinin-Mediated Angioedema: Outcomes from an Angioedema Expert Consensus Meeting", Int. Arch. Allergy Immunol., 2014, 165(2), 119-127.
Database Registry [Online] Chemical Abstracts Service, Columbus, Ohio, US; Dec. 18, 2008 (Dec. 18, 2008), Chemical catalogue: AKos Consulting and Solutions GmbH: "2-Thiophenecarboxamide", XP055244196.
Davis III et al.; "Biological activities of C1 inhibitor"; Molecular Immunology; Oct. 2008; vol. 45; p. 4057-4063.
deMaat et al., "Factor XII truncation accelerates activation in solution", J. Thromb Haemost., Jan. 2019, 17(1), 183-194.
DeNinno, M. P. et al., "1,5-Substituted nipecotic amides: Selective PDE8 inhibitors displaying diastereomer-dependent microsomal stability", Bioorganic & Medicinal Chemistry Letters, 2011, vol. 21, 3095-3098.
Drzewiecki et al.; "Theory of the Oscillometric Maximum and the Systolic and Diastolic Detection Ratios"; Annals of Biomedical Engineering; vol. 22; 1994; p. 88-96.
Durairaj et al., "Prediction of Vitreal Half-Life Based on Drug Physiochemical Properties: Quantitative Structure-Pharmacokinetic Relationships (QSPKR)", Pharmaceutical Research, 2009, 26(5), 1236-1260.
Elman et al., "Randomized Trial Evaluating Ranibizumab Plus Prompt or Deferred Laser or Triamcinolone Plus Prompt Laser for Diabetic Macular Edema", Ophthalmology, Jun. 2010, 117(6), e35, 1064-1077.
Enamine website on Jul. 25, 2013 from the Internet Archive Way Back Machine {https://web.archive.org/web/20130725053127/http://www.enamine.net/index.php?option=com_content&task=view&id=22.
European Patent Office Communication in Application 17728612.7, dated Apr. 1, 2020, 5 pages. (Year: 2020).
Evans et al., "Selective Inhibitors of Plasma Kallikrein", Immunopharmacology, May 1996, 32(1-3), 115-116.
Federal Register, Wednesday, Feb. 9, 2011, vol. 76, No. 27, p. 7166.
Feener et al.; "Role of plasma kallikrein in diabetes and metabolism"; Thrombosis and Haemostasis; Sep. 2013; vol. 110(3); p. 434-441.
Feingold et al., "Crossover trails with censored data", Statistics in Medicine, 1996, 15(10), 953-967.
Frohlich et al., "Angioedema in Stroke Patients With Thrombolysis—A Lesion Mapping Study", Stroke, Jun. 2019, 11, 50, 1682-1687.
Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), 60-71.
Giard et al., "Angio-Oedema Induced by Oestrogen Contraceptives Is Mediated by Bradykinin and Is Frequently Associated with Urticaria", Dermatology, 2012, 225(1), 62-69.
Golub, et al., "Molecular Classification of Cancer: Class Discovery and Class Prediction by Gene Expression Monitoring", Science, Oct. 15, 1999, vol. 286, 531-537.

Greisbacher et al.; "Involvement of tissue kallikrein but not plasma kallikrein in the development of symptoms mediated by endogenous kinins in acute pancreatitis in rats"; British Journal of Pharmacology; Nov. 2002; vol. 137(5); p. 692-700.
Han et al.,"Increased vascular permeability in C1 inhibitor-deficient mice mediated by the bradykinin type 2 receptor", The Journal of Clinical Investigation, 2002, 109, 1057-1063.
Hermanrud et al., "Recurrent angioedema associated with pharmacological inhibition of dipeptidyl peptidase IV", BMJ Case Reports, Jan. 2017, 10, 4 pages.
Hilfiker et al., "Polymorphism: In the Pharmaceutical Industry", 2006, 1-19.
Hofman et al., "Angioedema attacks in patients with hereditary angioedema: Local manifestations of a systemic activation process", Clin. Rev. Allergy Immunol., 2016, 138, 359-366.
Hwang et al., "Oral plasma kallikrein inhibitor BCX7353 for treatment of hereditary angioedema", Immunotherapy, 2019, 11(17), 1439-1444.
Ikeda et al., "Flost Stromal Bradykinin B.sub.2 Receptor Signaling Facilitates Tumor-Associated Angiogenesis and Tumor Growth", Cancer Research, Aug. 2004, 64, 5178-5185.
International Patent Application No. PCT/GB2015/053613: International Search Report dated Jun. 2, 2016, 5 pages.
International Patent Application No. PCT/IB2019/053640; Int'l Written Opinion and Search Report; dated Sep. 20, 2019; 24 pages.
International Search Report for PCT/GB2014/051592 completed Jul. 23, 2014.
Jaffa et al.; "A Risk Marker for Hypertension and Nephropathy in Type 1 Diabetes"; Diabetes; May 2003; vol. 52; p. 1215-1221.
Johansen et al., "Assay of Kallikrein Inhibitors and Levels of Acetone-Activated Kallikrein in Plasma Specimens From Reactors to Dextran or to Contrast Media", Bioscience Ed, Int. J. Tiss. Reac., 1986, 185-192.
Katsuura et al., "Effects of a Highly Selective Synthetic Inhibitor of Plasma Kallikrein on Disseminated Intravascular Coagulation in Rats", Thrombosis Research, 1996, vol. 82, No. 4, 361-368.
Kedarisetty et al., "Air Pollution and Angioedema," Otolaryngol Head Neck Surg., Apr. 2019, 30, 431-438.
Kenniston, J Bio Chem, "Inhibition of Plasma Kallikrein by a Highly Specific Active Site Blocking Antibody", vol. 289 (34), 2014, 23596-23608.
Khadka et al. "Pharmaceutical particle technologies: An approach to improve drug solubility, dissolution and bioavailability." Asian Journal of Pharmaceutical Sciences, 2014, 9:304-316 (Year: 2014).
Kim et al., "Clinical experiences and case review of angiotensin II receptor blocker-related angioedema in Korea Basic", Clin. Pharmacol. Toxicol., Jan. 2019, 124(1), 115-122.
Kolte et al., "Biochemical Characterization of a Novel High-Affinity and Specific Kallikrein Inhibitor", British Journal of Pharmacology, Apr. 2011, 162(7), pp. 1639-1649.
Koohi et al.; "Coefficient-Free Blood Pressure Estimation Based on Arterial Lumen Area Oscillations in Oscillometric Methods"; IEEE 9th Int'l Symposium on Intelligent Signal Processing; 2015; 6 pages.
Lala, et al., "Role of nitric oxide in tumor progression: Lessons from experimental tumors", Cancer and Metastasis Reviews, 1998, 17: 91-106.
Langewouters et al.; "Pressure-diameter relationships of segments of human finger arteries"; Clinical Physics and Physiological Measurement; vol. 7; 1986; p. 43-56.
Lehmann, "Ecallanlide (DX-88), A Plasma Kallikrein Inhibitor for the Treatment of Hereditary Angioedema and the Prevention of Blood Loss in On-Pump Cardiolhoracic Surgery", Expert Opinion on Biological Therapy, Jul. 2008, 8(8), 1187-1199.
Leibfried et al., "C1 Esterase Inhibitor (Berinert) for ACE Inhibitor-Induced Angioedema: Two Case Reports," J. Pharm Pract., 2017, pp. 668-671.
Leinweber et al, "Possible Physiological Roles of Carboxylic Esler Hydrolases", Drug Metabolism Reviews, Jan. 1987, 18(4), 379-439.
Liang et al. "Fast-Dissolving Intraoral Drug Delivery Systems", Expert Opinion in Therapeutic Patents, 2001, 11(6), 981-986.
Ambinter Sari: "1 H-Pyrazole-4-carboxamides" In: Chemical Catalog, Sep. 11, 2011 (Sep. 11, 2011), Ambinter SARL, XP055601375.

(56) References Cited

OTHER PUBLICATIONS

Anderson, N.G., "Practical Process Research and Development" A guide for organic chemists, Second Edition, 2012, pp. 472.
Aulton's pharmaceutics the design and manufacture of medicines, 3rd Ed, Churchill LivingstoneElsevier, Hungary, 2007, p. 356.
Babu et al., "A Simple, Sensitive and Selective Fluorogenic Assay to Monitor Plasma Kallikrein Inhibitory Activity of BCX4161 in Activated Plasma", Journal of Allergy and Clinical Immunology, Feb. 2014, 133(2 Supp), Abstract AB40, p. 1.
Babu, "Drug Discovery at BioCryst Pharmaceuticals Inc.", Presentation, http://files.shareholder.com/downloads/BCRX/0x0x403076/97a18d6e-1621-4fc6--8f5fd0828bddab4f/, Sep. 16, 2010, 18 pages.
Baeriswyl et al., "A Synthetic Factor XIIa Inhibitor Blocks Selectively Intrinsic Coagulation Initiation", ACS Chem. Biol., 2015, 10(8), 1861-1870.
Bank et al.; "Direct Effects of Smooth Muscle Relaxation and Contraction on In Vivo Human Brachial Artery Elastic Properties"; Circulation Research; vol. 77; Nov. 1995; p. 1008-1016.
Bas et al., N. Engl. J. Med., 2015, 1866-1868.
Bernstein et al., "Polymorphism in Molecular Crystals", 2002, pp. 1-8.
Bhoola et al., "Bioregulation of Kinins: Kallikreins, Kininogens and Kinases", Pharmacological Rev., Mar. 1992, 44(1), 1-80.
Bhoola et al., "Kallikrein-Kinin Cascade" Encyclopedia of Respiratory Medicine, 2006, pp. 483-493.
Bird et al.; Effects of plasma kallikrein deficiency on haemostasis and thrombosis in mice: Murine Ortholog of the Fletcher Trait Thrombosis and Haemostasis; Mar. 8, 2012; vol. 107; p. 1141-50.
Bjorkqvist et al., "Plasma kallikrein: the bradykinin-producing enzyme", Thrombosis and Haemotasis, 2013, 110, 399-407.
Bouckaert et al., "Synthesis, evaluation and structure-activity relationship of new 3-carboxamide coumarins as FXIIa inhibitors", European Journal of Medicinal Chemistry, 2016, 110, 181-194.
Brittain et al., "Polymorphism in Pharmaceutical Solids", 1999,234-239.
Bryant et al., "Human plasma kallikrein-kinin system: Physiological and biochemical parameters", Cardiovascular & Hematological Agents in Medicinal Chemistry, Jul. 2009, 7(3), 234-250.
Byrn et al., "Solid-State Chemistry of Drugs", 1999, 1-17, 233-247.
Caddick et al., "Convenient Synthesis of Protected Primary Amines from Nitriles", Tetrahedron Letters, Apr. 29, 2000, 41(18), 3513-3516.
Calderone et al., "1,2,3-Triazol-Carboxanilides and 1,2,3-Triazol-(N-Benzyl)-Carboxamides as BK-Potassium Channel Activators. XII" European Journal of Medicinal Chemistry 43, 2008, pp. 2618-2626.
Campbell, "Towards Understanding the Kallikrein-Kinin System: Insights from the Measurement of Kinin Peptides", Brazilian Journal of Medical and Biological Research, 2000, 33(6), 665-677.
Cannon, Chapter Nineteen in Burger's Medicinal Chemistry and Drug Discovery, Fifth Edition, vol. 1: Principles and Practice, Wiley-Interscience 1995, pp. 783-802.
CAS abstract accession No. 1990:515202, corresponding to Ried et al. Liebigs Annalen der Chemie, 1990, 8, 2 pages.
CAS abstract accession No. 2013:1177162, corresponding to Ye et al. Chemical Science, 2013, 4(9), 4 pages.
CAS abstract accession No. 2013:1592386, corresponding to FR2989085 A1 (Commissariat Energie Atomique), 3 pages.
CAS abstract accession Nos. 2009:769551 and 2009:846114, corresponding to U.S. Publication 2009-0163545A1, 5 pages.
CAS extract for Compound 1180236-10-5; Sep. 4, 2009.
CAS extract for Compound 1180808-34-7; Sep. 6, 2009.
CAS Extract for Compound 1197490-19-9, dated Dec. 16, 2009, 1 page.
CAS Extract for Compound 120842-43-4, dated Apr. 18, 2011, 1 page.
CAS extract for Compound 1288265-35-9; May 1, 2011.
CAS extract for Compound 1288488-40-3; May 1, 2011.
CAS extract for Compound 1288531-53-2; May 1, 2011.
CAS extract for Compound 1293757-54-6; May 12, 2011.
CAS extract for Compound 1297493-36-7; May 19, 2011.
CAS Extract for Compound 1386962-55-5, dated Aug. 6, 2012, 1 page.
CAS Extract for Compound 1388550-15-9, dated Aug. 9, 2012, 1 page.
CAS Extract for Compound 1626023-22-0, dated Sep. 25, 2014, 1 page.
CAS Structures cited in WO201683818 Written Opinion dated Jun. 2, 2016, 290 pages.
Chemical & Engineering News, Feb. 24, 2003, pp. 32-35.
Chemical Abstract Service, CHEMCATS, RN 1424383-07-2, Mar. 15, 2013.
Chemical Abstracts Registry No. 1147797-44-1, indexed in the Registry file on STN CAS ONLINE May 20, 2009.
Chemical Abstracts Registry No. 1217027-87-6, indexed in the Registry file on STN CAS ONLINE Apr. 5, 2010.
Chemical Abstracts Registry No. 1241137-33-6, indexed in the Registry file on STN CAS ONLINE Sep. 15, 2010.
Chemical Abstracts Registry No. 1295467-87-6, indexed in the Registry file on STN CAS ONLINE May 16, 2011.
Chemical Abstracts Registry No. 1296846-83-7, indexed in the Registry file on STN CAS ONLINE May 18, 2011.
Chemical Abstracts Registry No. 1297526-11-4, indexed in the Registry file on STN CAS ONLINE May 19, 2011.
Chemical Abstracts Registry No. 1389653-06-8, indexed in the Registry file on STN CAS ONLINE Aug. 12, 2012.
Chemical Abstracts Registry No. 1575116-26-5, indexed in the Registry file on STN CAS ONLINE Mar. 28, 2014.
Chemical Abstracts Registry No. 942731-43-3, indexed in the Registry file on STN CAS ONLINE Jul. 19, 2007.
Siebeck et al., "Inhibition of Plasma Kallikrein With Aprotinin in Porcine Endotoxin Shock", The Journal of Trauma, 1993, vol. 34, No. 2, 193-198.
Simao et al., "Plasma kallikrein mediates brain hemorrhage and edema caused by tissue plasminogen activator therapy in mice after stroke", Blood, Apr. 20, 2017, 129(16), 2280-2290.
Stahl, "A Handbook of Pharmaceutical Salts: Properties, Selection and Use", Wiley-VCH, Weinheim, Germany, 2002, 24(3), 1 page.
Stegemann et al., When Poor Solubility Becomes an Issue: From Early Stage to Proof of Concept, European Journal of Pharmaceutical Sciences, 2007, 31, 249-261.
Stergiopulos et al.; "Physical basis of pressure transfer from periphery to aorta: a model-based study"; vol. 274; 1998; H1386-H1392.
STN Registry, "5-Pyrimidinecarboxamide, 1,6-dihydro-N-[1-(6-methyl-1 H-benzimidazol-2-yl)ethyl]-2-oxo-2-(1 H-1,2,4-triazol-1-ylmethyl)", CAS No. 1422635-37-7, Mar. 8, 2013.
STN Registry, "5-Pyrimidinecarboxamide, N-[1-(1H-benzimidazol-2-yl)ethyl]-1,6-dihydro-6-oxo-2-(phenoxymethyl)", CAS No. 1434334-41-4, Jun. 5, 2013.
Sturzbecher et al., "Novel Plasma Kallikrein Inhibitors of the Benzamidine Type", Brazilian J. Med. Biol. Res., 1994, 27, 1929-1934.
Sturzebecher et al., "Inhibition of Human Mast Cell Tryptase by Benzamidine Derivatives", Biological Chemistry Hoppe-Seyler, Oct. 1992, 373(2), 1025-1030.
Tanaka et al., Thrombosis Research 2004, "Evaluation of a novel kallikrein inhibitor on hemostatic activation in vitro"; 113, 333-339.
Teno et al., "Development of Active Center-Directed Plasmin and Plasma Kallikrein Inhibitors and Studies on the Structure-Inhibitory Activity Relationship", Chem. Pharm. Bull., Jun. 1993, 41, 1079-1090.
Tombran-Tink et al., "Opthamology Research", Visual Dysfunction in Diabetes the Science of Patient Impairment and Health Care, 2012, 4 pages.
Ulven et al.; "6-Acylamino-2-amino-4-methylquinolines as potent melanin-concentrating hormone 1 receptor antagonists: Structure-activity exploration of eastern and western parts"; Bioorganic & Medicinal Chemistry Letters; vol. 16 Issue 4; Feb. 2006; p. 1070-1075.
van den Elzen et al., "Efficacy of 1-45 Treatment of Non-hereditary Angioedema", Clinical Reviews in Allergy and Immunology, Humana Press, Totowa, NJ, US, Sep. 27, 2016, vol. 54, No. 3, 412-431.

(56) References Cited

OTHER PUBLICATIONS

Veronez et al., "Genetic Variation of Kallikrein-Kinin System and Related Genes in Patients With Hereditary Angioedema", Frontiers in Medicine, Feb. 2019, 21, 6, 28, 6 pages.
Wang et al., "Determination of In Vitro Permeability of Drug Candidates through a Caco-2 Cell Monolayer by Liquid Chromatography/Tandem Mass Spectrometry" J. Mass Spectrom 35(1); 71-76, 2000.
Wermuth et al., Handbook of Pharmaceutical Salts: Properties, Selection and Use, 2002 vol. 24, No. 3, p. 20.
Wermuth, "The Practice of Medicinal Chemistry", 2003, 2nd Ed., 561-585.
Wintenberger et al., "Tranexamic acid as maintenance treatment for non-histaminergic angioedema: analysis of efficacy and safety in 37 patients", British Society for Immunology, Clinical and Experimental Immunology, 2014, 178, 112-117.
Young et al., "Small Molecule Inhibitors of Plasma Kallikrein", Bioorg. Med. Chem. Letts., Apr. 2006, 16(7), pp. 2034-2036.
Zhang et al., "Discovery of Highly Potent Small Molecule Kallikrein Inhibitors"; Medicinal Chemistry, Nov. 2006, 2(6), 545-553.
Bouillet, "Hereditary angioedema with normal C1 inhibitor: clinical characteristics and treatment response with plasma-derived human C1 inhibitor concentrate (Berinert®) in a French cohort," Eur. J. Dermatol., Apr. 1, 2017, 27(2), 155-159.
Diestro et al., "Hemilingual Angioedema after Thrombolysis in a Patient on an Angiotensin II Receptor Blocker," J. Stroke Cerebrovasc Dis., May 2019, 28(5), e44-e45.
Hill et al., "Hemi-orolingual angioedema and ACE inhibition after alteplase treatment of stroke," Neurology, May 13, 2003, 60(9), 1525-1527.
Jose et al., "Evaluating satisfaction of patients with hereditary angioedema with their past and present treatments: Implications for future therapies," Allergy Asthma Proc., Jan. 1, 2018, 39(1), 74-80.
Lekoubou et al., "Audit report and systematic review of orolingual angioedemain post-acute stroke thrombolysis," Neurol. Res., Jul. 2014, 36(7), 687-694.
Magerl et al., "Hereditary Angioedema with Normal C1 Inhibitor: Update on Evaluation and Treatment," Immunol Allergy Clin North Am., Aug. 2017, 37(3), 571-584.
Scott et al., "Dipeptidyl Peptidase-4 Inhibitor Induced Angioedema—An Overlooked Adverse Drug Reaction?," Curr Diabetes Rev., 2018, 14(4), 327-333.
Stone et al., "Angiotensin-converting Enzyme Inhibitor and Other Drug-associated Angioedema," Immunol Allergy Clin North Am., Aug. 2017, 37(3), 483-495.
Lieberman et al. Pharmaceutical Dosage Forms: Tablets, Second Edition, vol. 2, 1989, XP008099925; 15 pages (front page and list of contents included), 145-157.
Liu et al.; "Hyperglycemia Induced Cerebral Hematoma Expansion is Mediated by Plasma Kallikrein"; Nat. Med.; Feb. 2011; vol. 17(2); p. 206-210.
Long et al., "Negatively Charged Silver Nanoparticles Cause Retinal Vascular Permeability by Activating Plasma Contact System and Disrupting Adherens Junction", Nanotxicology, 2016, 10(4), 501-511.
Lussis et al.; "A single synthetic small molecule that generates force against a load"; Nature Nanotechnology; vol. 6; 2011; p. 553-557.
Lussis et al.; "A single synthetic small molecule that generates force against a load"; Nature Nanotechnology; vol. 6; 2011; p. S1-S25 (Supplemental Information).
Luthin et al., "The Discovery of Novel Small Molecule Non-peptide Gonadotropin Releasing Hormone (GnRH) Receptor Antagonists" Bioorg Med Chem Lett, 12, 2002, pp. 3467-3470.
Maas et al., "Misfolded proteins activate Factor XII in humans, leading to kallikrein formation without initiating coagulation", J. Clinical Invest., Sep. 2008, 118(9), 3208-3218.
Magerl et al., "Characterization of prodromal symptoms in a large population of patients with hereditary angio-oedema", Clinical and Experimental Dermatology, 2014, 39, 298-303.
Mansi et al., 2014 the Association for the publication of the Journal of Internal Medicine Journal of Internal Medicine, 2015, 277, 585-593.
Marceau et al., "Bradykinin Receptor Ligands: Therapeutic Perspectives", Nature Review, Drug Discovery 2004, Oct. 2004, 3, 845-852.
Marra et al, "Solution Formulation Development of a VEGF Inhibitor for Intravitreal Injection", 2011, 12(1), 362-370.
Maurer et al., "Hereditary Angioedema Attacks Resolve Faster and Are Shorter after Early Icatibant Treatment", PLoS ONE, 2013, 8(2), e53773, 7 pages.
Maurice, "Review: Practical Issues in Intravitreal Drug Delivery", Journal of Ocular Pharmacology and Therapeutics, 2001, 17(4), 393-401.
MedicineNet (2004) Web:<http://www.medterms.com>.
Obach, "Prediction of human clearance of twenty-nine drugs from hepatic microsomal intrinsicclearance data: An examination of in vitro half-life approach and nonspecific binding tomicrosomes", Drug Metabolism and Disposition, 1999, 27(11), 1350-13592.
Okada et al., "Development of Potent and Selective Plasmin and Plasma Kallikrein Inhibitors and Studies on the Structure-Activity Relationship", Chem. Pharm. Bull., 2000, 48, 12, 1964-1972.
Pace, et al., "4-Hydroxy-5-pynolinone-3-carboxamide HIV-1 integrase inhibitors", Bioorganic & Medicinal Chemistry Letters., 18, Jun. 2008, pp. 3865-3869.
Patel et al. An overview of size reduction technologies in the field of pharmaceutical manufacturing. Asian Journal of Pharmaceutical Sciences. Oct.-Dec. 2008:216-220. (Year: 2008).
Patel et al., "Ecall anti de for treatment of acute attacks of acquired CI esterase inhibitor deficiency", Allergy and Asthma Proceedings, Oceanside Publications, Inc., US, Nov. 30, 2012, vol. 34, No. 1, 72-77.
Patel, "Combination Therapy for Age-Related Macular Degeneration", Retina, Jun. 2009, 29(6), S45-S48.
Patel, et al: Allery and Asthma Proceedings; Ecallantide for treatment of acute attacks of acquired C1 esterase inhibitor deficiency; Jan.-Feb. 2013, vol. 34, No. 1, 72-77.
Prassas, "Unleashing the therapeutic potential of human kallikrein-related serine proteases", Nature Reviews Drug Discovery, vol. 14, 183-202, 2015.
Prescott's Test, "The comparison of success rates in cross-over trails in the presence of an order effect", Applied Statistics, 1981, 30, 9-15.
PubChem Compound 40150888 May 30, 2009.
PubChem Compound 51143945 May 3, 2011.
PubChem Compound 52011740 May 20, 2011.
PubChem Compound 52011741 May 20, 2001.
PubChem Compound 52011742 May 20, 2011.
PubChem Compound 52011935 May 20, 2011.
PubChem Compound 52011936 May 20, 2011.
PubChem Compound 52011937 May 20, 2011.
PubChem Compound 52011938 May 20, 2011.
PubChem Compound 55389827 Jan. 25, 2012.
PubChem Compound 55408484 Jan. 25, 2012.
PubChem Compound 55408530 Jan. 25, 2012.
PubChem Compound 55408677 Jan. 25, 2012.
PubChem Compound 55408742 Jan. 25, 2012.
PubChem Compound 55408894 Jan. 25, 2012.
PubChem Compound 55438190 Jan. 25, 2012.
PubChem Compound 55494217 Jan. 25, 2012.
PubChem Compound 55650494 Jan. 25, 2012.
PubChem Compound 60376550 Oct. 18, 2012.
PubChem Compound ID 22830339 Dec. 5, 2007.
PubChem Compound ID 24488625 Feb. 29, 2008.
PubChem Compound ID 38284485 May 29, 2009.
PubChem Compound ID 38284487 May 29, 2009.
PubChem Compound ID 46438580 Jul. 23, 2010.
Rathbun, "Angioedema after thrombolysis with tissue plasminogen activator: an airway emergency", Oxf. Med Case Reports, Jan. 24, 2019, (1), 11-13.

(56) References Cited

OTHER PUBLICATIONS

Recke et al., "Identification of the recently described plasminogen gene mutation p.Lys330Glu in a family from Northern Germany with hereditary angioedema", Clin. Transl. Allergy. Feb. 2019, 14; 9, 9, 4 pages.
Registry No. 1015534-45-8, Chemical Library—FCG Group, Apr. 18, 2008, 1 page.
Registry No. 1027627-81-1, Chemical Library—FCG Group, Jun. 12, 2008, 1 page.
Registry No. 1028093-96-0, Chemical Library—FCG Group, Jun. 13, 2008, 1 page.
Registry No. 1028094-50-9, Chemical Library—FCG Group, Jun. 13, 2008, 1 page.
Registry No. 1028096-34-5, Chemical Library—FCG Group, Jun. 13, 2008, 1 page.
Registry No. 1028361-95-6, Chemical Library—FCG Group, Jun. 16, 2008, 1 page.
Registry No. 1061709-51-0, Chemical Library—FCG Group, Oct. 15, 2008, 1 page.
Registry No. 1062408-24-5, Chemical Library—FCG Group, Oct. 17, 2008, 1 page.
Registry No. 1086603-37-3, Chemical Library—AKos Consulting and Solutions GmbH, CHEMCATS, dated Dec. 18, 2008, 1 page.
Registry No. 1086603-42-0, Chemical Library—AKos Consulting and Solutions GmbH, CHEMCATS, dated Dec. 18, 2008, 1 page.
Registry No. 1086603-52-2, Chemical Library—AKos Consulting and Solutions GmbH, CHEMCATS, dated Dec. 18, 2008, 1 page.
Registry No. 1094996-93-6, Chemical Library—AKos Consulting and Solutions GmbH, CHEMCATS, dated Jan. 22, 2009, 1 page.
Registry No. 1103271-51-7, Chemical Library—FCG Group, Feb. 9, 2009, 1 page.
Registry No. 1170030-40-6, Chemical Library—FCG Group, Jul. 29, 2009, 1 page.
Registry No. 1171669-07-0, Chemical Library—FCG Group, Aug. 2, 2009, 1 page.
Registry No. 1171693-25-6, Chemical Library—Ambinter, CHEMCATS, dated Aug. 2, 2017, 1 page.
Registry No. 1278351-92-0, Chemical Library—FCG Group, Apr. 11, 2011, 1 page.
Registry No. 1280842-43-4, Chemical Library—FCG Group, Apr. 18, 2011, 1 page.
Registry No. 1317328-27-0, Chemical Library—FCG Group, Aug. 14, 2011, 1 page.
Registry No. 1317855-54-1, Chemical Library—FCG Group, Aug. 15, 2011, 1 page.
Registry No. 1318167-86-0, Chemical Library—FCH Group, CHEMCATS, dated Aug. 15, 2011, 1 page.
Registry No. 1318604-27-1, Chemical Library—FCG Group, Aug. 16, 2011, 1 page.
Registry No. 1320653-15-3, Chemical Library—FCG Group, Aug. 21, 2011, 1 page.
Registry No. 1321195-15-6, Chemical Library—FCG Group, Aug. 21, 2011, 1 page.
Registry No. 1321521-84-9, Chemical Library—FCG Group, Aug. 12, 2011, 1 page.
Registry No. 1386189-59-8, Chemical Library—Ukrorgsyntez Ltd., CHEMCATS, dated Aug. 3, 2012, 1 page.
Registry No. 1390613-03-2, Chemical Library—FCG Group, Aug. 13, 2012, 1 page.
Registry No. 1569406-35-4, Chemical Library—FCG Group, Mar. 18, 2014, 1 page.
Registry No. 1570266-44-2, Chemical Library—FCG Group, Mar. 19, 2014, 1 page.
Registry No. 1572436-72-6, Chemical Library—FCG Group, Mar. 24, 2014, 1 page.
Registry No. 1572751-33-7, Chemical Library—FCH Group, dated Mar. 24, 2014.
Registry No. 1572946-10-1, Chemical Library—FCG Group, Mar. 25, 2014, 1 page.
Registry No. 1573976-69-8, Chemical Library—FCG Group, Mar. 26, 2014, 1 page.
Registry No. 1575214-30-0, Chemical Library—FCG Group, Mar. 28, 2014, 1 page.
Registry No. 1580327-09-8, Chemical Library—FCH Group, Apr. 4, 2014, 1 page.
Registry No. 1625594-62-8, Chemical Library—FCG Group, Sep. 24, 2014, 1 page.
Registry No. 879195-72-9, Chemical Library—FCG Group, Apr. 4, 2006, 1 page.
Registry No. 879300-81-9, Chemical Library—FCG Group, Apr. 5, 2006, 1 page.
Registry No. 955867-36-4, Chemical Library—FCG Group, Nov. 23, 2007, 1 page.
Registry No. 956190-38-8, Chemical Library—FCG Group, Nov. 28, 2007, 1 page.
Registry No. 956290-77-0, Chemical Library—FCG Group, Nov. 29, 2007, 1 page.
Registry No. 956444-80-7, Chemical Library—FCG Group, Dec. 2, 2007, 1 page.
Registry No. 956521-49-6, Chemical Library—FCG Group, Dec. 3, 2007, 1 page.
Registry No. 956529-72-9, Chemical Library—FCG Group, Dec. 3, 2007, 1 page.
Registry No. 956747-39-0, Chemical Library—FCG Group, Dec. 5, 2007, 1 page.
Reichman et al., "Antihypertensive drug associated angioedema: effect modification by race/ethnicity," Pharmacoepidermiol Drug Saf., Oct. 2017, 26(10), 1190-1196.
Remington: Practice of the Science and Pharmacy; 19th Edition; Mack Publishing Company, 1995, 5 pages.
Revenko et al.; "Selective depletion of plasma prekallikrein or coagulation factor XII inhibits thrombosis in mice without increased risk of bleeding"; Blood; Aug. 5, 2011; 118; p. 5302-5311.
Rodriguez-Spong, et al: General principles of pharmaceutical solid polymorphism: a supramolecular perspective; 56, 2004, 241-274.
Savjani et al. "Drug Solubility: Importance and Enhancement Techniques". ISRN Pharm. vol. 2012, article ID 195727, 10 pages. (Year: 2012).
Shari et al., "New Specific Assays for Tonin and Tissue Kallikrein Activities in Rat Submandibular Glands: Assays Reveal Differences in the Effects of Sympathetic and Parasympathetic Stimulation on Proteinases in Saliva", Biochemical Pharmacology, Mar. 17, 1992, 43(6), pp. 1209-1217.

ENZYME INHIBITORS

CROSS-REFERENCE TO RELATED APPLICATIONS

This application is a continuation of International Patent Application No. PCT/GB2020/050331, filed Feb. 13, 2020, which claims priority to International Patent Application No. PCT/GB2019/052252, filed Aug. 9, 2019, the disclosures of which are incorporated by reference herein.

FIELD OF THE INVENTION

This invention relates to enzyme inhibitors that are inhibitors of plasma kallikrein, and to the pharmaceutical compositions, and uses of, such inhibitors.

BACKGROUND TO THE INVENTION

The heterocyclic derivatives of the present invention are inhibitors of plasma kallikrein and have a number of therapeutic applications, particularly in the treatment of bradykinin-mediated angioedema hereditary angioedema and bradykinin-mediated angioedema non-hereditary (BK-AEnH).

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and can be synthesized in the liver, as well as other tissues. It is secreted by hepatocytes as an inactive plasma prekallikrein that circulates in plasma as a heterodimer complex bound to high molecular weight kininogen (HK) which is activated to give the active plasma kallikrein. This contact activation system (or contact system) can be activated by negatively charged surfaces that activate Factor XII (FXII) to Factor XIIa (FXIIa), by certain proteases e.g. plasmin (Hofman et al Clin Rev Allergy Immunol 2016), which may not require negative surfaces, or by misfolded proteins (Maas et al J Clinical Invest 2008). FXIIa mediates conversion of plasma prekallikrein to plasma kallikrein and the subsequent cleavage of high molecular weight kininogen (HK) to generate bradykinin, a potent inflammatory hormone. Kinins are potent mediators of inflammation that act through G protein-coupled receptors and antagonists of kinins (such as bradykinin receptor antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen (HK) liberating bradykinin leading to increased vascular permeability. "Hereditary angioedema" can thus be defined as any disorder characterised by recurrent episodes of bradykinin-mediated angioedema (e.g. severe swelling) caused by an inherited dysfunction/fault/mutation. There are currently three known categories of HAE: (i) HAE type 1, (ii) HAE type 2, and (iii) normal C1 inhibitor HAE (normal C1-Inh HAE). However, the HAE field is developing quickly so it is expected that further types of HAE might be defined in the future.

Without wishing to be bound by theory, it is thought that HAE type 1 is caused by mutations in the SERPING1 gene that lead to reduced levels of C1 inhibitor in the blood. Without wishing to be bound by theory, it is thought that HAE type 2 is caused by mutations in the SERPING1 gene that lead to dysfunction of the C1 inhibitor in the blood. Without wishing to be bound by theory, the cause of normal C1-Inh HAE is less well defined and the underlying genetic dysfunction/fault/mutation can sometimes remain unknown. What is known is that the cause of normal C1-Inh HAE is not related to reduced levels or dysfunction of the C1 inhibitor (in contrast to HAE types 1 and 2). Normal C1-Inh HAE can be diagnosed by reviewing the family history and noting that angioedema has been inherited from a previous generation (and thus it is hereditary angioedema). Normal C1-Inh HAE can also be diagnosed by determining that there is a dysfunction/fault/mutation in a gene other than those related to C1 inhibitor. For example, it has been reported that dysfunction/fault/mutation with plasminogen can cause normal C1-Inh HAE (see e.g. Veronez et al., Front Med (Lausanne). 2019 Feb. 21; 6:28. doi: 10.3389/fmed.2019.00028; or Recke et al., Clin Transl Allergy. 2019 Feb. 14; 9:9. doi: 10.1186/s13601-019-0247-x.). It has also been reported that dysfunction/fault/mutation with Factor XII can cause normal C1-Inh HAE (see e.g. Mansi et al. 2014 The Association for the Publication of the Journal of Internal Medicine Journal of Internal Medicine, 2015, 277; 585-593; or Maat et al. *J Thromb Haemost*. 2019 January; 17(1):183-194. doi: 10.1111/jth.14325).

However, angioedemas are not necessarily inherited. Indeed, another class of angioedema is bradykinin-mediated angioedema non-hereditary (BK-AEnH), which is not caused by an inherited genetic dysfunction/fault/mutation. Often the underlying cause of BK-AEnH is unknown and/or undefined.

However, the signs and symptoms of BK-AEnH are similar to those of HAE, which without being bound by theory, is thought to be on account of the shared bradykinin-mediated pathway between HAE and BK-AEnH. Specifically, BK-AEnH is characterised by recurrent acute attacks where fluids accumulate outside of the blood vessels, blocking the normal flow of blood or lymphatic fluid and causing rapid swelling of tissues such as in the hands, feet, limbs, face, intestinal tract, airway or genitals.

Specific types of BK-AEnH include: non-hereditary angioedema with normal C1 Inhibitor (AE-nC1 Inh), which can be environmental, hormonal, or drug-induced; acquired angioedema; anaphylaxis associated angioedema; angiotensin converting enzyme (ACE) inhibitor-induced angioedema; dipeptidyl peptidase-4 inhibitor-induced angioedema; and tPA-induced angioedema (tissue plasminogen activator-induced angioedema). However, reasons why these factors and conditions cause angioedema in only a relatively small proportion of individuals are unknown.

Environmental factors that can induce AE-nC1 Inh include air pollution (Kedarisetty et al, Otolaryngol Head Neck Surg. 2019 Apr. 30:194599819846446. doi: 10.1177/

0194599819846446) and silver nanoparticles such as those used as antibacterial components in healthcare, biomedical and consumer products (Long et al., Nanotoxicology. 2016; 10(4):501-11. doi: 10.3109/17435390.2015.1088589).

Various publications suggest a link between the bradykinin and contact system pathways and BK-AEnHs, and also the potential efficacy of treatments, see e.g.: Bas et al. (N Engl J Med 2015; Leibfried and Kovary. J Pharm Pract 2017); van den Elzen et al. (Clinic Rev Allerg Immunol 2018); Han et al (JCI 2002). tPA-induced angioedema is discussed in various publications as being a potentially life-threatening complication following thrombolytic therapy in acute stroke victims (see e.g. Simão et al., Blood. 2017 Apr. 20; 129(16):2280-2290. doi: 10.1182/blood-2016-09-740670; Fröhlich et al., Stroke. 2019 Jun. 11:STROKEAHA119025260. doi: 10.1161/STROKEAHA.119.025260; Rathbun, Oxf Med Case Reports. 2019 Jan. 24; 2019(1):omy112. doi: 10.1093/omcr/omy112; Lekoubou et al., Neurol Res. 2014 July; 36(7): 687-94. doi: 10.1179/1743132813Y.0000000302; Hill et al., Neurology. 2003 May 13; 60(9):1525-7).

Stone et al. (Immunol Allergy Clin North Am. 2017 August; 37(3):483-495.) reports that certain drugs can cause angioedema.

Scott et al. (Curr Diabetes Rev. 2018; 14(4):327-333. doi: 10.2174/1573399813666170214113856) reports cases of dipeptidyl Peptidase-4 Inhibitor induced angioedema.

Hermanrud et al., (BMJ Case Rep. 2017 Jan. 10; 2017. pii: bcr2016217802) reports recurrent angioedema associated with pharmacological inhibition of dipeptidyl peptidase IV and also discusses acquired angioedema related to angiotensin-converting enzyme inhibitors (ACEI-AAE). Kim et al. (Basic Clin Pharmacol Toxicol. 2019 January; 124(1): 115-122. doi: 10.1111/bcpt.13097) reports angiotensin II receptor blocker (ARB)-related angioedema. Reichman et al., (Pharmacoepidemiol Drug Saf. 2017 October; 26(10): 1190-1196. doi: 10.1002/pds.4260) also reports angioedema risk for patients taking ACE inhibitors, ARB inhibitors and beta blockers. Diestro et al. (J Stroke Cerebrovasc Dis. 2019 May; 28(5):e44-e45. doi: 10.1016/j.jstrokecerebrovasdis.2019.01.030) also reports a possible association between certain angioedemas and ARBs.

Giard et al. (Dermatology. 2012; 225(1):62-9. doi: 10.1159/000340029) reports that bradykinin-mediated angioedema can be precipitated by oestrogen contraception.

Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" Expert Opin. Biol. Ther. 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" Diabetes, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . " J. Peptide Res. 52, p 62-71 (1998)), T. Griesbacher et al. ("Involvement of tissue kallikrein but not plasma kallikrein in the development of symptoms mediated by endogenous kinins in acute pancreatitis in rats" British Journal of Pharmacology 137, p 692-700 (2002)), Evans ("Selective dipeptide inhibitors of kallikrein" WO03/076458), Szelke et al. ("Kininogenase inhibitors" WO92/04371), D. M. Evans et al. (Immunopharmacology, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Sturzbecher et al. (Brazilian J. Med. Biol. Res 27, p 1929-34 (1994)), Kettner et al. (U.S. Pat. No. 5,187,157), N. Teno et al. (Chem. Pharm. Bull. 41, p 1079-1090 (1993)), W. B. Young et al. ("Small molecule inhibitors of plasma kallikrein" Bioorg. Med. Chem. Letts. 16, p 2034-2036 (2006)), Okada et al. ("Development of potent and selective plasmin and plasma kallikrein inhibitors and studies on the structure-activity relationship" Chem. Pharm. Bull. 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" Medicinal Chemistry 2, p 545-553 (2006)), Sinha et al. ("Inhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, no small molecule synthetic plasma kallikrein inhibitor has been approved for medical use. The molecules described in the known art suffer from limitations such as poor selectivity over related enzymes such as KLK1, thrombin and other serine proteases, and poor oral availability. The large protein plasma kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the vast majority of molecules in the known art feature a highly polar and ionisable guanidine or amidine functionality. It is well known that such functionalities may be limiting to gut permeability and therefore to oral availability. For example, it has been reported by Tamie J. Chilcote and Sukanto Sinha ("ASP-634: An Oral Drug Candidate for Diabetic Macular Edema", ARVO 2012 May 6th-May 9, 2012, Fort Lauderdale, Fla., Presentation 2240) that ASP-440, a benzamidine, suffers from poor oral availability. It is further reported that absorption may be improved by creating a prodrug such as ASP-634. However, it is well known that prodrugs can suffer from several drawbacks, for example, poor chemical stability and potential toxicity from the inert carrier or from unexpected metabolites. In another report, indole amides are claimed as compounds that might overcome problems associated with drugs possessing poor or inadequate ADME-tox and physicochemical properties although no inhibition against plasma kallikrein is presented or claimed (Griffioen et al, "Indole amide derivatives and related compounds for use in the treatment of neurodegenerative diseases", WO2010142801).

Other plasma kallikrein inhibitors known in the art are generally small molecules, some of which include highly polar and ionisable functional groups, such as guanidines or amidines. Recently, plasma kallikrein inhibitors that do not feature guanidine or amidine functionalities have been reported. For example Brandl et al. ("N-((6-amino-pyridin-3-yl)methyl)-heteroaryl-carboxamides as inhibitors of plasma kallikrein" WO2012/017020), Evans et al. ("Benzylamine derivatives as inhibitors of plasma kallikrein" WO2013/005045), Allan et al. ("Benzylamine derivatives" WO2014/108679), Davie et al. ("Heterocyclic derivates" WO2014/188211), Davie et al. ("N-((het)arylmethyl)-heteroaryl-carboxamides compounds as plasma kallikrein inhibitors" WO2016/083820) and Davie et al. ("Pyrazole derivatives as plasma kallikrein inhibitors" WO2017/207983).

However, there remains a need to develop new plasma kallikrein inhibitors that will have utility to treat a wide range of disorders, in particular bradykinin-mediated angioedema such as hereditary angioedema. In particular, there remains a need to develop new plasma kallikrein inhibitors that have high selectivity for plasma kallikrein and possess a good pharmacokinetic profile for oral delivery (e.g. possessing good bioavailability).

DETAILED DESCRIPTION OF THE DRAWINGS

DESCRIPTION OF THE INVENTION

Figure 1:
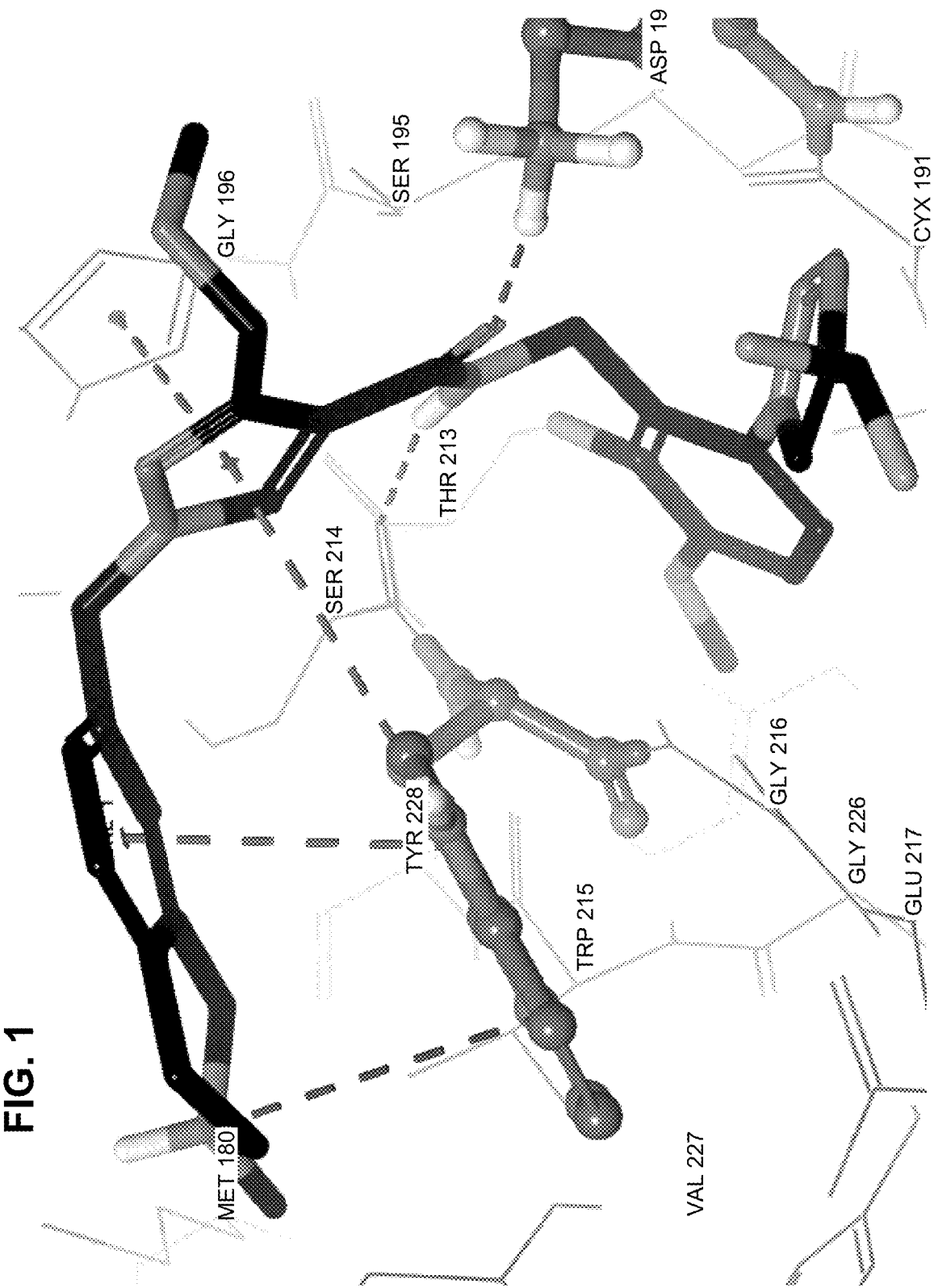
FIG. 1 is a diagram showing key interactions of Example 1 with human plasma kallikrein.

The present invention relates to a series of heterocyclic derivatives that are inhibitors of plasma kallikrein. These compounds demonstrate good selectivity for plasma kallikrein and are potentially useful in the treatment of bradykinin-mediated angioedemas such as impaired visual acuity, diabetic retinopathy, macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post-operative surgery. The invention further relates to pharmaceutical compositions of the inhibitors, to the use of the compositions as therapeutic agents, and to methods of treatment using these compositions.

In a first aspect, the present invention provides compounds of formula (I):

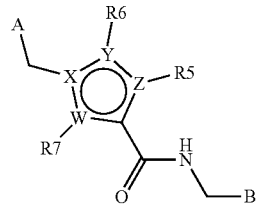

Formula (I)

wherein

W, X, Y and Z are independently selected from C, C(R16)-C, C(R16)=C, C=N, O and N, such that the ring containing W, X, Y and Z is a 5-, or 6-membered heteroaryl;

R5, R6, and R7 are independently absent or independently selected from H, alkyl, cycloalkyl, alkoxy, halo, OH, CN, $CF_3$, aryl, heteroaryl$^a$, N-linked pyrrolidinyl, N-linked piperidinyl, N-linked morpholinyl, N-linked piperazinyl, —NR13R14, —COOR13, —CONR13R14, and —NR13COR14;

R16 is independently selected from H, alkyl, cycloalkyl, alkoxy, halo, OH, CN, $CF_3$, aryl, heteroaryl$^a$, N-linked pyrrolidinyl, N-linked piperidinyl, N-linked morpholinyl, N-linked piperazinyl, —NR13R14, —COOR13, —CONR13R14, and —NR13COR14; or W, X, Y and Z are independently selected from C, C(R16)-C, C(R16)=C, C=N and N, and one of R5, R6, R7 or R16 is oxo such that the ring containing W, X, Y and Z is 2-pyridone or 4-pyridone; wherein the others of R5, R6, R7 and R16 are independently absent or independently selected from H, alkyl, cycloalkyl, alkoxy, halo, OH, CN, $CF_3$, aryl, heteroaryl$^a$, N-linked pyrrolidinyl, N-linked piperidinyl, N-linked morpholinyl, N-linked piperazinyl, —NR13R14, —COOR13, —CONR13R14, and —NR13COR14;

B is of Formula (II) comprising aromatic rings B' and B" that are linked by a bond:

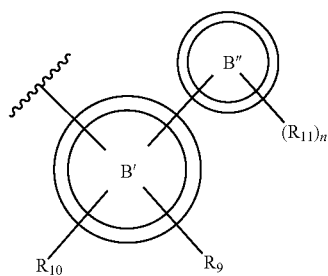

Formula (II)

B' is phenyl or pyridyl;
B" is pyrrole, pyrazole, triazole, or tetrazole;
n is 0, 1, or 2;
R9 and R10 are independently selected from H, alkyl, cycloalkyl, alkoxy, halo, OH, CN, and CF$_3$;
Each R11 is independently alkyl, cycloalkyl, alkoxy, halo, OH, —COOR13, —CONR13NR14, CN, and CF$_3$;
A is a heterocyclic ring of Formula (III) comprising an aromatic ring (A') fused to a non-aromatic ring (A"):

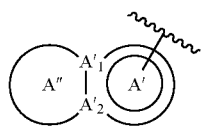

Formula (III)

A'1 and A'2 are independently C or N;
A' is heteroaryl or phenyl, wherein phenyl may be optionally substituted with 1, 2, or 3 substituents independently selected from alkyl, alkoxy, OH, OCF$_3$, halo, CN, and CF$_3$, and wherein heteroaryl may be optionally substituted as stated below;
A" is heterocycloalkyl;
  optionally wherein a carbon ring atom on A" is substituted with an alkylene or a heteroalkylene such that the carbon ring atom on A" together with the alkylene or the heteroalkylene forms a cycloalkyl or heterocycloalkyl$^a$ that is spiro to ring A"; and/or
  optionally wherein two ring atoms on A" are linked by an alkylene or heteroalkylene to form a non-aromatic ring containing 5, 6, or 7 ring members;
alkyl is a linear saturated hydrocarbon having up to 10 carbon atoms ($C_1$-$C_{10}$) or a branched saturated hydrocarbon of between 3 and 10 carbon atoms ($C_3$-$C_{20}$); alkyl may optionally be substituted with 1 or 2 substituents independently selected from ($C_1$-$C_6$)alkoxy, OH, —NR13R14, —COOR13, —CONR13R14, CN, CF$_3$, halo;
alkyl$^b$ is a linear saturated hydrocarbon having up to 10 carbon atoms ($C_1$-$C_{10}$) or a branched saturated hydrocarbon of between 3 and 10 carbon atoms ($C_3$-$C_{10}$); alkyl$^b$ may optionally be substituted with 1 or 2 substituents independently selected from ($C_1$-$C_6$)alkoxy, OH, CN, CF$_3$, halo;
alkylene is a bivalent linear saturated hydrocarbon having 1 to 5 carbon atoms ($C_1$-$C_5$); alkylene may optionally be substituted with 1 or 2 substituents independently selected from alkyl, ($C_1$-$C_6$)alkoxy, OH, CN, CF$_3$, halo;

aryl is phenyl, biphenyl or naphthyl; aryl may be optionally substituted with 1, 2 or 3 substituents independently selected from alkyl, alkoxy, methylenedioxy, ethylenedioxy, OH, halo, CN, heteroaryl$^a$, —(CH$_2$)$_{0-3}$—O-heteroaryl$^a$, aryl$^b$, —O-aryl$^b$, —(CH$_2$)$_{1-3}$-aryl$^b$, —(CH$_2$)$_{1-3}$-heteroaryl$^a$, —COOR13, —CONR13R14, —(CH$_2$)$_{0-3}$—NR13R14, OCF$_3$ and CF$_3$;
aryl$^b$ is phenyl, biphenyl or naphthyl, which may be optionally substituted with 1, 2 or 3 substituents independently selected from alkyl$^b$, alkoxy, OH, halo, CN, and CF$_3$;
heteroalkylene is a bivalent linear saturated hydrocarbon having 2 to 5 carbon atoms ($C_2$-$C_5$), wherein at least one of the 2 to 5 carbon atoms is replaced with NR8, S, or O; heteroalkylene may optionally be substituted with 1 or 2 substituents independently selected from alkyl, ($C_1$-$C_6$)alkoxy, OH, CN, CF$_3$, halo;
cycloalkyl is a monocyclic saturated hydrocarbon ring of between 3 and 6 carbon atoms ($C_3$-$C_6$); cycloalkyl may optionally be substituted with 1 or 2 substituents independently selected from alkyl ($C_1$-$C_6$)alkoxy, OH, CN, CF$_3$, halo;
alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1 or 2 substituents independently selected from OH, CN, CF$_3$, and fluoro;
halo is F, Cl, Br, or I;
heteroaryl is a 5- or 6-membered carbon-containing aromatic ring containing one, two or three ring members that are selected from N, NR8, S, and O; heteroaryl may be optionally substituted with 1, 2 or 3 substituents independently selected from alkyl, alkoxy, OH, OCF$_3$, halo, CN, and CF$_3$;
heteroaryl$^a$ is a 5, 6, 9 or 10 membered mono- or bi-cyclic aromatic ring, containing, where possible, 1, 2, 3 or 4 ring members independently selected from N, NR12, S and O; heteroaryl$^a$ may be optionally substituted with 1, 2 or 3 substituents independently selected from alkyl, alkoxy, OH, OCF$_3$, halo, CN, aryl$^b$, —(CH$_2$)$_{1-3}$-aryl$^b$, —(CH$_2$)$_{0-3}$—NR13R14, heteroaryl$^b$, —COOR13, —CONR13R14 and CF$_3$;
heteroaryl$^b$ is a 5, 6, 9 or 10 membered mono- or bi-cyclic aromatic ring, containing, where possible, 1, 2 or 3 ring members independently selected from N, NR12, S and O; wherein heteroaryl$^b$ may be optionally substituted with 1, 2 or 3 substituents independently selected from alkyl$^b$, alkoxy, OH, halo, CN, aryl$^b$, —(CH$_2$)$_{1-3}$-aryl$^b$, and CF$_3$;
heterocycloalkyl is a non-aromatic carbon-containing monocyclic ring containing 5, 6, or 7 ring members, wherein one or two ring members are independently selected from N, NR8, S, SO, SO$_2$, and O; wherein heterocycloalkyl may be optionally substituted with 1, 2, or 3 substituents independently selected from alkyl, alkoxy, OH, OCF$_3$, halo, oxo and CN;
heterocycloalkyl$^a$ is a non-aromatic carbon-containing monocyclic ring containing 3, 4, 5, or 6, ring members, wherein at least one ring member is independently selected from NR8, S, SO, SO$_2$, and O; heterocycloalkyl$^a$ may be optionally be substituted with 1 or 2 substituents independently selected from alkyl, ($C_1$-$C_6$) alkoxy, OH, CN, CF$_3$, halo;
R8 is independently selected from H, alkyl, cycloalkyl, or heterocycloalkyl$^b$;
heterocycloalkyl$^b$ is a non-aromatic carbon-containing monocyclic ring containing 3, 4, 5, or 6, ring members, wherein at least one ring member is independently selected from N, NR12, S, and O; heterocycloalkyl$^b$ may be optionally be substituted with 1 or 2 substituents independently selected from alkyl, (C$_1$-C$_6$)alkoxy, OH, CN, CF$_3$, halo;

R12 is independently selected from H, alkyl$^b$, or cycloalkyl;

R13 and R14 are independently selected from H, alkyl$^b$, aryl$^b$ and heteroaryl$^b$ or R13 and R14 together with the nitrogen atom to which they are attached form a carbon-containing 4-, 5-, 6- or 7-membered heterocyclic ring, optionally containing an additional heteroatom selected from N, NR12, S, SO, SO$_2$ and O, which may be saturated or unsaturated with 1 or 2 double bonds and which may be optionally mono- or di-substituted with substituents selected from oxo, alkyl$^b$, alkoxy, OH, halo and CF$_3$;

and tautomers, isomers, stereoisomers (including enantiomers, diastereoisomers and racemic and scalemic mixtures thereof), deuterated isotopes, and pharmaceutically acceptable salts and/or solvates thereof.

The compounds of formula (I) have been carefully developed to be particularly suitable for oral delivery (e.g. possessing an excellent pharmacokinetic profile, in particular bioavailability). As shown by the examples, the inventors have demonstrated that compounds of formula (I) have surprisingly excellent solubility. More surprisingly, compounds of formula (I) exhibit these advantageous effects whilst being highly selective inhibitors of plasma kallikrein, including making key binding interactions.

The present invention also provides a prodrug of a compound of formula (I) as herein defined, or a pharmaceutically acceptable salt and/or solvate thereof.

The present invention also provides an N-oxide of a compound of formula (I) as herein defined, or a prodrug or pharmaceutically acceptable salt and/or solvate thereof.

It will be understood that certain compounds of the present invention may exist in solvated, for example hydrated, as well as unsolvated forms. It is to be understood that the present invention encompasses all such solvated forms.

It will be understood that "pharmaceutically acceptable salts and/or solvates thereof" means "pharmaceutically acceptable salts thereof", "pharmaceutically acceptable solvates thereof", and "pharmaceutically acceptable solvates of salts thereof".

It will be understood that, for the purposes of naming, each of rings A' and A" are defined separately. For example, when A is

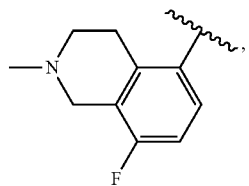

A' is phenyl and A" is piperidine. For example, when A is

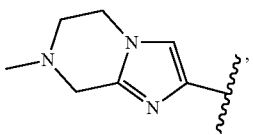 [SMILES: *c1cn2c(n1)CN(C)CC2]

A' is imidazole and A" is piperazine.

It will be understood that the compounds of the invention comprise several ring systems. When any of these ring systems is defined more specifically herein, the substituents/optional substituents to these groups described above also apply, unless stated otherwise. For example, "A' can be pyrazole" allows the pyrazole to be "optionally substituted with 1, 2 or 3 substituents independently selected from alkyl, alkoxy, OH, OCF$_3$, halo, CN, and CF$_3$", which is permitted by the above definition of heteroaryl.

It will be understood that in Formula (III)

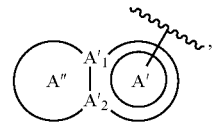

A'1 is directly bonded to A'2.

It will be understood that "alkylene" has two free valencies i.e. it is bivalent, meaning that it is capable of being bonded to twice. For example, when two adjacent ring atoms on A" are linked by an alkylene to form a cyclopentane, the alkylene will be —CH$_2$CH$_2$CH$_2$—.

It will be understood that when any variable (e.g. R11, etc) occurs more than once, its definition on each occurrence is independent of every other occurrence.

It will be understood that combinations of substituents and variables are permissible only if such combinations result in stable compounds.

It will be understood that lines drawn into the ring systems from substituents represent that the indicated bond can be attached to any of the substitutable ring atoms. For example, in Formula (II), R10 and R9 can be attached to any of the substitutable ring atoms on B', and R11 (if present) can be attached to any of the substitutable ring atoms on B".

Formula (II)

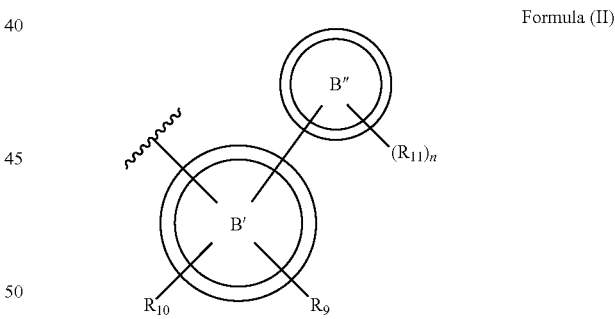

As noted above, "heteroalkylene" is a bivalent linear saturated hydrocarbon having 2 to 5 carbon atoms (C$_2$-C$_5$), wherein at least one of the 2 to 5 carbon atoms is replaced with NR8, S, or O. For example, —CH$_2$O— is a "heteroalkylene" having 2 carbon atoms wherein one of the 2 carbon atoms has been replaced with O.

As used herein the term "bradykinin-mediated angioedema" means hereditary angioedema, and any non-hereditary bradykinin-mediated angioedema. For example, "bradykinin-mediated angioedema" encompasses hereditary angioedema and acute bradykinin-mediated angioedema of unknown origin.

As used herein, the term "hereditary angioedema" means any bradykinin-mediated angioedema caused by an inherited genetic dysfunction, fault, or mutation. As a result, the term "HAE" includes at least HAE type 1, HAE type 2, and normal C1 inhibitor HAE (normal C1-Inh HAE).

W, X, Y and Z can be independently selected from C, C(R16)-C, C(R16)=C, C=N, O and N, such that the ring containing W, X, Y and Z is a 5-, or 6-membered heteroaryl;

R5, R6, and R7 can be independently absent or independently selected from H, alkyl, cycloalkyl, alkoxy, halo, OH, CN, and $CF_3$;

R16 can be independently selected from H, alkyl, cycloalkyl, alkoxy, halo, OH, CN, and $CF_3$; or W, X, Y and Z can be independently selected from C, C(R16)-C, C(R16)=C, C=N and N, and one of R5, R6, R7 or R16 can be oxo such that the ring containing W, X, Y and Z is 2-pyridone or 4-pyridone;

wherein the others of R5, R6, R7 and R16 can be independently absent or independently selected from H, alkyl, cycloalkyl, alkoxy, halo, OH, CN, and $CF_3$.

W, X, Y and Z can be independently selected from C, C(R16)-C, C(R16)=C, C=N, O and N, such that the ring containing W, X, Y and Z is a 5-, or 6-membered heteroaryl;

R5, R6, and R7 can be independently absent or independently selected from H, alkyl, cycloalkyl, alkoxy, halo, OH, CN, $CF_3$, aryl, heteroaryl$^a$, N-linked pyrrolidinyl, N-linked piperidinyl, N-linked morpholinyl, N-linked piperazinyl, NR13R14, COOR13, CONR13R14, and NR13COR14;

R16 can be independently selected from H, alkyl, cycloalkyl, alkoxy, halo, OH, CN, $CF_3$, aryl, heteroaryl$^a$, N-linked pyrrolidinyl, N-linked piperidinyl, N-linked morpholinyl, N-linked piperazinyl, NR13R14, COOR13, CONR13R14, and NR13COR14.

When at least one of W, X, Y and Z is O, W, X, Y, Z can form a 5-membered heteroaryl selected from furan, oxazole, isoxazole, 1,2,3-oxadiazole, and furazan.

More specifically, W, X, Y and Z can be independently selected from C, C(R16)-C, C(R16)=C, C=N and N, such that the ring containing W, X, Y and Z is a 5-, or 6-membered heteroaryl; R5, R6, and R7 can be independently absent or independently selected from H, alkyl, cycloalkyl, alkoxy, halo, OH, CN, $CF_3$, aryl, heteroaryl$^a$, N-linked pyrrolidinyl, N-linked piperidinyl, N-linked morpholinyl, N-linked piperazinyl, NR13R14, COOR13, CONR13R14, and NR13COR14;

R16 can be independently selected from H, alkyl, cycloalkyl, alkoxy, halo, OH, CN, $CF_3$, aryl, heteroaryl$^a$, N-linked pyrrolidinyl, N-linked piperidinyl, N-linked morpholinyl, N-linked piperazinyl, NR13R14, COOR13, CONR13R14, and NR13COR14.

More specifically, W, X, Y and Z can be independently selected from C, C(R16)-C, C(R16)=C, C=N and N, such that the ring containing W, X, Y and Z is a 5-, or 6-membered heteroaryl;

R5, R6, and R7 can be independently absent or independently selected from H, alkyl, cycloalkyl, alkoxy, halo, OH, CN, and $CF_3$;

R16 can be independently selected from H, alkyl, cycloalkyl, alkoxy, halo, OH, CN, $CF_3$.

W, X, Y and Z can be independently selected from C, C(R16)-C, C(R16)=C, C=N and N, such that the ring containing W, X, Y and Z is a 6-membered heteroaryl. More specifically, W, X, Y and Z can be independently selected from C and N, such that the ring containing W, X, Y and Z is a 6-membered heteroaryl selected from pyridine, pyridazine, pyrimidine, and pyrazine.

Preferably, W, X, Y and Z are independently selected from C and N, such that the ring containing W, X, Y and Z is a 5-membered heteroaryl. More specifically, W, X, Y and Z can be independently selected from C and N, such that the ring containing W, X, Y and Z is a 5-membered heteroaryl selected from pyrrole, pyrazole, imidazole, 1,2,3-triazole, 1,2,4-triazole. Preferably, W, X, Y and Z are independently selected from C and N, such that the ring containing W, X, Y and Z is pyrazole, in particular when X and Y are N, and W and Z are C. Specifically, the compounds of formula (I) can be selected from:

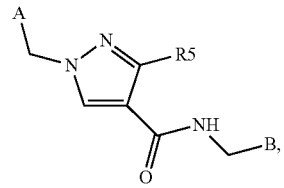

wherein R5 is as defined above, and in particular, small alkyl. More specifically, R5 can be selected from methyl and —$CH_2OMe$.

Alternatively, it is preferred that W, X, Y and Z are independently selected from C and N, such that the ring containing W, X, Y and Z is imidazole. Specifically, the compounds of formula (I) can be:

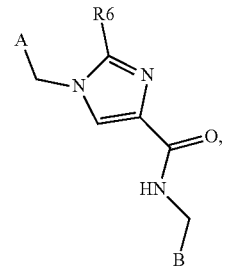

wherein R6 is as defined above, and in particular, small alkyl. More specifically, R6 can be selected from methyl and —$CH_2OMe$.

As noted above, R5, R6, and R7 are independently absent or independently selected from H, alkyl, cycloalkyl, alkoxy, halo, OH, CN, $CF_3$, aryl, heteroaryl$^a$, N-linked pyrrolidinyl, N-linked piperidinyl, N-linked morpholinyl, N-linked piperazinyl, —NR13R14, —COOR13, —CONR13R14, and —NR13COR14. More specifically, R5, R6, and R7 can be independently absent or independently selected from H, alkyl, cycloalkyl, alkoxy, halo, OH, CN, $CF_3$. At least one of R5, R6, or R7 can be present and not H (i.e. selected from alkyl, cycloalkyl, alkoxy, halo, OH, CN, $CF_3$, aryl, heteroaryl, N-linked pyrrolidinyl, N-linked piperidinyl, N-linked morpholinyl, N-linked piperazinyl, —NR13R14, —COOR13, —CONR13R14, and —NR13COR14). Additionally, or alternatively, R7 can be H.

At least one of R5, R6, or R7 can be selected from H, alkyl, cycloalkyl, and $CF_3$. Alternatively, at least two of R5, R6, or R7 can be independently selected from H, alkyl, cycloalkyl, and $CF_3$. Alternatively, R5, R6, or R7 can be independently selected from H, alkyl, cycloalkyl, and $CF_3$.

R5 can be alkyl. For example, the compounds of formula (I) can be:

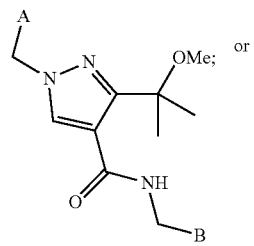

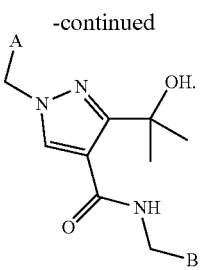

Alternatively, R5 can be H. Alternatively, R5 can be CF$_3$. Alternatively, R5 can be cycloalkyl.

R6 can be alkyl. R6 can be H. R6 can be CF$_3$. R6 can be cycloalkyl.

R7 can be alkyl. R7 can be H. R7 can be CF$_3$. R7 can be cycloalkyl. R7 is preferably H.

R16 (when present) can be selected from H, alkyl, cycloalkyl, and CF$_3$.

When any of R5, R6, R7, and/or R16 is alkyl, it is preferable that R5, R6, R7 and/or R16 is alkyl substituted by at least alkoxy, in particular, —CH$_2$OMe.

Alternatively, at least one of R5 or R6 can be —CHF$_2$. R5 can be —CHF$_2$. R6 can be —CHF$_2$.

When any of R5, R6, R7, and/or R16 is cycloalkyl, it is preferable that R5, R6, R7, and/or R16 is cyclopropane, optionally substituted with alkoxy, in particular, —OMe. Specifically, the compounds of formula (I) can be:

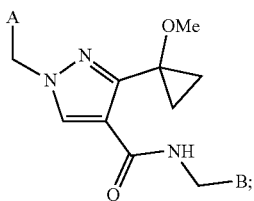 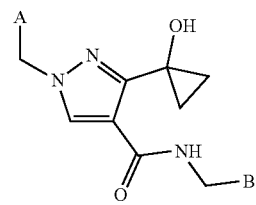

Preferably, R5 is alkyl substituted by at least alkoxy, in particular, —CH$_2$OMe. R6 is alkyl substituted by at least alkoxy, in particular, —CH$_2$OMe is also preferred. More specifically, one of R5 or R6 can be absent and one of R5 or R6 can be alkyl substituted by alkoxy, in particular, —CH$_2$OMe. For example, it is preferred when R5 is alkyl substituted by alkoxy, in particular, CH$_2$OMe and R6 is absent. It is also preferred when R5 is absent and R6 is alkyl substituted by alkoxy, in particular, CH$_2$OMe.

Preferably: (i) W, X, Y and Z are independently selected from C and N, such that the ring containing W, X, Y and Z is a pyrazole, (ii) one of R5 or R6 is absent and one of R5 or R6 is alkyl substituted by alkoxy, and (iii) R7 is H. More specifically: (i) W, X, Y and Z are independently selected from C and N, such that the ring containing W, X, Y and Z is a pyrazole, in particular when X and Y are N, and W and Z are C, (ii) R5 is alkyl substituted with alkoxy, in particular —CH$_2$OMe, (iii) R6 is absent; and (iv) R7 is H.

B' can be phenyl. B' can be pyridyl.

R9 and R10 can be independently H, alkyl, halo, or alkoxy. More specifically, R9 and R10 can be independently halo or alkoxy. For example, one of R9 or R10 can be halo, in particular F. Alternatively, one of R9 or R10 can be alkoxy, specifically, —OMe, or —Ocyclopropyl, in particular —OMe. Preferably, R9 is halo (in particular F) and R10 is alkoxy (in particular —OMe).

Preferably, B' is phenyl, R9 is halo (in particular F) and R10 is alkoxy (in particular-OMe). More specifically, the preferred B' group is

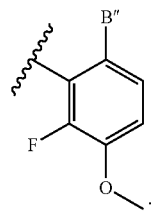

As noted above, B" is pyrrole, pyrazole, triazole, or tetrazole. Preferably, B" can be pyrazole or triazole. When B" is triazole, B" can be 1,2,3-triazole. Alternatively, when B" is triazole, B" can be 1,2,4-triazole.

B" can be bonded to B' through any of the ring atoms on B". Preferably, B" is bonded to B' through a nitrogen atom on B"

B" can be pyrrole. B" can be pyrrole, n can be 1, and R11 can be selected from alkyl, cycloalkyl, CN, and CF$_3$. Preferably, B" is pyrrole, n is 1, and R11 is selected from small alkyl, cyclopropyl, CN, and CF$_3$ B" can be pyrazole. B" can be pyrazole, n can be 1, and R11 can be selected from alkyl, cycloalkyl, CN, and CF$_3$. Preferably, B" is pyrazole, n is 1, and R11 is selected from small alkyl, cyclopropyl, CN, and CF$_3$. Specifically, B" can be selected from:

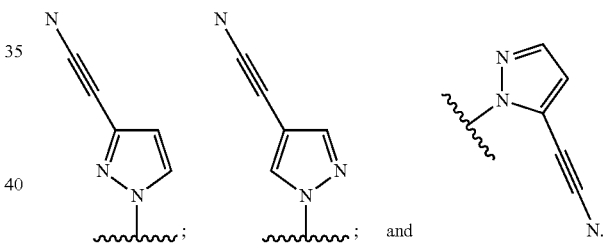

B" can be 1,2,3-triazole. B" can be 1,2,3-triazole, n can be 1, and R11 can be alkyl. More specifically, B" can be 1,2,3-triazole, n can be 1, and R11 can be selected from CN and small alkyl. Preferably, when B" is 1,2,3-triazole, n is 1, and R11 is selected from CN, methyl, ethyl, and CHF$_2$. Specifically, B" can be:

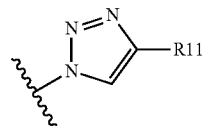

wherein R11 is as defined above.

B" can be 1,2,4-triazole. B" can be 1,2,4-triazole, n can be 1 or 2, and each R11 can be independently alkyl, cycloalkyl, CF$_3$. More specifically, B" can be 1,2,4-triazole, n can be 1, and R11 can be alkyl, cycloalkyl, CF$_3$. Additionally, when B" is 1,2,4-triazole and n is 1, R11 can be selected from CN, CF$_3$, and small alkyl, and in particular, CN, methyl, ethyl, CHF$_2$, CF$_3$. When B" is 1,2,4-triazole and n is 2, both R11 groups are preferably methyl. Specifically, B" can be:

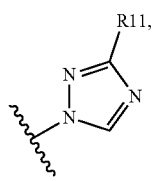

wherein R11 is as defined above.

B" can be 1,2,4-triazole, n can be 1, and R11 can be CF$_3$.

B" can be 1,2,5-triazole. B" can be 1,2,5-triazole, n can be 1, and R11 can be alkyl. Preferably, when B" is 1,2,5-triazole, n is 1, and R11 is selected from methyl and CHF$_2$.

Specific B" groups include:

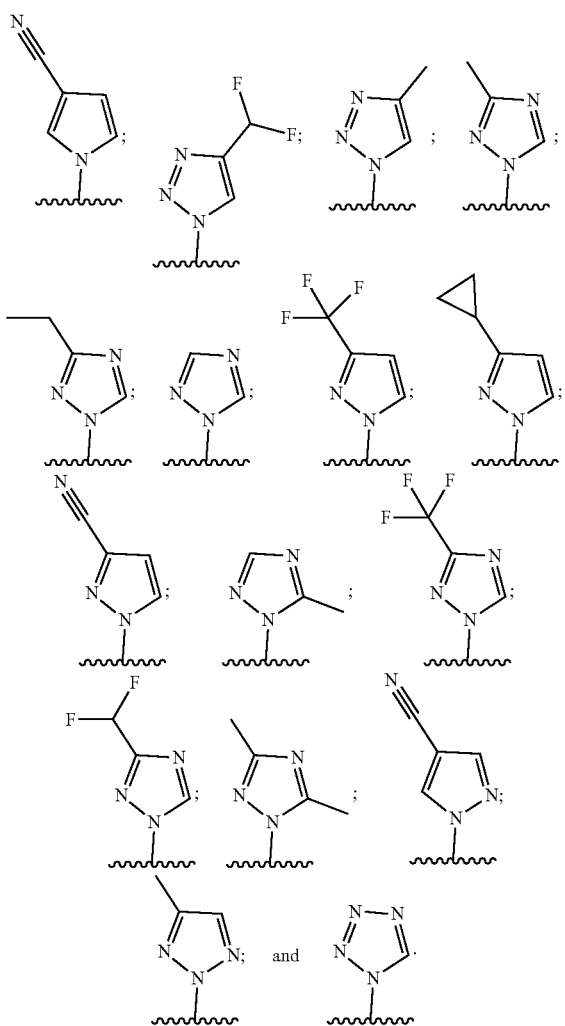

Preferred B" groups include:

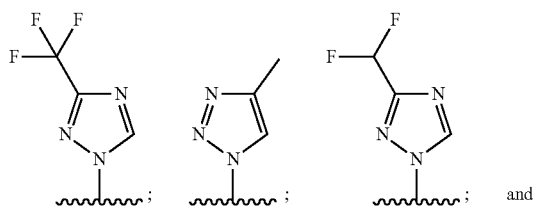

and in particular

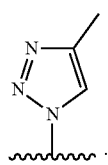

Preferably: (i) B' is phenyl, (ii) R9 is halo, (iii) R10 is alkoxy, and (iv) B" is 1,2,3-triazole. In addition, (v) n can be 1, and (vi) R11 can be alkyl. More specifically, R9 can be F, R10 can be —OMe, n can be 1, and R11 can be methyl.

Preferably, (i) B' is phenyl, (ii) R9 is halo, (iii) R10 is alkoxy, and (iv) B" is 1,2,3-triazole. In addition, (v) n can be 1, (vi) R11 can be alkyl, (vii) W, X, Y and Z are independently selected from C and N, such that the ring containing W, X, Y and Z is a pyrazole, (viii) one of R5 or R6 is absent and one of R5 or R6 is alkyl substituted by alkoxy, (ix) R7 is H, (x) B' is phenyl, (xi) R9 is halo, (xii) R10 is alkoxy, and (xiii) B" is 1,2,3-triazole. In addition, (viii) n can be 1, and (ix) R11 can be alkyl. More specifically: W, X, Y and Z are independently selected from C and N, such that the ring containing W, X, Y and Z is a pyrazole when X and Y are N, and W and Z are C, R5 can be —CH$_2$OMe, R6 can be absent, R7 can be H, and R11 can be methyl.

Alternatively: (i) B' is phenyl, (ii) R9 is halo, (iii) R10 is alkoxy, and (iv) B" is 1,2,4-triazole. In addition, (v) n can be 1, (vi) R11 can be CF$_3$, (vii) W, X, Y and Z are independently selected from C and N, such that the ring containing W, X, Y and Z is a pyrazole, (viii) one of R5 or R6 is absent and one of R5 or R6 is alkyl substituted by alkoxy, (ix) R7 is H, (x) B' is phenyl, (xi) R9 is halo, (xii) R10 is alkoxy, and (xiii) B" is 1,2,4-triazole. In addition, (viii) n can be 1, and (ix) R11 can be CF$_3$. More specifically: W, X, Y and Z are independently selected from C and N, such that the ring containing W, X, Y and Z is a pyrazole when X and Y are N, and W and Z are C, R5 can be —CH$_2$OMe, R6 can be absent, R7 can be H, and R11 can be methyl.

A'1 can be C. A'1 can be N. A'2 can be C. A'2 can be N. A' can be phenyl.

Alternatively, A' can be heteroaryl. When A' is heteroaryl, A' can be heteroaryl selected from thiophene, furan, pyrrole, pyrazole, imidazole, oxazole, isoxazole, thiazole, isothiazole, triazole, oxadiazole, thiadiazole, pyridine, pyridazine, pyrimidine, and pyrazine. A' can be a 5-membered heteroaryl, preferably selected from pyrrole or imidazole. Alternatively, A' can be a 6-membered heteroaryl, preferably pyridine.

A" can be a non-aromatic carbon-containing monocyclic ring containing 5 ring members, wherein one or two ring members are independently selected from N, NR8, S, and O. For example, A" can be selected from pyrrolidine, tetrahydrofuran, tetrahydrothiophene, pyrazolidine, imidazolidine, 3-dioxolane, thiazolidine, and isoxazolidine. When A" is a non-aromatic carbon-containing monocyclic ring containing 5 ring members, A" is preferably pyrrolidine.

Alternatively, A" can be a non-aromatic carbon-containing monocyclic ring containing 6 ring members, wherein one or two ring members are independently selected from N, NR8, S, and O. For example, A" can be selected from piperidine, piperazine, morpholine, 1,4-dioxane, thiomorpholine, 1,4-oxathiane, and 1,4-dithiane. When A" is a non-aromatic carbon-containing monocyclic ring containing 6 ring members, A" is preferably piperidine.

Alternatively, A" can be a non-aromatic carbon-containing monocyclic ring containing 7 ring members, wherein one or two ring members are independently selected from N, NR8, S, and O. For example, A" can be selected from azepane, oxepane, oxazepane (in particular, a 1,4-oxazapane), thiepane, and diazepane. When A" is a non-aromatic carbon-containing monocyclic ring containing 7 ring members, A" is preferably azepane.

A carbon ring atom on A" can be substituted with an alkylene such that the carbon ring atom on A" together with the alkylene forms a cycloalkyl that is spiro to ring A". More specifically, the spiro ring formed can be cyclopropane. Alternatively, the spiro ring formed can be cyclobutane. Alternatively, the spiro ring formed can be cyclopentane. Alternatively, the spiro ring formed is cyclohexane. When a spiro ring is present on A", a preferred spiro ring is cyclopropane.

A carbon ring atom on A" can be substituted with a heteroalkylene such that the carbon ring atom on A" together with the heteroalkylene forms a heterocycloalkyl$^a$ that is spiro to ring A". More specifically, the spiro ring formed can be 3-membered, e.g. selected from aziridine, oxirane, and thiirane. Alternatively, the spiro ring formed can be 4-membered, e.g. selected from azetidine, oxetane, and thietane. Alternatively, the spiro ring formed can be 5-membered, e.g. selected from pyrrolidine, tetrahydrofuran, tetrahydrothiophene, pyrazolidine, imidazolidine, 3-dioxolane, thiazolidine, and isoxazolidine. Alternatively, the spiro ring formed can be 6-membered, e.g. selected from piperidine, piperazine, morpholine, 1,4-dioxane, thiomorpholine, 1,4-oxathiane, and 1,4-dithiane.

Two ring atoms on A" can be linked by an alkylene to form a non-aromatic ring containing 5, 6, or 7 ring members. More specifically, two ring atoms on A" can be linked by an alkylene to form a non-aromatic ring containing 5 ring members, e.g. cyclopentane. Alternatively, the two ring atoms on A" can be linked by an alkylene to form a non-aromatic ring containing 6 ring members, e.g. cyclohexane. Alternatively, the two ring atoms on A" can be linked by an alkylene to form a non-aromatic ring containing 7 ring members, e.g. cycloheptane.

Two ring atoms on A" can be linked by a heteroalkylene to form a non-aromatic ring containing 5, 6, or 7 ring members. More specifically, the two ring atoms on A" can be linked by a heteroalkylene to form a non-aromatic ring containing 5 ring members, e.g. selected from thiophene, furan, pyrrole, pyrazole, imidazole, oxazole, isoxazole, thiazole, isothiazole, triazole, oxadiazole, thiadiazole, pyridine, pyridazine, pyrimidine, and pyrazine. Alternatively, the two ring atoms on A" can be linked by a heteroalkylene to form a non-aromatic ring containing 6 ring members e.g. selected from piperidine, piperazine, morpholine, 1,4-dioxane, thiomorpholine, 1,4-oxathiane, and 1,4-dithiane. Alternatively, the two ring atoms on A" can be linked by a heteroalkylene to form a non-aromatic ring containing 7 ring members, e.g. selected from azepane, oxepane, oxazepane (in particular, a 1,4-oxazapane), thiepane, and diazepane.

Specific A groups include:

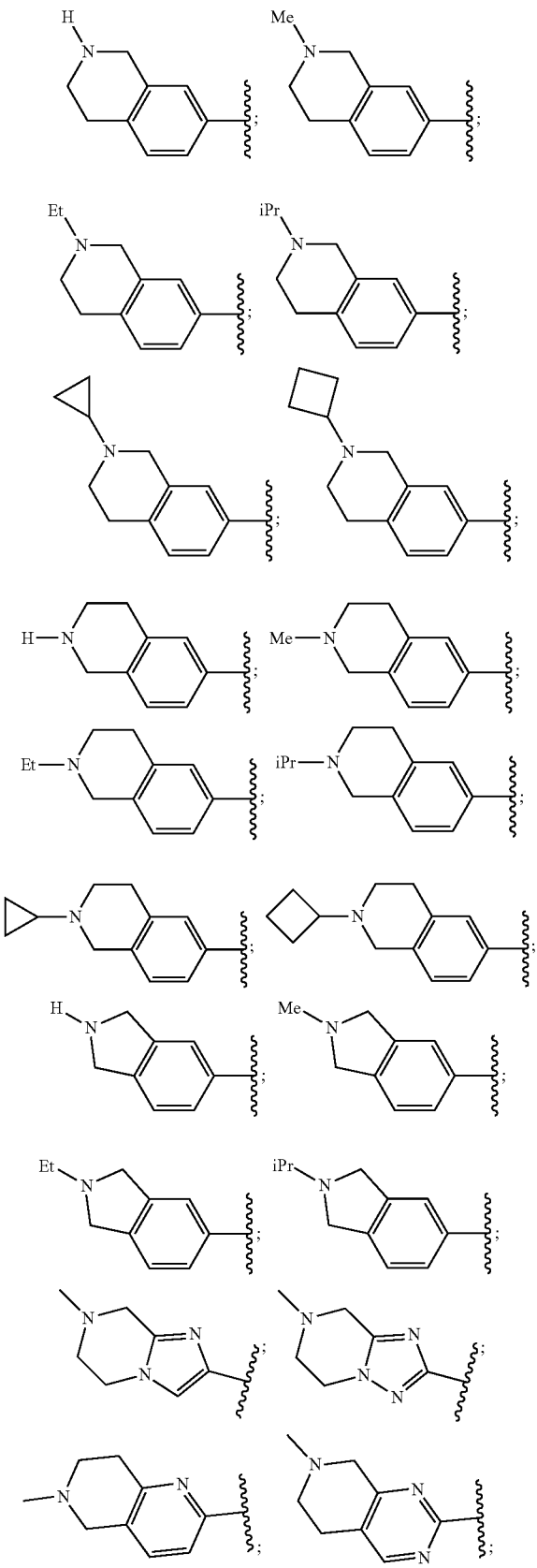

-continued
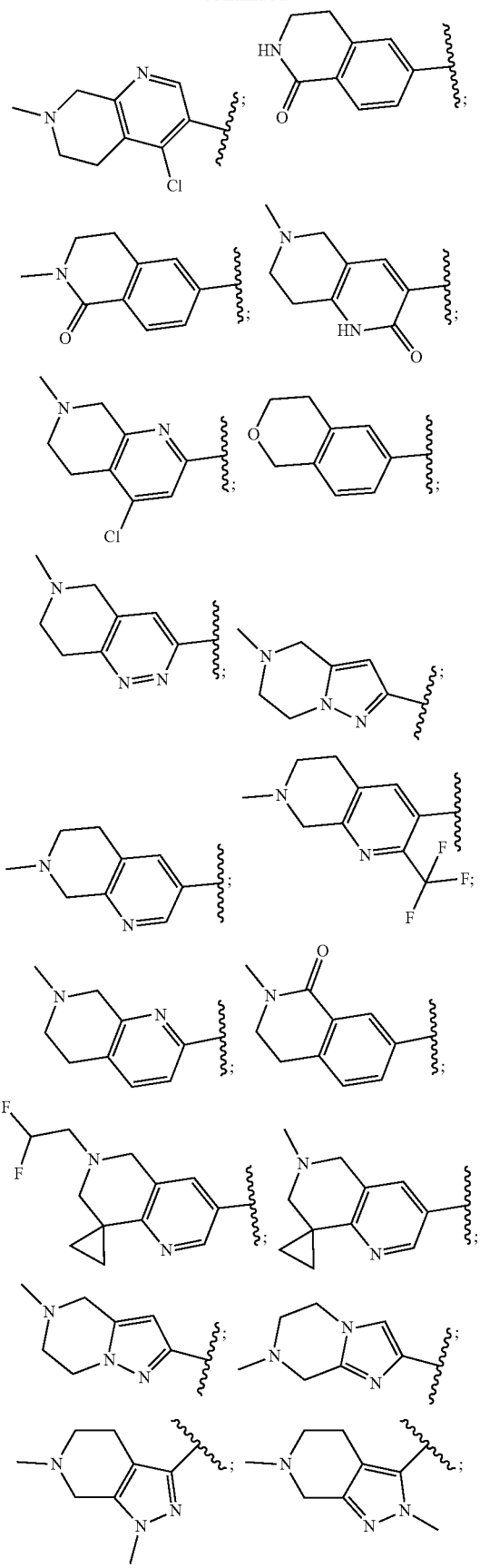
-continued
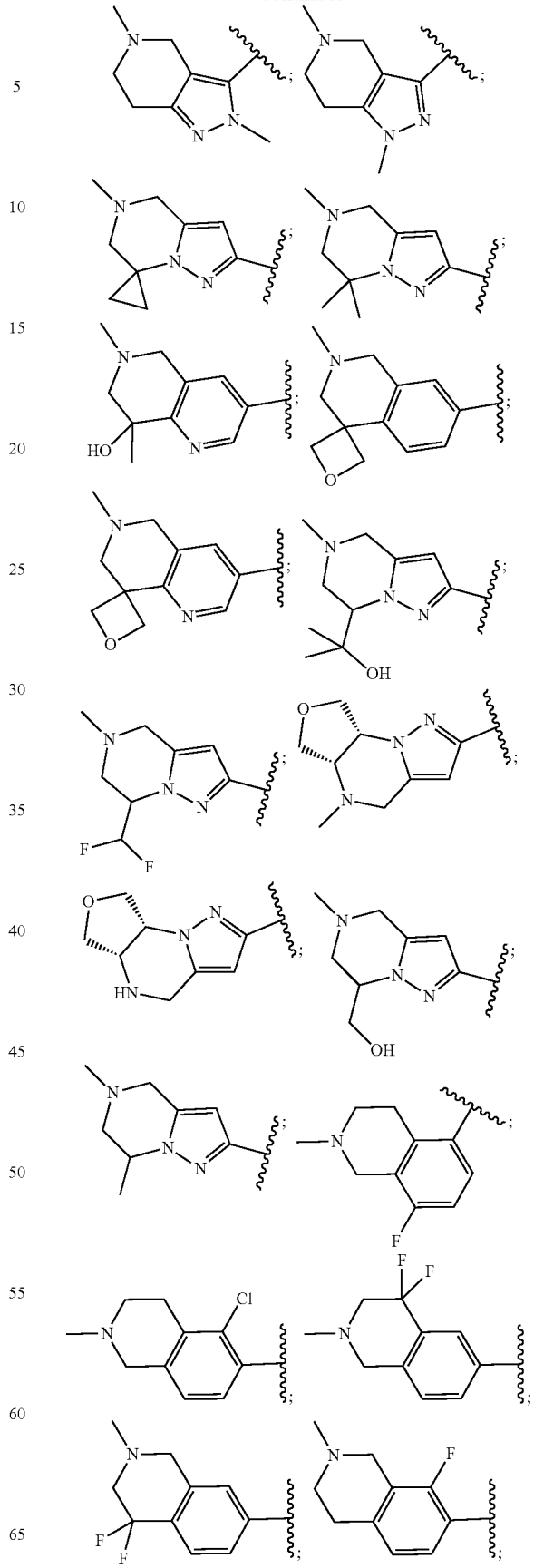

-continued
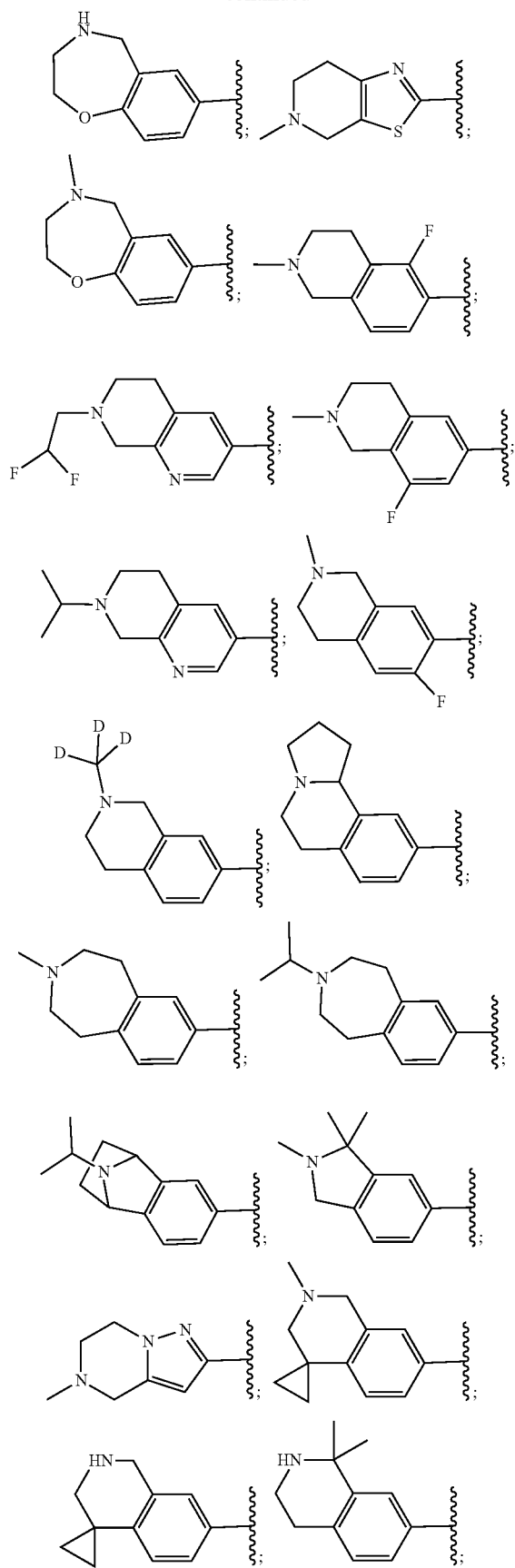
-continued
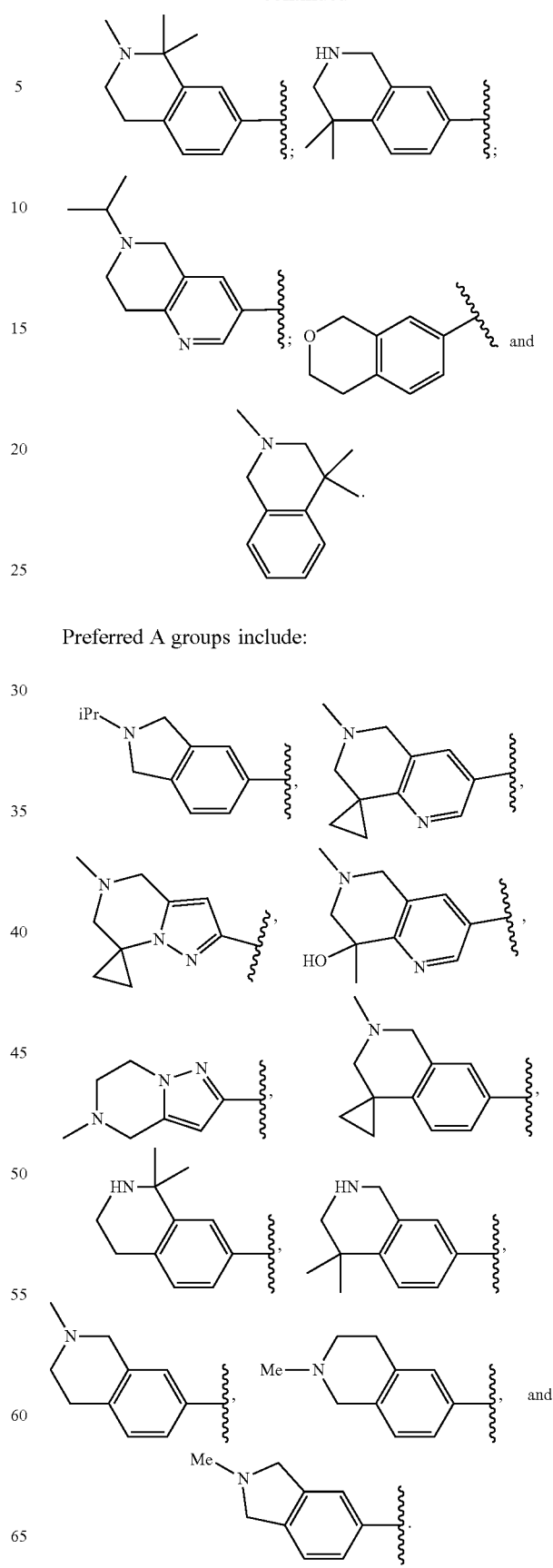
Preferred A groups include:

More preferred A groups include:

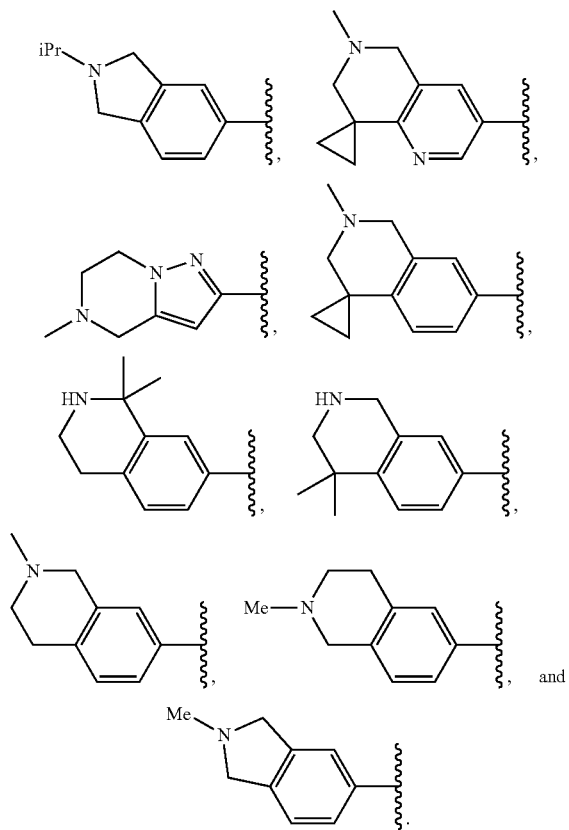

Even more preferred A groups include:

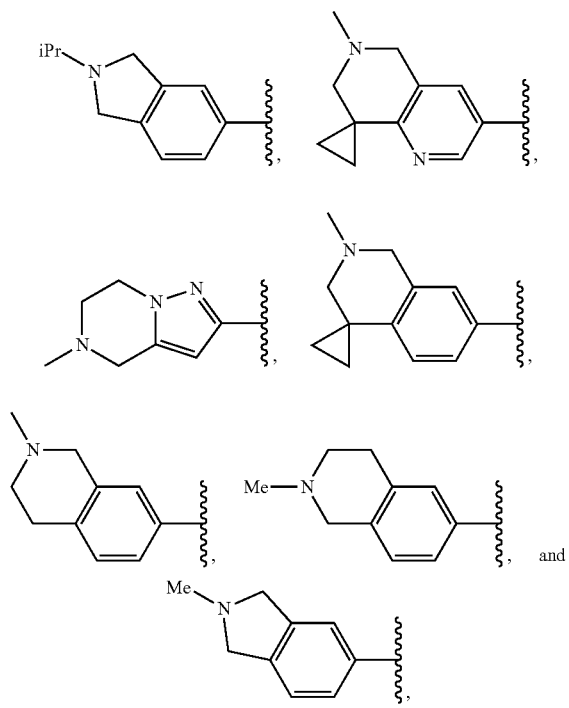

in particular

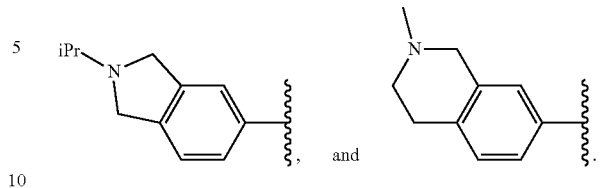

Preferably: (i) A' is phenyl, and (ii) A" is piperidine. More specifically, (i) A' can be phenyl, and (ii) A" can be piperidine substituted with methyl.

Preferably: (i) A' is phenyl, (ii) A" is piperidine, (iii) B' is phenyl, (iv) R9 is halo, (v) R10 is alkoxy, and (vi) B" is 1,2,3-triazole. In addition, (vii) n can be 1, and (viii) R11 can be alkyl. More specifically, A" can be piperidine substituted with methyl, R9 can be F, R10 can be —OMe, n can be 1, and R11 can be methyl.

Preferably: (i) A' is phenyl, (ii) A" is piperidine, (iii) B' is phenyl, (iv) R9 is halo, (v) R10 is alkoxy, and (vi) B" is 1,2,3-triazole. In addition, (vii) n can be 1, (viii) R11 can be alkyl, (ix) W, X, Y and Z can be independently selected from C and N, such that the ring containing W, X, Y and Z is a pyrazole, (x) one of R5 or R6 can be absent and one of R5 or R6 can be alkyl substituted by alkoxy, and (xi) R7 is H. In addition, (xii) n can be 1, and (xiii) R11 can be alkyl. More specifically: W, X, Y and Z are independently selected from C and N, such that the ring containing W, X, Y and Z is a pyrazole, in particular when X and Y can be N, and W and Z can be C, R5 can be —CH$_2$OMe, R6 can be absent, R7 can be H, R11 can be methyl, A" can be piperidine substituted with methyl.

Alternatively: (i) A' is phenyl, (ii) A" is piperidine, (iii) B' is phenyl, (iv) R9 is halo, (v) R10 is alkoxy, and (vi) B" is 1,2,4-triazole. In addition, (vii) n can be 1, (viii) R11 can be CF$_3$, (ix) W, X, Y and Z can be independently selected from C and N, such that the ring containing W, X, Y and Z is a pyrazole, (x) one of R5 or R6 can be absent and one of R5 or R6 can be alkyl substituted by alkoxy, and (xi) R7 is H. In addition, (xii) n can be 1, and (xiii) R11 can be alkyl. More specifically: W, X, Y and Z are independently selected from C and N, such that the ring containing W, X, Y and Z is a pyrazole, in particular when X and Y can be N, and W and Z can be C, R5 can be —CH$_2$OMe, R6 can be absent, R7 can be H, R11 can be CF$_3$, A" can be piperidine substituted with methyl.

Alternatively: (i) A' is phenyl, and (ii) A" is pyrrolidine. More specifically, (i) A' can be phenyl, and (ii) A" can be pyrrolidine substituted with methyl.

Alternatively: (i) A' is phenyl, (ii) A" is pyrrolidine, (iii) B' is phenyl, (iv) R9 is halo, (v) R10 is alkoxy, and (vi) B" is 1,2,3-triazole. In addition, (vii) n can be 1, and (viii) R11 can be alkyl. More specifically, A" can be piperidine substituted with methyl, R9 can be F, R10 can be —OMe, n can be 1, and R11 can be methyl.

Alternatively: (i) A' is phenyl, (ii) A" is pyrrolidine, (iii) B' is phenyl, (iv) R9 is halo, (v) R10 is alkoxy, and (vi) B" is 1,2,3-triazole. In addition, (vii) n can be 1, (viii) R11 can be alkyl, (ix) W, X, Y and Z can be independently selected from C and N, such that the ring containing W, X, Y and Z is a pyrazole, (x) one of R5 or R6 can be absent and one of R5 or R6 can be alkyl substituted by alkoxy, and (xi) R7 is H. In addition, (xii) n can be 1, and (xiii) R11 can be alkyl. More specifically: W, X, Y and Z are independently selected from C and N, such that the ring containing W, X, Y and Z is a pyrazole, in particular when X and Y can be N, and W and Z can be C, R5 can be —CH$_2$OMe, R6 can be absent, R7 can be H, R11 can be methyl, A" can be pyrrolidine substituted with methyl.

As noted above, R8 is independently selected from H, alkyl, cycloalkyl, or heterocycloalkyl$^b$. When R8 is heterocycloalkyl$^b$, it is preferably a non-aromatic carbon-containing monocyclic ring containing 4 ring members, in particular, oxetane. More specifically, R8 can be independently selected from H, alkyl, or cycloalkyl. When R8 is alkyl, it is preferably methyl. When R8 is cycloalkyl, it is preferably cyclopropyl.

When A' is phenyl and A" is piperidine, specific A groups can be selected from:

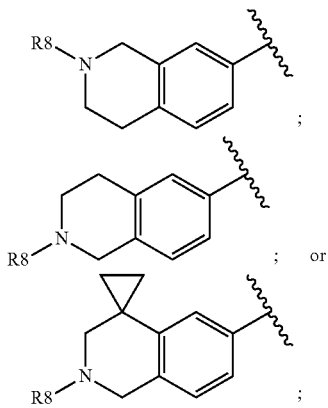

wherein R8 is as defined above, and more specifically small alkyl, and in particular, methyl.

Specific A groups can also be selected from:

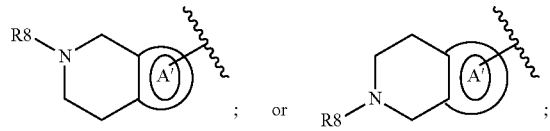

wherein A' is pyridine, and R8 is as defined above, and more specifically small alkyl, and in particular, methyl.

Specific A groups also include:

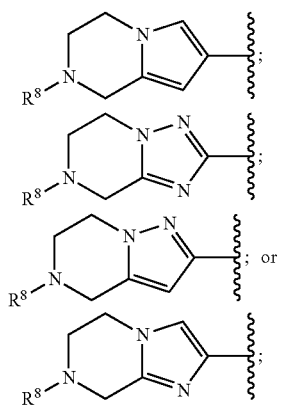

Specific A groups also include:

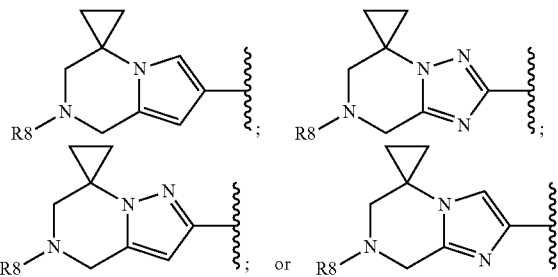

wherein R8 is as defined above, and more specifically small alkyl, and in particular, methyl.

R13 and R14 can be independently selected from H, alkyl$^b$, aryl$^b$ and heteroaryl$^b$. More specifically, R13 and R14 can be in independently selected from H and small alkyl.

Alternatively, R13 and R14 can together with the nitrogen atom to which they are attached form a carbon-containing 4-, 5-, 6- or 7-membered heterocyclic ring, optionally containing an additional heteroatom selected from N, N12, S, SO, SO$_2$, and O, which may be saturated or unsaturated with 1 or 2 double bonds and which may be optionally mono- or di-substituted with substituents selected from oxo, alkyl$^b$, alkoxy, OH, halo and CF$_3$.

The invention provides a compound of formula (I), as set out below, which may be combined with the above disclosure:

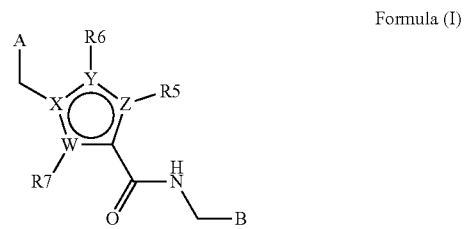

Formula (I)

wherein
W, X, Y and Z are independently selected from C and N, such that the ring containing W, X, Y and Z is a 5-membered heteroaryl (preferably pyrazole);
R5, R6, and R7 are independently absent or independently selected from H, alkyl, cycloalkyl, alkoxy, halo, OH, CN, and CF$_3$;
B is of Formula (II) comprising aromatic rings B' and B" that are linked by a bond:

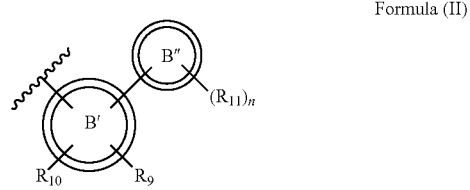

Formula (II)

B' is phenyl;
B" is pyrrole, pyrazole, 1,2,3-triazole, 1,2,4-triazole, or 1,2,5-triazole;
n is 0, 1, or 2;

R9 is halo (preferably F) and R10 is alkoxy (preferably —OMe);

Each R11 are independently selected from alkyl, cycloalkyl, alkoxy, halo, OH, CN, and $CF_3$;

A is a heterocyclic ring of Formula (III) comprising an aromatic ring (A') fused to a non-aromatic ring (A"):

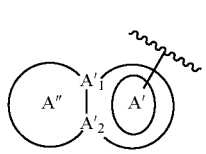

Formula (III)

A'1 and A'2 are independently C or N;

A' is heteroaryl or phenyl, wherein phenyl may be optionally substituted with 1, 2, or 3 substituents independently selected from alkyl, alkoxy, OH, $OCF_3$, halo, CN, and $CF_3$, and wherein heteroaryl may be optionally substituted as described herein;

A" is heterocycloalkyl; wherein A" may be optionally substituted with 1, 2, or 3 substituents independently selected from alkyl, alkoxy, OH, $OCF_3$, halo, oxo and CN;

optionally wherein a carbon ring atom on A" is substituted with an alkylene or a heteroalkylene such that the carbon ring atom on A" together with the alkylene or the heteroalkylene forms a cycloalkyl or heterocycloalkyl$^a$ that is spiro to ring A"; and/or optionally wherein two ring atoms on A" are linked by an alkylene or heteroalkylene to form a non-aromatic ring containing 5, 6, or 7 ring members;

and tautomers, isomers, stereoisomers (including enantiomers, diastereoisomers and racemic and scalemic mixtures thereof), deuterated isotopes, and pharmaceutically acceptable salts and/or solvates thereof.

The invention also provides a compound of formula (I), as set out below, which may be combined with the above disclosure:

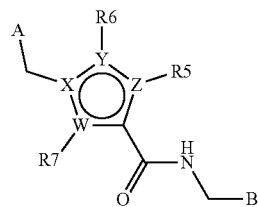

Formula (I)

wherein

W, X, Y and Z are independently selected from C and N, such that the ring containing W, X, Y and Z is a 5-membered heteroaryl (preferably pyrazole);

R5, R6, and R7 are independently absent or independently selected from H, alkyl, cycloalkyl, alkoxy, halo, OH, CN, and $CF_3$ provided that at least one of R5, R6, or R7 is present and is not H (i.e. independently selected from alkyl, cycloalkyl, alkoxy, halo, OH, CN, and $CF_3$), preferably, wherein one of R5 or R6 is absent and one of R5 or R6 is alkyl substituted by alkoxy (in particular, $CH_2OMe$), and R7 is H;

B is of Formula (II) comprising aromatic rings B' and B" that are linked by a bond:

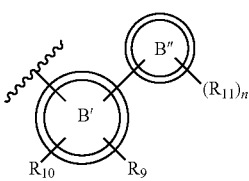

Formula (II)

B' is phenyl;

B" is pyrrole, pyrazole, 1,2,3-triazole, 1,2,4-triazole, or 1,2,5-triazole;

n is 0, 1, or 2;

R9 is halo (preferably F) and R10 is alkoxy (preferably —OMe);

R11 are independently selected from alkyl, cycloalkyl, alkoxy, halo, OH, CN, and $CF_3$;

A is a heterocyclic ring of Formula (III) comprising an aromatic ring (A') fused to a non-aromatic ring (A"):

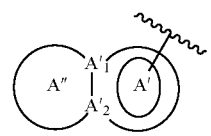

Formula (III)

A'1 and A'2 are independently C or N;

A' is heteroaryl or phenyl, wherein phenyl may be optionally substituted with 1, 2, or 3 substituents independently selected from alkyl, alkoxy, OH, $OCF_3$, halo, CN, and $CF_3$, and wherein heteroaryl may be optionally substituted described herein;

A" is heterocycloalkyl; wherein A" may be optionally substituted with 1, 2, or 3 substituents independently selected from alkyl, alkoxy, OH, $OCF_3$, halo, oxo and CN;

optionally wherein a carbon ring atom on A" is substituted with an alkylene or a heteroalkylene such that the carbon ring atom on A" together with the alkylene or the heteroalkylene forms a cycloalkyl or heterocycloalkyl$^a$ that is spiro to ring A"; and/or optionally wherein two ring atoms on A" are linked by an alkylene or heteroalkylene to form a non-aromatic ring containing 5, 6, or 7 ring members;

and tautomers, isomers, stereoisomers (including enantiomers, diastereoisomers and racemic and scalemic mixtures thereof), deuterated isotopes, and pharmaceutically acceptable salts and/or solvates thereof.

The invention also provides a compound of formula (I), as set out below, which may be combined with the above disclosure:

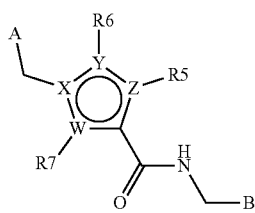

Formula (I)

wherein
W, X, Y and Z are independently selected from C and N, such that the ring containing W, X, Y and Z is a 5-membered heteroaryl (preferably pyrazole);
R5, R6, and R7 are independently absent or independently selected from H, alkyl, cycloalkyl, alkoxy, halo, OH, CN, and $CF_3$ provided that at least one of R5, R6, or R7 is present and is not H (preferably, wherein one of R5 or R6 is absent and one of R5 or R6 is alkyl substituted by alkoxy (in particular, $CH_2OMe$), and R7 is H;
B is of Formula (II) comprising aromatic rings B' and B" that are linked by a bond:

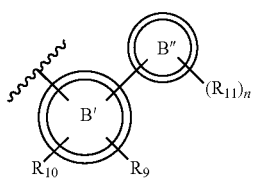

Formula (II)

B' is phenyl;
B" is 1,2,3-triazole;
n is 1;
R9 is halo (preferably F) and R10 is alkoxy (preferably —OMe);
R11 is alkyl (preferably methyl);
A is a heterocyclic ring of Formula (III) comprising an aromatic ring (A') fused to a non-aromatic ring (A"):

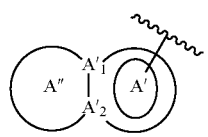

Formula (III)

A'1 and A'2 are independently C or N;
A' is heteroaryl or phenyl, wherein phenyl may be optionally substituted with 1, 2, or 3 substituents independently selected from alkyl, alkoxy, OH, $OCF_3$, halo, CN, and $CF_3$, and wherein heteroaryl may be optionally substituted described herein;
A" is heterocycloalkyl selected from pyrrolidine, piperidine, or azepane; wherein A" may be optionally substituted with 1, 2, or 3 substituents independently selected from alkyl, alkoxy, OH, $OCF_3$, halo, oxo and CN;
  optionally wherein a carbon ring atom on A" is substituted with an alkylene or a heteroalkylene such that the carbon ring atom on A" together with the alkylene or the heteroalkylene forms a cycloalkyl or heterocycloalkyl$^a$ that is spiro to ring A"; and/or
  optionally wherein two ring atoms on A" are linked by an alkylene or heteroalkylene to form a non-aromatic ring containing 5, 6, or 7 ring members;

and tautomers, isomers, stereoisomers (including enantiomers, diastereoisomers and racemic and scalemic mixtures thereof), deuterated isotopes, and pharmaceutically acceptable salts and/or solvates thereof.

The invention also provides a compound of formula (I), as set our below, which may be combined with the above disclosure:

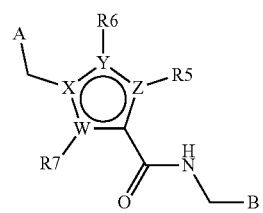

Formula (I)

wherein
W, X, Y and Z are independently selected from C and N, such that the ring containing W, X, Y and Z is a 5-membered heteroaryl (preferably pyrazole);
R5, R6, and R7 are independently absent or independently selected from H, alkyl, cycloalkyl, alkoxy, halo, OH, CN, and $CF_3$ provided that at least one of R5, R6, or R7 is present and is not H (preferably, wherein one of R5 or R6 is absent and one of R5 or R6 is alkyl substituted by alkoxy (in particular, $CH_2OMe$), and R7 is H;
B is of Formula (II) comprising aromatic rings B' and B" that are linked by a bond:

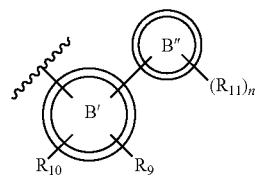

Formula (II)

B' is phenyl;
B" is 1,2,3-triazole;
n is 1;
R9 is halo (preferably F) and R10 is alkoxy (preferably —OMe);
R11 is alkyl (preferably methyl);
A is a heterocyclic ring of Formula (III) comprising an aromatic ring (A') fused to a non-aromatic ring (A"):

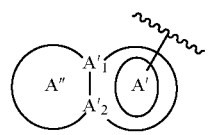

Formula (III)

A'1 and A'2 are independently C or N;
A' is phenyl, wherein phenyl may be optionally substituted with 1, 2, or 3 substituents independently selected from alkyl, alkoxy, OH, $OCF_3$, halo, CN, and $CF_3$;
A" is heterocycloalkyl selected from pyrrolidine, piperidine, or azepane; wherein A" may be optionally substituted with 1, 2, or 3 substituents independently selected from alkyl, alkoxy, OH, $OCF_3$, halo, oxo and CN;

optionally wherein a carbon ring atom on A" is substituted with an alkylene or a heteroalkylene such that the carbon ring atom on A" together with the alkylene or the heteroalkylene forms a cycloalkyl or heterocycloalkyl$^a$ that is spiro to ring A"; and/or optionally wherein two ring atoms on A" are linked by an alkylene or heteroalkylene to form a non-aromatic ring containing 5, 6, or 7 ring members;

and tautomers, isomers, stereoisomers (including enantiomers, diastereoisomers and racemic and scalemic mixtures thereof), deuterated isotopes, and pharmaceutically acceptable salts and/or solvates thereof.

The invention also provides a compound of formula (I), as set our below, which may be combined with the above disclosure:

Formula (I)

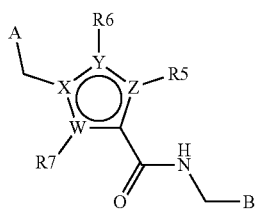

wherein

W, X, Y and Z are independently selected from C and N, such that the ring containing W, X, Y and Z is a 5-membered heteroaryl (preferably pyrazole);

R5, R6, and R7 are independently absent or independently selected from H, alkyl, cycloalkyl, alkoxy, halo, OH, CN, and $CF_3$ provided that at least one of R5, R6, or R7 is present and is not H (preferably, wherein one of R5 or R6 is absent and one of R5 or R6 is alkyl substituted by alkoxy (in particular, $CH_2OMe$), and R7 is H;

B is of Formula (II) comprising aromatic rings B' and B" that are linked by a bond:

Formula (II)

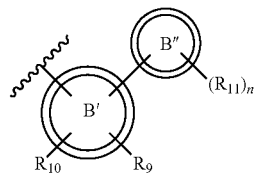

B' is phenyl;
B" is 1,2,4-triazole;
n is 1;
R9 is halo (preferably F) and R10 is alkoxy (preferably —OMe);
R11 is $CF_3$;

A is a heterocyclic ring of Formula (III) comprising an aromatic ring (A') fused to a non-aromatic ring (A"):

Formula (III)

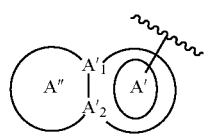

A'1 and A'2 are independently C or N;
A' is phenyl, wherein phenyl may be optionally substituted with 1, 2, or 3 substituents independently selected from alkyl, alkoxy, OH, $OCF_3$, halo, CN, and $CF_3$;

A" is heterocycloalkyl selected from pyrrolidine, piperidine, or azepane; wherein A" may be optionally substituted with 1, 2, or 3 substituents independently selected from alkyl, alkoxy, OH, $OCF_3$, halo, oxo and CN;

optionally wherein a carbon ring atom on A" is substituted with an alkylene or a heteroalkylene such that the carbon ring atom on A" together with the alkylene or the heteroalkylene forms a cycloalkyl or heterocycloalkyl$^a$ that is spiro to ring A"; and/or optionally wherein two ring atoms on A" are linked by an alkylene or heteroalkylene to form a non-aromatic ring containing 5, 6, or 7 ring members;

and tautomers, isomers, stereoisomers (including enantiomers, diastereoisomers and racemic and scalemic mixtures thereof), deuterated isotopes, and pharmaceutically acceptable salts and/or solvates thereof.

The present invention also encompasses, but is not limited to, the below compounds:

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]pyrazole-4-carboxamide;

N-{[2-fluoro-3-methoxy-6-(3-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-{[6-(3-ethyl-1,2,4-triazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)pyrazol-1-yl]phenyl}methyl)-3-(methoxymethyl)-1-[(2-methyl-3,4-dihydro-1H-isoquinolin-7-yl)methyl]pyrazole-4-carboxamide;

N-{[6-(3-cyclopropylpyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(5-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-7-yl)methyl]pyrazole-4-carboxamide;

1-[(2-cyclopropyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

1-[(2-ethyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(2-cyclopropyl-3,4-dihydro-1H-isoquinolin-7-yl)methyl]-N-({6-[3-(difluoromethyl)-1,2,4-triazol-1-yl]-2-fluoro-3-methoxyphenyl}methyl)-3-(methoxymethyl)pyrazole-4-carboxamide;

1-[(2-cyclopropyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-{[6-(3-cyanopyrazol-1-yl)-2-fluoro-3-methoxyphenyl]methyl}-1-[(2-cyclopropyl-3,4-dihydro-1H-isoquinolin-7-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-7-yl)methyl]-3-(methoxymethyl)pyrazole-4-carboxamide;

N-{[6-(dimethyl-1,2,4-triazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

N-{[6-(dimethyl-1,2,4-triazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[6-(4-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]pyrazole-4-carboxamide;

3-(difluoromethyl)-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]pyrazole-4-carboxamide;

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

1-[(2-cyclopropyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(2-cyclobutyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-6-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-6-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-6-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-6-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-6-yl)methyl]-3-(methoxymethyl)pyrazole-4-carboxamide;

1-[(2-cyclopropyl-3,4-dihydro-1H-isoquinolin-6-yl)methyl]-N-({6-[3-(difluoromethyl)-1,2,4-triazol-1-yl]-2-fluoro-3-methoxyphenyl}methyl)-3-(methoxymethyl)pyrazole-4-carboxamide;

1-[(2-cyclopropyl-3,4-dihydro-1H-isoquinolin-6-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-{[6-(3-cyanopyrazol-1-yl)-2-fluoro-3-methoxyphenyl]methyl}-1-[(2-cyclopropyl-3,4-dihydro-1H-isoquinolin-6-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-6-yl)methyl]-3-(methoxymethyl)pyrazole-4-carboxamide;

1-(2,3-dihydro-1H-isoindol-5-ylmethyl)-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1,3-dihydroisoindol-5-yl)methyl]pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-3-(methoxymethyl)pyrazole-4-carboxamide;

1-[(2-ethyl-1,3-dihydroisoindol-5-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-1,3-dihydroisoindol-5-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-1,3-dihydroisoindol-5-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-1,3-dihydroisoindol-5-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-1,3-dihydroisoindol-5-yl)methyl]-3-(methoxymethyl)pyrazole-4-carboxamide;

N-{[2-fluoro-3-methoxy-6-(4-methyl-1,2,3-triazol-1-yl)phenyl]methyl}-1-({7-methyl-5H,6H,8H-imidazo[1,2-a]pyrazin-2-yl}methyl)-3-(trifluoromethyl)pyrazole-4-carboxamide;

N-{[2-fluoro-3-methoxy-6-(4-methyl-1,2,3-triazol-1-yl)phenyl]methyl}-1-({7-methyl-5H,6H,8H-pyrido[3,4-d]pyrimidin-2-yl}methyl)-3-(trifluoromethyl)pyrazole-4-carboxamide;

1-[(4-chloro-7-methyl-6,8-dihydro-5H-1,7-naphthyridin-3-yl)methyl]-N-{[2-fluoro-3-methoxy-6-(4-methyl-1,2,3-triazol-1-yl)phenyl]methyl}-3-(methoxymethyl)pyrazole-4-carboxamide;

1-(3,4-dihydro-1H-2-benzopyran-6-ylmethyl)-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-({5-methyl-4H,6H,7H-pyrazolo[1,5-a]pyrazin-2-yl}methyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1-oxo-3,4-dihydroisoquinolin-7-yl)methyl]pyrazole-4-carboxamide;

3-(difluoromethyl)-N-(2-fluoro-3-methoxy-6-(4-methyl-1H-1,2,3-triazol-1-yl)benzyl)-1-((5'-methyl-5',6'-dihydro-4'H-spiro[cyclopropane-1,7'-pyrazolo[1,5-a]pyrazin]-2'-yl)methyl)-1H-pyrazole-4-carboxamide;

N-{[2-fluoro-3-methoxy-6-(4-methyl-1,2,3-triazol-1-yl)phenyl]methyl}-3-(methoxymethyl)-1-[(7-methyl-6,8-dihydro-5H-1,7-naphthyridin-3-yl)methyl]pyrazole-4-carboxamide;

1-[(7-fluoro-2-methyl-3,4-dihydro-1H-isoquinolin-5-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(5-chloro-2-methyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(4,4-difluoro-2-methyl-1,3-dihydroisoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(4,4-difluoro-2-methyl-1,3-dihydroisoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(8-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(4-methyl-3,5-dihydro-2H-1,4-benzoxazepin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-({5-methyl-4H,6H,7H-[1,3]thiazolo[5,4-c]pyridin-2-yl}methyl)pyrazole-4-carboxamide;

N-{[2-fluoro-3-methoxy-6-(4-methyl-1,2,3-triazol-1-yl)phenyl]methyl}-3-(methoxymethyl)-1-(2,3,4,5-tetrahydro-1,4-benzoxazepin-7-ylmethyl)pyrazole-4-carboxamide;

1-[(5-fluoro-2-methyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-{[7-(2,2-difluoroethyl)-6,8-dihydro-5H-1,7-naphthyridin-3-yl]methyl}-N-{[2-fluoro-3-methoxy-6-(4-methyl-1,2,3-triazol-1-yl)phenyl]methyl}-3-(methoxymethyl)pyrazole-4-carboxamide;

1-[(8-fluoro-2-methyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-1-[(7-isopropyl-6,8-dihydro-5H-1,7-naphthyridin-3-yl)methyl]-3-(methoxymethyl)pyrazole-4-carboxamide;

1-[(6-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{[2-($^{2}H_3$)methyl-3,4-dihydro-1H-isoquinolin-7-yl]methyl}pyrazole-4-carboxamide;

1-{1H,2H,3H,5H,6H,10bH-pyrrolo[2,1-a]isoquinolin-9-ylmethyl}-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(3-methyl-1,2,4,5-tetrahydro-3-benzazepin-7-yl)methyl]pyrazole-4-carboxamide;

N-{[2-fluoro-3-methoxy-6-(4-methyl-1,2,3-triazol-1-yl)phenyl]methyl}-1-[(3-isopropyl-1,2,4,5-tetrahydro-3-benzazepin-7-yl)methyl]-3-(methoxymethyl)pyrazole-4-carboxamide;

N-{[2-fluoro-3-methoxy-6-(4-methyl-1,2,3-triazol-1-yl)phenyl]methyl}-1-({11-isopropyl-11-azatricyclo[6.2.1.0^{2,7}]undeca-2(7),3,5-trien-4-yl}methyl)-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2,3,3-trimethyl-1H-isoindol-5-yl)methyl]pyrazole-4-carboxamide;

N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)-3-(trifluoromethyl)pyrazole-4-carboxamide;

N-{[2-fluoro-3-methoxy-6-(4-methyl-1,2,3-triazol-1-yl)phenyl]methyl}-3-(methoxymethyl)-1-{2'-methyl-1',3'-dihydrospiro[cyclopropane-1,4'-isoquinoline]-7'-ylmethyl}pyrazole-4-carboxamide;

1-{2',3'-dihydro-1'H-spiro[cyclopropane-1,4'-isoquinoline]-7'-ylmethyl}-N-{[2-fluoro-3-methoxy-6-(4-methyl-1,2,3-triazol-1-yl)phenyl]methyl}-3-(methoxymethyl)pyrazole-4-carboxamide;

1-[(1,1-dimethyl-3,4-dihydro-2H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(1,1,2-trimethyl-3,4-dihydroisoquinolin-7-yl)methyl]pyrazole-4-carboxamide;

1-[(4,4-dimethyl-2,3-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1H-1,2,3-triazol-1-yl)phenyl]methyl}-1-[(7-methyl-5,6,7,8-tetrahydro-1,7-naphthyridin-2-yl)methyl]-3-(trifluoromethyl)-1H-pyrazole-4-carboxamide;

N-{[2-fluoro-3-methoxy-6-(4-methyl-1H-1,2,3-triazol-1-yl)phenyl]methyl}-3-(methoxymethyl)-1-{[6-(propan-2-yl)-5,6,7,8-tetrahydro-1,6-naphthyridin-3-yl]methyl}-1H-pyrazole-4-carboxamide;

1-(3,4-dihydro-1H-2-benzopyran-7-ylmethyl)-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2,4,4-trimethyl-1,3-dihydroisoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1-oxo-3,4-dihydroisoquinolin-6-yl)methyl]pyrazole-4-carboxamide;

3-(difluoromethyl)-N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)pyrazole-4-carboxamide;

3-(difluoromethyl)-N-{[2-fluoro-3-methoxy-6-(4-methyl-1,2,3-triazol-1-yl)phenyl]methyl}-1-[(7-methyl-6,8-dihydro-5H-1,7-naphthyridin-3-yl)methyl]pyrazole-4-carboxamide;

N-{[2-fluoro-3-methoxy-6-(4-methyl-1,2,3-triazol-1-yl)phenyl]methyl}-1-[(6-methyl-7,8-dihydro-5H-1,6-naphthyridin-2-yl)methyl]-3-(trifluoromethyl)pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-2-(methoxymethyl)imidazole-4-carboxamide;

N-{[2-fluoro-3-methoxy-6-(4-methyl-1,2,3-triazol-1-yl)phenyl]methyl}-2-(methoxymethyl)-1-[(2-methyl-3,4-dihydro-1H-isoquinolin-7-yl)methyl]imidazole-4-carboxamide;

2-cyclopropyl-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]imidazole-4-carboxamide;

2-cyclopropyl-N-{[2-fluoro-3-methoxy-6-(4-methyl-1,2,3-triazol-1-yl)phenyl]methyl}-1-[(2-isopropyl-1,3-dihydroisoindol-5-yl)methyl]imidazole-4-carboxamide;

N-{[2-fluoro-3-methoxy-6-(4-methyl-1,2,3-triazol-1-yl)phenyl]methyl}-2-methyl-1-[(2-methyl-3,4-dihydro-1H-isoquinolin-7-yl)methyl]imidazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-1,2,3-triazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-1,2,3-triazole-4-carboxamide;

N-({3-chloro-6-[3-(difluoromethyl)-1,2,4-triazol-1-yl]-2-fluorophenyl}methyl)-3-(methoxymethyl)-1-[(2-methyl-3,4-dihydro-1H-isoquinolin-7-yl)methyl]pyrazole-4-carboxamide;

N-({2-chloro-6-[3-(difluoromethyl)-1,2,4-triazol-1-yl]-3-methoxyphenyl}methyl)-3-(methoxymethyl)-1-[(2-methyl-3,4-dihydro-1H-isoquinolin-7-yl)methyl]pyrazole-4-carboxamide;

N-{[3-(1,1-difluoroethyl)-6-[3-(difluoromethyl)-1,2,4-triazol-1-yl]-2-fluorophenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(3-methyl-1,2,4,5-tetrahydro-3-benzazepin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-2-oxopyridine-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-6-oxopyridine-3-carboxamide;

N-{[2-fluoro-3-methoxy-6-(4-methyl-1,2,3-triazol-1-yl)phenyl]methyl}-5-[(2-methyl-3,4-dihydro-1H-isoquinolin-7-yl)methyl]pyridine-3-carboxamide;

N-{[2-fluoro-3-methoxy-6-(4-methyl-1,2,3-triazol-1-yl)phenyl]methyl}-1-[(1-hydroxy-2-methyl-3,4-dihydro-1H-isoquinolin-7-yl)methyl]-3-(methoxymethyl)pyrazole-4-carboxamide.

The present invention also encompasses, but is not limited to, the below compounds:

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]pyrazole-4-carboxamide;

N-{[2-fluoro-3-methoxy-6-(3-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-{[6-(3-ethyl-1,2,4-triazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)pyrazol-1-yl]phenyl}methyl)-3-(methoxymethyl)-1-[(2-methyl-3,4-dihydro-1H-isoquinolin-7-yl)methyl]pyrazole-4-carboxamide;

N-{[6-(3-cyclopropylpyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(5-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-7-yl)methyl]pyrazole-4-carboxamide;

1-[(2-cyclopropyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

1-[(2-ethyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(2-cyclopropyl-3,4-dihydro-1H-isoquinolin-7-yl)methyl]-N-({6-[3-(difluoromethyl)-1,2,4-triazol-1-yl]-2-fluoro-3-methoxyphenyl}methyl)-3-(methoxymethyl)pyrazole-4-carboxamide;

1-[(2-cyclopropyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-{[6-(3-cyanopyrazol-1-yl)-2-fluoro-3-methoxyphenyl]methyl}-1-[(2-cyclopropyl-3,4-dihydro-1H-isoquinolin-7-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-7-yl)methyl]-3-(methoxymethyl)pyrazole-4-carboxamide;

N-{[6-(dimethyl-1,2,4-triazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[6-(4-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]pyrazole-4-carboxamide;

3-(difluoromethyl)-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]pyrazole-4-carboxamide;

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

1-[(2-cyclopropyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(2-cyclobutyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-6-yl)methyl]pyrazole-4-carboxamide;

N-{[6-(3-cyanopyrazol-1-yl)-2-fluoro-3-methoxyphenyl]
  methyl}-3-(methoxymethyl)-1-[(2-methyl-3,4-dihydro-
  1H-isoquinolin-6-yl)methyl]pyrazole-4-carboxamide;
N-({6-[3-(difluoromethyl)-1,2,4-triazol-1-yl]-2-fluoro-3-
  methoxyphenyl}methyl)-1-[(2-isopropyl-3,4-dihydro-
  1H-isoquinolin-6-yl)methyl]-3-(methoxymethyl)pyra-
  zole-4-carboxamide;
N-({2-fluoro-3-methoxy-6-[3-(trifluoromethyl)-1,2,4-tri-
  azol-1-yl]phenyl}methyl)-1-[(2-isopropyl-3,4-dihydro-
  1H-isoquinolin-6-yl)methyl]-3-(methoxymethyl)pyra-
  zole-4-carboxamide;
N-{[6-(3-cyanopyrazol-1-yl)-2-fluoro-3-methoxyphenyl]
  methyl}-1-[(2-isopropyl-3,4-dihydro-1H-isoquinolin-6-
  yl)methyl]-3-(methoxymethyl)pyrazole-4-carboxamide;
1-[(2-cyclopropyl-3,4-dihydro-1H-isoquinolin-6-yl)
  methyl]-N-({6-[3-(difluoromethyl)-1,2,4-triazol-1-yl]-2-
  fluoro-3-methoxyphenyl}methyl)-3-(methoxymethyl)
  pyrazole-4-carboxamide;
1-[(2-cyclopropyl-3,4-dihydro-1H-isoquinolin-6-yl)
  methyl]-N-({2-fluoro-3-methoxy-6-[3-(trifluoromethyl)-
  1,2,4-triazol-1-yl]phenyl}methyl)-3-(methoxymethyl)
  pyrazole-4-carboxamide;
N-{[6-(3-cyanopyrazol-1-yl)-2-fluoro-3-methoxyphenyl]
  methyl}-1-[(2-cyclopropyl-3,4-dihydro-1H-isoquinolin-
  6-yl)methyl]-3-(methoxymethyl)pyrazole-4-carboxam-
  ide;
N-({6-[3-(difluoromethyl)-1,2,4-triazol-1-yl]-2-fluoro-3-
  methoxyphenyl}methyl)-1-[(2-ethyl-3,4-dihydro-1H-iso-
  quinolin-6-yl)methyl]-3-(methoxymethyl)pyrazole-4-car-
  boxamide;
1-[(2-ethyl-3,4-dihydro-1H-isoquinolin-6-yl)methyl]-N-
  ({2-fluoro-3-methoxy-6-[3-(trifluoromethyl)-1,2,4-tri-
  azol-1-yl]phenyl}methyl)-3-(methoxymethyl)pyrazole-4-
  carboxamide;
N-{[6-(3-cyanopyrazol-1-yl)-2-fluoro-3-methoxyphenyl]
  methyl}-1-[(2-ethyl-3,4-dihydro-1H-isoquinolin-6-yl)
  methyl]-3-(methoxymethyl)pyrazole-4-carboxamide;
1-(2,3-dihydro-1H-isoindol-5-ylmethyl)-N-{[2-fluoro-3-
  methoxy-6-(4-methyl-1,2,3-triazol-1-yl)phenyl]methyl}-
  3-(methoxymethyl)pyrazole-4-carboxamide;
N-{[2-fluoro-3-methoxy-6-(4-methyl-1,2,3-triazol-1-yl)
  phenyl]methyl}-3-(methoxymethyl)-1-[(2-methyl-1,3-di-
  hydroisoindol-5-yl)methyl]pyrazole-4-carboxamide;
N-{[2-fluoro-3-methoxy-6-(4-methyl-1,2,3-triazol-1-yl)
  phenyl]methyl}-1-[(2-isopropyl-1,3-dihydroisoindol-5-
  yl)methyl]-3-(methoxymethyl)pyrazole-4-carboxamide;
1-[(2-ethyl-1,3-dihydroisoindol-5-yl)methyl]-N-{[2-fluoro-
  3-methoxy-6-(4-methyl-1,2,3-triazol-1-yl)phenyl]
  methyl}-3-(methoxymethyl)pyrazole-4-carboxamide;
N-({6-[3-(difluoromethyl)-1,2,4-triazol-1-yl]-2-fluoro-3-
  methoxyphenyl}methyl)-3-(methoxymethyl)-1-[(2-
  methyl-1,3-dihydroisoindol-5-yl)methyl]pyrazole-4-car-
  boxamide;
N-({2-fluoro-3-methoxy-6-[3-(trifluoromethyl)-1,2,4-tri-
  azol-1-yl]phenyl}methyl)-3-(methoxymethyl)-1-[(2-
  methyl-1,3-dihydroisoindol-5-yl)methyl]pyrazole-4-car-
  boxamide;
N-({6-[3-(difluoromethyl)-1,2,4-triazol-1-yl]-2-fluoro-3-
  methoxyphenyl}methyl)-1-[(2-isopropyl-1,3-dihydroi-
  soindol-5-yl)methyl]-3-(methoxymethyl)pyrazole-4-car-
  boxamide;
N-({2-fluoro-3-methoxy-6-[3-(trifluoromethyl)-1,2,4-tri-
  azol-1-yl]phenyl}methyl)-1-[(2-isopropyl-1,3-dihydroi-
  soindol-5-yl)methyl]-3-(methoxymethyl)pyrazole-4-car-
  boxamide;
N-{[2-fluoro-3-methoxy-6-(4-methyl-1,2,3-triazol-1-yl)
  phenyl]methyl}-1-({7-methyl-5H,6H,8H-imidazo[1,2-a]
  pyrazin-2-yl}methyl)-3-(trifluoromethyl)pyrazole-4-car-
  boxamide;
1-[(4-chloro-7-methyl-6,8-dihydro-5H-1,7-naphthyridin-3-
  yl)methyl]-N-{[2-fluoro-3-methoxy-6-(4-methyl-1,2,3-
  triazol-1-yl)phenyl]methyl}-3-(methoxymethyl)pyra-
  zole-4-carboxamide;
1-(3,4-dihydro-1H-2-benzopyran-6-ylmethyl)-N-{[2-
  fluoro-3-methoxy-6-(4-methyl-1,2,3-triazol-1-yl)phenyl]
  methyl}-3-(methoxymethyl)pyrazole-4-carboxamide;
N-{[2-fluoro-3-methoxy-6-(4-methyl-1,2,3-triazol-1-yl)
  phenyl]methyl}-3-(methoxymethyl)-1-({5-methyl-4H,
  6H,7H-pyrazolo[1,5-a]pyrazin-2-yl}methyl)pyrazole-4-
  carboxamide;
N-{[2-fluoro-3-methoxy-6-(4-methyl-1,2,3-triazol-1-yl)
  phenyl]methyl}-3-(methoxymethyl)-1-[(2-methyl-1-oxo-
  3,4-dihydroisoquinolin-7-yl)methyl]pyrazole-4-carbox-
  amide;
3-(difluoromethyl)-N-(2-fluoro-3-methoxy-6-(4-methyl-
  1H-1,2,3-triazol-1-yl)benzyl)-1-((5'-methyl-5',6'-di-
  hydro-4'H-spiro[cyclopropane-1,7'-pyrazolo[1,5-a]
  pyrazin]-2'-yl)methyl)-1H-pyrazole-4-carboxamide;
N-{[2-fluoro-3-methoxy-6-(4-methyl-1,2,3-triazol-1-yl)
  phenyl]methyl}-3-(methoxymethyl)-1-[(7-methyl-6,8-di-
  hydro-5H-1,7-naphthyridin-3-yl)methyl]pyrazole-4-car-
  boxamide;
1-[(7-fluoro-2-methyl-3,4-dihydro-1H-isoquinolin-5-yl)
  methyl]-N-{[2-fluoro-3-methoxy-6-(4-methyl-1,2,3-tri-
  azol-1-yl)phenyl]methyl}-3-(methoxymethyl)pyrazole-4-
  carboxamide;
1-[(5-chloro-2-methyl-3,4-dihydro-1H-isoquinolin-6-yl)
  methyl]-N-{[2-fluoro-3-methoxy-6-(4-methyl-1,2,3-tri-
  azol-1-yl)phenyl]methyl}-3-(methoxymethyl)pyrazole-4-
  carboxamide;
1-[(4,4-difluoro-2-methyl-1,3-dihydroisoquinolin-6-yl)
  methyl]-N-{[2-fluoro-3-methoxy-6-(4-methyl-1,2,3-tri-
  azol-1-yl)phenyl]methyl}-3-(methoxymethyl)pyrazole-4-
  carboxamide;
1-[(4,4-difluoro-2-methyl-1,3-dihydroisoquinolin-7-yl)
  methyl]-N-{[2-fluoro-3-methoxy-6-(4-methyl-1,2,3-tri-
  azol-1-yl)phenyl]methyl}-3-(methoxymethyl)pyrazole-4-
  carboxamide;
1-[(8-fluoro-2-methyl-3,4-dihydro-1H-isoquinolin-7-yl)
  methyl]-N-{[2-fluoro-3-methoxy-6-(4-methyl-1,2,3-tri-
  azol-1-yl)phenyl]methyl}-3-(methoxymethyl)pyrazole-4-
  carboxamide;
N-{[2-fluoro-3-methoxy-6-(4-methyl-1,2,3-triazol-1-yl)
  phenyl]methyl}-3-(methoxymethyl)-1-[(4-methyl-3,5-di-
  hydro-2H-1,4-benzoxazepin-7-yl)methyl]pyrazole-4-car-
  boxamide;
N-{[2-fluoro-3-methoxy-6-(4-methyl-1,2,3-triazol-1-yl)
  phenyl]methyl}-3-(methoxymethyl)-1-({5-methyl-4H,
  6H,7H-[1,3]thiazolo[5,4-c]pyridin-2-yl}methyl)pyra-
  zole-4-carboxamide;
N-{[2-fluoro-3-methoxy-6-(4-methyl-1,2,3-triazol-1-yl)
  phenyl]methyl}-3-(methoxymethyl)-1-(2,3,4,5-tetra-
  hydro-1,4-benzoxazepin-7-ylmethyl)pyrazole-4-carbox-
  amide;
1-[(5-fluoro-2-methyl-3,4-dihydro-1H-isoquinolin-6-yl)
  methyl]-N-{[2-fluoro-3-methoxy-6-(4-methyl-1,2,3-tri-
  azol-1-yl)phenyl]methyl}-3-(methoxymethyl)pyrazole-4-
  carboxamide;
1-{[7-(2,2-difluoroethyl)-6,8-dihydro-5H-1,7-naphthyridin-
  3-yl]methyl}-N-{[2-fluoro-3-methoxy-6-(4-methyl-1,2,
  3-triazol-1-yl)phenyl]methyl}-3-(methoxymethyl)pyra-
  zole-4-carboxamide;

1-[(8-fluoro-2-methyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-1-[(7-isopropyl-6,8-dihydro-5H-1,7-naphthyridin-3-yl)methyl]-3-(methoxymethyl)pyrazole-4-carboxamide;

1-[(6-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{[2-($^2H_3$)methyl-3,4-dihydro-1H-isoquinolin-7-yl]methyl}pyrazole-4-carboxamide;

1-{1H,2H,3H,5H,6H,10bH-pyrrolo[2,1-a]isoquinolin-9-ylmethyl}-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(3-methyl-1,2,4,5-tetrahydro-3-benzazepin-7-yl)methyl]pyrazole-4-carboxamide;

N-{[2-fluoro-3-methoxy-6-(4-methyl-1,2,3-triazol-1-yl)phenyl]methyl}-1-[(3-isopropyl-1,2,4,5-tetrahydro-3-benzazepin-7-yl)methyl]-3-(methoxymethyl)pyrazole-4-carboxamide;

N-{[2-fluoro-3-methoxy-6-(4-methyl-1,2,3-triazol-1-yl)phenyl]methyl}-1-({11-isopropyl-11-azatricyclo[6.2.1.0^{2,7}]undeca-2(7),3,5-trien-4-yl}methyl)-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2,3,3-trimethyl-1H-isoindol-5-yl)methyl]pyrazole-4-carboxamide;

N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)-3-(trifluoromethyl)pyrazole-4-carboxamide;

N-{[2-fluoro-3-methoxy-6-(4-methyl-1,2,3-triazol-1-yl)phenyl]methyl}-3-(methoxymethyl)-1-{2'-methyl-1',3'-dihydrospiro[cyclopropane-1,4'-isoquinoline]-7'-ylmethyl}pyrazole-4-carboxamide;

1-{2',3'-dihydro-1'H-spiro[cyclopropane-1,4'-isoquinoline]-7'-ylmethyl}-N-{[2-fluoro-3-methoxy-6-(4-methyl-1,2,3-triazol-1-yl)phenyl]methyl}-3-(methoxymethyl)pyrazole-4-carboxamide;

1-[(1,1-dimethyl-3,4-dihydro-2H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(1,1,2-trimethyl-3,4-dihydroisoquinolin-7-yl)methyl]pyrazole-4-carboxamide;

1-[(4,4-dimethyl-2,3-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1H-1,2,3-triazol-1-yl)phenyl]methyl}-1-[(7-methyl-5,6,7,8-tetrahydro-1,7-naphthyridin-2-yl)methyl]-3-(trifluoromethyl)-1H-pyrazole-4-carboxamide;

N-{[2-fluoro-3-methoxy-6-(4-methyl-1H-1,2,3-triazol-1-yl)phenyl]methyl}-3-(methoxymethyl)-1-{[6-(propan-2-yl)-5,6,7,8-tetrahydro-1,6-naphthyridin-3-yl]methyl}-1H-pyrazole-4-carboxamide;

1-(3,4-dihydro-1H-2-benzopyran-7-ylmethyl)-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2,4,4-trimethyl-1,3-dihydroisoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1-oxo-3,4-dihydroisoquinolin-6-yl)methyl]pyrazole-4-carboxamide;

3-(difluoromethyl)-N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)pyrazole-4-carboxamide;

3-(difluoromethyl)-N-{[2-fluoro-3-methoxy-6-(4-methyl-1,2,3-triazol-1-yl)phenyl]methyl}-1-[(7-methyl-6,8-dihydro-5H-1,7-naphthyridin-3-yl)methyl]pyrazole-4-carboxamide;

N-{[2-fluoro-3-methoxy-6-(4-methyl-1,2,3-triazol-1-yl)phenyl]methyl}-1-[(6-methyl-7,8-dihydro-5H-1,6-naphthyridin-2-yl)methyl]-3-(trifluoromethyl)pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-2-(methoxymethyl)imidazole-4-carboxamide;

N-{[2-fluoro-3-methoxy-6-(4-methyl-1,2,3-triazol-1-yl)phenyl]methyl}-2-(methoxymethyl)-1-[(2-methyl-3,4-dihydro-1H-isoquinolin-7-yl)methyl]imidazole-4-carboxamide;

2-cyclopropyl-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]imidazole-4-carboxamide;

2-cyclopropyl-N-{[2-fluoro-3-methoxy-6-(4-methyl-1,2,3-triazol-1-yl)phenyl]methyl}-1-[(2-isopropyl-1,3-dihydroisoindol-5-yl)methyl]imidazole-4-carboxamide;

N-{[2-fluoro-3-methoxy-6-(4-methyl-1,2,3-triazol-1-yl)phenyl]methyl}-2-methyl-1-[(2-methyl-3,4-dihydro-1H-isoquinolin-7-yl)methyl]imidazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-1,2,3-triazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-1,2,3-triazole-4-carboxamide;

N-({3-chloro-6-[3-(difluoromethyl)-1,2,4-triazol-1-yl]-2-fluorophenyl}methyl)-3-(methoxymethyl)-1-[(2-methyl-3,4-dihydro-1H-isoquinolin-7-yl)methyl]pyrazole-4-carboxamide;

N-({2-chloro-6-[3-(difluoromethyl)-1,2,4-triazol-1-yl]-3-methoxyphenyl}methyl)-3-(methoxymethyl)-1-[(2-methyl-3,4-dihydro-1H-isoquinolin-7-yl)methyl]pyrazole-4-carboxamide;

N-{[3-(1,1-difluoroethyl)-6-[3-(difluoromethyl)-1,2,4-triazol-1-yl]-2-fluorophenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(3-methyl-1,2,4,5-tetrahydro-3-benzazepin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-2-oxopyridine-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-6-oxopyridine-3-carboxamide;

N-{[2-fluoro-3-methoxy-6-(4-methyl-1,2,3-triazol-1-yl)phenyl]methyl}-5-[(2-methyl-3,4-dihydro-1H-isoquinolin-7-yl)methyl]pyridine-3-carboxamide.

The present invention also encompasses, but is not limited to, the below compounds:

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(3-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-7-yl)methyl]pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-7-yl)methyl]-3-(methoxymethyl)pyrazole-4-carboxamide;

N-{[6-(4-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

1-[(2-cyclopropyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(2-cyclobutyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-6-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-6-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-6-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-6-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-6-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1,3-dihydroisoindol-5-yl)methyl]pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-3-(methoxymethyl)pyrazole-4-carboxamide;

N-{[2-fluoro-3-methoxy-6-(4-methyl-1,2,3-triazol-1-yl)phenyl]methyl}-1-[(7-isopropyl-6,8-dihydro-5H-1,7-naphthyridin-3-yl)methyl]-3-(methoxymethyl)pyrazole-4-carboxamide;

1-[(6-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{[2-($^2H_3$)methyl-3,4-dihydro-1H-isoquinolin-7-yl]methyl}pyrazole-4-carboxamide;

N-{[2-fluoro-3-methoxy-6-(4-methyl-1,2,3-triazol-1-yl)phenyl]methyl}-1-[(3-isopropyl-1,2,4,5-tetrahydro-3-benzazepin-7-yl)methyl]-3-(methoxymethyl)pyrazole-4-carboxamide;

N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)-3-(trifluoromethyl)pyrazole-4-carboxamide;

N-{[2-fluoro-3-methoxy-6-(4-methyl-1,2,3-triazol-1-yl)phenyl]methyl}-3-(methoxymethyl)-1-{2'-methyl-1',3'-dihydrospiro[cyclopropane-1,4'-isoquinoline]-7'-ylmethyl}pyrazole-4-carboxamide;

1-{2',3'-dihydro-1'H-spiro[cyclopropane-1,4'-isoquinoline]-7'-ylmethyl}-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1H-1,2,3-triazol-1-1)phenyl]methyl}-3-(methoxymethyl)-1-{[6-(propan-2-yl)-5,6,7,8-tetrahydro-1,6-naphthyridin-3-yl]methyl}-1H-pyrazole-4-carboxamide;

1-(3,4-dihydro-1H-2-benzopyran-7-ylmethyl)-N-{[2-fluoro-3-methoxy-6-(4-methyl-1,2,3-triazol-1-yl)phenyl]methyl}-3-(methoxymethyl)pyrazole-4-carboxamide;

3-(difluoromethyl)-N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)pyrazole-4-carboxamide;

3-(difluoromethyl)-N-{[2-fluoro-3-methoxy-6-(4-methyl-1,2,3-triazol-1-yl)phenyl]methyl}-1-[(7-methyl-6,8-dihydro-5H-1,7-naphthyridin-3-yl)methyl]pyrazole-4-carboxamide;

N-{[2-fluoro-3-methoxy-6-(4-methyl-1,2,3-triazol-1-yl)phenyl]methyl}-1-[(6-methyl-7,8-dihydro-5H-1,6-naphthyridin-2-yl)methyl]-3-(trifluoromethyl)pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-2-(methoxymethyl)imidazole-4-carboxamide;

N-{[2-fluoro-3-methoxy-6-(4-methyl-1,2,3-triazol-1-yl)phenyl]methyl}-2-(methoxymethyl)-1-[(2-methyl-3,4-dihydro-1H-isoquinolin-7-yl)methyl]imidazole-4-carboxamide;

2-cyclopropyl-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]imidazole-4-carboxamide;

N-{[2-fluoro-3-methoxy-6-(4-methyl-1,2,3-triazol-1-yl)phenyl]methyl}-2-methyl-1-[(2-methyl-3,4-dihydro-1H-isoquinolin-7-yl)methyl]imidazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-1,2,3-triazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-1,2,3-triazole-4-carboxamide;

N-({2-chloro-6-[3-(difluoromethyl)-1,2,4-triazol-1-yl]-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-6-oxopyridine-3-carboxamide;

N-{[2-fluoro-3-methoxy-6-(4-methyl-1,2,3-triazol-1-yl)phenyl]methyl}-5-[(2-methyl-3,4-dihydro-1H-isoquinolin-7-yl)methyl]pyridine-3-carboxamide.

The present invention also encompasses, but is not limited to, the below compounds:

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]pyrazole-4-carboxamide;

N-{[2-fluoro-3-methoxy-6-(3-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-{[6-(3-ethyl-1,2,4-triazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)pyrazol-1-yl]phenyl}methyl)-3-(methoxymethyl)-1-[(2-methyl-3,4-dihydro-1H-isoquinolin-7-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(5-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-7-yl)methyl]pyrazole-4-carboxamide;

1-[(2-cyclopropyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

1-[(2-ethyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(2-cyclopropyl-3,4-dihydro-1H-isoquinolin-7-yl)methyl]-N-({6-[3-(difluoromethyl)-1,2,4-triazol-1-yl]-2-fluoro-3-methoxyphenyl}methyl)-3-(methoxymethyl)pyrazole-4-carboxamide;

1-[(2-cyclopropyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-{[6-(3-cyanopyrazol-1-yl)-2-fluoro-3-methoxyphenyl]methyl}-1-[(2-cyclopropyl-3,4-dihydro-1H-isoquinolin-7-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-7-yl)methyl]-3-(methoxymethyl)pyrazole-4-carboxamide;

N-{[6-(dimethyl-1,2,4-triazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[6-(4-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]pyrazole-4-carboxamide;

3-(difluoromethyl)-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]pyrazole-4-carboxamide;

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(2-cyclobutyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-6-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-6-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-6-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-6-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-6-yl)methyl]-3-(methoxymethyl)pyrazole-4-carboxamide;

N-{[6-(3-cyanopyrazol-1-yl)-2-fluoro-3-methoxyphenyl]methyl}-1-[(2-cyclopropyl-3,4-dihydro-1H-isoquinolin-6-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-6-yl)methyl]-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1,3-dihydroisoindol-5-yl)methyl]pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-3-(methoxymethyl)pyrazole-4-carboxamide;

1-[(2-ethyl-1,3-dihydroisoindol-5-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-1,3-dihydroisoindol-5-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-1,3-dihydroisoindol-5-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-1,3-dihydroisoindol-5-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-1,3-dihydroisoindol-5-yl)methyl]-3-(methoxymethyl)pyrazole-4-carboxamide;

1-(3,4-dihydro-1H-2-benzopyran-6-ylmethyl)-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-({5-methyl-4H,6H,7H-pyrazolo[1,5-a]pyrazin-2-yl}methyl)pyrazole-4-carboxamide;

3-(difluoromethyl)-N-(2-fluoro-3-methoxy-6-(4-methyl-1H-1,2,3-triazol-1-yl)benzyl)-1-((5'-methyl-5',6'-dihydro-4'H-spiro[cyclopropane-1,7'-pyrazolo[1,5-a]pyrazin]-2'-yl)methyl)-1H-pyrazole-4-carboxamide;

N-{[2-fluoro-3-methoxy-6-(4-methyl-1,2,3-triazol-1-yl)phenyl]methyl}-3-(methoxymethyl)-1-[(7-methyl-6,8-dihydro-5H-1,7-naphthyridin-3-yl)methyl]pyrazole-4-carboxamide;

1-[(4,4-difluoro-2-methyl-1,3-dihydroisoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(4,4-difluoro-2-methyl-1,3-dihydroisoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(8-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(5-fluoro-2-methyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-{[7-(2,2-difluoroethyl)-6,8-dihydro-5H-1,7-naphthyridin-3-yl]methyl}-N-{[2-fluoro-3-methoxy-6-(4-methyl-1,2,3-triazol-1-yl)phenyl]methyl}-3-(methoxymethyl)pyrazole-4-carboxamide;

1-[(8-fluoro-2-methyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-1-[(7-isopropyl-6,8-dihydro-5H-1,7-naphthyridin-3-yl)methyl]-3-(methoxymethyl)pyrazole-4-carboxamide;

1-[(6-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{[2-($^2$H$_3$)methyl-3,4-dihydro-1H-isoquinolin-7-yl]methyl}pyrazole-4-carboxamide;

1-{1H,2H,3H,5H,6H,10bH-pyrrolo[2,1-a]isoquinolin-9-ylmethyl}-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(3-methyl-1,2,4,5-tetrahydro-3-benzazepin-7-yl)methyl]pyrazole-4-carboxamide;

N-{[2-fluoro-3-methoxy-6-(4-methyl-1,2,3-triazol-1-yl)phenyl]methyl}-1-[(3-isopropyl-1,2,4,5-tetrahydro-3-benzazepin-7-yl)methyl]-3-(methoxymethyl)pyrazole-4-carboxamide;

N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)-3-(trifluoromethyl)pyrazole-4-carboxamide;

N-{[2-fluoro-3-methoxy-6-(4-methyl-1,2,3-triazol-1-yl)phenyl]methyl}-3-(methoxymethyl)-1-{2'-methyl-1',3'-dihydrospiro[cyclopropane-1,4'-isoquinoline]-7'-ylmethyl}pyrazole-4-carboxamide;

1-{2',3'-dihydro-1'H-spiro[cyclopropane-1,4'-isoquinoline]-7'-ylmethyl}-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(1,1,2-trimethyl-3,4-dihydroisoquinolin-7-yl)methyl]pyrazole-4-carboxamide;

1-[(4,4-dimethyl-2,3-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1H-1,2,3-triazol-1-yl)phenyl]methyl}-1-[(7-methyl-5,6,7,8-tetrahydro-1,7-naphthyridin-2-yl)methyl]-3-(trifluoromethyl)-1H-pyrazole-4-carboxamide;

N-{[2-fluoro-3-methoxy-6-(4-methyl-1H-1,2,3-triazol-1-yl)phenyl]methyl}-3-(methoxymethyl)-1-{[6-(propan-2-yl)-5,6,7,8-tetrahydro-1,6-naphthyridin-3-yl]methyl}-1H-pyrazole-4-carboxamide;

1-(3,4-dihydro-1H-2-benzopyran-7-ylmethyl)-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2,4,4-trimethyl-1,3-dihydroisoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1-oxo-3,4-dihydroisoquinolin-6-yl)methyl]pyrazole-4-carboxamide;

3-(difluoromethyl)-N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)pyrazole-4-carboxamide;

3-(difluoromethyl)-N-{[2-fluoro-3-methoxy-6-(4-methyl-1,2,3-triazol-1-yl)phenyl]methyl}-1-[(7-methyl-6,8-dihydro-5H-1,7-naphthyridin-3-yl)methyl]pyrazole-4-carboxamide;

N-{[2-fluoro-3-methoxy-6-(4-methyl-1,2,3-triazol-1-yl)phenyl]methyl}-1-[(6-methyl-7,8-dihydro-5H-1,6-naphthyridin-2-yl)methyl]-3-(trifluoromethyl)pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-2-(methoxymethyl)imidazole-4-carboxamide;

N-{[2-fluoro-3-methoxy-6-(4-methyl-1,2,3-triazol-1-yl)phenyl]methyl}-2-(methoxymethyl)-1-[(2-methyl-3,4-dihydro-1H-isoquinolin-7-yl)methyl]imidazole-4-carboxamide;

2-cyclopropyl-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]imidazole-4-carboxamide;

2-cyclopropyl-N-{[2-fluoro-3-methoxy-6-(4-methyl-1,2,3-triazol-1-yl)phenyl]methyl}-1-[(2-isopropyl-1,3-dihydroisoindol-5-yl)methyl]imidazole-4-carboxamide;

N-{[2-fluoro-3-methoxy-6-(4-methyl-1,2,3-triazol-1-yl)phenyl]methyl}-2-methyl-1-[(2-methyl-3,4-dihydro-1H-isoquinolin-7-yl)methyl]imidazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-1,2,3-triazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-1,2,3-triazole-4-carboxamide;

N-({2-chloro-6-[3-(difluoromethyl)-1,2,4-triazol-1-yl]-3-methoxyphenyl}methyl)-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(3-methyl-1,2,4,5-tetrahydro-3-benzazepin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-6-oxopyridine-3-carboxamide;

N-{[2-fluoro-3-methoxy-6-(4-methyl-1,2,3-triazol-1-yl)phenyl]methyl}-5-[(2-methyl-3,4-dihydro-1H-isoquinolin-7-yl)methyl]pyridine-3-carboxamide.

The present invention also encompasses, but is not limited to, the below compounds:

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(3-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-7-yl)methyl]pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-7-yl)methyl]-3-(methoxymethyl)pyrazole-4-carboxamide;

N-{[6-(4-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(2-cyclobutyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-6-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-6-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-6-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-6-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-6-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1,3-dihydroisoindol-5-yl)methyl]pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-3-(methoxymethyl)pyrazole-4-carboxamide;

N-{[2-fluoro-3-methoxy-6-(4-methyl-1,2,3-triazol-1-yl)phenyl]methyl}-1-[(7-isopropyl-6,8-dihydro-5H-1,7-naphthyridin-3-yl)methyl]-3-(methoxymethyl)pyrazole-4-carboxamide;

1-[(6-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{[2-($^{2}H_3$)methyl-3,4-dihydro-1H-isoquinolin-7-yl]methyl}pyrazole-4-carboxamide;

N-{[2-fluoro-3-methoxy-6-(4-methyl-1,2,3-triazol-1-yl)phenyl]methyl}-1-[(3-isopropyl-1,2,4,5-tetrahydro-3-benzazepin-7-yl)methyl]-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{2'-methyl-1',3'-dihydrospiro[cyclopropane-1,4'-isoquinoline]-7'-ylmethyl}pyrazole-4-carboxamide;

1-{2',3'-dihydro-1'H-spiro[cyclopropane-1,4'-isoquinoline]-7'-ylmethyl}-N-{[2-fluoro-3-methoxy-6-(4-methyl-1,2,3-triazol-1-yl)phenyl]methyl}-3-(methoxymethyl)pyrazole-4-carboxamide;

3-(difluoromethyl)-N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)pyrazole-4-carboxamide;

3-(difluoromethyl)-N-{[2-fluoro-3-methoxy-6-(4-methyl-1,2,3-triazol-1-yl)phenyl]methyl}-1-[(7-methyl-6,8-dihydro-5H-1,7-naphthyridin-3-yl)methyl]pyrazole-4-carboxamide;

N-{[2-fluoro-3-methoxy-6-(4-methyl-1,2,3-triazol-1-yl)phenyl]methyl}-1-[(6-methyl-7,8-dihydro-5H-1,6-naphthyridin-2-yl)methyl]-3-(trifluoromethyl)pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-2-(methoxymethyl)imidazole-4-carboxamide;

N-{[2-fluoro-3-methoxy-6-(4-methyl-1,2,3-triazol-1-yl)phenyl]methyl}-2-(methoxymethyl)-1-[(2-methyl-3,4-dihydro-1H-isoquinolin-7-yl)methyl]imidazole-4-carboxamide;

2-cyclopropyl-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]imidazole-4-carboxamide;

N-{[2-fluoro-3-methoxy-6-(4-methyl-1,2,3-triazol-1-yl)phenyl]methyl}-2-methyl-1-[(2-methyl-3,4-dihydro-1H-isoquinolin-7-yl)methyl]imidazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-1,2,3-triazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-1,2,3-triazole-4-carboxamide;

N-({2-chloro-6-[3-(difluoromethyl)-1,2,4-triazol-1-yl]-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-6-oxopyridine-3-carboxamide;

N-{[2-fluoro-3-methoxy-6-(4-methyl-1,2,3-triazol-1-yl)phenyl]methyl}-5-[(2-methyl-3,4-dihydro-1H-isoquinolin-7-yl)methyl]pyridine-3-carboxamide.

The present invention also encompasses, but is not limited to, the below compounds:

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]pyrazole-4-carboxamide;

N-{[2-fluoro-3-methoxy-6-(3-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-{[6-(3-ethyl-1,2,4-triazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(5-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-7-yl)methyl]pyrazole-4-carboxamide;

1-[(2-cyclopropyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

1-[(2-ethyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(2-cyclopropyl-3,4-dihydro-1H-isoquinolin-7-yl)methyl]-N-({6-[3-(difluoromethyl)-1,2,4-triazol-1-yl]-2-fluoro-3-methoxyphenyl}methyl)-3-(methoxymethyl)pyrazole-4-carboxamide;

N-{[6-(3-cyanopyrazol-1-yl)-2-fluoro-3-methoxyphenyl]methyl}-1-[(2-cyclopropyl-3,4-dihydro-1H-isoquinolin-7-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-7-yl)methyl]-3-(methoxymethyl)pyrazole-4-carboxamide;

N-{[6-(dimethyl-1,2,4-triazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-{[6-(4-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]pyrazole-4-carboxamide;

3-(difluoromethyl)-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]pyrazole-4-carboxamide;

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-6-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-6-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-6-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-6-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-6-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-6-yl)methyl]-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1,3-dihydroisoindol-5-yl)methyl]pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-3-(methoxymethyl)pyrazole-4-carboxamide;

1-[(2-ethyl-1,3-dihydroisoindol-5-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-1,3-dihydroisoindol-5-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-1,3-dihydroisoindol-5-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-1,3-dihydroisoindol-5-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-1,3-dihydroisoindol-5-yl)methyl]-3-(methoxymethyl)pyrazole-4-carboxamide;

3-(difluoromethyl)-N-(2-fluoro-3-methoxy-6-(4-methyl-1H-1,2,3-triazol-1-yl)benzyl)-1-((5'-methyl-5',6'-dihydro-4'H-spiro[cyclopropane-1,7'-pyrazolo[1,5-a]pyrazin]-2'-yl)methyl)-1H-pyrazole-4-carboxamide;

N-{[2-fluoro-3-methoxy-6-(4-methyl-1,2,3-triazol-1-yl)phenyl]methyl}-3-(methoxymethyl)-1-[(7-methyl-6,8-dihydro-5H-1,7-naphthyridin-3-yl)methyl]pyrazole-4-carboxamide;

1-[(4,4-difluoro-2-methyl-1,3-dihydroisoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(4,4-difluoro-2-methyl-1,3-dihydroisoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(8-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(8-fluoro-2-methyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

1-[(6-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{[2-($^2$H$_3$)methyl-3,4-dihydro-1H-isoquinolin-7-yl]methyl}pyrazole-4-carboxamide;

1-{1H,2H,3H,5H,6H,10bH-pyrrolo[2,1-a]isoquinolin-9-yl-methyl}-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(3-methyl-1,2,4,5-tetrahydro-3-benzazepin-7-yl)methyl]pyrazole-4-carboxamide;

N-{[2-fluoro-3-methoxy-6-(4-methyl-1,2,3-triazol-1-yl)phenyl]methyl}-1-[(3-isopropyl-1,2,4,5-tetrahydro-3-benzazepin-7-yl)methyl]-3-(methoxymethyl)pyrazole-4-carboxamide;

N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)-3-(trifluoromethyl)pyrazole-4-carboxamide;

N-{[2-fluoro-3-methoxy-6-(4-methyl-1,2,3-triazol-1-yl)phenyl]methyl}-3-(methoxymethyl)-1-{2'-methyl-1',3'-dihydrospiro[cyclopropane-1,4'-isoquinoline]-7'-ylmethyl}pyrazole-4-carboxamide;

1-{2',3'-dihydro-1'H-spiro[cyclopropane-1,4'-isoquinoline]-7'-ylmethyl}-N-{[2-fluoro-3-methoxy-6-(4-methyl-1,2,3-triazol-1-yl)phenyl]methyl}-3-(methoxymethyl)pyrazole-4-carboxamide;

3-(difluoromethyl)-N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)pyrazole-4-carboxamide;

3-(difluoromethyl)-N-{[2-fluoro-3-methoxy-6-(4-methyl-1,2,3-triazol-1-yl)phenyl]methyl}-1-[(7-methyl-6,8-dihydro-5H-1,7-naphthyridin-3-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-1,2,3-triazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-1,2,3-triazole-4-carboxamide;

N-({2-chloro-6-[3-(difluoromethyl)-1,2,4-triazol-1-yl]-3-methoxyphenyl}methyl)-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(3-methyl-1,2,4,5-tetrahydro-3-benzazepin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-6-oxopyridine-3-carboxamide;

N-{[2-fluoro-3-methoxy-6-(4-methyl-1,2,3-triazol-1-yl)phenyl]methyl}-5-[(2-methyl-3,4-dihydro-1H-isoquinolin-7-yl)methyl]pyridine-3-carboxamide.

The present invention also encompasses, but is not limited to, the below compounds:

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(3-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-7-yl)methyl]pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-7-yl)methyl]-3-(methoxymethyl)pyrazole-4-carboxamide;

N-{[6-(4-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-6-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-6-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-6-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-6-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-6-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1,3-dihydroisoindol-5-yl)methyl]pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-3-(methoxymethyl)pyrazole-4-carboxamide;

1-[(6-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{[2-($^2$H$_3$)methyl-3,4-dihydro-1H-isoquinolin-7-yl]methyl}pyrazole-4-carboxamide;

N-{[2-fluoro-3-methoxy-6-(4-methyl-1,2,3-triazol-1-yl)phenyl]methyl}-1-[(3-isopropyl-1,2,4,5-tetrahydro-3-benzazepin-7-yl)methyl]-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{2'-methyl-1',3'-dihydrospiro[cyclopropane-1,4'-isoquinoline]-7'-ylmethyl}pyrazole-4-carboxamide;

1-{2',3'-dihydro-1'H-spiro[cyclopropane-1,4'-isoquinoline]-7'-ylmethyl}-N-{[2-fluoro-3-methoxy-6-(4-methyl-1,2,3-triazol-1-yl)phenyl]methyl}-3-(methoxymethyl)pyrazole-4-carboxamide;

3-(difluoromethyl)-N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)pyrazole-4-carboxamide;

3-(difluoromethyl)-N-{[2-fluoro-3-methoxy-6-(4-methyl-1,2,3-triazol-1-yl)phenyl]methyl}-1-[(7-methyl-6,8-dihydro-5H-1,7-naphthyridin-3-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-1,2,3-triazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-1,2,3-triazole-4-carboxamide;

N-({2-chloro-6-[3-(difluoromethyl)-1,2,4-triazol-1-yl]-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-6-oxopyridine-3-carboxamide;

N-{[2-fluoro-3-methoxy-6-(4-methyl-1,2,3-triazol-1-yl)phenyl]methyl}-5-[(2-methyl-3,4-dihydro-1H-isoquinolin-7-yl)methyl]pyridine-3-carboxamide.

The present invention also encompasses, but is not limited to, the below compounds:

N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-7-yl)methyl]pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-6-yl)methyl]-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1,3-dihydroisoindol-5-yl)methyl]pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{2'-methyl-1',3'-dihydrospiro[cyclopropane-1,4'-isoquinoline]-7'-ylmethyl}pyrazole-4-carboxamide.

Therapeutic Applications

As previously mentioned, the compounds of the present invention are potent and selective inhibitors of plasma kallikrein. They are therefore useful in the treatment of disease conditions for which over-activity of plasma kallikrein is a causative factor.

Accordingly, the present invention provides a compound of formula (I) for use in medicine.

The present invention also provides for the use of a compound of formula (I) in the manufacture of a medicament for the treatment or prevention of a disease or condition in which plasma kallikrein activity is implicated.

The present invention also provides a compound of formula (I) for use in the treatment or prevention of a disease or condition in which plasma kallikrein activity is implicated.

The present invention also provides a method of treatment of a disease or condition in which plasma kallikrein activity is implicated comprising administration to a subject in need thereof a therapeutically effective amount of a compound of formula (I).

In particular, the disease or condition in which plasma kallikrein activity is implicated is a bradykinin-mediated angioedema.

The bradykinin-mediated angioedema can be non-hereditary. For example, the non-hereditary bradykinin-mediated angioedema can be selected from non-hereditary angioedema with normal C1 Inhibitor (AE-nC1 Inh), which can be environmental, hormonal, or drug-induced; acquired angioedema; anaphylaxis associated angioedema; angiotensin converting enzyme (ACE or ace) inhibitor-induced angioedema; dipeptidyl peptidase-4 inhibitor-induced angioedema; and tPA-induced angioedema (tissue plasminogen activator-induced angioedema).

Alternatively, and preferably, the bradykinin-mediated angioedema can be hereditary angioedema (HAE), which is angioedema caused by an inherited dysfunction/fault/mutation. Types of HAE that can be treated with compounds according to the invention include HAE type 1, HAE type 2, and normal C1 inhibitor HAE (normal C1 Inh HAE).

The disease or condition in which plasma kallikrein activity is implicated is selected from impaired visual acuity, diabetic retinopathy, diabetic macular edema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery. More specifically, the disease or condition in which plasma kallikrein activity is implicated can be retinal vascular permeability associated with diabetic retinopathy and diabetic macular edema.

Combination Therapy

The compounds of the present invention may be administered in combination with other therapeutic agents. Suitable combination therapies include a compound of formula (I) combined with one or more agents selected from agents that inhibit platelet-derived growth factor (PDGF), endothelial growth factor (VEGF), integrin alpha5beta1, steroids, other agents that inhibit plasma kallikrein and other inhibitors of inflammation. Specific examples of therapeutic agents that may be combined with the compounds of the present invention include those disclosed in EP2281885A and by S. Patel in $Retina$, 2009 June; 29(6 Suppl):S45-8.

When combination therapy is employed, the compounds of the present invention and said combination agents may exist in the same or different pharmaceutical compositions, and may be administered separately, sequentially or simultaneously.

The compounds of the present invention can be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema" Ophthalmology. 27 Apr. 2010).

Definitions

As noted above, the term "alkyl" is a linear saturated hydrocarbon having up to 10 carbon atoms ($C_1$-$C_{10}$) or a branched saturated hydrocarbon of between 3 and 10 carbon atoms ($C_3$-$C_{10}$); alkyl may optionally be substituted with 1 or 2 substituents independently selected from ($C_1$-$C_6$) alkoxy, OH, —NR13R14, —COOR13, —CONR13R14, CN, $CF_3$, halo. As noted above, the term "alkyl$^b$" is a linear saturated hydrocarbon having up to 10 carbon atoms ($C_1$-$C_{10}$) or a branched saturated hydrocarbon of between 3 and 10 carbon atoms ($C_3$-$C_{10}$); alkyl may optionally be substituted with 1 or 2 substituents independently selected from ($C_1$-$C_6$)alkoxy, OH, CN, $CF_3$, and halo. Examples of such alkyl or alkyl$^b$ groups include, but are not limited, to C1-methyl, $C_2$-ethyl, $C_3$-propyl and $C_4$-n-butyl, $C_3$-isopropyl, $C_4$-sec-butyl, $C_4$-iso-butyl, $C_4$-tert-butyl and $C_5$-neo-pentyl), optionally substituted as noted above. More specifically, "alkyl" or "alkyl$^b$" can be a linear saturated hydrocarbon having up to 6 carbon atoms ($C_1$-$C_6$) or a branched saturated hydrocarbon of between 3 and 6 carbon atoms ($C_3$-$C_6$), optionally substituted as noted above. Even more specifically, "alkyl" or "alkyl$^b$" can be a linear saturated hydrocarbon having up to 4 carbon atoms ($C_1$-$C_4$) or a branched saturated hydrocarbon of between 3 and 4 carbon atoms ($C_3$-$C_4$), optionally substituted as noted above, which is herein called "small alkyl" or "small alkyl$^b$", respectively. Preferably, "alkyl" or "alkyl$^b$" can be defined as a "small alkyl" or "small alkyl$^b$".

As noted above, the term "alkylene" is a bivalent linear saturated hydrocarbon having 1 to 5 carbon atoms ($C_1$-$C_5$); alkylene may optionally be substituted with 1 or 2 substituents independently selected from alkyl, ($C_1$-$C_6$)alkoxy, OH, CN, $CF_3$, halo. More specifically, alkylene can be a bivalent linear saturated hydrocarbon having 2 to 4 carbon atoms ($C_2$-$C_4$), more specifically having 2 to 3 carbon atoms ($C_2$-$C_3$), optionally substituted as noted above.

Aryl and aryl$^b$ are as defined above. Typically, aryl or aryl$^b$ will be optionally substituted with 1, 2 or 3 substituents. Optional substituents are selected from those stated above. Examples of suitable aryl or aryl$^b$ groups include phenyl and naphthyl (each optionally substituted as stated above). Preferably aryl is selected from phenyl, substituted phenyl (wherein said substituents are selected from those stated above) and naphthyl.

As noted above, the term "heteroalkylene" is a bivalent linear saturated hydrocarbon having 2 to 5 carbon atoms ($C_2$-$C_5$), wherein at least one of the 2 to 5 carbon atoms is replaced with NR8, S, or O; heteroalkylene may optionally be substituted with 1 or 2 substituents independently selected from alkyl ($C_1$-$C_6$)alkoxy, OH, CN, $CF_3$, halo. More specifically, heteroalkylene can be a valent linear saturated hydrocarbon having 2 to 4 carbon atoms ($C_2$-$C_4$), wherein at least one of the 2 to 4 carbon atoms is replaced with NR8, S, or O, or having 2 to 3 carbon atoms ($C_2$-$C_3$), wherein at least one of the 2 to 3 carbon atoms is replaced with NR8, S, or O, each optionally substituted as noted above.

As noted above, the term "cycloalkyl" is a monocyclic saturated hydrocarbon ring of between 3 and 6 carbon atoms ($C_3$-$C_6$); cycloalkyl may optionally be substituted with 1 or 2 substituents independently selected from alkyl ($C_1$-$C_6$) alkoxy, OH, CN, $CF_3$, halo. Examples of suitable monocyclic cycloalkyl groups include cyclopropyl, cyclobutyl, cyclopentyl, and cyclohexyl), optionally substituted as noted above. More specifically, cycloalkyl can be a monocyclic saturated hydrocarbon ring of between 3 and 5 carbon atoms, more specifically, between 3 and 4 carbon atoms), optionally substituted as noted above.

As noted above, the term "alkoxy" is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1 or 2 substituents independently selected from OH, CN, $CF_3$, and fluoro. Examples of such alkoxy groups include, but are not limited to, $C_1$-methoxy, $C_2$-ethoxy, $C_3$-n-propoxy and $C_4$-n-butoxy for linear alkoxy, and $C_3$-iso-propoxy, and $C_4$-sec-butoxy and tert-butoxy for branched alkoxy, optionally substituted as noted above. More specifically, alkoxy can be linear groups of between 1 and 4 carbon atoms ($C_1$-$C_4$), more specifically, between 1 and 3 carbon atoms ($C_1$-$C_3$). More specifically, alkoxy can be branched groups of between 3 and 4 carbon atoms ($C_3$-$C_4$), optionally substituted as noted above.

Halo can be selected from Cl, F, Br and I. More specifically, halo can be selected from Cl and F.

As noted above, heteroaryl is a 5- or 6-membered carbon-containing aromatic ring containing one, two or three ring members that are selected from N, NR8, S, and O; heteroaryl may be optionally substituted with 1, 2 or 3 substituents independently selected from alkyl, alkoxy, OH, $OCF_3$, halo, CN, and $CF_3$. For example, heteroaryl can be selected from thiophene, furan, pyrrole, pyrazole, imidazole, oxazole, isoxazole, thiazole, isothiazole, triazole, oxadiazole, thiadiazole, pyridine, pyridazine, pyrimidine, and pyrazine, optionally substituted as noted above.

Heteroaryl$^a$ and heteroaryl$^b$ are as defined above. Typically, heteroaryl$^a$ or heteroaryl$^b$ will be optionally substituted with 1, 2 or 3 substituents. Optional substituents are selected from those stated above.

Examples of suitable heteroaryl$^a$ or heteroaryl$^b$ groups include thienyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above).

As noted above, "heterocycloalkyl" is a non-aromatic carbon-containing monocyclic ring containing 5, 6, or 7 ring members, wherein one or two ring members are independently selected from N, NR8, S, SO, SO2, and O. More specifically, "heterocycloalkyl" can be a non-aromatic carbon-containing monocyclic ring containing 5, 6, or 7 ring members, wherein one or two ring members are independently selected from N, NR8, and O, optionally substituted as noted above. More specifically, "heterocycloalkyl" can be a non-aromatic carbon-containing monocyclic ring containing 5, 6, or 7 ring members, wherein one or two ring members are independently selected from N or NR8.

As noted above, "heterocycloalkyl$^a$" is a non-aromatic carbon-containing monocyclic ring containing 3, 4, 5, or 6, ring members, wherein at least one ring member is independently selected from NR8, S, SO, $SO_2$, and O; heterocycloalkyl$^a$ may be optionally substituted with 1 or 2 substituents independently selected from alkyl ($C_1$-$C_6$)alkoxy, OH, CN, $CF_3$, halo. More specifically, "heterocycloalkyl$^a$" can be a non-aromatic carbon-containing monocyclic ring containing 3, 4, 5, or 6, ring members, wherein at least one ring member is independently selected from NR8, and O; heterocycloalkyl$^a$ may be optionally substituted with 1 or 2 substituents independently selected from alkyl ($C_1$-$C_6$) alkoxy, OH, CN, $CF_3$, halo.

The term "O-linked", such as in "O-linked hydrocarbon residue", means that the hydrocarbon residue is joined to the remainder of the molecule via an oxygen atom.

The term "N-linked", such as in "N-linked pyrrolidinyl", means that the heterocycloalkyl group is joined to the remainder of the molecule via a ring nitrogen atom.

In groups such as —$(CH_2)_{1-3}$-aryl, "-" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming prodrugs are described in 'The Practice of Medicinal Chemistry, $2^{nd}$ Ed. pp 561-585 (2003) and in F. J. Leinweber, *Drug Metab. Res.*, 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

Unless otherwise stated, the compounds of the invention include compounds that differ only in the presence of one or more isotopically enriched atoms. For example, compounds wherein hydrogen is replaced by deuterium or tritium, or wherein carbon is replaced by $^{13}C$ or $^{14}C$, are within the scope of the present invention. Such compounds are useful, for example, as analytical tools or probes in biological assays.

In the context of the present invention, references herein to "treatment" include references to curative, palliative and prophylactic treatment.

General Methods

The compounds of the invention may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Compounds of the invention intended for pharmaceutical use may be administered as a solid or liquid, such as a tablet, capsule or solution. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of the invention and a pharmaceutically acceptable carrier, diluent or excipient.

For the treatment of conditions such as retinal vascular permeability associated with diabetic retinopathy and diabetic macular edema, the compounds of the invention may be administered in a form suitable for injection into the ocular region of a patient, in particular, in a form suitable for intra-vitreal injection. It is envisaged that formulations suitable for such use will take the form of sterile solutions of a compound of the invention in a suitable aqueous vehicle. The compositions may be administered to the patient under the supervision of the attending physician.

The compounds of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, mannitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of the invention used in the preparation of parenteral solutions may be increased by the use of appropriate formulation techniques, such as the incorporation of co-solvents and/or solubility-enhancing agents such as surfactants, micelle structures and cyclodextrins.

The compounds of the invention can be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solids and liquids (including multiple phases or dispersed systems). Exemplary formulations suitable for oral administration include tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents, 2001, 11(6), 981-986.

The formulation of tablets is discussed in Pharmaceutical Dosage Forms: Tablets, Vol. 1, by H. Lieberman and L. Lachman (Marcel Dekker, New York, 1980).

For administration to human patients, the total daily dose of the compounds of the invention is typically in the range 0.1 mg and 10,000 mg, or between 1 mg and 5000 mg, or between 10 mg and 1000 mg depending, of course, on the mode of administration. If administered by intra-vitreal injection a lower dose of between 0.0001 mg (0.1 µg) and 0.2 mg (200 µg) per eye is envisaged, or between 0.0005 mg (0.5 µg) and 0.05 mg (50 µg) per eye.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The compounds of the present invention can be prepared according to the procedures of the following schemes and examples, using appropriate materials, and are further exemplified by the specific examples provided herein below. Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions, processes and order in which the synthetic steps are performed in the following preparative procedures can be used to prepare these compounds.

The compounds and intermediates of the invention may be isolated in the form of their pharmaceutically acceptable salts, such as those described previously herein above. The interconversion between free form and salt form would be readily known to those skilled in the art.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 4$^{th}$ Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvent. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr, or by stirring with borane tribromide in an organic solvent such as DCM. Alternatively where a hydroxy group is protected as a benzyl ether, deprotection conditions comprise hydrogenation with a palladium catalyst under a hydrogen atmosphere.

Examples of synthetic methods that may be used to prepare 4-carboxyimidazoles are described in EP 1426364 A1 ("Imidazole-derivatives as factor Xa inhibitors", p 27-28).

Examples of synthetic methods that may be used to prepare 4-carboxyoxazoles and 5-carboxyoxazoles are described in WO2018011628 ("Preparation of heterocyclic compounds for inhibiting plasma kallikrein").

Examples of synthetic methods that may be used to prepare 4-carboxypyrazoles are described in WO2012009009 ("Novel 2-amino-4-pyrazolyl-thiazole derivatives and their use as allosteric modulators of metabotropic glutamate receptors"); also U.S. Pat. No. 3,515,715 ("Quaternized pyrazolylazo dyes"); also WO2016083820 ("Preparation of N-((het)arylmethyl)heteroaryl-carboxamides compounds as plasma kallikrein inhibitors"); also WO2017103611 ("Preparation of pyrazole derivatives as kinase inhibitors"); also WO2014152738 ("Preparation of pyrazolyl-biphenyl compounds as LXR modulators")

The compounds according to general formula I can be prepared using conventional synthetic methods for example, but not limited to, the route outlined in Schemes 1a and 1b.

Scheme 1a

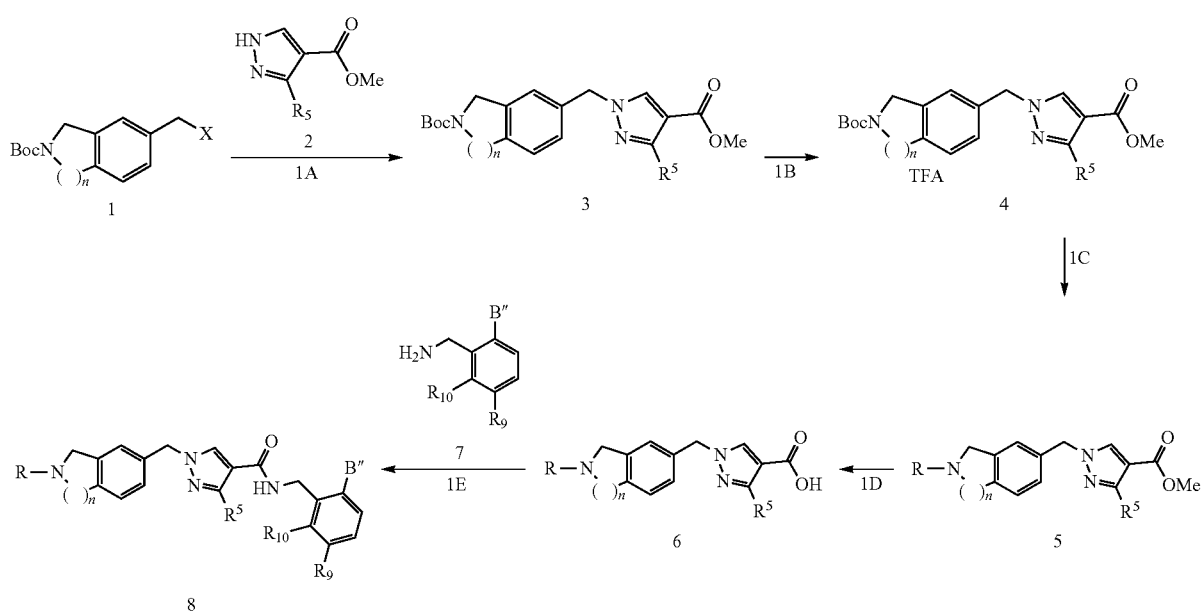

Scheme 1b

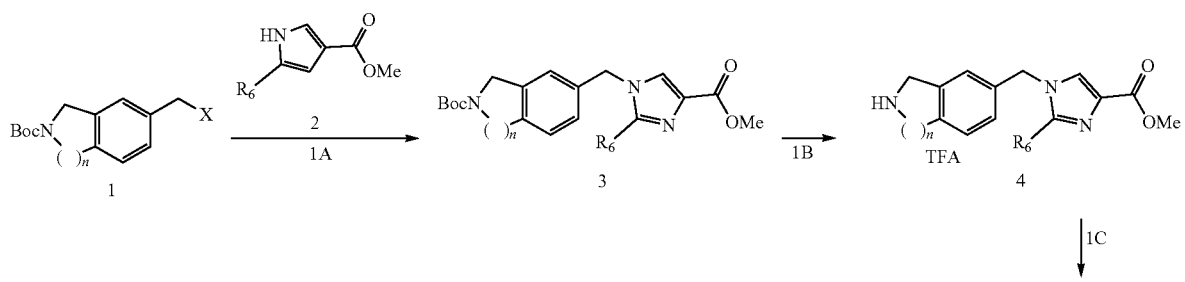

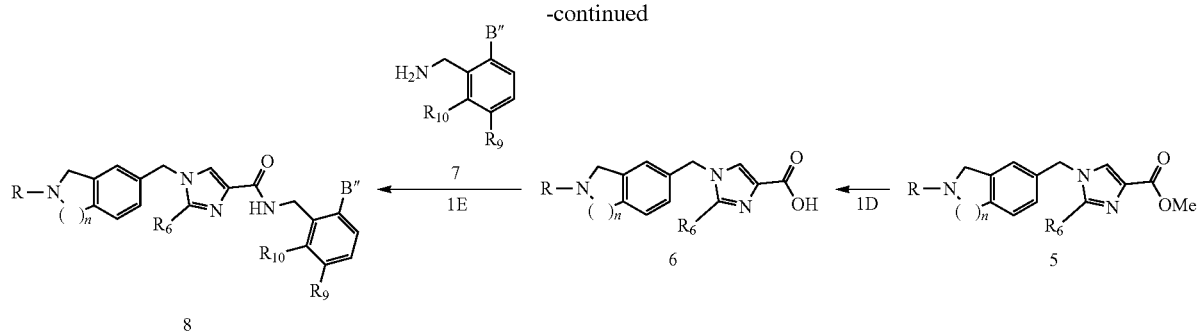

In both Schemes 1a and 1b, the halide 1 is reacted with a substituted heterocycle 2, for example substituted pyrazole as shown in Scheme 1a or substituted imidazole as shown in Scheme 1b, (Step 1A) typically using for example potassium carbonate or cesium carbonate to give ester 3, requiring separation of regioisomers confirming their identity by NOESY NMR. The Boc protecting group is removed (Step 1B) using acidic conditions such as trifluoroacetic acid to give amine 4. Typically this intermediate would be isolated in the form of the acid salt, for example the trifluoroacetate. Methylation of the amine (Step 1C) may be carried out using standard conditions for such a transformation. For example amine 4 is treated with formaldehyde (37% in water) followed by the addition of a reducing agent such as sodium triacetoxyborohydride to give compound 5. Alternative alkylations may be carried out by use of the appropriate alkanone, for example amine 4 is treated with the alkenone, for example acetone, in an organic solvent such as DCM followed by the addition of a reducing agent such as sodium triacetoxyborohydride to give compound 5. Alternative reducing agents include sodium borohydride and sodium cyanoborohydride. The ester is hydrolysed (Step 1D) using standard literature conditions such as NaOH, KOH, or LiOH. The acid (or salt) 6 is coupled to amine (or salt) 7 (Step 1E) to give compound 8. This coupling is typically carried out using standard coupling conditions such as hydroxybenzotriazole (HOBt) and carbodiimide such as water soluble carbodiimide in the presence of an organic base. Other standard coupling methods include the reaction of acids with amines in the presence of 2-(1H-benzotriazole-1-yl)-1,1,3,3-tetramethylaminium hexafluorophosphate (HBTU) or benzotriazole-1-yl-oxy-tris-pyrrolidino-phosphoium hexafluorophosphate (PyBOP) or bromo-trispyrolidino-phosphonium hexafluorophosphate (PyBroP) or 2-(3H-[1,2,3]triazolo[4,5-b]pyridin-3-yl)-1,1,3,3-tetramethylisouronium hexafluorophosphate(V) (HATU), or 1-ethyl-3-(3-dimethylaminopropyl)carbodiimide (EDC) in the presence of organic bases such as triethylamine, diisopropylethylamine or N-methylmorpholine. Alternatively, the amide formation can take place via an acid chloride in the presence of an organic base. Such acid chlorides can be formed by methods well known in the literature, for example reaction of the acid with oxalyl chloride or thionyl chloride. Alternatively, the carboxylic acid can be activated using 1,1'-carbonyldiimidazole (CDI) and then amine added.

The halide 1 in Scheme 1 above may be prepared from readily available starting materials using methods known in the art, for example as shown in Scheme 2.

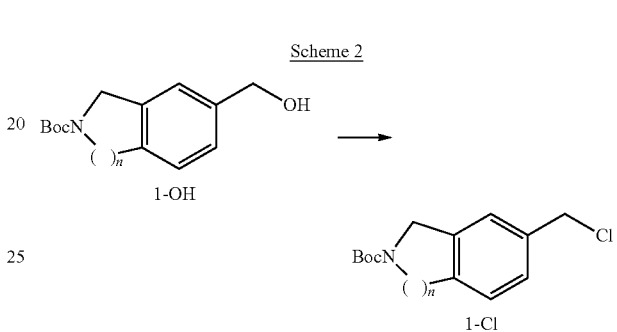

In Scheme 2 the alcohol 1-OH may be converted to the chloride 1-Cl. Methods for such transformations are known in the art, for example reaction with methanesulfonyl chloride in the presence of a base such as N,N-diisopropylethylamine (DIPEA) in a solvent such as dichloromethane. 4-Dimethylaminopyridine (DMAP) may be added.

Alternatively, Step A can be carried out via in situ sulfonyl transfer (see Jane Panteleev et al., "Alkylation of Nitrogen-Containing Heterocycles via In Situ Sulfonyl Transfer", *Synlett* 26(08)), as shown in Scheme 3.

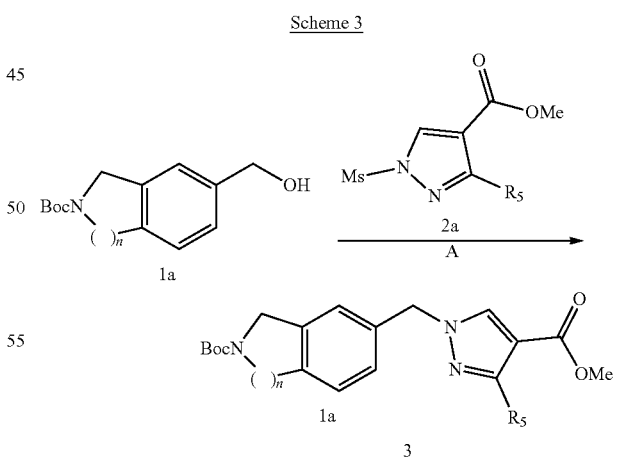

The pyrazole mesylate 2a is prepared by treating pyrazole 2 with methanesulfanyl chloride (MsCl) with a base such as triethylamine in a solvent such as dichloromethane. The pyrazole mesylate 2a may then be coupled to the alcohol 1a in the presence of a base such as caesium carbonate in a solvent such as acetonitrile, typically heating to reflux.

The compounds according to general formula I can thus be prepared using conventional synthetic methods for example, but not limited to, the route outlined in Scheme 4.

Scheme 4

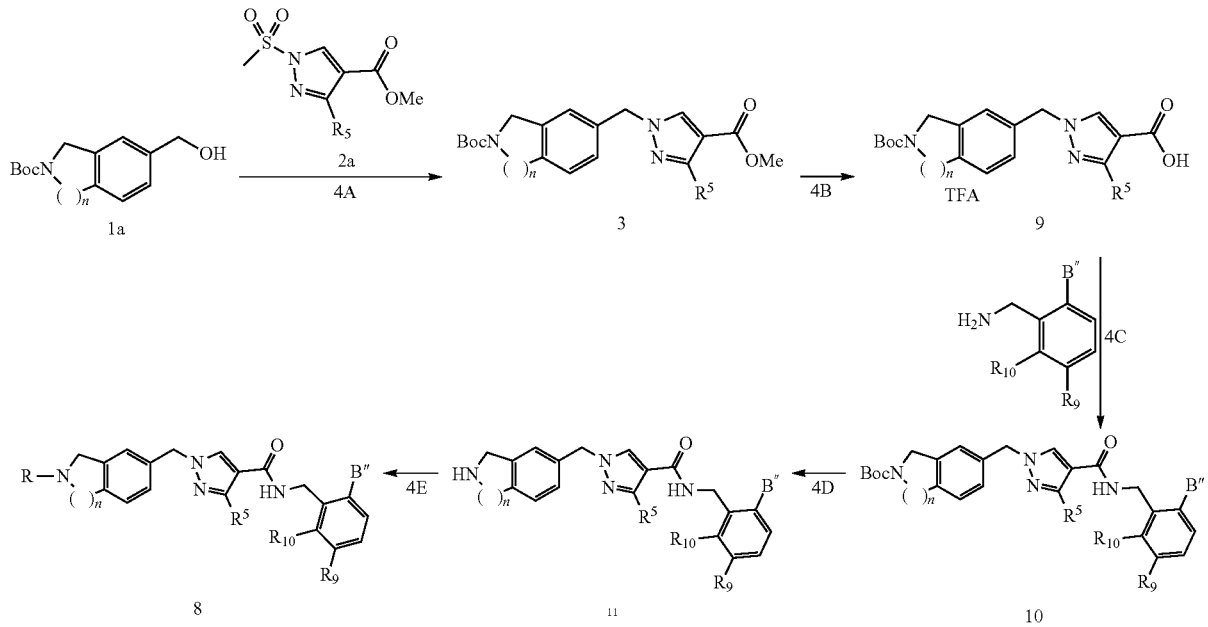

The alcohol 1a is reacted with substituted pyrazole mesylate 2a (Step 4A) in the presence of a base such as caesium carbonate in a solvent such as acetonitrile, typically heating to reflux to give ester 3, requiring separation of regioisomers confirming their identity by NOESY NMR. The ester is hydrolysed (Step 4B) using standard literature conditions such as NaOH, KOH, or LiOH. The acid (or salt) 9 is coupled to amine 7 (or salt) (Step 4C) to give compound 10. This coupling is typically carried out using standard coupling conditions such as hydroxybenzotriazole (HOBt) and carbodiimide such as water soluble carbodiimide in the presence of an organic base. Other standard coupling methods include the reaction of acids with amines in the presence of 2-(1H-benzotriazole-1-yl)-1,1,3,3-tetramethylaminium hexafluorophosphate (HBTU) or benzotriazole-1-yl-oxy-tris-pyrrolidino-phosphoium hexafluorophosphate (PyBOP) or bromo-trispyrolidino-phosphonium hexafluorophosphate (PyBroP) or 2-(3H-[1,2,3]triazolo[4,5-b]pyridin-3-yl)-1,1,3,3-tetramethylisouronium hexafluorophosphate(V) (HATU), in the presence of organic bases such as triethylamine, diisopropylethylamine or N-methylmorpholine. Alternatively, the amide formation can take place via an acid chloride in the presence of an organic base. Such acid chlorides can be formed by methods well known in the literature, for example reaction of the acid with oxalyl chloride or thionyl chloride. Alternatively, the carboxylic acid can be activated using 1,1'-carbonyldiimidazole (CDI) and then amine added. The Boc protecting group is removed (Step 4D) using acidic conditions such as trifluoroacetic acid or hydrogen chloride to give amine 11. Typically this intermediate would be isolated in the form of the acid salt, for example the trifluoroacetate or the hydrochloride. Alkylation of the amine 11 (Step 4E) may be carried out using standard conditions for such a transformation, for example reductive alkylation. For example, amine 11 is treated with formaldehyde (37% in water) followed by the addition of a reducing agent such as sodium triacetoxyborohydride to give compound 8. Alternative alkylations may be carried out by use of the appropriate alkanone, for example amine 11 is treated with the alkenone, for example acetone, in an organic solvent such as DCM followed by the addition of a reducing agent such as sodium triacetoxyborohydride to give compound 8. Alternative reducing agents include sodium borohydride and sodium cyanoborohydride.

EXAMPLES

The invention is illustrated by the following non-limiting examples in which the following abbreviations and definitions are used:

| | |
|---|---|
| aq | Aqueous solution |
| AIBN | Azobisisobutyronitrile |
| tBu | Tert-Butyl |
| CDI | 1,1'-Carbonyldiimidazole |
| DCM | Dichloromethane |
| DIPEA | N,N-Diisopropylethylamine |
| DMF | N,N-Dimethylformamide |
| DMSO | Dimethyl sulfoxide |
| eq | Equivalent |
| Et$_2$O | Diethyl ether |
| Et | Ethyl |
| EtOH | Ethanol |
| EtOAc | Ethyl Acetate |
| HATU | 2-(3H-[1,2,3]triazolo[4,5-b]pyridin-3-yl)-1,1,3,3-tetramethylisouronium hexafluorophosphate(V) |
| hrs | Hours |
| HOBt | Hydroxybenzotriazole |
| LCMS | Liquid chromatography mass spectrometry |
| Me | Methyl |
| MeCN | Acetonitrile |
| MsCl | Methanesulfonyl chloride |
| MeOH | Methanol |
| min | Minutes |
| MS | Mass spectrum |
| Ms | Methanesulfonyl |

| | |
|---|---|
| NMR | Nuclear magnetic resonance spectrum |
| NMP | N-Methyl-2-pyrrolidone |
| Pet. Ether | Petroleum ether fraction boiling at 60-80° C. |
| Ph | Phenyl |
| iPr | Iso-propyl |
| nPr | n-Propyl |
| SWFI | Sterile water for injection |
| rt | room temperature |
| TBDMS | tert-Butyldimethylsilyl |
| TBME | tert-Butyl methyl ether |
| THF | Tetrahydrofuran |
| TEA | Triethylamine |
| TFA | Trifluoroacetic acid |

All reactions were carried out under an atmosphere of nitrogen unless specified otherwise.

$^1$H NMR spectra were recorded on a Bruker (500 MHz or 400 MHz) spectrometer and reported as chemical shift (ppm).

Molecular ions were obtained using LCMS with appropriate conditions selected from Chromolith Speedrod RP-18e column, 50×4.6 mm, with a linear gradient 10% to 90% 0.1% HCO$_2$H/MeCN into 0.1% HCO$_2$H/H$_2$O over 13 min, flow rate 1.5 mL/min;

Agilent, X-Select, acidic, 5-95% MeCN/water over 4 min. Data was collected using a Thermofinnigan Surveyor MSQ mass spectrometer with electrospray ionisation in conjunction with a Thermofinnigan Surveyor LC system;

LCMS (Waters Acquity UPLC, C18, Waters X-Bridge UPLC C18, 1.7 μm, 2.1×30 mm, Basic (0.1% Ammonium Bicarbonate) 3 min method;

LCMS (Agilent, X-Select, Waters X-Select C18, 2.5 μm, 4.6×30 mm, Acidic 4 min method, 95-5 MeCN/water);

LCMS (Agilent, Basic, Waters X-Bridge C18, 2.5 μm, 4.6×30 mm, Basic 4 min method, 5-95 MeCN/water;

Acquity UPLC BEH C18 1.7 μM column, 50×2.1 mm, with a linear gradient 10% to 90% 0.1% HCO2H/MeCN into 0.1% HCO2H/H2O over 3 minutes, flow rate 1 mL/min. Data was collected using a Waters Acquity UPLC mass spectrometer with quadropole dalton, photodiode array and electrospray ionisation detectors.

Flash chromatography was typically carried out over 'silica' (silica gel for chromatography, 0.035 to 0.070 mm (220 to 440 mesh) (e.g. Merck silica gel 60)), and an applied pressure of nitrogen up to 10 p.s.i accelerated column elution. Alternatively, pre-prepared cartridges of silica gel were used. Reverse phase preparative HPLC purifications were carried out using a Waters 2525 binary gradient pumping system at flow rates of typically 20 mL/min using a Waters 2996 photodiode array detector.

All solvents and commercial reagents were used as received.

Chemical names were generated using automated software such as ChemDraw (PerkinElmer) or the Autonom software provided as part of the ISIS Draw package from MDL Information Systems or the Chemaxon software provided as a component of MarvinSketch or as a component of the IDBS E-WorkBook.

Synthesis of Intermediates

Ethyl (Z)-3-(dimethylamino)-2-(1-methoxycyclopropane-1-carbonyl)acrylate

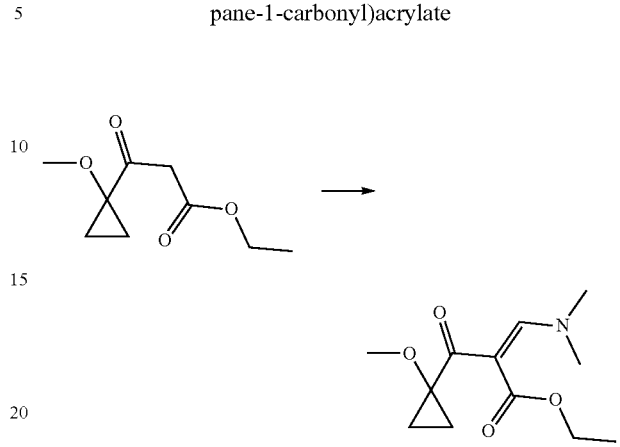

To ethyl 3-(1-methoxycyclopropyl)-3-oxopropanoate (reported in WO2015022073) (2.25 g, 11.4 mmol) was added 1,1-dimethoxy-N,N-dimethyl-methanamine (2.3 mL, 17.3 mmol) and stirred at rt for 72 hrs. The mixture was concentrated in vacuo to afford the title compound (2.95 g, quantitative).

Ethyl 3-(1-methoxycyclopropyl)-1H-pyrazole-4-carboxylate

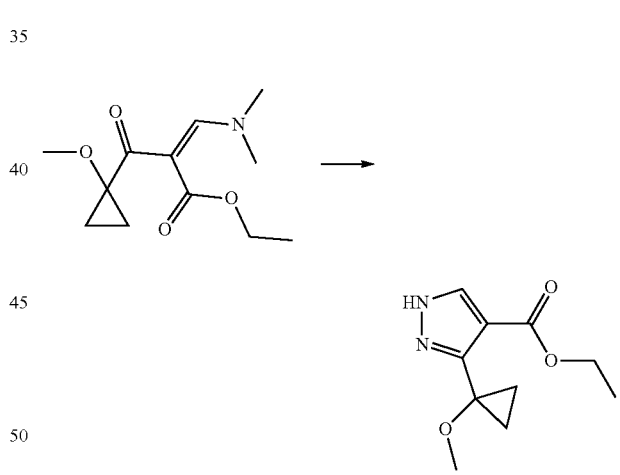

To a solution of ethyl (Z)-3-(dimethylamino)-2-(1-methoxycyclopropane-1-carbonyl)acrylate (2.95 g, 11.4 mmol) in EtOH (20 mL) was added hydrazine hydrate (50-60%, 1.2 mL) and the mixture heated at reflux for 2 hrs. The mixture was concentrated in vacuo and the residue purified by flash chromatography (0-100% EtOAc in isohexanes) to afford the title compound (2.01 g, 80%) as a white solid.

[M+H]$^+$=211.1

$^1$H NMR (DMSO-d6) 0.95 (2H, s), 1.07 (2H, s), 1.26 (3H, t, J=7.1 Hz), 3.07 (3H, s), 4.19 (2H, q, J=7.1 Hz), 7.97 (1H, s), 13.45 (1H, s)

Tert-Butyl 7-((5-(methoxycarbonyl)pyridin-3-yl)methyl)-3,4-dihydroisoquinoline-2(1H)-carboxylate

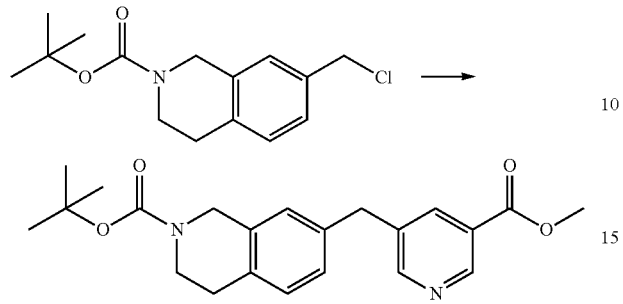

A mixture of methyl 5-(4,4,5-trimethyl-1,3,2-dioxaborolan-2-yl)pyridine-3-carboxylate (115 mg, 0.46 mmol), tert-butyl 7-(chloromethyl)-3,4-dihydro-1H-isoquinoline-2-carboxylate (100 mg, 0.36 mmol), K$_2$CO$_3$ (98 mg, 0.71 mmol), 1,4-dioxane (1.5 mL) and water (0.5 mL) were combined and degassed briefly with N$_2$. Tetrakis(triphenylphosphine)palladium (0) (41 mg, 0.04 mmol) was added and the mixture degassed with N$_2$ again and heated to 90° C. for 60 min. The mixture was cooled and stored in a freezer overnight. The mixture was partitioned between EtOAc (20 mL) and saturated NaHCO$_3$(aq) (15 mL). The aqueous layer was extracted with EtOAc and the combined organic layers washed with brine, dried over MgSO$_4$ and concentrated in vacuo to afford the title compound which was used without further purification.

5-((2-(tert-Butoxy carbonyl)-1,2,3,4-tetrahydroisoquinolin-7-yl)methyl) nicotinic Acid

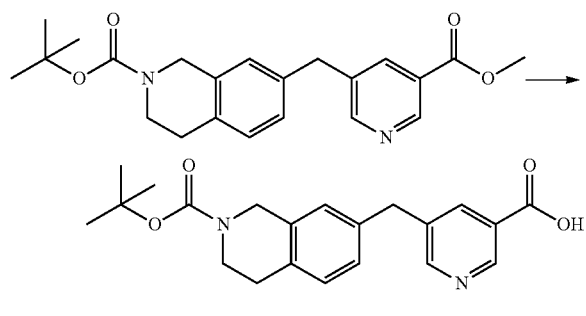

A solution of lithium hydroxide (12 mg, 0.50 mmol) in water (2 mL) was added to a mixture of tert-butyl 7-[(5-methoxycarbonyl-3-pyridyl)methyl]-3,4-dihydro-1H-isoquinoline-2-carboxylate (190 mg, 0.34 mmol) in THF (2 mL) and MeOH (4 mL) and stirred at 50° C. for 20 hrs. The mixture was concentrated in vacuo and the residue azeotroped with toluene. The residue was treated with 1M HCl(aq) (0.75 mL) and again azeotroped with toluene to afford the title compound (200 mg) that was used without further purification.

Tert-Butyl 7-((5-((2-fluoro-3-methoxy-6-(4-methyl-1H-1,2,3-triazol-1-yl)benzyl)carbamoyl)pyridin-3-yl)methyl)-3,4-dihydroisoquinoline-2(1H)-carboxylate

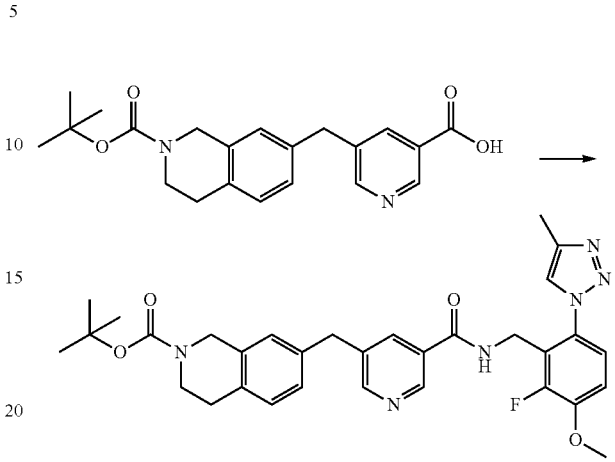

DIPEA (215 mg, 1.66 mmol) was added to a solution of (2-fluoro-3-methoxy-6-(4-methyl-1H-1,2,3-triazol-1-yl)phenyl)methanamine hydrochloride (97.8 mg, 0.36 mmol), HATU (136 mg, 0.36 mmol) and 5-((2-(tert-butoxycarbonyl)-1,2,3,4-tetrahydroisoquinolin-7-yl)methyl)nicotinic acid (200 mg, 0.33 mmol) in DCM (2 mL) and NMP (2 mL) and stirred for 20 hrs. The mixture was diluted with EtOAc (30 mL), washed with water and brine, dried over MgSO$_4$ and concentrated in vacuo. Flash chromatography (30 to 100% EtOAc/isohexanes and then 0-30% MeOH/EtOAc) afforded the title compound (120 mg, 62%) as a colourless oil.

$^1$H NMR (DMSO-d6) 1.42 (9H, s), 2.25 (3H, s), 2.72 (2H, t, J=6.0 Hz), 3.52 (2H, t, J=5.8 Hz), 3.92 (3H, s), 3.95 (2H, s), 4.35 (2H, d, J=4.8 Hz), 4.45 (2H, s), 7.03-7.11 (3H, m), 7.24-7.35 (2H, m), 7.87 (1H, t, J=2.2 Hz), 8.13 (1H, s), 8.60 (1H, d, J=2.1 Hz), 8.67 (1H, d, J=2.1 Hz), 8.77 (1H, t, J=4.9 Hz).

Tert-Butyl 5-(azidomethyl)isoindoline-2-carboxylate

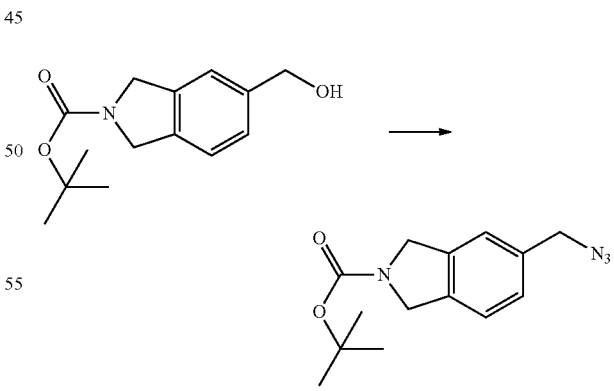

To a solution of tert-butyl 5-(hydroxymethyl)-2,3-dihydro-1H-isoindole-2-carboxylate (0.5 g, 2.0 mmol) in toluene (8 mL) and 1,4-dioxane (8 mL) was added diphenyl phosphorylazide (0.85 mL, 3.9 mmol) and 2,3,4,6,7,8,9,10-octahydropyrimido[1,2-a]azepine (0.95 mL, 6.4 mmol) whilst cooling in an ice/water bath. The mixture was allowed to warm to rt and stirred overnight. The mixture was partitioned between EtOAc and water and the aqueous layer extracted with EtOAc. The combined organic layers were dried over MgSO₄ and concentrated in vacuo. Flash chromatography (0-40% EtOAc in hexane) afforded the title compound which was used without further purification.

(M-tBu+H)⁺=219.1

Tert-Butyl 5-[(4-methoxycarbonyltriazol-1-yl)methyl]isoindoline-2-carboxylate

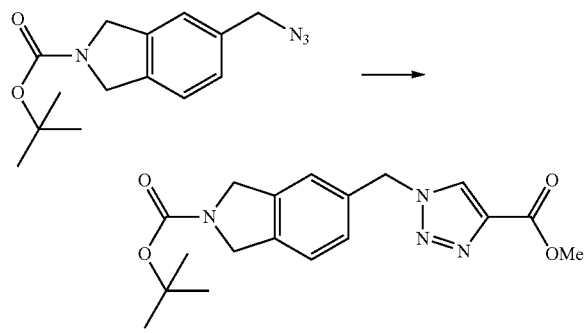

To a solution of tert-butyl 5-(azidomethyl)isoindoline-2-carboxylate (550 mg, 2.0 mmol) in DCM (6 mL) was added methyl prop-2-ynoate (0.2 mL, 2.3 mmol), water (2 mL), CuSO₄.H₂O (20 mg) and sodium ascorbate (45 mg). The mixture was stirred overnight, separated and the aqueous phase extracted with DCM. The combined organic layers were washed with brine, dried over MgSO₄ and concentrated in vacuo. Flash chromatography (0-30% EtOAc in hexane) afforded the title compound (284 mg, 39%). Regiochemistry was confirmed by ROSEY NMR experiment.

¹H NMR (DMSO-d6) 1.45 (9H, s), 3.83 (3H, s), 4.56 (4H, d, J=11.7 Hz), 5.66 (2H, s), 7.27-7.37 (3H, m), 8.88 (1H, d, J=3.6 Hz)

Methyl 1-(isoindolin-5-ylmethyl)triazole-4-carboxylate hydrochloride

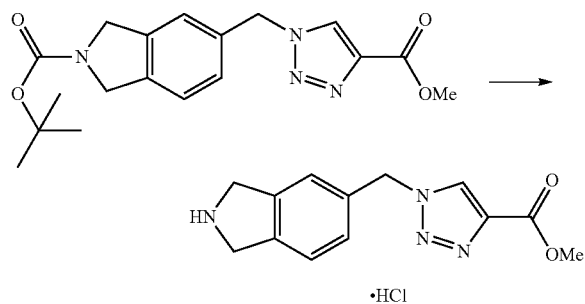

tert-Butyl 5-[(4-methoxycarbonyltriazol-1-yl)methyl]isoindoline-2-carboxylate (284 mg, 0.79 mmol) was added to a mixture of 4M HCl in dioxane (4 mL) and water (4 mL) and stirred for 36 hrs. The mixture was reduced in vacuo to afford the title compound (233 mg, 99%) and used without further purification.

Methyl 1-[(2-isopropylisoindolin-5-yl)methyl]triazole-4-carboxylate

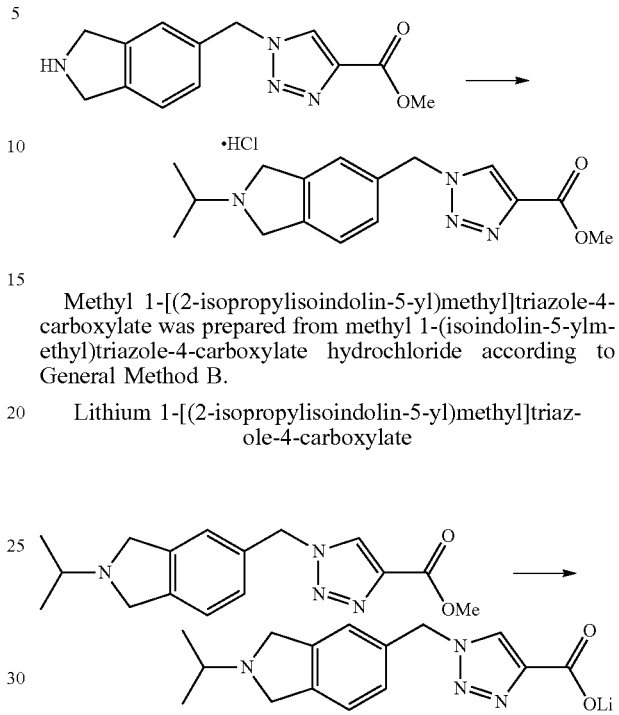

Methyl 1-[(2-isopropylisoindolin-5-yl)methyl]triazole-4-carboxylate was prepared from methyl 1-(isoindolin-5-ylmethyl)triazole-4-carboxylate hydrochloride according to General Method B.

Lithium 1-[(2-isopropylisoindolin-5-yl)methyl]triazole-4-carboxylate

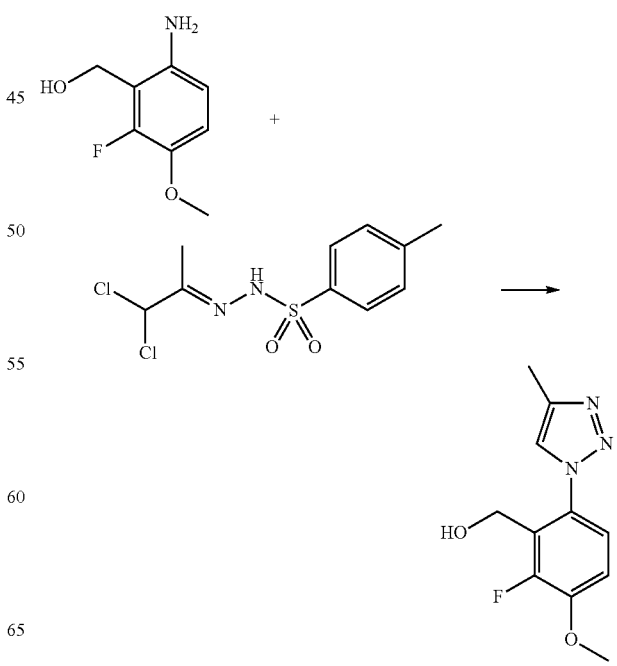

Lithium 1-[(2-isopropylisoindolin-5-yl)methyl]triazole-4-carboxylate was prepared from methyl 1-[(2-isopropylisoindolin-5-yl)methyl]triazole-4-carboxylate according to procedure L5a.

[2-Fluoro-3-methoxy-6-(4-methyl-1H-1,2,3-triazol-1-yl)phenyl]methanol (R1a)

To a solution of (6-amino-2-fluoro-3-methoxyphenyl)methanol (300 mg, 1.45 mmol) and DIPEA (560 mg, 4.34 mmol) in EtOH (30 mL) at 0° C. was added α,α-dichloroacetone p-toluenesulfonylhydrazone (555 mg, 1.88 mmol) and the reaction mixture stirred at rt for 18 hrs. The solvent was removed in vacuo and the residue dissolved in EtOAc (100 mL), was washed with water (30 mL), brine (30 mL), dried over Na₂SO₄ and evaporated in vacuo. Flash chromatography (2% MeOH, 98% CHCl₃) afforded a white solid identified as the title compound (340 mg, 99%).

[M+H]⁺=238.2

1-[2-(Bromomethyl)-3-fluoro-4-methoxyphenyl]-4-methyl-1H-1,2,3-triazole (R2a)

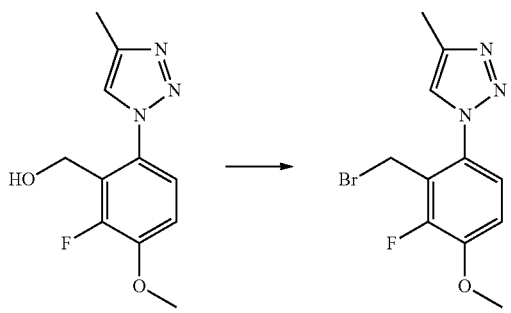 [SMILES: COc1ccc(-n2cc(C)nn2)c(CO)c1F ; COc1ccc(-n2cc(C)nn2)c(CBr)c1F]

[2-Fluoro-3-methoxy-6-(4-methyl-1H-1,2,3-triazol-1-yl)phenyl]methanol (340 mg, 1.43 mmol) was dissolved in DCM (50 mL). To this solution was added phosphorous tribromide (776 mg, 2.87 mmol). The reaction mixture was stirred at rt for 18 hrs and diluted with CHCl₃ (100 mL) the filtrate was washed with saturated NaHCO₃(aq), water, brine, dried over Na₂SO₄ and concentrated in vacuo to give the title compound as white solid (430 mg, 100%).

[M+H]⁺=302.8

2-{[2-Fluoro-3-methoxy-6-(4-methyl-1H-1,2,3-triazol-1-yl)phenyl]methyl}-2,3-dihydro-1H-isoindole-1,3-dione (R3a)

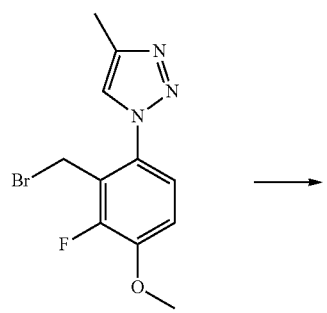

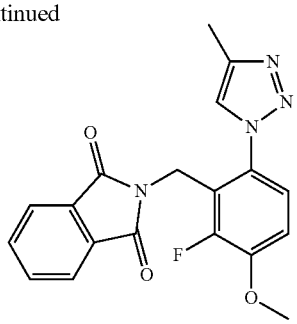

Potassium phthalimide (291 mg, 1.58 mmol) was added to a solution of 1-[2-(bromomethyl)-3-fluoro-4-methoxyphenyl]-4-methyl-1H-1,2,3-triazole (430 mg, 1.43 mmol) in DMF (20 mL). The mixture was stirred at 50° C. for 18 hrs. The mixture was diluted with EtOAc (50 mL), washed with water, brine and dried over Na₂SO₄ and concentrated in vacuo. Flash chromatography (2% MeOH, 98% CHCl₃) afforded the title compound as an orange solid (225 mg, 64%).

[M+H]⁺=367.2

(2-Fluoro-3-methoxy-6-(4-methyl-1H-1,2,3-triazol-1-yl)phenyl)methanamine (R4a)

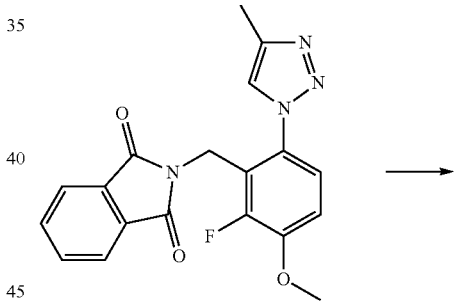

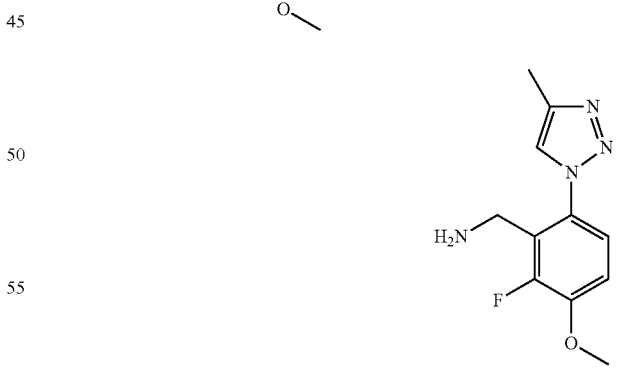

A solution of 2-{[2-fluoro-3-methoxy-6-(4-methyl-1H-1,2,3-triazol-1-yl)phenyl]methyl}-2,3-dihydro-1H-isoindole-1,3-dione (220 mg, 0.60 mmol) and hydrazine hydrate (50-60% solution, 0.35 mL) in EtOH (50 mL) was stirred at 80° C. for 60 min and for a further 18 hrs at rt. The resulting solid was filtered off, washed with EtOH and discarded. The filtrate was reduced in vacuo and the residue triturated with EtOAc, filtered off and discarded. The EtOAc filtrate was reduced in vacuo to give the title compound as a yellow oil (130 mg, 92%).

(2-Fluoro-6-iodo-3-methoxyphenyl)methanol (R1b)

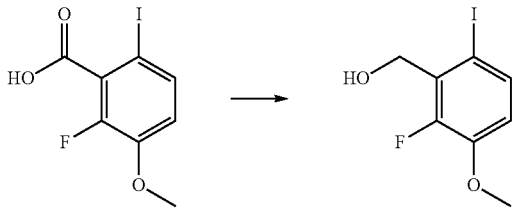

To a solution of 2-fluoro-6-iodo-3-methoxy-benzoic acid (10.0 g, 33.6 mmol) in THF was added 4-methyl morpholine (3.9 mL, 36 mmol) and isobutyl chloroformate (4.4 mL, 34 mmol) dropwise. After 60 min the reaction was filtered and washed with a minimum amount of THF. The filtrate was cooled in an ice-bath and a solution of sodium borohydride (2.0 g, 59 mmol) in cold water (3 mL) was added portion-wise over 20 min. The resulting solution was stirred at rt for 18 hrs. The reaction was acidified with 1M HCl and extracted with TBME. The organic layer was washed sequentially with 2M NaOH(aq), 1M HCl(aq) and brine and dried over MgSO$_4$ and concentrated in vacuo. Flash chromatography (0-40% EtOAc in Hexanes) afforded the title compound (4.9 g, 49% yield).

[2-Fluoro-3-methoxy-6-(1,2,4-triazol-1-yl)phenyl]methanol (R2b)

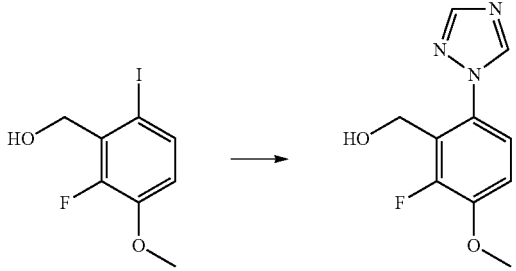 [SMILES: COc1ccc(I)c(CO)c1F ; COc1ccc(-n2cncn2)c(CO)c1F]

A mixture of (2-fluoro-6-iodo-3-methoxy-phenyl)methanol (2.0 g, 7.1 mmol), 1H-1,2,4-triazole (1.0 g, 14 mmol), (1S,2S)-N1,N2-dimethylcyclohexane-1,2-diamine (1.5 g, 11 mmol) and copper(I) iodide (96 mg, 0.50 mmol) was dissolved in DMF (12 mL) then treated with caesium carbonate (3.47 g, 10.7 mmol) and degassed with N$_2$, then heated at 120° C. for 60 min. The mixture was diluted with DCM (50 mL) and concentrated. Flash chromatography (0 to 50% MeCN/DCM) afforded the title compound (1.2 g, 58% yield).

[M+H]$^+$=223.9

1-[2-(Chloromethyl)-3-fluoro-4-methoxy-phenyl]-1,2,4-triazole (R3b)

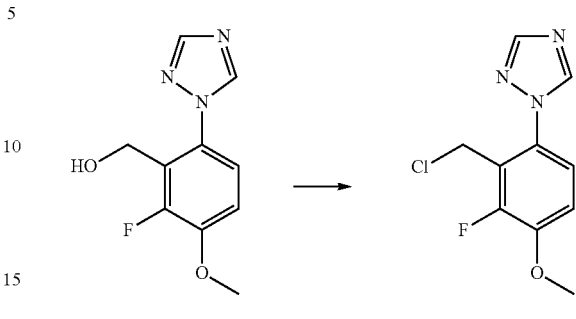

A stirred solution of [2-fluoro-3-methoxy-6-(1,2,4-triazol-1-yl)phenyl]methanol (909 mg, 4.07 mmol) in DCM (25 mL) was treated with TEA (0.91 mL, 6.5 mmol) and cooled in an ice-bath under N$_2$. Methanesulfonyl chloride (0.45 mL, 5.8 mmol) was added slowly then the ice-bath removed and the mixture allowed to warm to rt and stirred for 2 days. The mixture was diluted with DCM (20 mL) and partitioned over saturated NaHCO$_3$(aq). The aqueous layer was extracted with further DCM. The combined organics were washed with brine (30 mL), dried (Na$_2$SO$_4$) and concentrated in vacuo to afford the title compound as a viscous yellow oil (1.0 g, 96% yield).

[M+H]$^+$=241.9/243.9

2-[[2-Fluoro-3-methoxy-6-(1,2,4-triazol-1-yl)phenyl]methyl]isoindoline-1,3-dione (R4b)

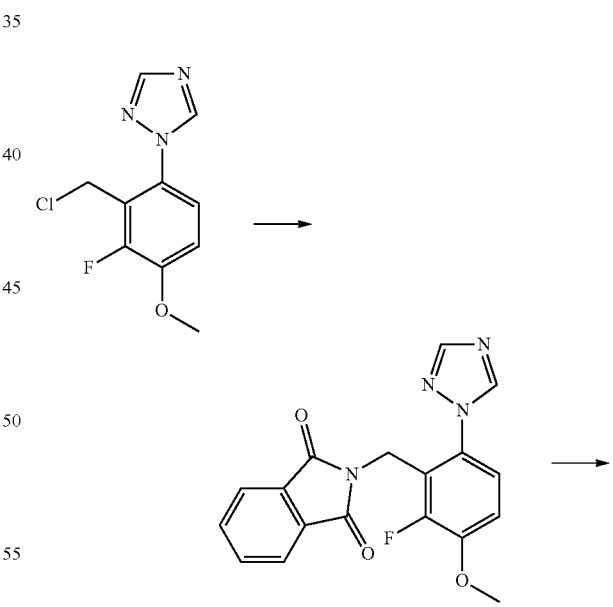

Potassium phthalimide (0.868 g, 4.69 mmol) was added to a solution of 1-[2-(chloromethyl)-3-fluoro-4-methoxy-phenyl]-1,2,4-triazole (1.03 g, 4.26 mmol) in DMF (10 mL) and the mixture warmed to 55° C. for 60 min. Water (30 mL) was added to form a thick precipitate which was filtered, washed with water and dried in vacuo in the presence of CaCl$_2$ to afford the title compound (1.12 g, 74% yield) as a white solid.

[M+H]$^+$=352.9

[2-Fluoro-3-methoxy-6-(1,2,4-triazol-1-yl)phenyl]methanamine (R5b)

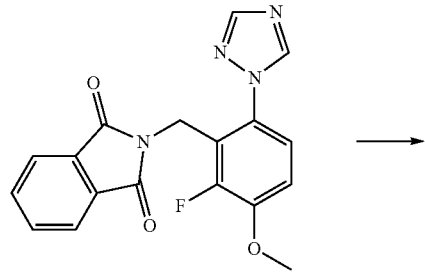

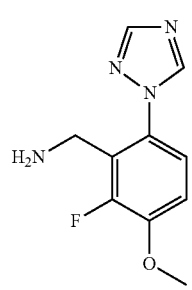

Hydrazine hydrate (50-60% solution, 0.24 mL) was added to a suspension of 2-[[2-fluoro-3-methoxy-6-(1,2,4-triazol-1-yl)phenyl]methyl]isoindoline-1,3-dione (1.12 g, 3.18 mmol) in MeOH (15 mL) and the reaction mixture heated to 70° C. for 3 hrs. Further hydrazine hydrate (50-60% solution, 0.2 mL) was added and the mixture heated at 70° C. for 60 min, then at rt overnight. The mixture was filtered and the filtrate concentrated in vacuo. The residue was taken up in TBME (40 mL) and sonicated. DCM (10 mL) was added and the mixture worked to a suspension with stirring and sonication. This was filtered and the filtrate concentrated in vacuo then dried in vacuo overnight to afford the title compound (563 mg, 72% yield) as a pale yellow solid.

$[M+H]^+=223.0$

Methyl 2-fluoro-3-methoxy-6-(3-methyl-1,2,4-triazol-1-yl)benzoate (R1c)

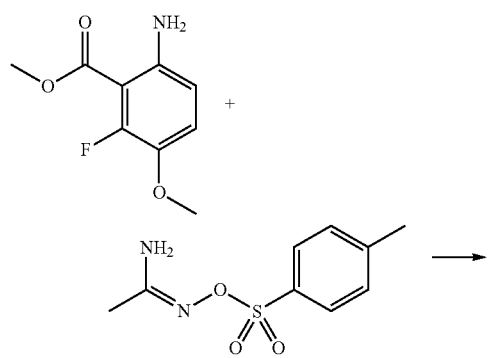

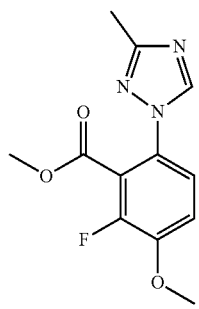

To a stirred solution of methyl 6-amino-2-fluoro-3-methoxy-benzoate (607 mg, 3.05 mmol) and N'-(tosyloxy)-acetimidamide (833 mg, 3.65 mmol) (prepared for example according to procedures in EP0795551) in THF (15 mL) was added triethylorthoformate (1.0 mL, 6.0 mmol) followed by ethanesulfonic acid (249 µL, 3.05 mmol). The mixture was sonicated then heated to 60° C. for 2 hrs. The reaction was cooled and concentrated in vacuo. Saturated $Na_2CO_3$(aq) and DCM were added to the residue and the mixture stirred vigorously for 15 min. The organic phase was isolated via hydrophobic frit and concentrated in vacuo. Flash chromatography (0-100% EtOAc in hexanes) afforded the title compound (597 mg, 72%) as a pale orange oil.

[2-Fluoro-3-methoxy-6-(3-methyl-1,2,4-triazol-1-yl)phenyl]methanol (R2c)

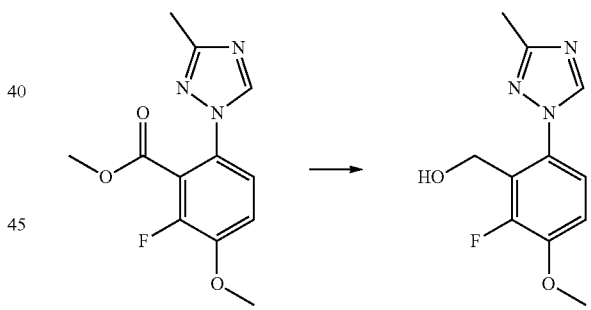

To a stirred solution of methyl 2-fluoro-3-methoxy-6-(3-methyl-1,2,4-triazol-1-yl)benzoate (619 mg, 2.33 mmol) in DCM (20 mL) at −78° C. was added diisobutylaluminium hydride (1M in DCM, 5.1 mL, 5.1 mmol) dropwise over 30 min. The solution was warmed to rt and stirred for 2 hrs. Additional diisobutylaluminium hydride (1M in DCM, 0.7 mL, 0.7 mmol) was added slowly and the reaction stirred for 18 hrs. The reaction was quenched with water (0.6 mL), 15% NaOH(aq) (0.6 mL) and further water (1.2 mL) and the mixture stirred for 30 min. The mixture was filtered through Celite rinsing with DCM. The filtrate was dried using a hydrophobic frit and concentrated in vacuo. Flash chromatography (50-100% EtOAc in hexanes) afforded the title compound as a white solid (390 mg, 68%).

$[M+H]^+=237.9$

1-[2-(Bromomethyl)-3-fluoro-4-methoxy-phenyl]-3-methyl-1,2,4-triazole (R3c)

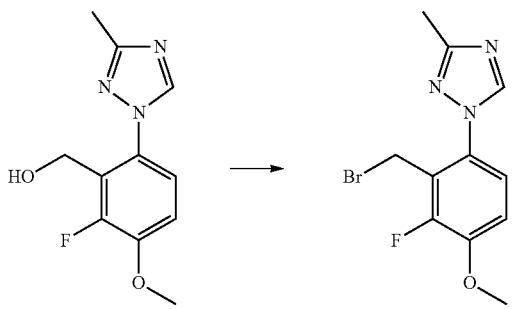 [SMILES: COc1ccc(-n2cnc(C)n2)c(CO)c1F ; COc1ccc(-n2cnc(C)n2)c(CBr)c1F]

To a stirred solution of [2-fluoro-3-methoxy-6-(3-methyl-1,2,4-triazol-1-yl)phenyl]methanol in DCM (5 mL) at 0° C. was added phosphorous tribromide (78 µL, 0.83 mmol). The resulting mixture was warmed to rt and stirred for 2 hrs. NaHCO$_3$(aq) (15 mL) was added and extracted with EtOAc. The combined organics were washed with brine (10 mL), dried over MgSO$_4$, filtered and concentrated in vacuo. Flash chromatography (50-100% EtOAc in hexanes) afforded the title compound as a white solid (96 mg, 19%).
[M+H]$^+$=299.8/301.8 tert-Butyl N-tert-butoxycarbonyl-N-[[2-fluoro-3-methoxy-6-(3-methyl-1,2,4-triazol-1-yl)phenyl]methyl]carbamate (R4c)

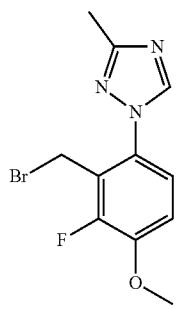

To a stirred solution of tert-butyl N-tert-butoxycarbonyl-carbamate (77 mg, 0.35 mmol) in MeCN (1 mL) was added potassium tert-butoxide (40 mg, 0.36 mmol) and the mixture stirred for 10 min. A solution of 1-[2-(bromomethyl)-3-fluoro-4-methoxy-phenyl]-3-methyl-1,2,4-triazole (96 mg, 0.32 mmol) in MeCN (3 mL) was added to the mixture and the reaction stirred for 18 hrs. Water was added and the mixture extracted with EtOAc (2×10 mL). The combined organic phase was washed with brine (5 mL), dried using a hydrophobic frit and concentrated in vacuo. Flash chromatography (0-100% EtOAc in hexanes) afforded the title compound as a white solid (100 mg, 70% yield).
[M+Na]$^+$=458.9

(2-Fluoro-3-methoxy-6-(3-methyl-1H-1,2,4-triazol-1-yl)phenyl)methanamine (R5c)

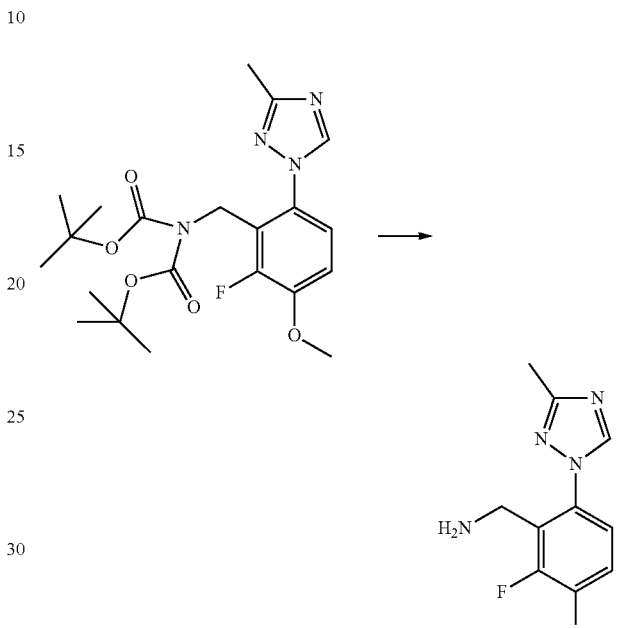

A solution of tert-butyl N-tert-butoxycarbonyl-N-[[2-fluoro-3-methoxy-6-(3-methyl-1,2,4-triazol-1-yl)phenyl]methyl]carbamate (100 mg, 0.23 mmol), in 4M HCl in dioxane (2 mL, 8 mmol) was stirred at rt for 2 hrs. The reaction was concentrated in vacuo to afford the title compound as the hydrochloride salt as a white solid.

tert-Butyl-[[2-fluoro-3-methoxy-6-(3-methyl-1,2,4-triazol-1-yl)phenyl]methoxy]-dimethyl-silane (R1d)

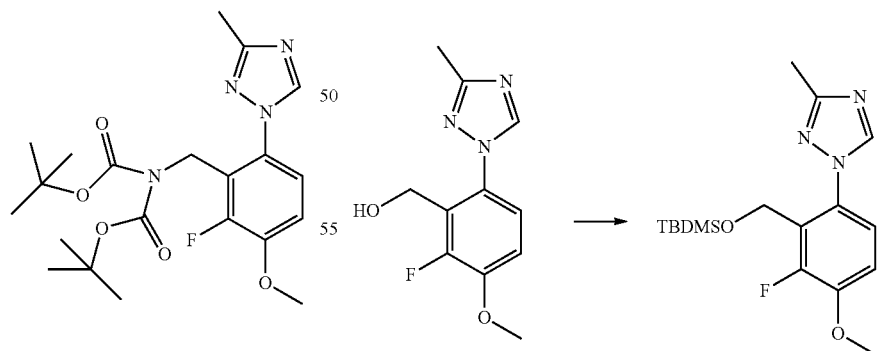

To a stirred solution of [2-fluoro-3-methoxy-6-(3-methyl-1,2,4-triazol-1-yl)phenyl]methanol (483 mg, 2.04 mmol) in DCM (15 mL) and DMF (1.5 mL) was added imidazole (209 mg, 3.08 mmol) followed by tert-butyldimethylsilyl chloride (326 mg, 2.16 mmol). The mixture was stirred at rt overnight then diluted with DCM (20 ml) and water (15 ml). The organic phase was washed with saturated NH₄Cl(aq) and brine, then dried via a hydrophobic frit and concentrated in vacuo. Flash chromatography (0-70% EtOAc in hexane) afforded the title compound (640 mg, 89% yield) as a clear, colourless oil which solidified to a white solid on standing.
[M+H]⁺=352.0

1-(2-(((tert-Butyldimethyl silyl)oxy)methyl)-3-fluoro-4-methoxyphenyl)-3,5-dimethyl-1H-1,2,4-triazole (R2d)

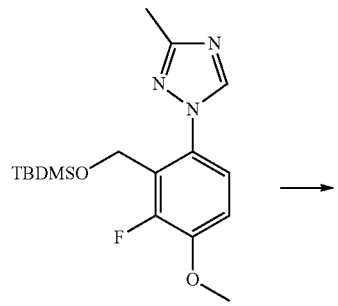

To a stirred solution of tert-butyl-[[2-fluoro-3-methoxy-6-(3-methyl-1,2,4-triazol-1-yl)phenyl]-methoxy]-dimethyl-silane (440 mg, 1.25 mmol) in THF (7 mL), whilst cooling in a cold bath at −78° C., was added n-butyl lithium (2.5M in hexane) (851 µL, 2.13 mmol) drop-wise and the reaction stirred for 30 min. Iodomethane (101 µL, 1.63 mmol) was added and the mixture allowed to warm to rt. Stirring was continued for 2 hrs. Saturated NH₄Cl(aq) was added and extracted with EtOAc. The organics were washed with brine, dried via hydrophobic frit and concentrated in vacuo. Flash chromatography (30-90% EtOAc in hexane) afforded the title compound (366 mg, 71% yield) as a yellow oil.
[M+H]⁺=366.0

(6-(3,5-Dimethyl-1H-1,2,4-triazol-1-yl)-2-fluoro-3-methoxyphenyl)methanol (R3d)

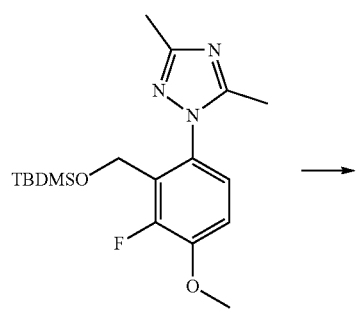

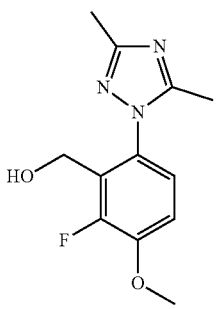

To a stirred solution of 1-(2-(((tert-butyldimethylsilyl)oxy)methyl)-3-fluoro-4-methoxyphenyl)-3,5-dimethyl-1H-1,2,4-triazole (484 mg, 1.18 mmol) in THF (6 mL) was added HCl (4M in dioxane) (1.3 mL, 5.2 mmol). The mixture was stirred at rt for 3 days. The mixture was concentrated in vacuo, triturated with TBME and filtered. The solid was washed with TBME and dried in vacuo to afford the title compound (275 mg, 93% yield) as a brown solid.
[M+H]⁺=251.9

(6-(3,5-Dimethyl-1H-1,2,4-triazol-1-yl)-2-fluoro-3-methoxyphenyl)methanamine (R4d)

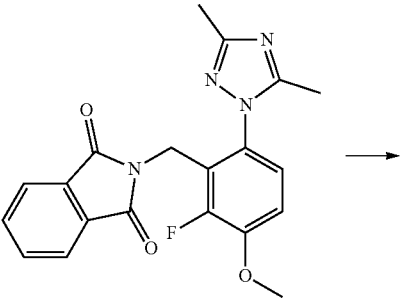

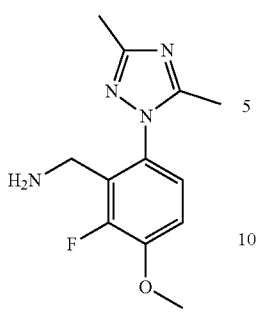

Starting with (6-(3,5-dimethyl-1H-1,2,4-triazol-1-yl)-2-fluoro-3-methoxyphenyl)methanol the title compound was synthesised using the methods described for the preparations of 1-[2-(chloromethyl)-3-fluoro-4-methoxy-phenyl]-1,2,4-triazole (R3b), 2-[[2-fluoro-3-methoxy-6-(1,2,4-triazol-1-yl)phenyl]methyl]isoindoline-1,3-dione (R4b) and [2-fluoro-3-methoxy-6-(1,2,4-triazol-1-yl)phenyl]methanamine (R5b).
[M+H]$^+$=251.2

(2-Fluoro-3-methoxy-6-(5-methyl-1H-1,2,4-triazol-1-yl)phenyl)methanamine (R1e)

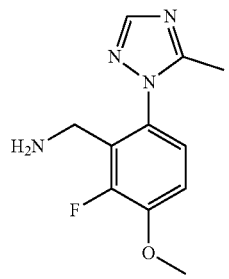 [SMILES: COc1ccc(-n2ncnc2C)c(CN)c1F]

Starting with [2-fluoro-3-methoxy-6-(1,2,4-triazol-1-yl)phenyl]methanol the title compound was synthesised using the methods described for the preparation of (6-(3,5-dimethyl-1H-1,2,4-triazol-1-yl)-2-fluoro-3-methoxyphenyl)methanamine (R4d).
[M+H]$^+$=237.0

[2-Fluoro-3-methoxy-6-[3-(trifluoromethyl)-1,2,4-triazol-1-yl]phenyl]methanamine (R1f)

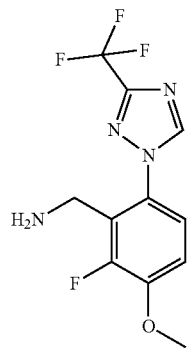 [SMILES: COc1ccc(-n2cnc(C(F)(F)F)n2)c(CN)c1F]

Starting with 3-(trifluoromethyl)-1H-1,2,4-triazole the title compound was prepared using methods described for the synthesis of [2-fluoro-3-methoxy-6-(1,2,4-triazol-1-yl)phenyl]methanamine (R5b).

[2-Fluoro-3-methoxy-6-[3-(difluoromethyl)-1,2,4-triazol-1-yl]phenyl]methanamine (R1g)

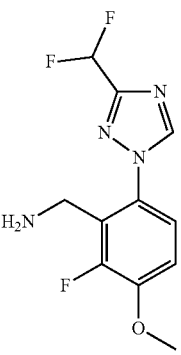 [SMILES: COc1ccc(-n2cnc(C(F)F)n2)c(CN)c1F]

Starting with 3-(difluoromethyl)-1H-1,2,4-triazole the title compound was prepared using methods described for the synthesis of [2-fluoro-3-methoxy-6-(1,2,4-triazol-1-yl)phenyl]methanamine (R5b).
[M+H]$^+$=256.1

(2-Fluoro-3-methoxy-6-(3-ethyl-1H-1,2,4-triazol-1-yl)phenyl)methanamine (R1h)

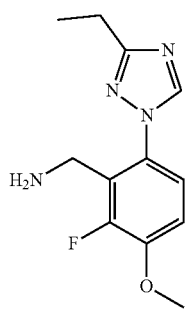 [SMILES: CCc1ncn(-c2ccc(OC)c(F)c2CN)n1]

Starting with N'-(tosyloxy)-propanimidamide (prepared for example according to analogous procedures in European Patent Application no. 97301695.9 (published as EP0795551A1) the title compound was prepared using methods described for the synthesis of (2-fluoro-3-methoxy-6-(3-methyl-1H-1,2,4-triazol-1-yl)phenyl)methanamine (R5c).
[M+H]$^+$=251.0

[2-Fluoro-3-methoxy-6-[3-(trifluoromethyl)pyrazol-1-yl]phenyl]methanamine (R1i)

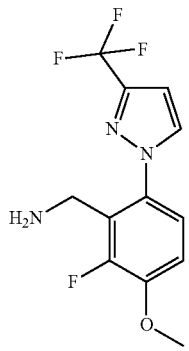 [SMILES: COc1ccc(-n2ccc(C(F)(F)F)n2)c(CN)c1F]

Starting with 3-(trifluoromethyl)-1H-pyrazole the title compound was prepared using methods described for the synthesis of [2-fluoro-3-methoxy-6-(1,2,4-triazol-1-yl)phenyl]methanamine (R5b).
[M+H]$^+$=289.9

[6-(3-Cyclopropylpyrazol-1-yl)-2-fluoro-3-methoxyphenyl]methanamine (R1j)

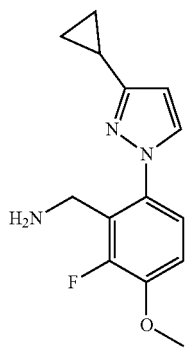 [SMILES: COc1ccc(-n2ccc(C3CC3)n2)c(CN)c1F]

Starting with 3-cyclopropyl-1H-pyrazole the title compound was prepared using methods described for the synthesis of [2-fluoro-3-methoxy-6-(1,2,4-triazol-1-yl)phenyl]methanamine (R5b).
[M+H]$^+$=262.0

[6-(3-Cyanopyrazol-1-yl)-2-fluoro-3-methoxyphenyl]methanamine (R1k)

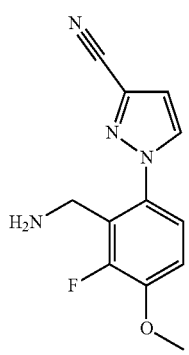 [SMILES: COc1ccc(-n2ccc(C#N)n2)c(CN)c1F]

Starting with 1H-pyrazole-3-carbonitrile the title compound was prepared using methods described for the synthesis of [2-fluoro-3-methoxy-6-(1,2,4-triazol-1-yl)phenyl]methanamine (R5b).
[M+H]$^+$=247.0

[6-(4-Cyanopyrazol-1-yl)-2-fluoro-3-methoxyphenyl]methanamine (R1o)

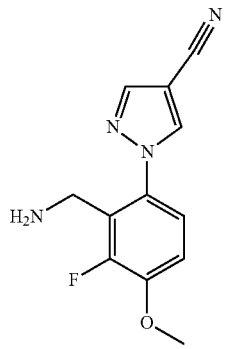 [SMILES: COc1ccc(-n2cc(C#N)cn2)c(CN)c1F]

Starting with 1H-pyrazole-4-carbonitrile the title compound was prepared using methods described for the synthesis of [2-fluoro-3-methoxy-6-(1,2,4-triazol-1-yl)phenyl]methanamine (R5b).

Ethyl 6-bromo-2-fluoro-3-methoxy-benzoate (R1l)

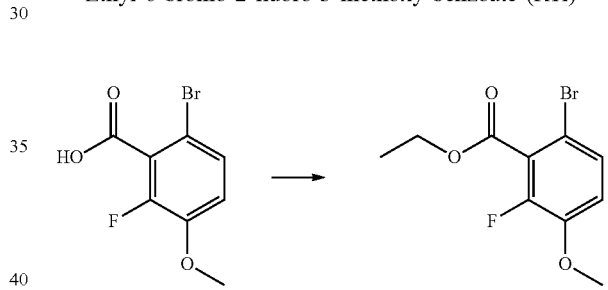

6-Bromo-2-fluoro-3-methoxy-benzoic acid (30.5 g, 123 mmol) was dissolved in MeCN (500 mL). Caesium carbonate (47.9 g, 147 mmol) was added followed by dropwise addition of iodoethane (15.2 mL, 189 mmol). The mixture was stirred at rt for 3 days. The mixture was filtered through Celite, washed with MeCN and concentrated in vacuo. The residue was separated between Et$_2$O (500 mL) and a brine-water mixture (1:2 brine:water, 750 mL). The aqueous phase was extracted with Et$_2$O (250 mL). The combined organics were dried over Na$_2$SO$_4$ and concentrated in vacuo to afford the title compound as an orange oil that solidified on standing (26.8 g, 79% yield).

Ethyl 6-((tert-butoxycarbonyl)amino)-2-fluoro-3-methoxybenzoate (R2l)

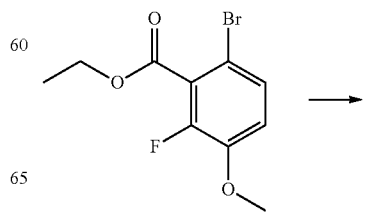

-continued

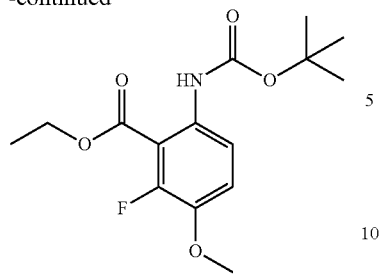

Ethyl 6-bromo-2-fluoro-3-methoxy-benzoate (10 g, 36 mmol) was dissolved in dioxane (250 mL). tert-Butyl carbamate (4.65 g, 39.7 mmol), 4,5-(bis(diphenylphospheno)-9,9-dimethylxanthene (2.09 g, 3.6 mmol), palladium (II) acetate (810 mg, 3.61 mmol) and caesium carbonate (23.5 g, 72.1 mmol) were added and the mixture was stirred for 18 hrs at 100° C. The mixture was cooled, diluted with EtOAc (250 mL) and filtered through Celite washing with EtOAc (150 mL). The combined filtrates were concentrated in vacuo. Flash chromatography (10% EtOAc, 90% Pet. Ether) afforded the title compound as a colourless oil that solidified on standing (8.45 g, 75% yield).

Ethyl 6-amino-2-fluoro-3-methoxybenzoate (R3l)

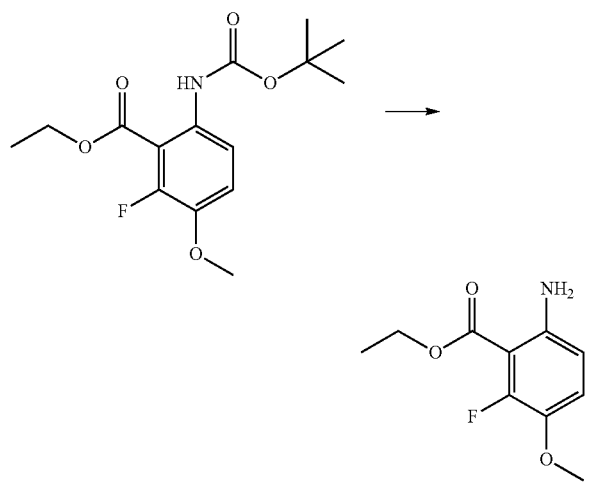

To ethyl 6-((tert-butoxycarbonyl)amino)-2-fluoro-3-methoxybenzoate (3.99 g, 12.7 mmol) was added 4M HCl in dioxane (50 mL) and the mixture stirred at rt for 6 hrs. The mixture was concentrated in vacuo to afford the HCl salt of the title compound as a beige solid. The solid was dissolved in MeOH and passed over polymer supported carbonate and reduced in vacuo to afford the free base of the title compound as an orange/brown oil (2.83 g, 89% yield).

Ethyl 2-fluoro-6-(4-(hydroxymethyl)-1H-1,2,3-triazol-1-yl)-3-methoxybenzoate (R4l)

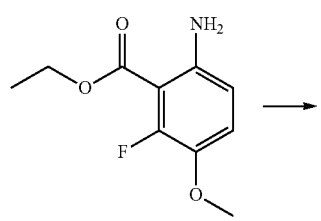

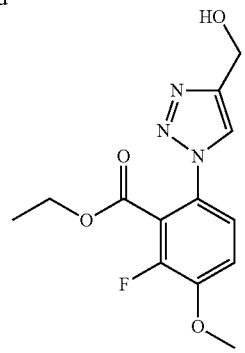

To ethyl 6-amino-2-fluoro-3-methoxybenzoate (500 mg, 2.35 mmol) in MeCN (50 mL) was added 3-methylbutyl nitrite (472 µL, 3.52 mmol) whilst cooling in an ice/water bath. Trimethylsilyl azide (467 µL, 3.52 mmol) was added dropwise. After 10 min the ice/water bath was removed and the mixture allowed to warm to rt and stirred for 3 hrs. The mixture was cooled in an ice/water bath and a further charge of 3-methylbutyl nitrite (100 µL, 0.74 mmol) and trimethylsilyl azide (100 µL, 0.75 mmol) added. The mixture was stirred at rt for 60 min. The mixture was concentrated in vacuo and the residue taken up in EtOAc, washed with water and brine, dried over MgSO4 and concentrated in vacuo to afford the intermediate azide.

1,4-Dioxane (50 mL) was added to the reaction flask containing the intermediate azide which was wrapped in foil to protect the reaction from light exposure. Propargyl alcohol (410 µL, 7.04 mmol), CuI (22 mg, 0.12 mmol) and sodium ascorbate (92 mg, 0.47 mmol) were added and the reaction heated at 80° C. overnight. A further charge of CuI (22 mg, 0.12 mmol) and sodium ascorbate (92 mg, 0.47 mmol) were added and heating continued at 80° C. for 24 hrs. The mixture was partitioned between EtOAc and saturated NH$_4$Cl(aq) and the layers separated. The organic layer was washed with brine, dried over Na$_2$SO$_4$ and concentrated. Flash chromatography (EtOAc/Pet. Ether) afforded the title compound as a beige solid (280 mg, 40%).

[M+H]$^+$=318.2

Ethyl 2-fluoro-6-(4-formyl-1H-1,2,3-triazol-1-yl)-3-methoxybenzoate (R5l)

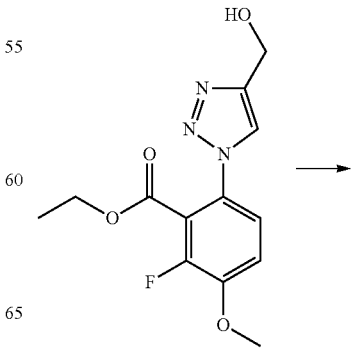

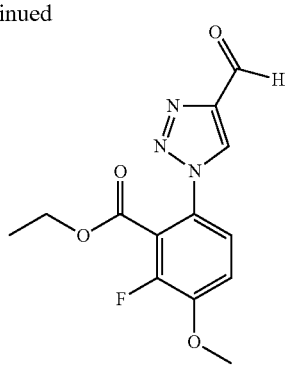

A solution of ethyl 2-fluoro-6-(4-(hydroxymethyl)-1H-1,2,3-triazol-1-yl)-3-methoxybenzoate (225 mg, 0.76 mmol) in EtOAc (75 mL) was treated with 2-iodoxybenzoic acid (1.42 g, 2.29 mmol) and stirred at vigorous reflux for 4 hrs. Additional 2-iodoxybenzoic acid (50 mg) was added and heating continued for a further 60 min. The mixture was cooled to rt and filtered through Celite, washing with EtOAc. The filtrates were concentrated in vacuo and flash chromatography (EtOAc/Pet. Ether) afforded the title compound as an off white solid, (223 mg, 100%).
[2M+H]$^+$=587.1

Ethyl 6-(4-(difluoromethyl)-1H-1,2,3-triazol-1-yl)-2-fluoro-3-methoxybenzoate (R6l)

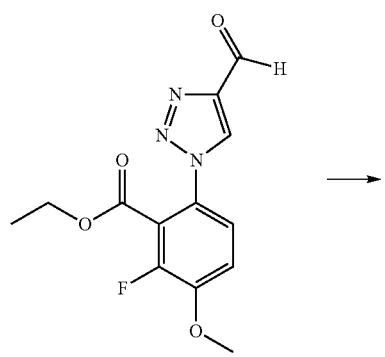

To ethyl 2-fluoro-6-(4-formyl-1H-1,2,3-triazol-1-yl)-3-methoxybenzoate (238 mg, 0.81 mmol) in DCM (5 mL) was added diethylaminosulfur trifluoride (161 μL, 1.22 mmol) and the mixture stirred at rt for 18 hrs. The mixture was poured into 20 mL of an iced solution of NaHCO$_3$(aq) and extracted with DCM. The organic phases were combined and washed with water and brine and dried over MgSO$_4$ and concentrated in vacuo. Flash chromatography (EtOAc/Pet. Ether) afforded the title compound as a pale yellow oil which solidified on standing (178 mg, 70%).

(6-(4-(Difluoromethyl)-1H-1,2,3-triazol-1-yl)-2-fluoro-3-methoxyphenyl)methanol (R7l)

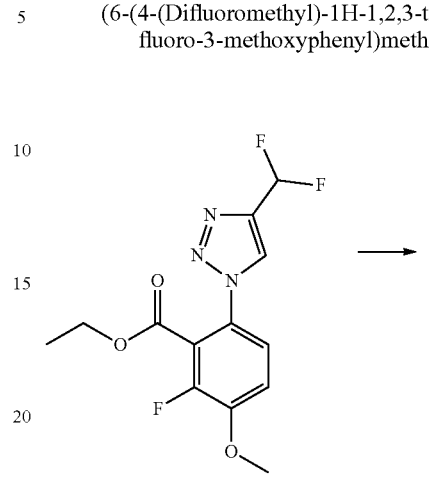

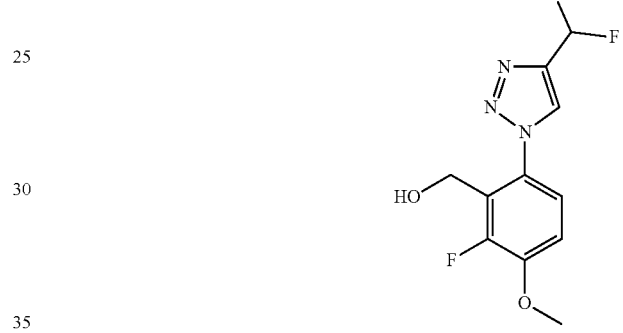

To a stirred solution of ethyl 6-(4-(difluoromethyl)-1H-1,2,3-triazol-1-yl)-2-fluoro-3-methoxybenzoate (228 mg, 0.72 mmol) in THF (15 mL) was added LiBH$_4$ (32 mg, 1.4 mmol) while cooling in an ice/water bath. The reaction was allowed to warm to 20° C., diluted with water (75 mL) and extracted with EtOAc. The combined organic phases were dried over MgSO$_4$ and concentrated in vacuo. Flash chromatography (Pet. Ether/EtOAc) afforded the title compound as a white crystalline solid (182 mg, 92%).
[M+H]$^+$=274.1

1-(2-(Bromomethyl)-3-fluoro-4-methoxyphenyl)-4-(difluoromethyl)-1H-1,2,3-triazole (R8l)

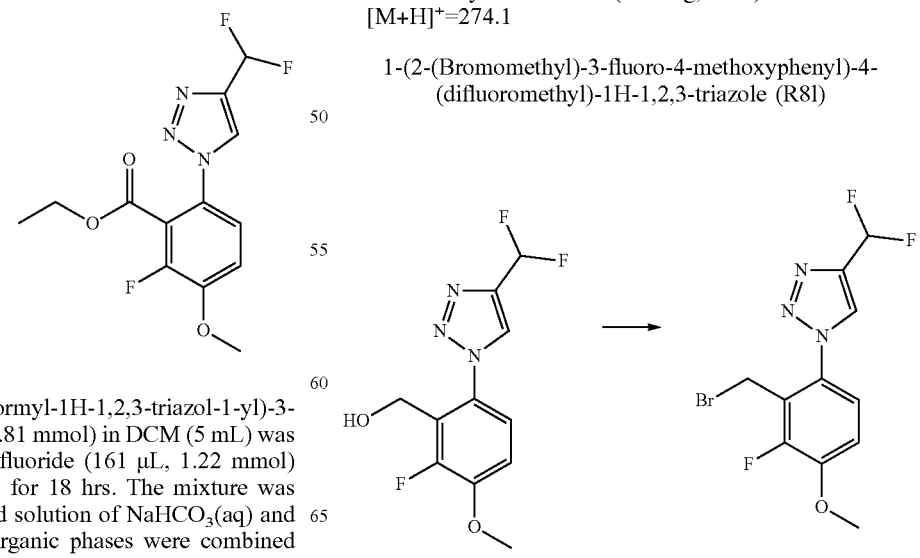

Starting with (6-(4-(difluoromethyl)-1H-1,2,3-triazol-1-yl)-2-fluoro-3-methoxyphenyl)methanol the title compound was prepared using methods described for the synthesis of 1-[2-(bromomethyl)-3-fluoro-4-methoxyphenyl]-4-methyl-1H-1,2,3-triazole (R2a).
[M+H]⁺=337.9

2-(6-(4-(Difluoromethyl)-1H-1,2,3-triazol-1-yl)-2-fluoro-3-methoxybenzyl)isoindoline-1,3-dione (R9l)

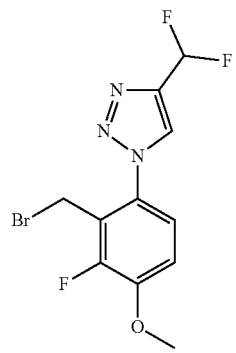

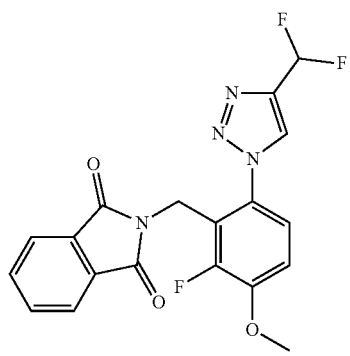

Starting with 1-(2-(bromomethyl)-3-fluoro-4-methoxyphenyl)-4-(difluoromethyl)-1H-1,2,3-triazole the title compound was prepared using methods described for the synthesis of 2-{[2-fluoro-3-methoxy-6-(4-methyl-1H-1,2,3-triazol-1-yl)phenyl]methyl}-2,3-dihydro-1H-isoindole-1,3-dione (R3a)
[M+H]⁺=403.0

(6-(4-(Difluoromethyl)-1H-1,2,3-triazol-1-yl)-2-fluoro-3-methoxyphenyl)methanamine (R10l)

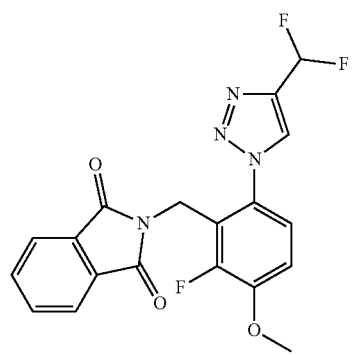

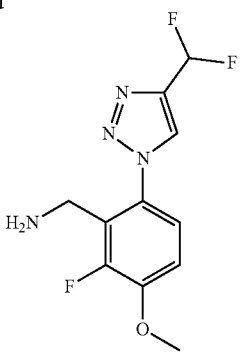

Starting with 2-(6-(4-(difluoromethyl)-1H-1,2,3-triazol-1-yl)-2-fluoro-3-methoxybenzyl)isoindoline-1,3-dione the title compound was prepared using methods described for the synthesis of [2-fluoro-3-methoxy-6-(1,2,4-triazol-1-yl)phenyl]methanamine (R5b).
[M+H]⁺=273.1

3-Chloro-2-fluoro-6-iodo-benzoic acid (R1m)

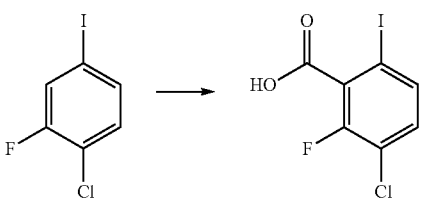 [SMILES: Fc1cc(I)ccc1Cl ; O=C(O)c1c(I)ccc(Cl)c1F]

1-Chloro-2-fluoro-4-iodo-benzene (5 g, 20 mmol) was dissolved in THF (40 mL) and cooled in a cold bath at −78° C. Lithium diisopropylamide (21 mmol in THF (10 mL)) was added dropwise to the mixture over 30 min and then the reaction stirred for 60 min. Solid CO₂ (35 g) was crushed and added to the mixture. The mixture was stirred and allowed to warm to rt overnight. The reaction was concentrated in vacuo, 1M NaOH(aq) was added and washed with TBME. The aqueous phase was acidified with 6M HCl(aq) to pH 1 and extracted with EtOAc. The EtOAc extracts were washed with brine, dried over MgSO₄ and concentrated in vacuo to afford the title compound as an off-white solid (4.8 g, 82%).

3-Chloro-6-[3-(difluoromethyl)-1,2,4-triazol-1-yl]-2-fluoro-benzoic Acid (R2m)

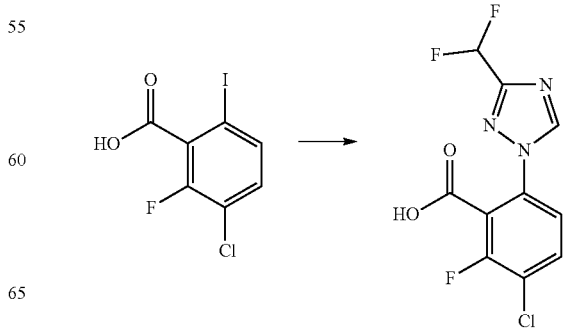

3-Chloro-2-fluoro-6-iodo-benzoic acid (1.8 g, 5.99 mmol) was added to a degassed mixture of (1S,2S)-N1,N2-dimethylcyclohexane-1,2-diamine (682 mg, 4.79 mmol), copper(I) iodide (79.5 mg, 0.417 mmol), 3-(difluoromethyl)-1H-1,2,4-triazole (1.43 g, 12 mmol) and caesium carbonate (2.93 g, 8.99 mmol) in anhydrous DMSO (27 mL) and heated to 40° C. for 18 hrs. Saturated NaHCO$_3$(aq) was added and the mixture washed with TBME. The aqueous layer was acidified to pH 1 with 6NHCl(aq) to form a precipitate which was filtered, washed with water and dried in vacuo over CaCl$_2$ to afford the title compound (927 mg, 48%) as a beige powder.
[M+H]$^+$=292.1/294.1

[3-Chloro-6-[3-(difluoromethyl)-1,2,4-triazol-1-yl]-2-fluorophenyl]methanol (R3m)

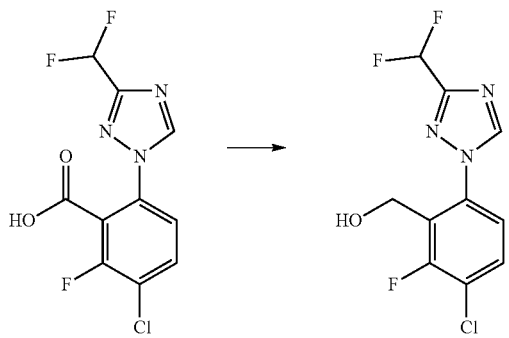 [SMILES: O=C(O)c1c(-n2cnc(C(F)F)n2)ccc(Cl)c1F ; OCc1c(-n2cnc(C(F)F)n2)ccc(Cl)c1F]

To a stirred solution of 3-chloro-6-[3-(difluoromethyl)-1,2,4-triazol-1-yl]-2-fluoro-benzoic acid (927 mg, 3.18 mmol) in THF (15 mL) at rt was added borane THF complex (11.5 mL, 11.5 mmol) dropwise. The mixture was heated at reflux for 2.5 hrs. MeOH (15 mL) was added cautiously followed by 4M HCl in dioxanes (15 mL). The mixture was stirred at rt for 30 min then concentrated in vacuo. DCM and saturated NaHCO$_3$(aq) were added and the layers separated and the aqueous layer further extracted with DCM. The combined organics were washed with 1M HCl(aq) and brine, dried over Na$_2$SO$_4$ and concentrated in vacuo. The residue solidified and was sonicated three times with a 5:1 mixture of Iso-Hexanes/TBME and the supernatant decanted each time to afford the title compound (481 mg, 54% yield) as an off-white solid
[M+H]$^+$=278.1/280.1

1-[4-Chloro-2-(chloromethyl)-3-fluoro-phenyl]-3-(difluoromethyl)-1,2,4-triazole (R4m)

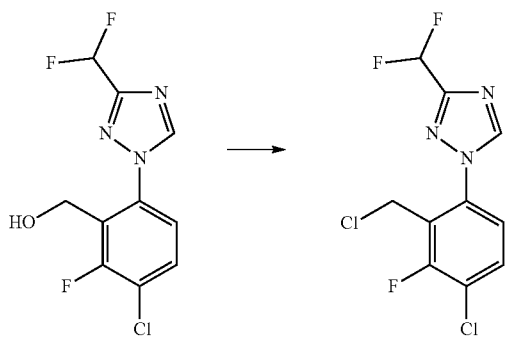 [SMILES: OCc1c(-n2cnc(C(F)F)n2)ccc(Cl)c1F ; Fc1c(Cl)ccc(-n2cnc(C(F)F)n2)c1CCl]

Starting with [3-chloro-6-[3-(difluoromethyl)-1,2,4-triazol-1-yl]-2-fluorophenyl]methanol the title compound was prepared using methods described for the synthesis of 1-[2-(chloromethyl)-3-fluoro-4-methoxy-phenyl]-1,2,4-triazole (R3b).
[M+H]$^+$=296.1/298.

2-[[3-Chloro-6-[3-(difluoromethyl)-1,2,4-triazol-1-yl]-2-fluorophenyl]methyl]isoindoline-1,3-dione (R5m)

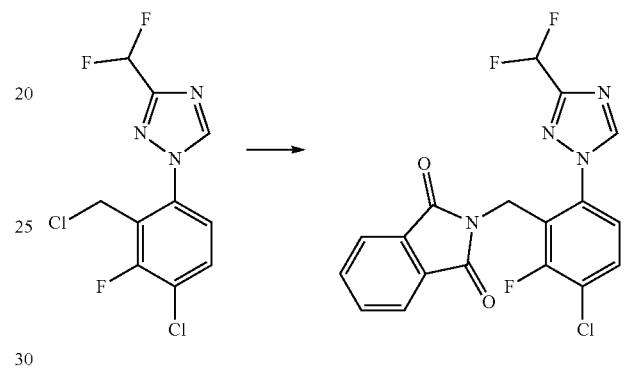

Starting with 1-[4-chloro-2-(chloromethyl)-3-fluoro-phenyl]-3-(difluoromethyl)-1,2,4-triazole the title compound was prepared using methods described for the synthesis of 2-[[2-Fluoro-3-methoxy-6-(1,2,4-triazol-1-yl)phenyl]methyl]isoindoline-1,3-dione (R4b).
[M+H]$^+$=407.2/409.2

[3-Chloro-6-[3-(difluoromethyl)-1,2,4-triazol-1-yl]-2-fluorophenyl]methanamine (R6m)

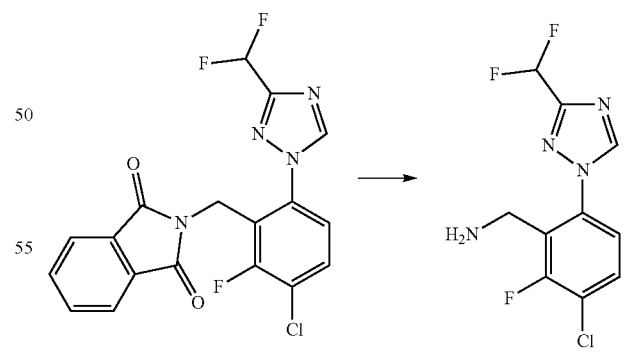

Starting with 2-[[3-chloro-6-[3-(difluoromethyl)-1,2,4-triazol-1-yl]-2-fluorophenyl]methyl]isoindoline-1,3-dione the title compound was prepared using methods described for the synthesis of [2-fluoro-3-methoxy-6-(1,2,4-triazol-1-yl)phenyl]methanamine (R5b).
[M+H]$^+$=273.2

103

[2-Chloro-6-[3-(difluoromethyl)-1,2,4-triazol-1-yl]-3-methoxy-phenyl]methanamine (R1n)

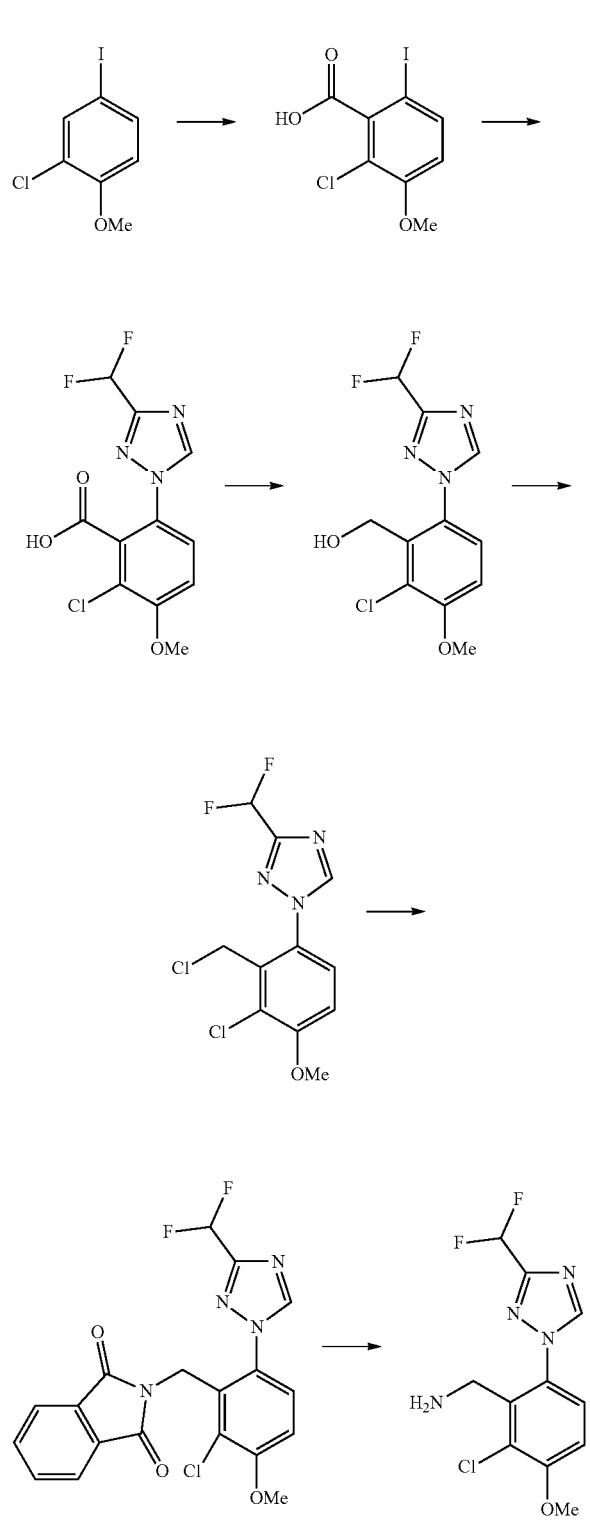

Starting with 2-chloro-4-iodo-1-methoxybenzene the title compound was prepared using methods described for the synthesis of [3-Chloro-6-[3-(difluoromethyl)-1,2,4-triazol-1-yl]-2-fluorophenyl]methanamine (R6m).

104

6-tert-Butoxycarbonylamino-2-fluoro-3-methoxy-benzoic Acid Methyl Ester

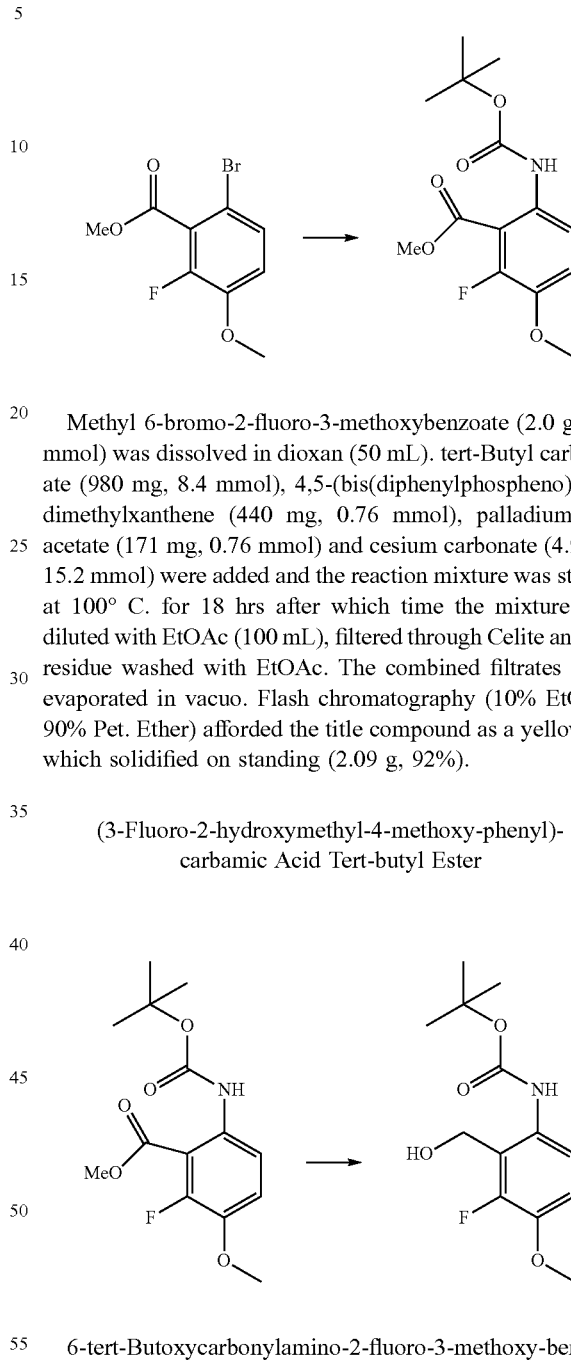

Methyl 6-bromo-2-fluoro-3-methoxybenzoate (2.0 g, 7.6 mmol) was dissolved in dioxan (50 mL). tert-Butyl carbamate (980 mg, 8.4 mmol), 4,5-(bis(diphenylphospheno)-9,9-dimethylxanthene (440 mg, 0.76 mmol), palladium (II) acetate (171 mg, 0.76 mmol) and cesium carbonate (4.95 g, 15.2 mmol) were added and the reaction mixture was stirred at 100° C. for 18 hrs after which time the mixture was diluted with EtOAc (100 mL), filtered through Celite and the residue washed with EtOAc. The combined filtrates were evaporated in vacuo. Flash chromatography (10% EtOAc, 90% Pet. Ether) afforded the title compound as a yellow oil which solidified on standing (2.09 g, 92%).

(3-Fluoro-2-hydroxymethyl-4-methoxy-phenyl)-carbamic Acid Tert-butyl Ester 6-tert-Butoxycarbonylamino-2-fluoro-3-methoxy-benzoic acid methyl ester (480 mg, 1.6 mmol) was dissolved in THF (50 mL) and cooled in an ice/water bath. A 2M solution of lithium borohydride in THF (1.6 mL, 3.21 mmol) was added dropwise. After 18 hrs at rt saturated $NH_4Cl(aq)$ was added slowly and the mixture extracted with EtOAc. The combined organic extracts were washed with water and brine, dried over $Na_2SO_4$ and evaporated in vacuo. Flash chromatography (60% EtOAc, 40% Pet. Ether) afforded the title compound as a white solid (426 mg, 98%).

$[MH]^+=277.7$

(6-Amino-2-fluoro-3-methoxy-phenyl)-methanol

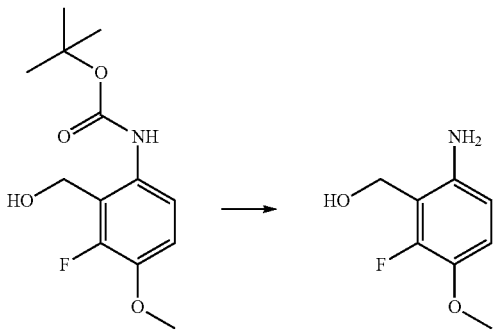 [SMILES: COc1ccc(NC(=O)OC(C)(C)C)c(CO)c1F ; COc1ccc(N)c(CO)c1F]

(3-Fluoro-2-hydroxymethyl-4-methoxy-phenyl)-carbamic acid tert-butyl ester (426 mg, 1.57 mmol) was dissolved in 4M HCl in dioxan (50 mL). After one hour at rt the solvent was removed in vacuo to give the title compound as a white solid (320 mg, 98%).

(2-Fluoro-3-methoxy-6-tetrazol-1-yl-phenyl)-methanol

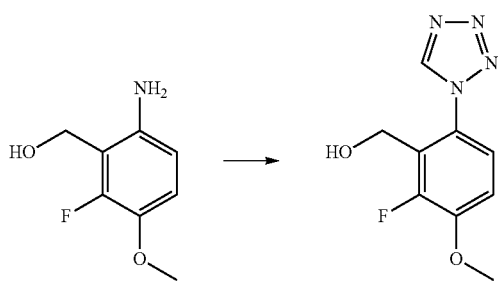 [SMILES: COc1ccc(N)c(CO)c1F ; COc1ccc(-n2cnnn2)c(CO)c1F]

(6-Amino-2-fluoro-3-methoxy-phenyl)-methanol (320 mg, 1.54 mmol) was dissolved in acetic acid (20 mL). Trimethyl orthoformate (491 mg, 4.62 mmol) and sodium azide (301 mg, 4.62 mmol) were added. The mixture was stirred at rt for 18 hrs after which time the mixture was poured into water (50 mL) and extracted with EtOAc. This solution was washed with water and brine, dried over $Na_2SO_4$ and evaporated in vacuo. Flash chromatography (60% EtOAc, 40% Pet. Ether) afforded the title compound as a yellow oil (160 mg, 46%).

[MH]$^+$=225.2

1-(2-Bromomethyl-3-fluoro-4-methoxy-phenyl)-1H-tetrazole

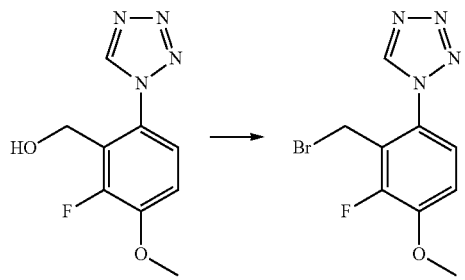 [SMILES: COc1ccc(-n2cnnn2)c(CO)c1F ; COc1ccc(-n2cnnn2)c(CBr)c1F]

(2-Fluoro-3-methoxy-6-tetrazol-1-yl-phenyl)-methanol (160 mg, 0.71 mmol) was dissolved in DCM (50 mL). To this solution was added phosphorous tribromide (386 mg, 1.43 mmol). The mixture was stirred at rt for 18 hrs and diluted with $CHCl_3$ (100 mL), washed with saturated $NaHCO_3$(aq), water and brine, dried over $Na_2SO_4$ and evaporated in vacuo to give the title compound as a white solid which was used without further purification (204 mg, 100%).

[M+H+MeCN]$^+$=330.1

1-(2-Azidomethyl-3-fluoro-4-methoxy-phenyl)-1H-tetrazole

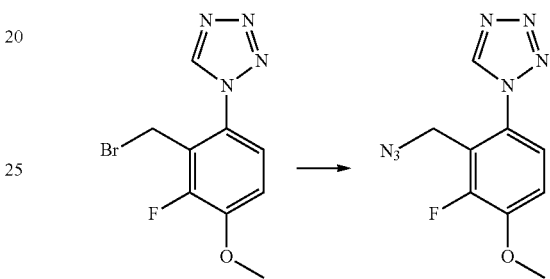

1-(2-Bromomethyl-3-fluoro-4-methoxy-phenyl)-1H-tetrazole (205 mg, 0.71 mmol) was dissolved in DMF (20 mL). Sodium azide (93 mg, 1.43 mmol) was added. The mixture was stirred at rt for 18 hrs after which time the mixture was diluted with EtOAc (100 mL). This solution was washed with water and brine, dried over $Na_2SO_4$ and evaporated in vacuo. Flash chromatography (60% Pet Ether, 40% EtOAc) afforded the title compound a white solid (128 mg, 72%).

[M+H+MeCN]$^+$=291.2

2-Fluoro-3-methoxy-6-tetrazol-1-yl-benzylamine

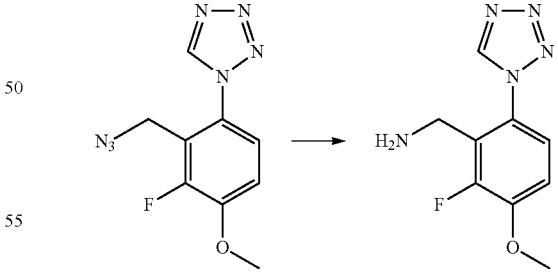

1-(2-Azidomethyl-3-fluoro-4-methoxy-phenyl)-1H-tetrazole (128 mg, 0.51 mmol) was dissolved in MeOH (40 mL) This solution was hydrogenated over 10% Pd/C (50 mg) at atmospheric pressure for 2 hrs after which time the catalyst was filtered off through Celite and the residue washed with MeOH (100 mL). The combined filtrates were evaporated in vacuo to give a yellow oil identified as 2-fluoro-3-methoxy-6-tetrazol-1-yl-benzylamine (100 mg, 87%).

107 tert-Butyl 7-(chloromethyl)-3,4-dihydroisoquinoline-2(1H)-carboxylate (L1a)

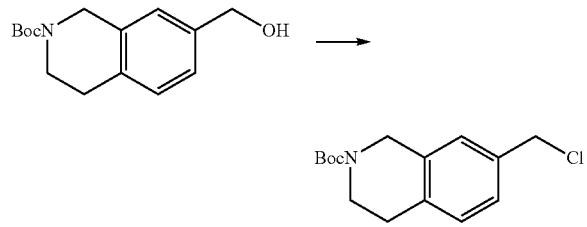

A solution of tert-butyl 7-(hydroxymethyl)-3,4-dihydroisoquinoline-2(1H)-carboxylate (935 mg, 3.6 mmol) in DCM (20 mL) was cooled in an ice-bath and treated with TEA (0.8 mL, 5.7 mmol) followed by methanesulfonyl chloride (0.40 mL, 5.1 mmol) dropwise. The ice-bath was removed and the mixture stirred at rt overnight. The mixture was diluted with DCM (30 mL) and washed with saturated NaHCO$_3$(aq). The aqueous layer was extracted with DCM and the combined organics washed with brine (30 mL), dried (Na$_2$SO$_4$), filtered and concentrated in vacuo. The residue was purified by flash chromatography on silica gel (0 to 40% EtOAc/Iso-Hexanes) to afford the title compound (630 mg, 62%) as a clear viscous oil.

m/z=226.0/228.0 (M-tBu+H)$^+$ tert-Butyl 7-((4-(methoxycarbonyl)-3-(methoxymethyl)-1H-pyrazol-1-yl)methyl)-3,4-dihydroisoquinoline-2(1H)-carboxylate (L2a)

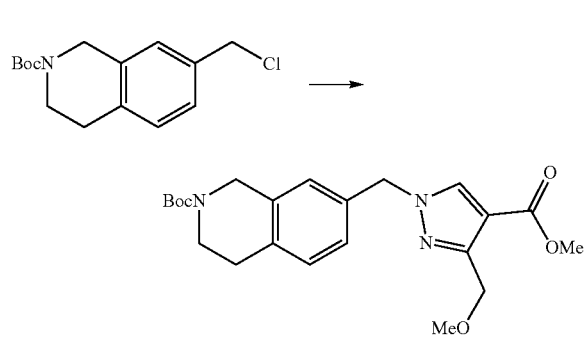

A mixture of potassium carbonate (460 mg, 3.33 mmol) in tert-butyl 7-(chloromethyl)-3,4-dihydroisoquinoline-2(1H)-carboxylate (625 mg, 2.22 mmol) and methyl-3-(methoxymethyl)-1H-pyrazole-4-carboxylate (378 mg, 2.22 mmol) in MeCN (6 mL) was heated to 50° C. overnight. The reaction mixture was cooled to rt and diluted with water. The mixture was extracted with EtOAc and the organic layers washed with brine, dried over MgSO$_4$ and concentrated in vacuo. Flash chromatography (0 to 100% EtOAc/Iso-Hexanes afforded the title compound as the second eluting of the two regioisomers (533 mg, 54%).

[M+H]$^+$=416.2

108

Methyl 3-(methoxymethyl)-1-((1,2,3,4-tetrahydroisoquinolin-7-yl)methyl)-1H-pyrazole-4-carboxylate (L3a)

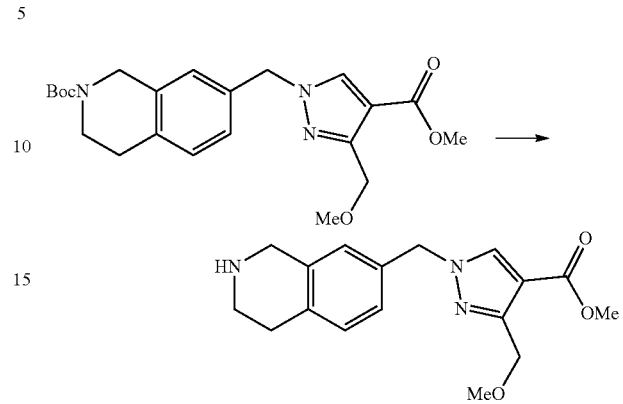

TFA (1 mL, 13 mmol) was added to a solution of tert-butyl 7-((4-(methoxycarbonyl)-3-(methoxymethyl)-1H-pyrazol-1-yl)methyl)-3,4-dihydroisoquinoline-2(1H)-carboxylate (513 mg, 1.23 mmol) in DCM (4 mL) and the reaction mixture was stirred at rt for 3 hrs. The reaction was diluted with MeCN (10 mL) and purified directly by SCX (~8 g), washing with MeOH, eluting with 1% NH$_3$/MeOH to afford the title compound (392 mg, 73% yield) as a clear gum.

[M+H]$^+$=316.2

Methyl 3-(methoxymethyl)-1-((2-methyl-1,2,3,4-tetrahydroisoquinolin-7-yl)methyl)-1H-pyrazole-4-carboxylate (L4a)

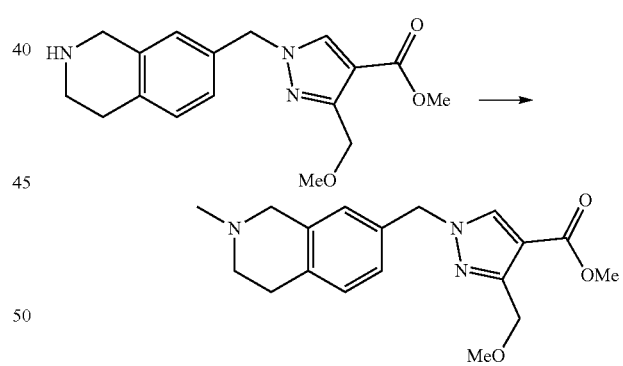

A mixture of methyl 3-(methoxymethyl)-1-((1,2,3,4-tetrahydroisoquinolin-7-yl)methyl)-1H-pyrazole-4-carboxylate (392 mg, 1.24 mmol), TEA (0.35 mL, 2.51 mmol) and formaldehyde (37% in water) (0.43 mL, 14.3 mmol) in DCM (7.5 mL) was stirred for 30 min at rt. Sodium triacetoxyborohydride (650 mg, 3.07 mmol) was added portionwise and the mixture was stirred for 4 hrs. The reaction mixture was partitioned between DCM and saturated NaHCO$_3$(aq), stirred and separated. The aqueous was further extracted with DCM. The combined organic layers were dried over Na$_2$SO$_4$ and concentrated in vacuo. Flash chromatography (0 to 10% MeOH (1% NH$_3$)/DCM) afforded the title compound (305 mg, 72%) as a clear gum.

[M+H]$^+$=330.2

Lithium 3-(methoxymethyl)-1-((2-methyl-1,2,3,4-tetrahydroisoquinolin-7-yl)methyl)-1H-pyrazole-4-carboxylate (L5a)

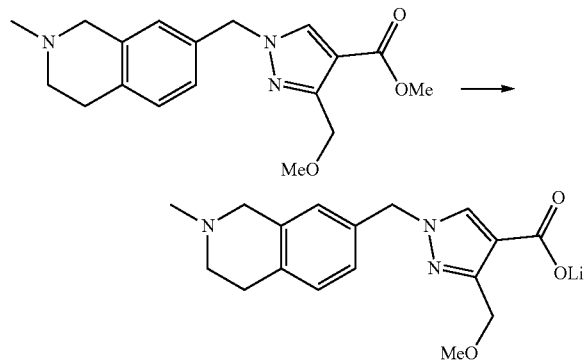

Lithium hydroxide monohydrate (33 mg, 1.4 mmol) was added to a solution of methyl 3-(methoxymethyl)-1-((2-methyl-1,2,3,4-tetrahydroisoquinolin-7-yl)methyl)-1H-pyrazole-4-carboxylate (301 mg, 0.91 mmol) in a 4:1 mixture of 1,4-dioxane:water (5 mL). The reaction was heated to 70° C. and stirred for 3 hrs before cooling to rt overnight. Solvent was removed in vacuo and the residue was azeotroped with toluene in order to afford the title compound (242 mg, 76%) as an off-white solid.

[M+H]⁺=316.2

Methyl 3-(methoxymethyl)-1-(methylsulfonyl)-1H-pyrazole-4-carboxylate (Lib)

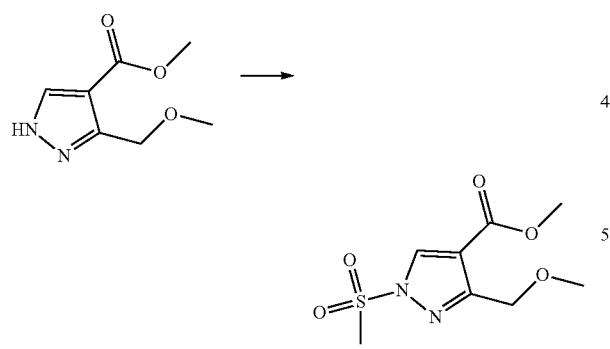

To a stirred solution of methyl 3-(methoxymethyl)-1H-pyrazole-4-carboxylate (10 g, 59 mmol) in DCM (200 mL) at 0° C. was added TEA (11 mL, 79 mmol) followed by methanesulfonyl chloride (5 mL, 64 mmol). The mixture was stirred for 10 min then allowed to warm to rt and stirred for an additional 30 min. The mixture was diluted with DCM (100 mL) and NH₄Cl(aq) (100 ml) was added. The aqueous phase was extracted with DCM and the combined organics dried over MgSO₄ and concentrated in vacuo to afford the title compound as a mixture of regioisomers (14 g, 95%).

tert-Butyl 5-((4-(methoxycarbonyl)-3-(methoxymethyl)-1H-pyrazol-1-yl)methyl)isoindoline-2-carboxylate (L2b)

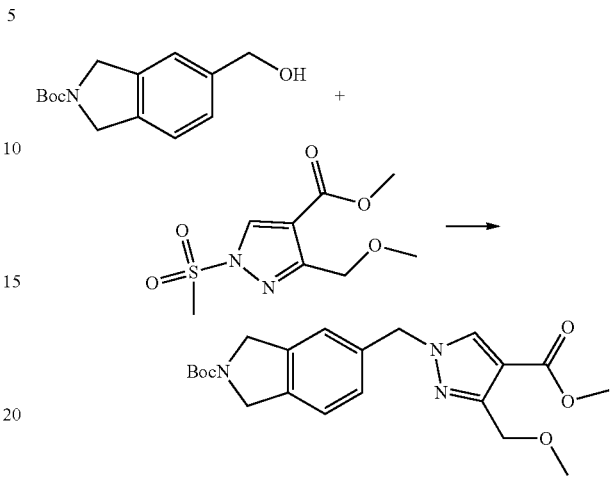

To a stirred suspension of tert-butyl 5-(hydroxymethyl)-2,3-dihydro-1H-isoindole-2-carboxylate (3.5 g, 13 mmol) and methyl 3-(methoxymethyl)-1-(methylsulfonyl)-1H-pyrazole-4-carboxylate (3.49 g, 13.9 mmol) in MeCN (140 mL) was added caesium carbonate (5.35 g, 16.4 mmol). The mixture was stirred at 90° C. for 2 hrs, cooled to rt and partitioned between EtOAc (400 mL) and brine (500 mL). The organic extracts were dried over MgSO₄ and concentrated in vacuo. Flash chromatography (0-100% EtOAc in isohexane) afforded the title compound (3.3 g, 55% yield) as a colourless oil.

[M+H]⁺=402.3

1-((2-(tert-Butoxycarbonyl)isoindolin-5-yl)methyl)-3-(methoxymethyl)-1H-pyrazole-4-carboxylic Acid (L3b)

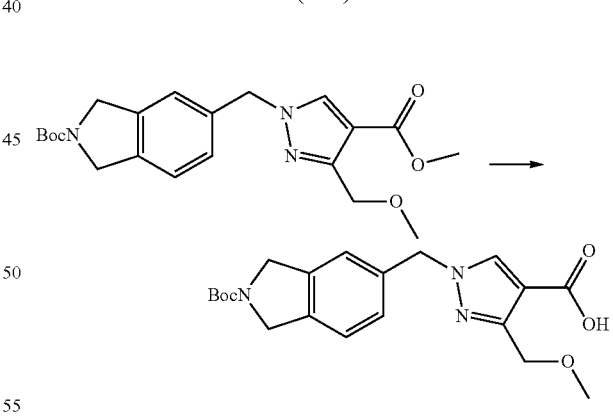

To a stirred solution of tert-butyl 5-((4-(methoxycarbonyl)-3-(methoxymethyl)-1H-pyrazol-1-yl)methyl)isoindoline-2-carboxylate (1.6 g, 4.0 mmol) in 1,4-dioxane (30 mL) was added lithium hydroxide (0.048 g, 2.0 mmol) in water (20 mL). The mixture was heated at 70° C. overnight. The mixture was cooled to rt and concentrated in vacuo. The residue was diluted with water (50 mL), acidified with 10 wt % aqueous citric acid, extracted into EtOAc, dried over MgSO₄ and concentrated in vacuo. Flash chromatography (0-10% MeOH in DCM) afforded the title compound (622 mg, 32% yield) as a white solid.

[M+H]⁺=388.3 tert-Butyl 5-((4-((2-fluoro-3-methoxy-6-(4-methyl-1H-1,2,3-triazol-1-yl)benzyl)carbamoyl)-3-(methoxymethyl)-1H-pyrazol-1-yl)methyl)isoindoline-2-carboxylate (L4b)

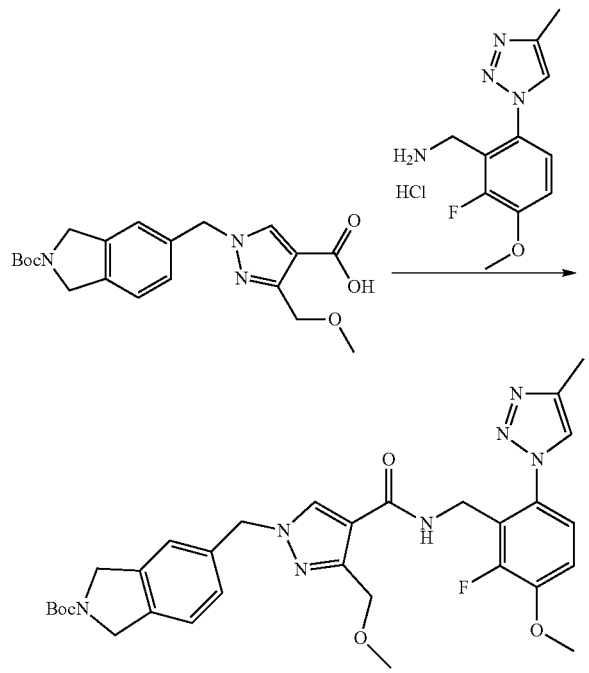

To a stirred suspension of 1-((2-(tert-butoxycarbonyl)isoindolin-5-yl)methyl)-3-(methoxymethyl)-1H-pyrazole-4-carboxylic acid (612 mg, 1.58 mmol), [2-fluoro-3-methoxy-6-(4-methyltriazol-1-yl)phenyl]methanamine hydrochloride (609 mg, 2.05 mmol) and HATU (781 mg, 2.05 mmol) in DCM/DMF (12 mL, 10:1) was added TEA (881 uL, 6.32 mmol) and stirred at rt overnight. The mixture was diluted with DCM (150 mL), washed with saturated NaHCO₃(aq), water and brine (150 mL). The organics were passed through a phase separator and concentrated in vacuo. Flash chromatography (0-5% MeOH in DCM) afforded the title compound (660 mg, 53% yield) as a colourless oil which solidified on standing.
[M+H]⁺=606.4

N-(2-Fluoro-3-methoxy-6-(4-methyl-1H-1,2,3-triazol-1-yl)benzyl)-1-(isoindolin-5-ylmethyl)-3-(methoxymethyl)-1H-pyrazole-4-carboxamide Hydrochloride (L5b)

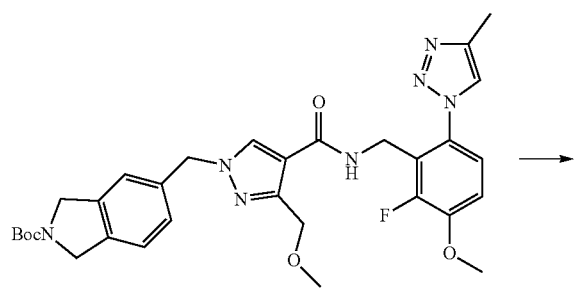

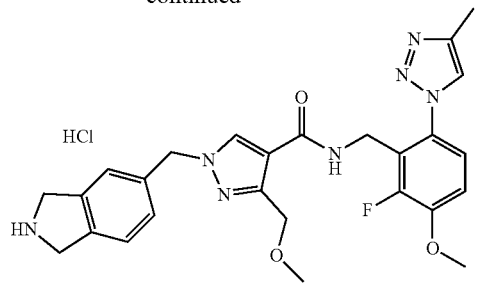

To a stirred solution of tert-butyl 5-((4-((2-fluoro-3-methoxy-6-(4-methyl-1H-1,2,3-triazol-1-yl)benzyl)carbamoyl)-3-(methoxymethyl)-1H-pyrazol-1-yl)methyl)isoindoline-2-carboxylate (602 mg, 0.77 mmol) in MeOH (5 mL) was added 4M HCl in 1,4-dioxanes (0.58 mL, 19 mmol). The mixture was stirred at rt for 2 hrs, concentrated in vacuo and azeotroped with toluene. The resulting residue was triturated with Et₂O/isohexane, filtered and dried to afford the title compound (460 mg, 100% yield) as a brown solid.
[M+H]⁺=506.3 tert-Butyl 6-(hydroxymethyl)-3,4-dihydroisoquinoline-2(1H)-carboxylate (L1c)

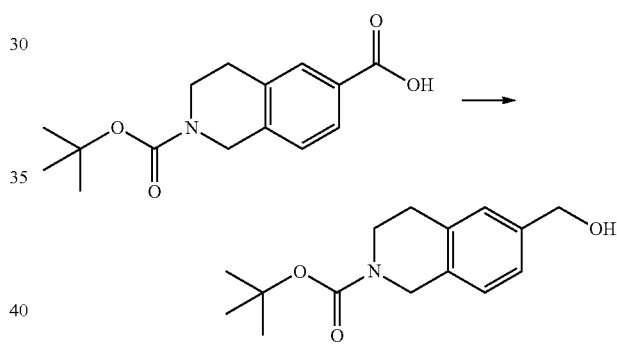

To a stirred solution of 2-tert-butoxycarbonyl-3,4-dihydro-1H-isoquinoline-6-carboxylic acid (500 mg, 1.8 mmol) in anhydrous THF (5 mL) at rt was added borane THF complex (1M, 4.5 mL, 4.5 mmol) dropwise over 5 min. The resulting solution was stirred for 20 hrs. Water (0.4 mL) was added dropwise followed by 2M Na₂CO₃(aq) (0.6 mL). The mixture was stirred for 30 min. EtOAc (20 mL) was added. The organics were separated from the aqueous sediment. The organics were washed with 1M HCl(aq) and brine, dried (hydrophobic frit), filtered and concentrated in vacuo. Flash chromatography (EtOAc/Pet. Ether) afforded the title compound as a colourless oil (478 mg, 99.7%).
[(M-tBu)+H]⁺=208.1 tert-Butyl 6-(bromomethyl)-3,4-dihydroisoquinoline-2(1H)-carboxylate (L2c)

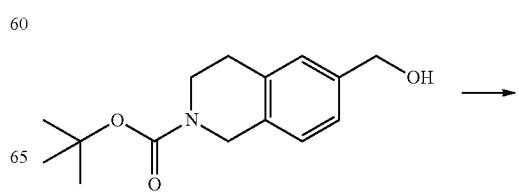

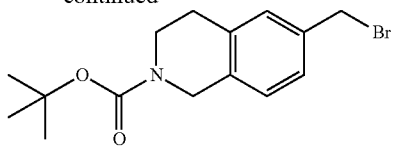

To a stirred solution of tert-butyl 6-(hydroxymethyl)-3,4-dihydroisoquinoline-2(1H)-carboxylate (478 mg, 1.82 mmol) in THF (10 mL) in an ice/water bath was added phosphorus tribromide (247 mg, 0.91 mmol) and the mixture allowed to warm to rt and stirred for 3 hrs. The mixture was quenched with saturated NaHCO$_3$(aq) (10 mL) and extracted with EtOAc. The combined organics were washed with brine, dried over MgSO$_4$, filtered and concentrated in vacuo. Flash chromatography (0-5% EtOAc/hexane) afforded the title compound (234 mg, 39%) as a colourless oil which solidified on standing.

[(M-tBu)+H]$^+$=270.0/272.0

7-(tert-butyl) 2-methyl 5,8-dihydropyrido[3,4-d]pyrimidine-2,7(6H)-dicarboxylate (L1d)

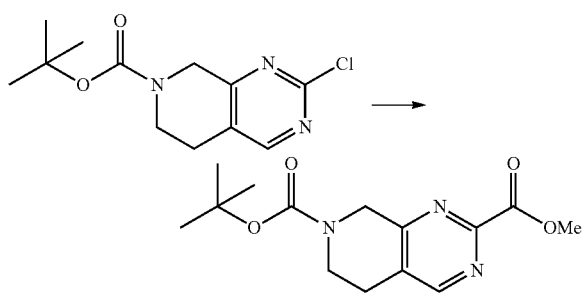

tert-Butyl 2-chloro-6,8-dihydro-5H-pyrido[3,4-d]pyrimidine-7-carboxylate (890 mg, 3.3 mmol) and 1,1'-bis(diphenylphosphino)ferrocenedichloro palladium(II) dichloromethane complex (130 mg, 0.16 mmol) were dissolved in DMF (45 mL) and MeOH (45 mL) before the addition of TEA (1.3 mL, 9.33 mmol). The resulting solution was purged 3 times with N$_2$ gas then 3 times with CO gas. The mixture was placed under a 4 bar atmosphere of CO, stirred and heated at 90° C. overnight. The mixture was concentrated in vacuo and the residue was diluted with DCM (50 mL) and NaHCO$_3$(aq) (30 mL). The layers were separated and aqueous layer was extracted with DCM. The organic layers were combined, washed with water and brine, dried over Na$_2$SO$_4$ and concentrated in vacuo. Flash chromatography (0 to 80% EtOAc/Iso-hexanes) gave the title compound (0.86 g, 88%) as a yellow oil which solidified to an orange solid on standing.

[(M-tBu)+H]$^+$=238.1 tert-Butyl 2-(hydroxymethyl)-6,8-dihydro-5H-pyrido[3,4-d]pyrimidine-7-carboxylate (L2d)

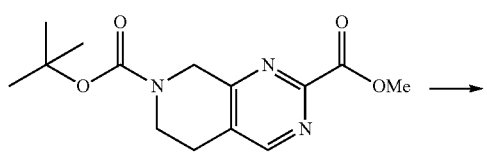

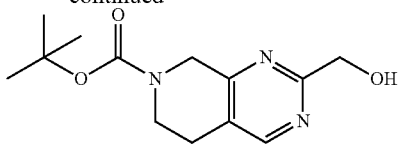

7-(tert-Butyl) 2-methyl 5,8-dihydropyrido[3,4-d]pyrimidine-2,7(6H)-dicarboxylate (240 mg, 0.82 mmol) was dissolved in THF (10 mL) before being cooled in an ice/water bath. Lithium borohydride (0.5 mL, 2 mmol) was added dropwise and the mixture was stirred in an ice/water bath for 1.5 hrs. MeOH (10 mL) was added and the mixture stirred for 30 min (until gas evolution had stopped). The mixture was concentrated in vacuo and the resulting residue was partitioned between EtOAc and brine. The aqueous phase was further extracted with EtOAc and the combined organic phases were dried over MgSO$_4$, filtered and concentrated in vacuo. Flash chromatography (50-100% EtOAc in Hexane) afforded the title compound (75 mg, 28%).

[(M-tBu)+2H]$^+$=210.2 tert-Butyl 2-(chloromethyl)-6,8-dihydro-5H-pyrido[3,4-d]pyrimidine-7-carboxylate (L3d)

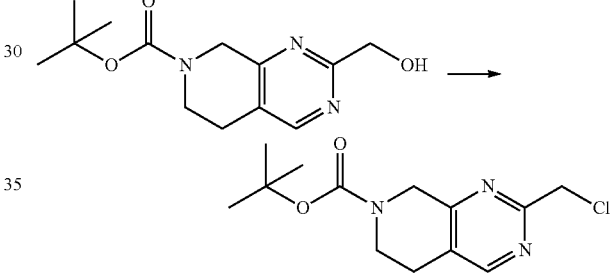

tert-Butyl 2-(hydroxymethyl)-6,8-dihydro-5H-pyrido[3,4-d]pyrimidine-7-carboxylate (75 mg, 0.28 mmol) was dissolved in DCM (3 mL) before the addition of TEA (60 µL, 0.43 mmol) and methanesulfonyl chloride (30 µL, 0.39 mmol). The mixture was stirred at rt for 18 hrs. Another equivalent of both methanesulfonyl chloride (30 µL, 0.39 mmol) and TEA (60 µL, 0.43 mmol) were added and the mixture stirred for a further 24 hrs. The mixture was diluted with DCM (5 mL) and washed with saturated NaHCO$_3$(aq) (5 mL). The aqueous layer was extracted with further DCM and the combined organics washed with brine, dried over MgSO$_4$, filtered and concentrated in vacuo to give the title compound (80 mg, 80%).

[M+H]$^+$=284.1

Tert-Butyl 5-chloro-6-hydroxy-3,4-dihydro-1H-isoquinoline-2-carboxylate (L1e)

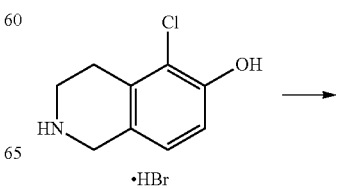

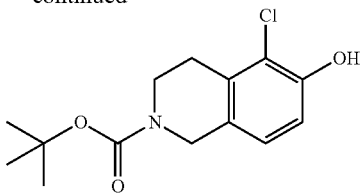

To a suspension of 5-chloro-1,2,3,4-tetrahydroisoquinoline-6-ol hydrobromide (2.98 g, 11.3 mmol) in DCM (30 mL) at rt was added TEA (4.8 mL, 34.4 mmol). To this suspension was added di-tert-butyl dicarbonate (2.7 g, 12.4 mmol) and the mixture stirred at rt overnight. The mixture was diluted with DCM (50 mL) and washed with water (30 mL) and brine (30 mL). The organic phase was dried via hydrophobic frit and concentrated in vacuo. Flash chromatography (0-100% EtOAc in hexane) afforded the title compound (955 mg, 28%) as a pale yellow solid.

$[(M-tBu)+H]^+ = 227.9$ tert-Butyl 5-chloro-6-(trifluoromethylsulfonyloxy)-3,4-dihydro-1H-isoquinoline-2-carboxylate (L2e)

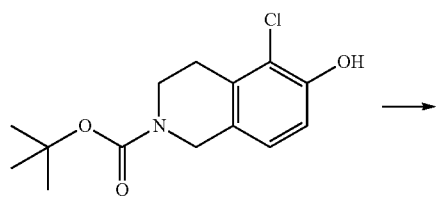

To a stirred solution of tert-butyl 5-chloro-6-hydroxy-3,4-dihydro-1H-isoquinoline-2-carboxylate (955 mg, 3.37 mmol) and TEA (1.4 mL, 10 mmol) in DCM (40 mL) in an ice/water bath was added 1,1,1-trifluoro-N-phenyl-N-(trifluoromethylsulfonyl)methanesulfonamide (1.32 g, 3.69 mmol). The mixture was warmed to rt and stirred overnight. The mixture was concentrated in vacuo and the residue purified by flash chromatography (0-10% EtOAc in hexane) to give the title compound (1.46 g, 84%) as a colourless oil.

$[(M-Boc)+H]^+ = 315.8$

2-(tert-Butyl) 6-methyl 5-chloro-3,4-dihydroisoquinoline-2,6(1H)-dicarboxylate (L3e)

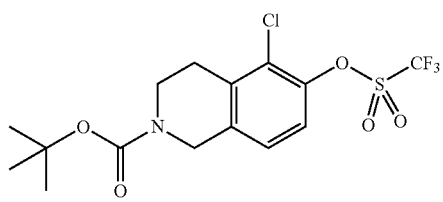

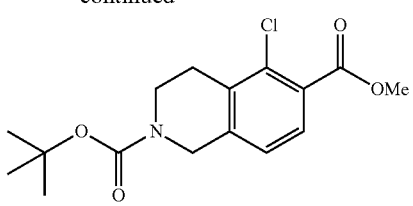

A solution of tert-butyl 5-chloro-6-(trifluoromethylsulfonyloxy)-3,4-dihydro-1H-isoquinoline-2-carboxylate (2.65 g, 6.37 mmol), 3-diphenylphosphanylpropyl(diphenyl)phosphane (265 mg, 0.64 mmol), DIPEA (4.5 mL, 25.8 mmol) and palladium (II) acetate (145 mg, 0.65 mmol) in a mixture of DMF (100 mL) and MeOH (50 mL) was degassed with $N_2$ gas and charged with CO gas. The resulting mixture was concentrated in vacuo and the residue suspended in MeOH (50 mL) and filtered through Celite. The filtrate was concentrated in vacuo. Flash chromatography (5-30% EtOAc in hexane) afforded the title compound (1.85 g, 86%) as a colourless oil.

$[(M-tBu)+H]^+ = 269.9$

2-(tert-Butoxycarbonyl)-5-chloro-1,2,3,4-tetrahydroisoquinoline-6-carboxylic Acid (L4e)

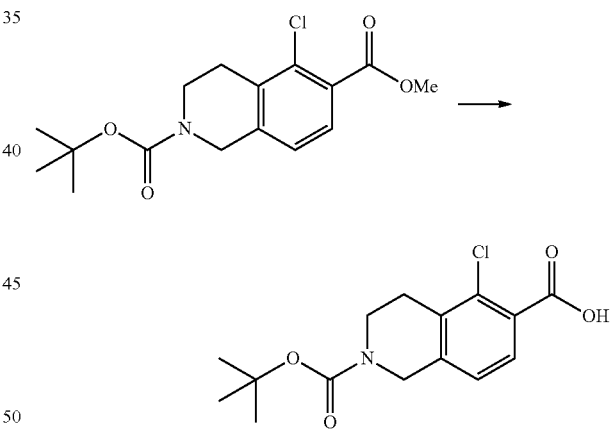

To a stirred solution of 2-(tert-butyl) 6-methyl 5-chloro-3,4-dihydroisoquinoline-2,6(1H)-dicarboxylate (50 mg, 0.15 mmol) in a mixture of THF (1 mL), MeOH (1 mL), water (0.5 mL) was added LiOH (35 mg, 1.5 mmol). The mixture was heated at 50° C. for 60 min. The mixture was cooled to rt and concentrated in vacuo. The residue was suspended in EtOAc (15 mL), partitioned with 1M HCl(aq) (10 mL) and separated. The organic phase was washed with additional 1M HCl and brine, dried over $MgSO_4$ and concentrated in vacuo to afford the title compound (53 mg, quantitative) as a colourless oil.

$[(M-tBu)+H]^+ = 255.9$

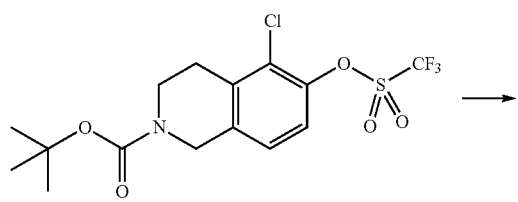

117 tert-Butyl 5-chloro-6-(hydroxymethyl)-3,4-dihydroisoquinoline-2(1H)-carboxylate (L5e)

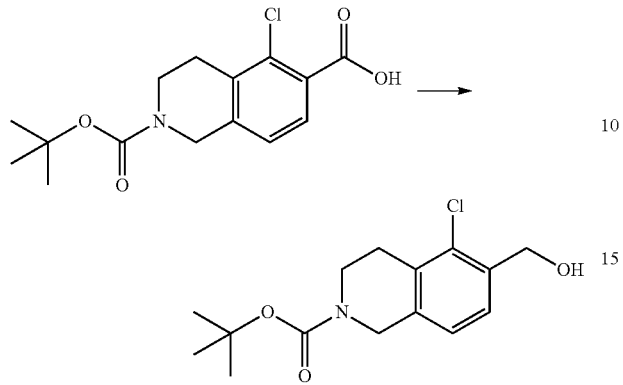

To a stirred solution of 2-(tert-butoxycarbonyl)-5-chloro-1,2,3,4-tetrahydroisoquinoline-6-carboxylic acid (1 g, 3.2 mmol), in THF (40 mL) at rt was added borane THF complex (1M in THF, 7 mL, 7 mmol). The mixture was stirred at rt for 4 hrs. The mixture was carefully quenched with MeOH (20 mL) portion-wise. The resulting solution was concentrated in vacuo to give a colourless gum. Flash chromatography (0-40% EtOAc/hexane) afforded the title compound (949 mg, 97%) as a colourless glass.

[(M-tBu)+H]$^+$=241.9 tert-Butyl 5-chloro-6-(chloromethyl)-3,4-dihydroisoquinoline-2(1H)-carboxylate (L6e)

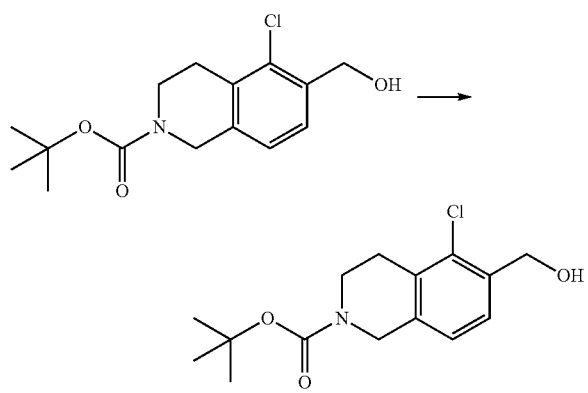

tert-Butyl 5-chloro-6-(hydroxymethyl)-3,4-dihydroisoquinoline-2(1H)-carboxylate (949 mg, 3.19 mmol) was dissolved in DCM (15 mL) and cooled in an ice/water bath. TEA (750 IL, 538 mmol) was added followed by the dropwise addition of methanesulfonyl chloride (30 μL, 0.39 mmol). The mixture was stirred at rt for 18 hrs. The mixture was diluted with DCM (30 mL) and washed with saturated NaHCO$_3$ (aq) (20 mL). The aqueous layer was extracted with further DCM and the combined organics washed with brine (10 mL), dried via a hydrophobic frit and concentrated in vacuo. Flash chromatography (10-40% EtOAc/hexane) afforded the title compound (874 mg, 86%).

[(M-tBu)+H]$^+$=259.9

118

7-(tert-Butyl) 2-ethyl 5,6-dihydroimidazo[1,2-a]pyrazine-2,7(8H)-dicarboxylate

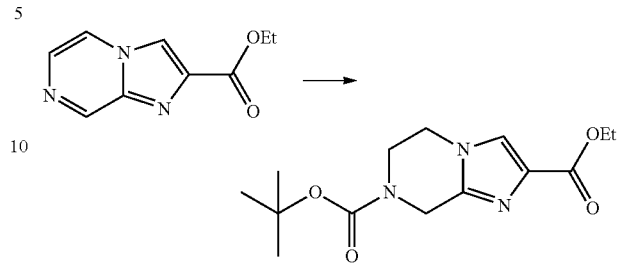

To a stirred solution of ethyl imidazo[1,2-a]pyrazine-2-carboxylate (3.5 g, 18.3 mmol) in EtOH (140 mL) was added di-tert-butyl dicarbonate (4.79 g, 22 mmol) and 5% palladium on carbon (1.95 g, 0.92 mmol). The resulting suspension was placed in a high-pressure hydrogenation vessel, flushed with N$_2$ gas then and H$_2$ gas. The vessel was charged with H$_2$ gas (3 Bar) and stirred overnight at rt. The mixture was filtered through Celite, washed with EtOH and concentrated in vacuo to afford the crude product. Flash chromatography (0-100% EtOAc in isohexane) afforded the title compound (2.09 g, 6.84 mmol, 37%) as a white solid.

[M+H]$^+$=296.3 tert-Butyl 2-(hydroxymethyl)-5,6-dihydroimidazo[1,2-a]pyrazine-7(8H)-carboxylate

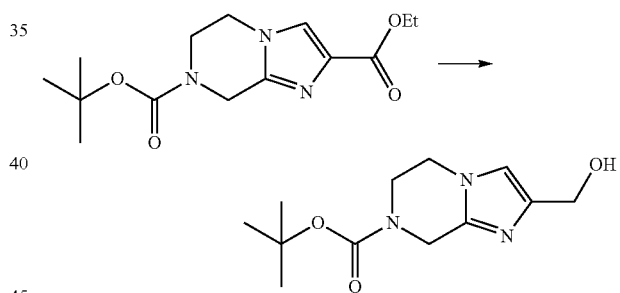

tert-Butyl 2-(hydroxymethyl)-5,6-dihydroimidazo[1,2-a]pyrazine-7(8H)-carboxylate was synthesised starting with 7-(tert-butyl) 2-ethyl 5,6-dihydroimidazo[1,2-a]pyrazine-2,7(8H)-dicarboxylate and using a similar method to that described for tert-butyl 2-(hydroxymethyl)-6,8-dihydro-5H-pyrido[3,4-d]pyrimidine-7-carboxylate (L2d).

Tert-Butyl 2-(hydroxymethyl)-5,6-dihydro-[1,2,4]triazolo[1,5-a]pyrazine-7(8H)-carboxylate

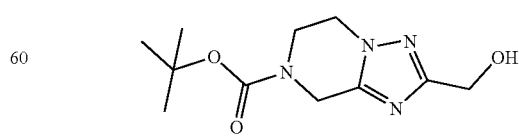

Synthesis of tert-butyl 2-(hydroxymethyl)-5,6-dihydro-[1,2,4]triazolo[1,5-a]pyrazine-7(8H)-carboxylate (CAS 265643-95-6) is reported in WO2000023449.

119

Methyl 4-hydroxy-7-methyl-6,8-dihydro-5H-1,7-naphthyridine-3-carboxylate

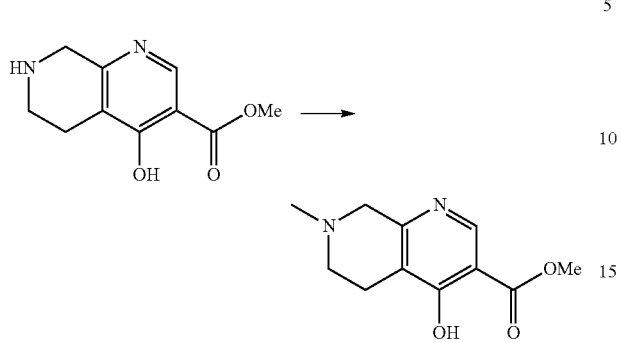

To a stirred solution of methyl 4-hydroxy-5,6,7,8-tetrahydro-1,7-naphthyridine-3-carboxylate (reported in WO2012027564) (200 mg, 0.96 mmol) in DCM (11 mL) was added TEA (550 IL, 3.95 mmol) and the mixture stirred for 30 min at rt. Formaldehyde solution (37% aq., 338 µL, 11.3 mmol) was added and the mixture stirred for a further 45 min before the addition of sodium triacetoxyborohydride (441 mg, 2.08 mmol). The resulting solution was stirred for 3 hrs. The mixture was quenched with 2.5 M HCl(aq) (0.3 mL), diluted with MeOH (20 mL) and purified directly by SCX, washing with MeOH (5×2 mL), eluting with 1% NH$_3$/MeOH (5×2 mL) to give the title compound (144 mg, 67%) as an orange solid.

$[M+H]^+=223.1$

Methyl 4-chloro-7-methyl-6,8-dihydro-5H-1,7-naphthyridine-3-carboxylate

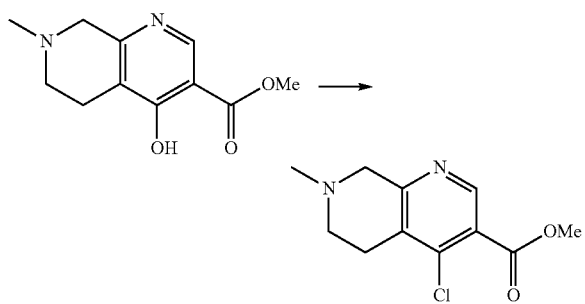

Methyl 4-hydroxy-7-methyl-6,8-dihydro-5H-1,7-naphthyridine-3-carboxylate (77 mg, 0.34 mmol) was heated at 80° C. in phosphorus oxychloride (0.5 mL, 5.36 mmol) for 90 min. The mixture was cooled to 0° C., poured into water (3 mL) and stirred for 20 min. The mixture was then basified to pH8 with saturated Na$_2$CO$_3$(aq) and extracted with EtOAc. The combined organic layers were combined, dried over Na$_2$SO$_4$ and concentrated in vacuo to give the title compound (54 mg, 65%) as a brown oil.

$[M+H]^+=241.1$

120

(4-Chloro-7-methyl-5,6,7,8-tetrahydro-1,7-naphthyridin-3-yl)methanol

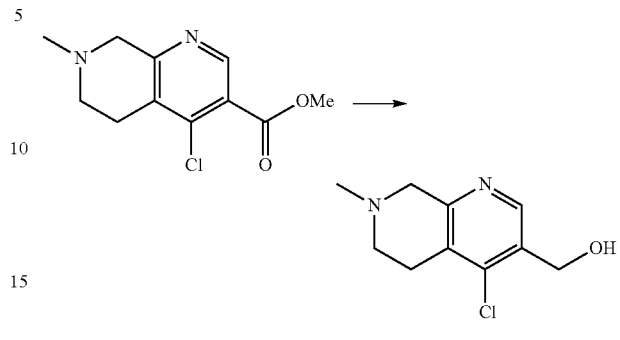

To a stirred solution of methyl 4-chloro-7-methyl-6,8-dihydro-5H-1,7-naphthyridine-3-carboxylate (54 mg, 0.22 mmol) in THF (2 mL) in a cold bath at −78° C. was added diisobutylaluminium hydride (1M in THF, 1.62 mL, 1.62 mmol) drop-wise. The resulting solution was stirred for 3 hrs, warmed to rt and stirred for 18 hrs. The mixture was quenched with water (0.1 mL) and 15% NaOH(aq) (0.1 mL). The mixture was gently warmed to melt the aqueous phase and additional water added. The mixture was stirred for 15 min before addition of MgSO$_4$ and the mixture was stirred for 15 min at rt. The mixture was filtered through Celite washing with MeOH. The filtrate was concentrated in vacuo to afford the title compound (47 mg, 99%) as a yellow gum.

$[M+H]^+=213.1$

Methyl isochromane-6-carboxylate

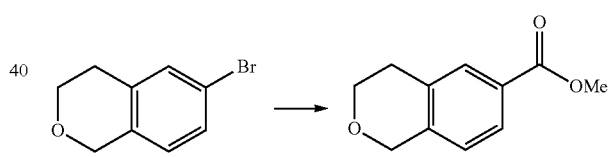

Methyl isochromane-6-carboxylate was prepared from 6-bromoisochromane using method L1d.

$[M+H]^+=192.1$

Isochroman-6-ylmethanol

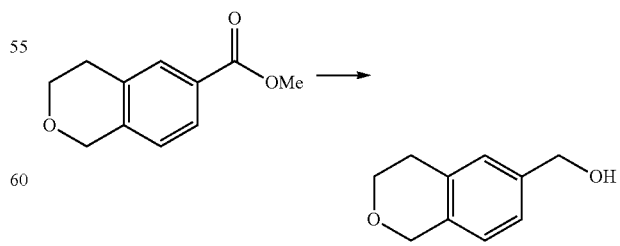

Isochroman-6-ylmethanol was prepared from methyl isochromane-6-carboxylate using procedure L2d.

$[M+H]^+=164.1$

121

Tert-Butyl 2-(hydroxymethyl)-6,7-dihydropyrazolo[1,5-a]pyrazine-5(4H)-carboxylate

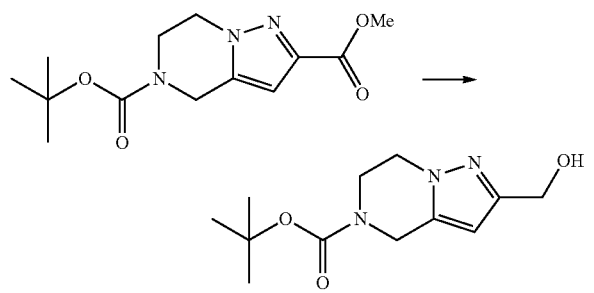

tert-Butyl 2-(hydroxymethyl)-6,7-dihydropyrazolo[1,5-a]pyrazine-5(4H)-carboxylate was prepared from 5-(tert-butyl) 2-methyl 6,7-dihydropyrazolo[1,5-a]pyrazine-2,5(4H)-dicarboxylate (reported in WO2010024258) using procedure L2d.

[M+H]$^+$=254.1

$^1$H NMR (DMSO-d6) 1.44 (9H, s), 3.78 (2H, t, J=5.5 Hz), 4.02 (2H, dd, J=6.4, 4.5 Hz), 4.35 (2H, d, J=5.9 Hz), 4.56 (2H, s), 4.95 (1H, t, J=5.7 Hz), 6.05 (1H, s).

7-(Hydroxymethyl)-2-methyl-3,4-dihydroisoquinolin-1(2H)-one

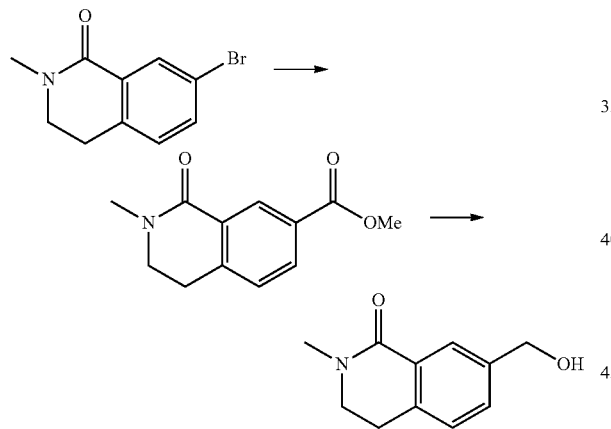

7-(Hydroxymethyl)-2-methyl-3,4-dihydroisoquinolin-1(2H)-one was prepared from 7-bromo-2-methyl-3,4-dihydroisoquinolin-1(2H)-one according to procedures L1d and L2d.

[M+H]$^+$=192.1

Di-tert-butyl 1-(1-cyanocyclopropyl)pyrazole-3,5-dicarboxylate

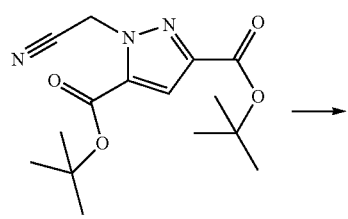

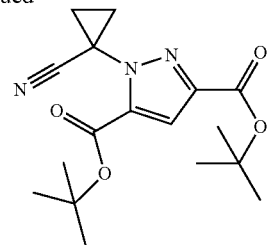

To an ice-cooled solution of di-tert-butyl 1-(cyanomethyl)pyrazole-3,5-dicarboxylate (5.02 g, 15 mmol) and 1-bromo-2-chloro-ethane (1.56 mL, 18.7 mmol) in anhydrous DMF (40 mL) was added sodium hydride (1.35 g, 33.8 mmol) portionwise over 60 min. The mixture was warmed to rt and stirred for 18 hrs. The mixture was carefully quenched with saturated NH$_4$Cl(aq) (30 mL) and stirred for 20 min before being poured into a mixture of water (500 mL) and EtOAc (500 mL) and stirred for 5 min. The organic layer was collected and the aqueous extracted with EtOAc (250 mL). The combined organics were washed with brine (200 mL), dried over MgSO4 and concentrated in vacuo to a brown oil. Flash chromatography (0 to 25% EtOAc/Iso-Hexanes) afforded the title compound (3.6 g, 65%) as a clear gum which crystallized on standing.

$^1$H NMR (DMSO-d6) 1.52 (9H, s), 1.59 (9H, s), 1.87-1.94 (2H, m), 1.99-2.05 (2H, m), 7.17 (1H, s).

Tert-butyl 4-oxospiro[5,6-dihydropyrazolo[1,5-a]pyrazine-7,1'-cyclopropane]-2-carboxylate

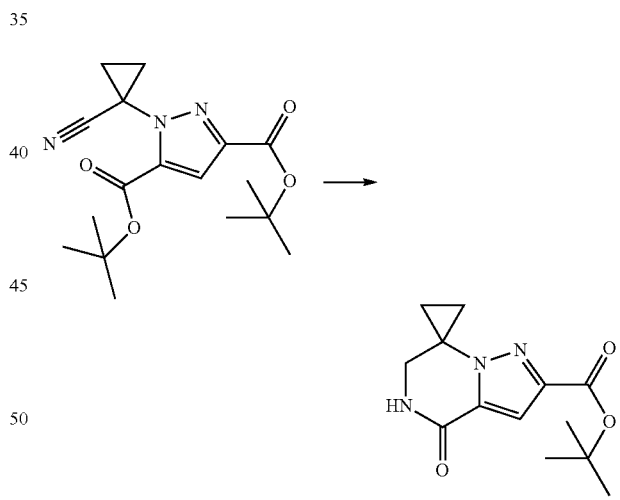

A solution of di-tert-butyl 1-(1-cyanocyclopropyl)pyrazole-3,5-dicarboxylate (100 mg, 0.3 mmol) in 1.75M ammonia in MeOH (6 mL, 10.5 mmol) was passed through a Ra-Ni CatCart using the H-Cube hydrogenation apparatus (30×4 mm, 30 bar, 50° C., 1 mL/min, 2 passes). The mixture was then stirred at rt. Solvents were removed in vacuo and flash chromatography (0 to 100% EtOAc/Iso-Hexanes) afforded the title compound (48 mg, 60%) as a white solid.

[(M-t-Bu+H)+H]$^+$=208.2

$^1$H NMR (DMSO-d6) 1.15-1.21 (2H, m), 1.41-1.45 (2H, m), 1.51 (9H, s), 3.62 (2H, d, J=2.8 Hz), 7.04 (1H, s), 8.49 (1H, s)

Tert-butyl 5-methyl-4-oxo-spiro[6H-pyrazolo[1,5-a]pyrazine-7,1'-cyclopropane]-2-carboxylate

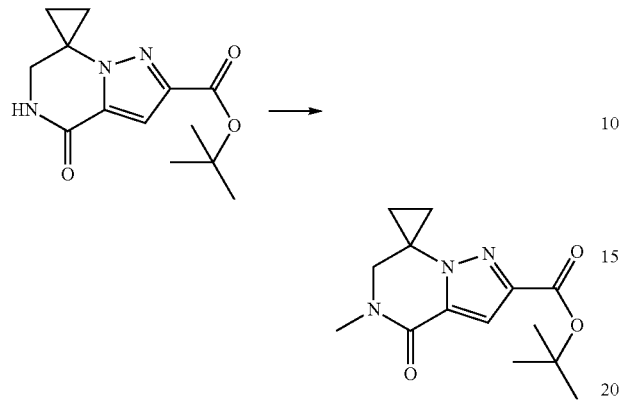

A solution of tert-butyl 4-oxospiro[5,6-dihydropyrazolo[1,5-a]pyrazine-7,1'-cyclopropane]-2-carboxylate (200 mg, 0.76 mmol) in anhydrous THF (6 mL) was treated with sodium hydride (61 mg, 1.53 mmol) in two portions, forming a white precipitate. The mixture was allowed to stir for 20 min, treated with iodomethane (95 μL, 1.53 mmol), heated to 55° C. for 60 min and stirred at rt for 18 hrs. Solvents were removed in vacuo and the residue partitioned between DCM (15 mL) and saturated NaHCO$_3$(aq) (15 mL). The aqueous layer was extracted with further DCM and the combined organics dried over Na$_2$SO$_4$ and concentrated in vacuo. The residue was sonicated with iso-hexanes (10 mL) and filtered to afford the title compound (167 mg, 78%) as a pale yellow solid.

[(M-t-Bu+H)+H]$^+$=222.2

$^1$H NMR (DMSO-d6) 1.19-1.24 (2H, m), 1.41-1.47 (2H, m), 1.51 (9H, s), 3.01 (3H, s), 3.80 (2H, s), 7.03 (1H, s)

2'-(hydroxymethyl)-5'-methyl-5',6'-dihydro-4'H-spiro[cyclopropane-1,7'-pyrazolo[1,5-a]pyrazin]-4'-one

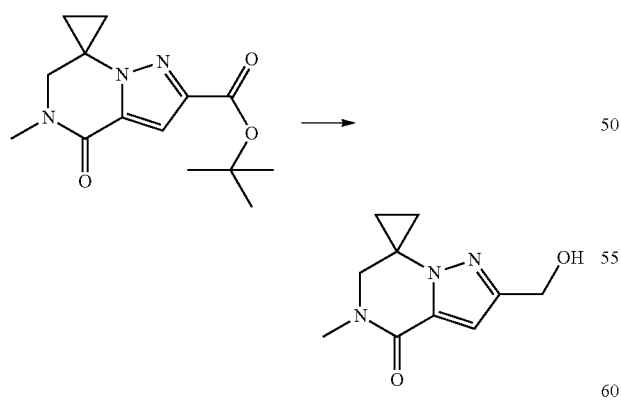

To tert-butyl 5-methyl-4-oxo-spiro[6H-pyrazolo[1,5-a]pyrazine-7,1'-cyclopropane]-2-carboxylate (182 mg, 0.66 mmol) in anhydrous THF (10 mL) cooled in an ice/water bath was added lithium aluminium hydride (25 mg, 0.66 mmol) portion-wise over 15 min. The mixture was stirred with ice bath in place for 2 hrs, carefully quenched with water (25 μL), 2M NaOH(aq) (25 μL) and further water (75 μL). MgSO$_4$ was added to the mixture and stirred for 15 min at rt. The mixture was filtered and concentrated in vacuo to afford the title compound (93 mg, 73%).

[M+H]$^+$=208.1

Tert-butyl 2-(hydroxymethyl)-7,8-dihydro-1,6-naphthyridine-6(5H)-carboxylate

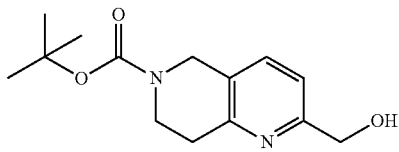 [SMILES: CC(C)(C)OC(=O)N1CCc2nc(CO)ccc2C1]

Synthesis of tert-butyl 2-(hydroxymethyl)-7,8-dihydro-1,6-naphthyridine-6(5H)-carboxylate is reported in WO2016014463.

Tert-Butyl 3-(hydroxymethyl)-5,8-dihydro-1,7-naphthyridine-7(6H)-carboxylate

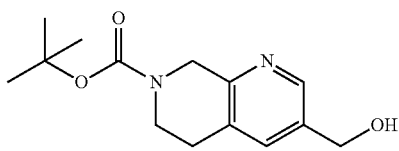 [SMILES: CC(C)(C)OC(=O)N1CCc2cc(CO)cnc2C1]

Synthesis of tert-butyl 3-(hydroxymethyl)-5,8-dihydro-1,7-naphthyridine-7(6H)-carboxylate is reported in WO2016014463.

Tert-Butyl 5-bromo-7-fluoro-3,4-dihydroisoquinoline-2(1H)-carboxylate

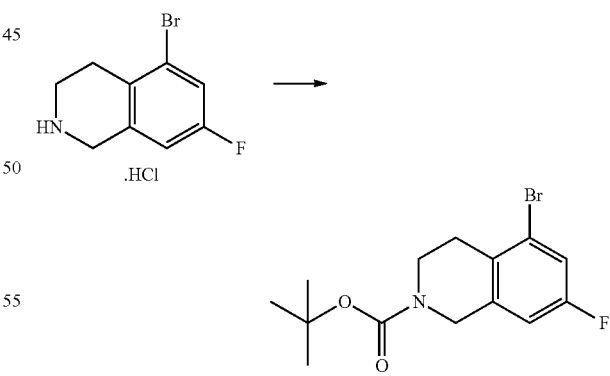

To a stirred suspension of 5-bromo-7-fluoro-1,2,3,4-tetrahydroisoquinoline HCl (500 mg, 1.88 mmol) in DCM (5 mL) at rt was added TEA (0.78 mL, 5.6 mmol). To this suspension was added di-tert-butyl dicarbonate (450 mg, 2.06 mmol) and the mixture stirred at rt for 18 hrs. The mixture was diluted with DCM (50 mL) and washed with water (2×25 mL) and brine (25 mL). The organic phase was dried via a hydrophobic frit and concentrated in vacuo. Flash chromatography (0-50% EtOAc in hexane) afforded the title compound (598 mg, 97%) as a colourless oil which solidified on standing.

[M+H]⁺=331.8/333.8

Tert-Butyl 7-fluoro-5-formyl-3,4-dihydroisoquinoline-2(1H)-carboxylate

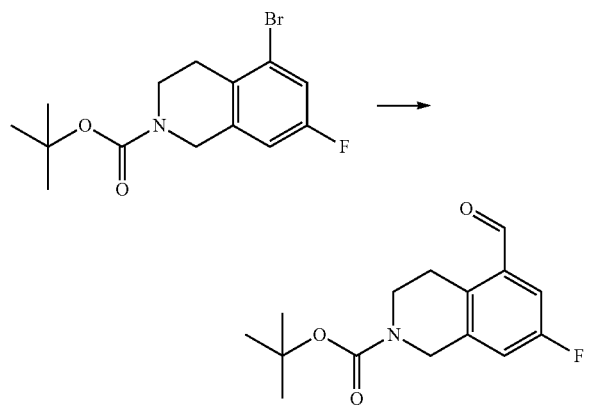

A solution of tert-butyl 7-fluoro-5-formyl-3,4-dihydroisoquinoline-2(1H)-carboxylate (598 mg, 1.81 mmol) and 1,1'-bis(diphenylphosphino)ferrocenedichloro palladium(ii) dichloromethane complex (72 mg, 0.09 mmol) in anhydrous DMF (20 mL) was treated with triethylsilane (580 μL, 3.63 mmol) and then TEA (730 μL, 5.24 mmol). The vessel was sealed and the resulting solution was purged 3 times with N₂, then 3 times with CO. The mixture was placed under a 4 bar atmosphere of CO, stirred and heated at 110° C. for 18 hrs. The mixture was filtered through Celite, washed with DCM and the filtrate concentrated in vacuo. The resulting residue was diluted with DCM (20 mL) and NaHCO₃(aq) (20 mL) and the layers were separated. The aqueous layer was extracted with DCM (2×50 mL), the organic layers were combined, washed with water, brine, dried over Na₂SO₄ and concentrated in vacuo. Flash chromatography (0 to 80% EtOAc/Isohexanes) afforded the title compound (0.86 g, 88%) as a colourless oil.

[(M-tBu)+H]=223.9

Tert-Butyl 7-fluoro-5-(hydroxymethyl)-3,4-dihydroisoquinoline-2(1H)-carboxylate

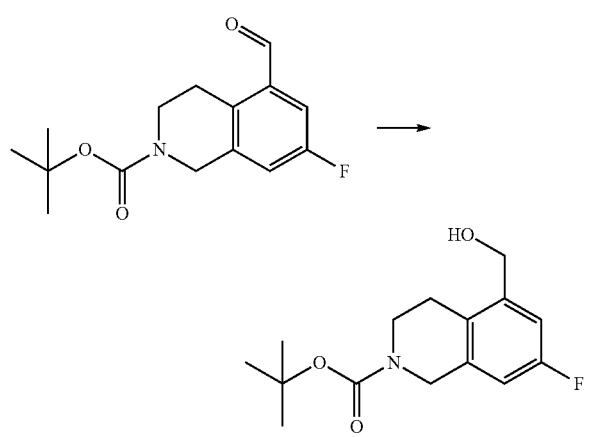

To a solution of tert-butyl 7-fluoro-5-formyl-3,4-dihydroisoquinoline-2(1H)-carboxylate (327 mg, 1.17 mmol) in a mixture of THF (8 mL) and MeOH (8 mL) was added NaBH₄ (71 mg, 1.88 mmol) and stirred in an ice/water bath for 60 min. Solvents were removed in vacuo and the residue partitioned between EtOAc (50 mL) and water (50 mL). The aqueous was extracted with further EtOAc and the combined organics washed with brine (50 mL), dried over MgSO₄ and concentrated in vacuo to afford the title compound (336 mg, 95%) as a clear gum.

[(M-tBu)+H]⁺=225.9

¹H NMR (DMSO-d6) 1.43 (9H, s), 2.62 (2H, t, J=6.3 Hz), 3.55 (2H, t, J=6.0 Hz), 4.42-4.56 (4H, m), 5.25 (1H, t, J=5.4 Hz), 6.93 (1H, dd, J=9.4, 2.7 Hz), 7.06 (1H, dd, J=10.1, 2.8 Hz).

Tert-Butyl 5-(chloromethyl)-7-fluoro-3,4-dihydroisoquinoline-2(1H)-carboxylate

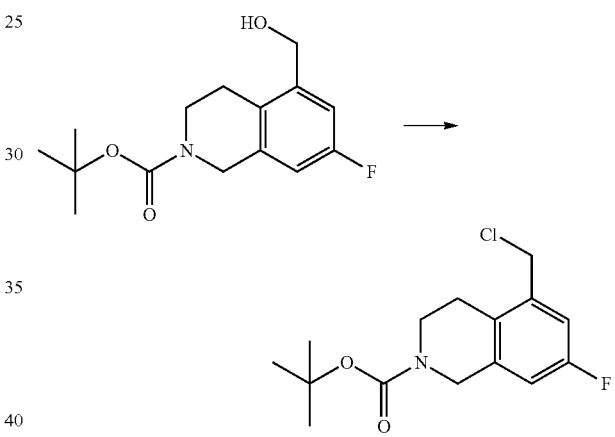

tert-Butyl 5-(chloromethyl)-7-fluoro-3,4-dihydroisoquinoline-2(1H)-carboxylate was prepared from tert-butyl 7-fluoro-5-(hydroxymethyl)-3,4-dihydroisoquinoline-2(1H)-carboxylate according to procedure L6e.

[(M-tBu)+H]⁺=243.9

Tert-Butyl 6-bromo-4,4-difluoro-1,3-dihydroisoquinoline-2-carboxylate (L1f)

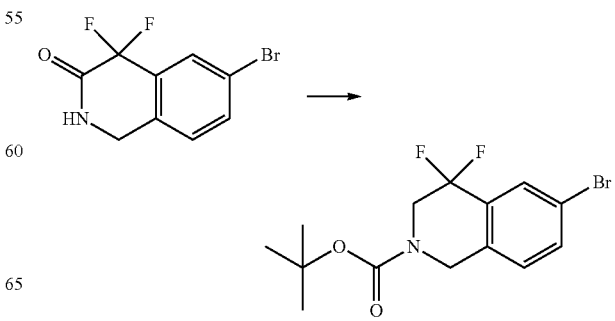

To a solution of 6-bromo-4,4-difluoro-1,2-dihydroisoquinolin-3-one (3.91 g, 14.9 mmol) in anhydrous THF (50 mL) was added borane tetrahydrofuran complex (75 mL, 75 mmol) dropwise and the mixture stirred at reflux for 2 hrs, cooled to rt and allowed to stir overnight. 1M HCl(aq) (60 mL, 60 mmol) was added carefully dropwise. On completion of the addition, the mixture was heated to reflux for 2 hrs and cooled to rt. The mixture was concentrated to low volume and water (75 mL) was added. The pH was adjusted to pH 10 with 2N NaOH(aq). The aqueous was extracted with EtOAc (3×100 mL). The combined organics were washed with brine (50 mL), dried over MgSO₄ and concentrated in vacuo to afford a clear oil. The oil was dissolved in THF (75 mL) and di-tert-butyl dicarbonate (3.26 g, 14.9 mmol) added. The mixture was stirred at rt for 60 min. Solvents were removed in vacuo and flash chromatography (silica, eluent: 0-40% EtOAc/Iso-Hexanes) afforded the title compound (4.79 g, 85%) as a clear gum.

[(M-tBu-HF)+H]⁺=272.1/274.1

¹H NMR (d6-DMSO) 1.43 (9H, s), 4.06 (2H, t, J=11.6 Hz), 4.62 (2H, s), 7.39 (1H, d, J=8.3 Hz), 7.73 (1H, d, J=8.4 Hz), 7.81 (1H, s).

Tert-Butyl 4,4-difluoro-6-formyl-1,3-dihydroisoquinoline-2-carboxylate (L2f)

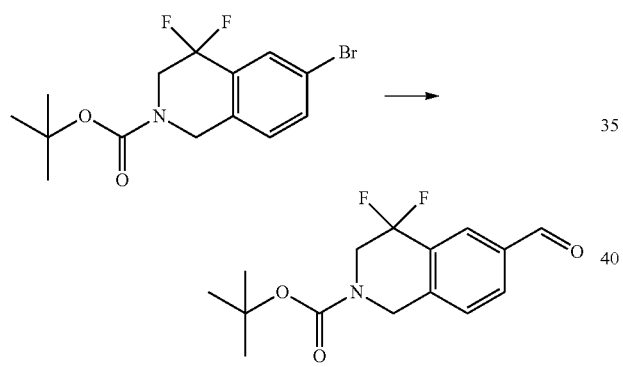

A stainless steel bomb with glass insert was used. A solution of tert-butyl 6-bromo-4,4-difluoro-1,3-dihydroisoquinoline-2-carboxylate (4.29 g, 12.3 mmol) and 1,1'-bis(diphenylphosphino)ferrocenedichloropalladium(II) dichloromethane complex (504 mg, 0.62 mmol) in DMF (150 mL) was treated with TEA (5.15 mL, 36.9 mmol) then triethylsilane (3.95 mL, 24.7 mmol). The vessel was sealed, purged with N₂ gas (×3) before purging with CO gas (×2) and finally pressurising to 4 bar with CO gas. The mixture was heated at 110° C. with stirring for 18 hrs then left at rt for 3 days. The pressure was released and the vessel purged with N₂ gas (×3) prior to opening. The crude mixture was filtered through Celite, washed with DCM and concentrated in vacuo. Flash chromatography (0-70% EtOAc/Iso-Hexanes) afforded the title compound (3.25 g, 80%) as a pale yellow viscous oil.

[(M-tBu-HF)+H]⁺=222.1

¹H NMR (d6-DMSO) 1.44 (9H, s), 4.12 (2H, t, J=11.7 Hz), 4.77 (2H, s), 7.64 (1H, d, J=8.1 Hz), 8.02 (1H, d, J=8.1 Hz), 8.21 (1H, s), 10.06 (1H, s).

Tert-Butyl 4,4-difluoro-6-(hydroxymethyl)-1,3-dihydroisoquinoline-2-carboxylate (L3f)

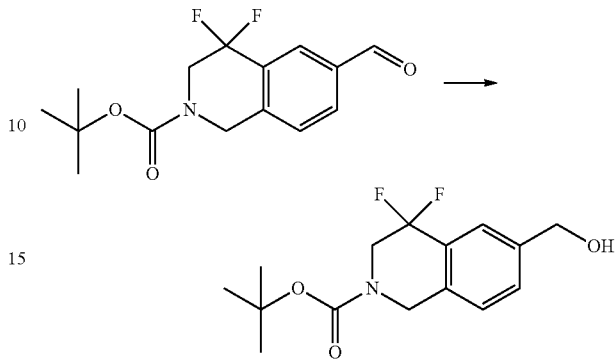

A solution of tert-butyl 4,4-difluoro-6-formyl-1,3-dihydroisoquinoline-2-carboxylate (3.25 g, 10.9 mmol) in MeOH (130 mL) was cooled in an ice-baths. NaBH₄ (0.83 g, 21.9 mmol) was added portion wise over 20 min and the mixture allowed to stir for 60 min. Solvents were removed in vacuo and the residue partitioned between EtOAc (50 mL) and water (50 mL). The aqueous was extracted with further EtOAc and the combined organics washed with brine (50 mL), dried over MgSO₄ and concentrated in vacuo. Flash chromatography (0-60% EtOAc/Iso-Hexanes) afforded the title compound (2.48 g, 68%) as a clear gum.

[(M-tBu-HF)+H]⁺=224.2

¹H NMR (d6-DMSO) 1.43 (9H, s), 4.01-4.10 (2H, m), 4.53 (2H, d, J=5.6 Hz), 4.63 (2H, s), 5.31 (1H, t, J=5.7 Hz), 7.32 (1H, d, J=8.0 Hz), 7.43 (1H, d, J=8.0 Hz), 7.60 (1H, s).

Tert-Butyl 6-(chloromethyl)-4,4-difluoro-1,3-dihydroisoquinoline-2-carboxylate (L4f)

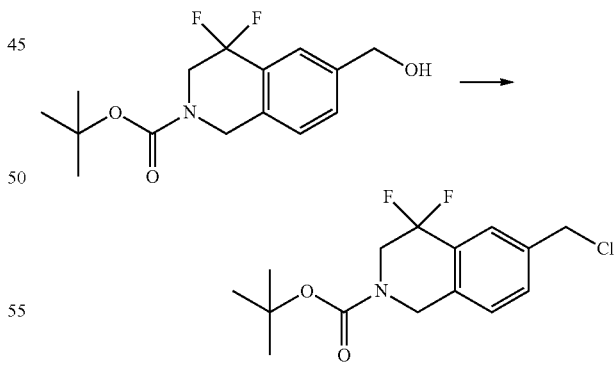

tert-Butyl 6-(chloromethyl)-4,4-difluoro-1,3-dihydroisoquinoline-2-carboxylate was prepared from tert-butyl 4,4-difluoro-6-(hydroxymethyl)-1,3-dihydroisoquinoline-2-carboxylate using procedure L3d.

[(M-tBu-HF)+H]⁺=242.2

¹H NMR (d6-DMSO) 1.43 (9H, s), 4.07 (2H, t, J=10.9 Hz), 4.66 (2H, s), 4.83 (2H, s), 7.41 (1H, d, J=8.0 Hz), 7.58 (1H, d, J=8.0 Hz), 7.74 (1H, s).

Tert-Butyl 7-(chloromethyl)-4,4-difluoro-3,4-dihydroisoquinoline-2(1H)-carboxylate

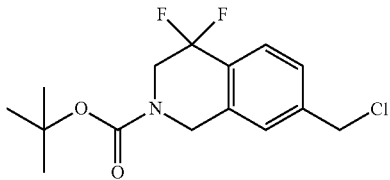 [SMILES: CC(C)(C)OC(=O)N1Cc2cc(CCl)ccc2C(F)(F)C1]

tert-butyl 7-(chloromethyl)-4,4-difluoro-3,4-dihydroisoquinoline-2(1H)-carboxylate was prepared from 7-bromo-4,4-difluoro-1,2-dihydroisoquinolin-3-one according to procedures L1f to L4f.

[(M-tBu-HF)+H]$^+$=242.2

$^1$H NMR (d6-DMSO) 1.43 (9H, s), 4.02-4.12 (2H, m), 4.66 (2H, s), 4.79 (2H, s), 7.46 (1H, s), 7.49 (1H, d, J=8.0 Hz), 7.68 (1H, d, J=8.0 Hz)

7-Bromo-8-fluoro-1,2,3,4-tetrahydroisoquinoline

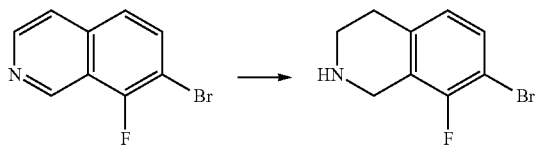 [SMILES: Fc1c(Br)ccc2ccncc12 ; Fc1c(Br)ccc2c1CNCC2]

NaBH$_4$ (1 g, 26.4 mmol) was dissolved in AcOH (40 mL) and 7-bromo-8-fluoro-isoquinoline (1.95 g, 8.63 mmol) was added and stirred for 60 min. A further portion of NaBH$_4$ (500 mg, 13.2 mmol) was added and the mixture stirred for an additional 2 hrs. The mixture was passed directly into 2M NaOH(aq) (200 mL) and washed in with TBME (100 mL). The layers were separated and the aqueous extracted further with TBME. The combined organic layers were washed with brine, dried over MgSO$_4$ and concentrated in vacuo to provide the title compound (1.31 g, 63%) as a colourless oil.

[M+H]$^+$=230.1

Tert-Butyl 7-bromo-8-fluoro-3,4-dihydro-1H-isoquinoline-2-carboxylate

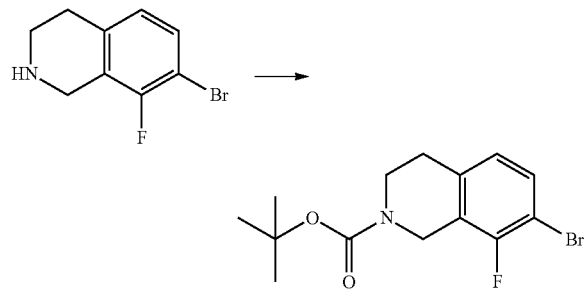

tert-Butyl 7-bromo-8-fluoro-3,4-dihydro-1H-isoquinoline-2-carboxylate was prepared from 7-bromo-8-fluoro-1,2,3,4-tetrahydroisoquinoline according to procedure L1e.

[(M-tBu)+H]$^+$=274.1

Tert-Butyl 8-fluoro-7-(hydroxymethyl)-3,4-dihydro-1H-isoquinoline-2-carboxylate

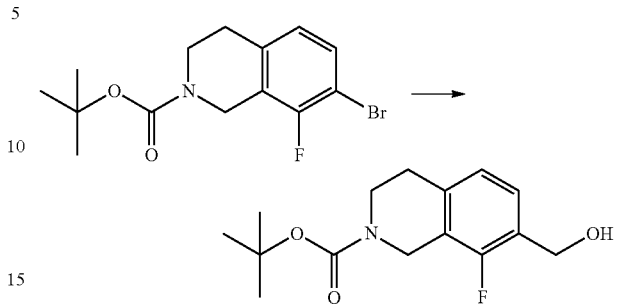

To a solution of tert-butyl 7-bromo-8-fluoro-3,4-dihydro-1H-isoquinoline-2-carboxylate (1.05 g, 3.18 mmol) in THF (10.5 mL) in a cold bath at −78° C. was added n-butyllithium in THF solution (1.8M, 2 mL, 3.6 mmol) and the solution stirred for 60 min. DMF (600 µL, 7.8 mmol) was added and the mixture stirred in a cold bath at −78° C. for 30 min. Acetic acid (200 µL, 3.49 mmol) was added and the mixture allowed to warm to rt and stirred overnight. To the mixture was added 1M HCl(aq) (20 mL) and DCM (20 mL) and the phases separated. The organics were concentrated in vacuo. The residue was dissolved in THF (5 mL), MeOH (5 mL) and water (5 mL) and NaBH$_4$ (132 mg, 3.5 mmol) added. On completion of the reaction DCM (5 mL) and 1M HCl (aq) (5 mL) were added and the mixture passed through a phase separator. The organics were collected and concentrated in vacuo. Flash chromatography (10-90% TBME in isohexanes) afforded the title compound (322 mg, 34%) as a colourless oil.

[(M-tBu-OH)+H]$^+$=208.0

$^1$H NMR (DMSO-d6,) 1.43 (9H, s), 2.77 (2H, d, J=5.8 Hz), 3.56 (2H, d, J=5.8 Hz), 4.44-4.55 (4H, m), 5.20 (1H, d, J=5.7 Hz), 7.00 (1H, d, J=7.8 Hz), 7.27 (1H, d, J=7.8 Hz).

Tert-Butyl 7-(chloromethyl)-8-fluoro-3,4-dihydro-1H-isoquinoline-2-carboxylate

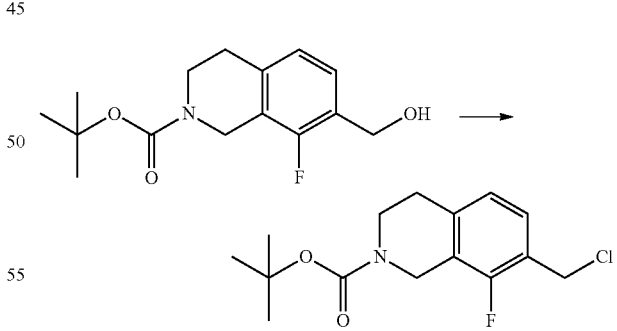

tert-Butyl 7-(chloromethyl)-8-fluoro-3,4-dihydro-1H-isoquinoline-2-carboxylate was prepared from tert-butyl 8-fluoro-7-(hydroxymethyl)-3,4-dihydro-1H-isoquinoline-2-carboxylate according to procedure L3d.

[(M-tBu)+H]$^+$=244.1

$^1$H NMR (DMSO-d6) 1.44 (9H, s), 2.81 (2H, d, J=5.8 Hz), 3.57 (2H, t, J=5.8 Hz), 4.52 (2H, s), 4.77 (2H, s), 7.04 (1H, d, J=7.8 Hz), 7.35 (1H, t, J=7.8 Hz).

Tert-Butyl 7-(hydroxymethyl)-2,3-dihydrobenzo[f][1,4]oxazepine-4(5H)-carboxylate

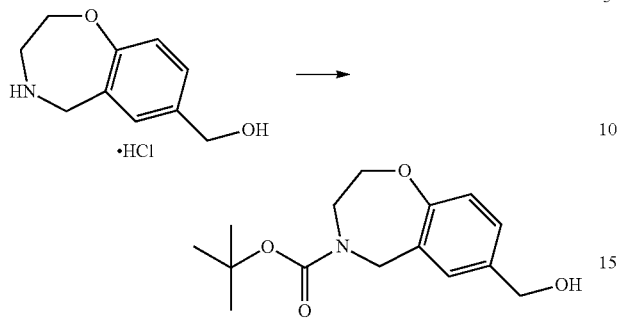

A suspension of 2,3,4,5-tetrahydro-1,4-benzoxazepin-7-ylmethanol hydrochloride (1 g, 4.6 mmol) in DCM (20 mL) was treated with DIPEA (1 mL, 5.73 mmol). To the stirred solution was added di-tert-butyl dicarbonate (1.2 g, 5.50 mmol). The solvent was removed in vacuo and flash chromatography (0-50% TBME in isohexanes) afforded the title compound (1.3 g, 82%) as a colourless oil.

[M−H]⁻=278.3

$^1$H NMR (CDCl$_3$) 1.41 (9H, s), 3.80 (2H, t, J=4.4 Hz), 3.98-4.06 (2H, m), 4.45 (2H, m), 4.64 (2H, s), 7.04 (1H, d, J=8.0 Hz), 7.20 (2H, s).

Tert-Butyl 2-(hydroxymethyl)-6,7-dihydrothiazolo[5,4-c]pyridine-5(4H)-carboxylate

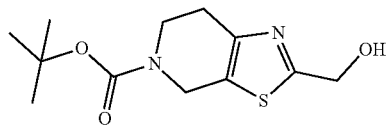 [SMILES: CC(C)(C)OC(=O)N1CCc2nc(CO)sc2C1]

Synthesis of tert-butyl 2-(hydroxymethyl)-6,7-dihydrothiazolo[5,4-c]pyridine-5(4H)-carboxylate (CAS 1190971-76-6) is reported in WO2009124746.

N-[2-(3-Bromo-2-fluoro-phenyl)ethyl]-2,2,2-trifluoro-acetamide

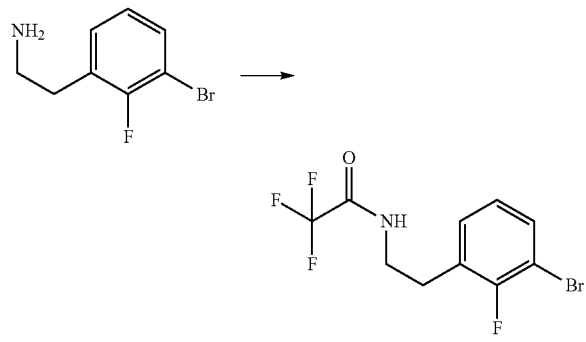

To a stirred solution of 2-(3-bromo-2-fluoro-phenyl)ethanamine (6.2 g, 11.7 mmol) in DCM (27 mL) was added TEA (2.7 mL, 19 mmol). The mixture was cooled in an ice/water bath and trifluoroacetic anhydride (3.1 mL, 22 mmol) slowly added. The mixture was warmed to rt and stirred for 90 min. TEA (1 mL, 7.2 mmol) and trifluoroacetic anhydride (1 mL, 7.1 mmol) were added. The mixture was stirred for 2 hrs, diluted with DCM (100 mL) and washed with saturated NaHCO$_3$(aq), NH$_4$Cl(aq) and brine. The organic layer was dried over MgSO$_4$ and concentrated in vacuo. Flash chromatography (EtOAc:Hexane 0-30%) afforded the title compound (2.5 g, 59%) as a white solid.

[M+H]⁺=330.8/332.8

1-(6-Bromo-5-fluoro-3,4-dihydro-1H-isoquinolin-2-yl)-2,2,2-trifluoro-ethanone

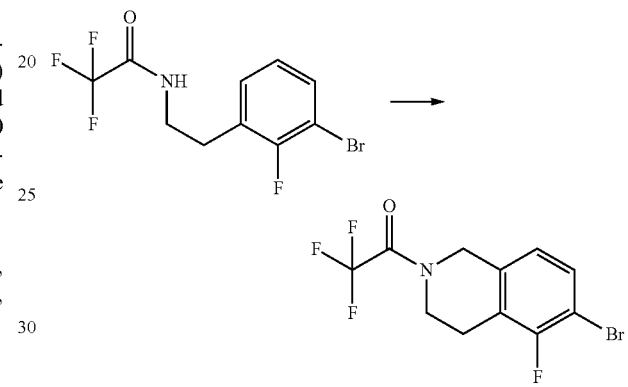

Paraformaldehyde (0.252 g, 8.39 mmol) was added to a solution of N-[2-(3-bromo-2-fluoro-phenyl)ethyl]-2,2,2-trifluoro-acetamide (1.5 g, 4.8 mmol) in AcOH (9 mL). Sulfuric acid (6 mL 113 mmol) was added dropwise and the mixture heated at 50° C. for 5 hrs and at rt overnight. The mixture was cooled to rt and partitioned between EtOAc (50 mL) and water (30 mL). The aqueous layer was extracted with EtOAc and the combined organic layers were washed with brine, dried over Na$_2$SO$_4$ and concentrated in vacuo. Flash chromatography (EtOAc:Hexane 0-30%) afforded the title compound (1.43 g, 85%) as a colourless oil that solidified upon standing.

[M+H]⁺=325.6/327.7

6-Bromo-5-fluoro-1,2,3,4-tetrahydroisoquinoline

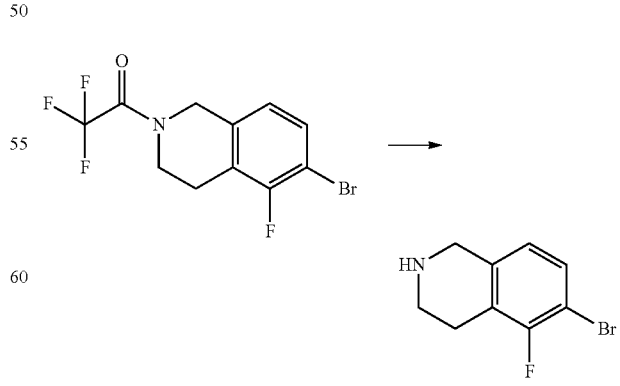

Water (3 mL) was added to a suspension of Na$_2$CO$_3$ (0.53 g, 5 mmol) and 1-(6-bromo-5-fluoro-3,4-dihydro-1H-isoquinolin-2-yl)-2,2,2-trifluoro-ethanone (1.46 g, 4.16 mmol) in MeOH (6 mL). The mixture was stirred at rt for 3 hrs. The mixture was concentrated in vacuo to remove MeOH and diluted with EtOAc (10 mL) and water (5 mL). The organic layer was separated and the aqueous phase was extracted with EtOAc. The organic layers were combined, dried over Na₂SO₄ and concentrated in vacuo to give the title compound (0.96 g, 99%) as a yellow oil.

[M+H]⁺=229.9/231.9

Tert-Butyl 6-bromo-5-fluoro-3,4-dihydro-1H-isoquinoline-2-carboxylate

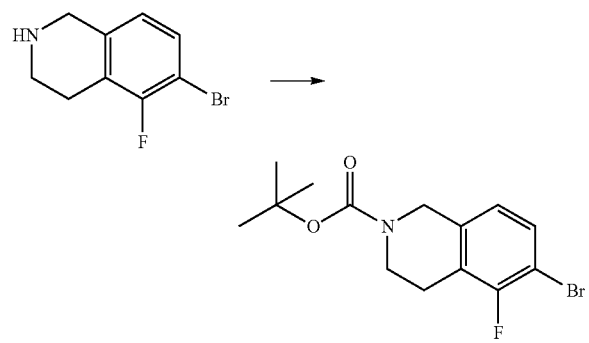

TEA (646 uL, 4.63 mmol) was added to a suspension of 6-bromo-5-fluoro-1,2,3,4-tetrahydroisoquinoline (0.964 g, 4.15 mmol) and di-tert-butyl dicarbonate (1.81 g, 8.3 mmol) in THF (24 mL). The mixture was stirred at rt overnight. The mixture was diluted with EtOAc (30 mL) and water (20 mL). The organic layer was separated, the aqueous layer was extracted with EtOAc and the organic layers were combined, dried over Na₂SO₄ and concentrated in vacuo to give a colourless oil. Flash chromatography (0-40% EtOAc in hexane) afforded the title compound (1.17 g, 84%) as a colourless oil.

[M+H]⁺=331.8/333.8

Tert-Butyl 5-fluoro-6-formyl-3,4-dihydro-1H-isoquinoline-2-carboxylate

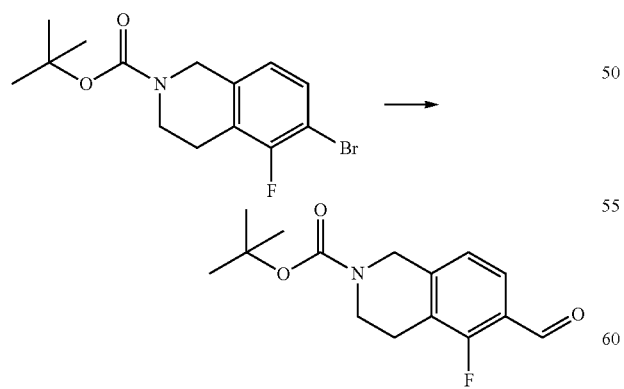

A stirred solution of tert-butyl 6-bromo-5-fluoro-3,4-dihydro-1H-isoquinoline-2-carboxylate (880 mg, 2.67 mmol) in THF (15 mL) was cooled in a cold bath at −78° C. ⁿBuLi in THF solution (1.5 mL, 2.5M, 3.75 mmol) was added dropwise over 15 min and the mixture stirred for 30 min. DMF (0.5 mL, 6.46 mmol) was added. The mixture was slowly warmed to rt and 5% citric acid (aq) solution (1 mL) was added. The mixture was extracted with TBME (100 mL) and the organic layer washed with brine (50 mL), dried over MgSO₄ and concentrated in vacuo. Flash chromatography (0-20 TBME/isohexane) afforded the title compound (230 mg, 29%) as a colourless solid ¹H NMR (CDCl₃) 1.48 (9H, s), 2.86 (2H, t, J=6.0 Hz), 3.69 (2H, t, J=5.9 Hz), 4.63 (2H, s), 6.81-7.04 (1H, m), 7.69 (1H, t, J=7.4 Hz), 10.33 (1H, s).

Tert-Butyl 5-fluoro-6-(hydroxymethyl)-3,4-dihydroisoquinoline-2(1H)-carboxylate

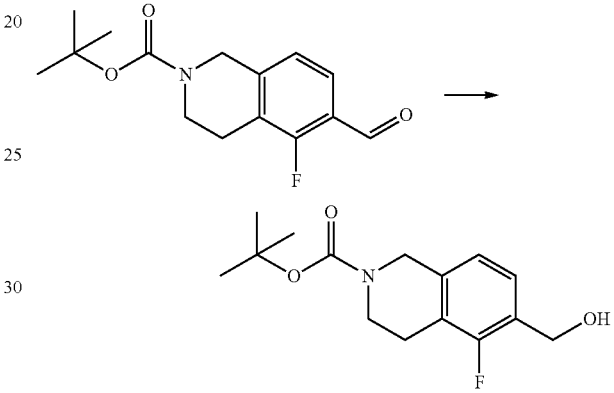

A stirred solution of tert-butyl 5-fluoro-6-formyl-3,4-dihydro-1H-isoquinoline-2-carboxylate (230 mg, 0.82 mmol) in EtOH (10 mL) was treated with NaBH₄ (31.2 mg, 0.82 mmol) and stirring continued for 30 min.

Brine (20 mL) was added and 5% citric acid (aq) (1 mL). The mixture was extracted with EtOAc and the combined organic layers were dried over MgSO₄ and concentrated in vacuo. Flash chromatography (0-50% EtOAc/isohexanes) afforded the title compound (190 mg, 78%) as a colourless oil.

¹H NMR (CDCl₃) 1.51 (9H, s), 2.83 (2H, t, J=6.0 Hz), 3.67 (2H, t, J=5.9 Hz), 4.59 (2H, s), 4.75 (2H, s), 6.93 (1H, t, J=7.9 Hz), 7.25 (1H, t, J=7.6 Hz).

Tert-Butyl 8-fluoro-6-(hydroxymethyl)-3,4-dihydroisoquinoline-2(1H)-carboxylate

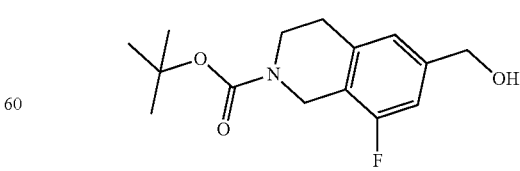

Synthesis of tert-butyl 8-fluoro-6-(hydroxymethyl)-3,4-dihydroisoquinoline-2(1H)-carboxylate is reported in WO2016014463.

N-[(3-Bromo-4-fluoro-phenyl)methyl]-2,2-dimethoxy-ethanamine

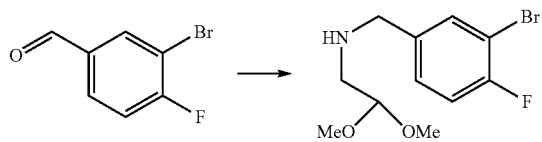 [SMILES: O=Cc1ccc(F)c(Br)c1 ; COC(CNCc1ccc(F)c(Br)c1)OC]

To 3-bromo-4-fluoro-benzaldehyde (5 g, 25 mmol) in toluene (25 mL) was added 2,2-dimethoxyethanamine (3 mL, 28 mmol) and the mixture stirred at rt. On completion of the reaction the mixture was concentrated in vacuo and the residue dissolved in MeOH (25 mL). NaBH$_4$ (1.1 g, 29 mmol) added portion wise. The mixture was stirred at rt for 2 hrs. Water (15 mL) was added and the volatile organics removed in vacuo. The resulting aqueous solution was extracted with EtOAc and the combined organic extracts dried over MgSO$_4$ and concentrated in vacuo to give the title compound (7.2 g, 100%).

N-[(3-Bromo-4-fluoro-phenyl)methyl]-N-(2,2-dimethoxyethyl)-4-methyl-benzenesulfonamide

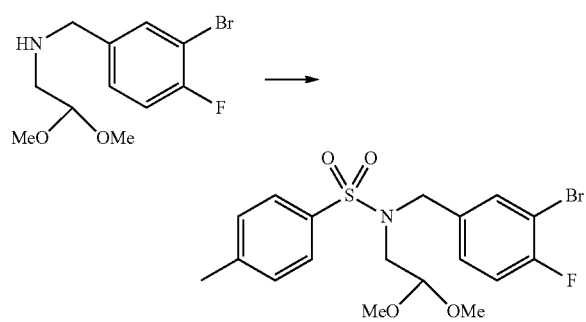

Pyridine (2.14 mL, 26.5 mmol) was added to a solution of N-[(3-bromo-4-fluoro-phenyl)methyl]-2,2-dimethoxyethanamine (7.2 g, 24.6 mmol) and p-toluenesulfonyl chloride (5.45 g, 28.6 mmol) in DCM (80 mL). The mixture was stirred at rt for 18 hrs, diluted with DCM (200 mL) and water (100 mL). The organic phase was separated and the aqueous phase extracted with DCM (200 mL). The combined organic phases were washed with brine, dried over Na$_2$SO$_4$ and concentrated in vacuo. Flash chromatography (50-100% EtOAc in hexane) afforded the tile compound (9 g, 81%) as a colourless oil.

[(M−2CH$_3$)+H]$^+$=413.8/415.8
$^1$H NMR (DMSO-d6) 2.41 (3H, s), 3.12 (6H, s), 3.17 (2H, d, J=5.3 Hz), 4.28 (1H, t, J=5.3 Hz), 4.34 (2H, s), 7.31-7.37 (2H, m), 7.41-7.45 (2H, m), 7.47-7.50 (1H, m), 7.72-7.77 (2H, m).

7-Bromo-6-fluoro-isoquinoline

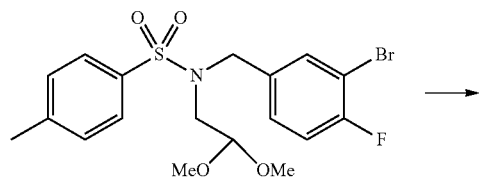

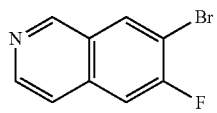

N-[3-Bromo-4-fluoro-phenyl)methyl]-N-(2,2-dimethoxyethyl)-4-methyl-benzenesulfonamide (9 g, 20 mmol) in DCM (160 mL) was treated with trichloroalumane (10.7 g, 80.2 mmol) and the mixture stirred at rt for 2 days. The mixture was slowly poured into a mixture of 2N NaOH (aq) (200 mL) and ice (200 g), diluted with DCM (300 mL) and the organic phase collected, dried over MgSO$_4$ and concentrated in vacuo. Flash chromatography (0-100% EtOAc in isohexanes) afforded the title compound (3 g, 55%) as an orange solid.

[M+H]$^+$=225.8/227.8

7-Bromo-6-fluoro-1,2,3,4-tetrahydroisoquinoline

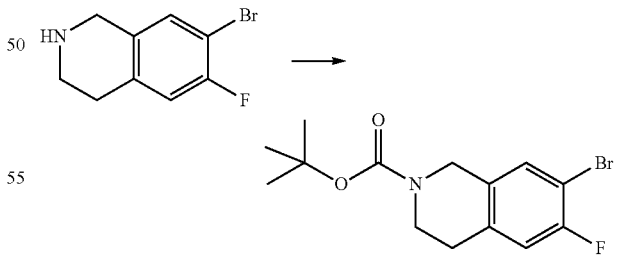

NaBH$_4$ (2.5 g, 66 mmol) was added portion wise to AcOH (300 mL) at rt. 7-Bromo-6-fluoro-isoquinoline (7.4 g, 32.7 mmol) was added and the mixture stirred at rt for 60 min. Additional NaBH$_4$ (2.5 g, 66.1 mmol) was added and the mixture stirred for a further 60 min. Additional NaBH$_4$ (0.25 g, 6.61 mmol) and the mixture stirred for a further 60 min. The mixture was quenched into water (300 mL) and TBME (600 mL) added. The layers were separated, and the aqueous layer extracted further with TBME. The organic layers were concentrated in vacuo and taken up in EtOAc (200 mL). The combined aqueous phases were basified to pH 10 using NaOH and extracted with EtOAc. The combined organic layers were dried over Na$_2$SO$_4$ and concentrated in vacuo to give the title compound (6.4 g, 78%).

[M+H]$^+$=230.0/232.1

Tert-Butyl 7-bromo-6-fluoro-3,4-dihydro-1H-isoquinoline-2-carboxylate

TEA (6.1 mL, 43.8 mmol) was added to a suspension of di-tert-butyl dicarbonate (14 g, 64.1 mmol) and 7-bromo-6-fluoro-1,2,3,4-tetrahydroisoquinoline (6.4 g, 25.6 mmol) in THF (150 mL). The mixture was stirred at rt overnight and diluted with EtOAc (200 mL) and water (100 mL). The organic layer was separated and the aqueous layer was extracted with EtOAc. The combined organic layers were washed with brine, dried over Na$_2$SO$_4$ and concentrated in vacuo. Flash chromatography (0-20% EtOAc in hexane) afforded the title compound (8.35 g, 83%) as a white solid.
[(M-tBu)+H]⁺=273.9/275.9
¹H NMR (DMSO-d6) 1.42 (9H, s), 2.74 (2H, t, J=6.0 Hz), 3.52 (2H, t, J=5.9 Hz), 4.42-4.49 (2H, m), 7.20 (1H, d, J=9.6 Hz), 7.57 (1H, d, J=7.1 Hz).

2-(tert-Butyl) 7-methyl 6-fluoro-3,4-dihydroisoquinoline-2,7(1H)-dicarboxylate

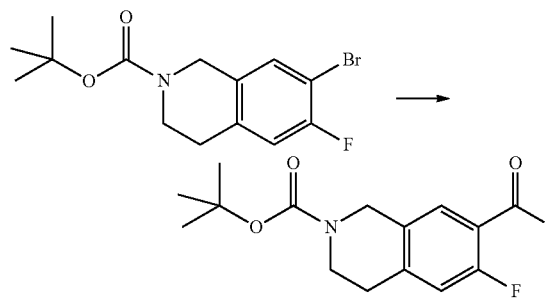

2-(tert-Butyl) 7-methyl 6-fluoro-3,4-dihydroisoquinoline-2,7(1H)-dicarboxylate was prepared from tert-butyl 7-bromo-6-fluoro-3,4-dihydro-1H-isoquinoline-2-carboxylate according to procedure L1d.
[(M-tBu)+H]⁺=254.0

Tert-Butyl 6-fluoro-7-(hydroxymethyl)-3,4-dihydro-(1H)-isoquinoline-2-carboxylate

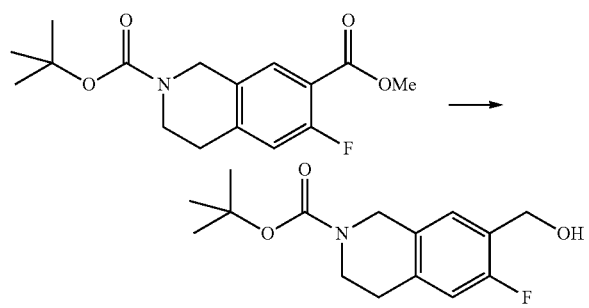

tert-Butyl 6-fluoro-7-(hydroxymethyl)-3,4-dihydro-(1H)-isoquinoline-2-carboxylate was prepared from 2-(tert-butyl) 7-methyl 6-fluoro-3,4-dihydroisoquinoline-2,7(1H)-dicarboxylate according to procedure L2d.
[(M-tBu-OH)+H]1=208.0

Methyl 3-(methoxymethyl)-1-((2-(methyl-d3)-1,2,3,4-tetrahydroisoquinolin-7-yl)methyl)-1H-pyrazole-4-carboxylate

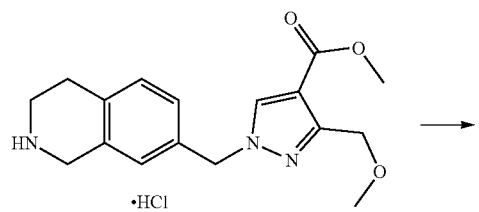

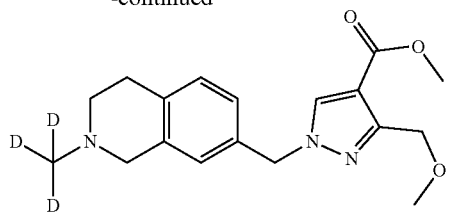

To a suspension of methyl 3-(methoxymethyl)-1-(1,2,3,4-tetrahydroisoquinolin-7-ylmethyl)pyrazole-4-carboxylate hydrochloride (600 mg, 1.71 mmol) and K₂CO₃ (707 mg, 5.12 mmol) in EtOH (6 mL) was added trideuterio(iodo)methane (0.13 mL, 2.13 mmol). The mixture was stirred at rt overnight, concentrated in vacuo and partitioned between DCM (30 mL) and brine (30 mL). The organic layer was passed through a phase separator and concentrated in vacuo. Flash chromatography (0-10% MeOH in DCM) afforded the title compound (130 mg, 21%) as an orange oil.
[M+H]⁺=333.3
¹H NMR (DMSO-d6) 2.55-2.60 (2H, m), 2.75-2.80 (2H, m), 3.23 (3H, s), 3.45 (2H, s), 3.72 (3H, s), 4.50 (2H, s), 5.25 (2H, s), 6.94-6.98 (1H, m), 7.01-7.05 (1H, m), 7.06-7.09 (1H, m), 8.38 (1H, s).

1-[2-(4-Bromophenyl)ethyl]pyrrolidine-2,5-dione

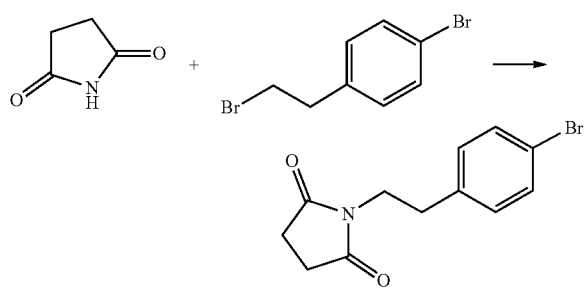

To a solution of pyrrolidine-2,5-dione (2.24 g, 22.6 mmol) in DMF (39.5 mL) was added NaH (1.00 g, 24.9 mmol) portion wise at rt. The mixture was stirred for 60 min and a solution of 1-bromo-4-(2-bromoethyl)benzene (6.59 g, 25 mmol) in DMF (13 mL) was added dropwise. The mixture was heated at 50° C. for 2 hrs and cooled in an ice-bath. EtOAc (100 mL) and brine (60 mL) were added and the mixture was stirred for 30 min and partitioned. The organic layer was washed with brine, dried over MgSO₄ and concentrated in vacuo. The residue was slurried in TBME (40 mL) overnight. The mixture was filtered and air-dried to afford the title compound (4.78 g, 74%) as a white solid.
[M+H]⁺=281.9/283.9

1-[2-(4-Bromophenyl)ethyl]-5-hydroxy-pyrrolidin-2-one

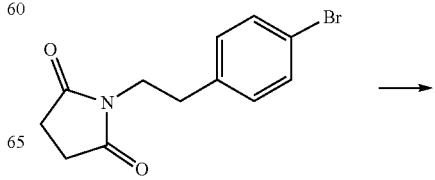

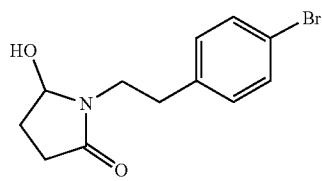

1-[2-(4-bromophenyl)ethyl]pyrrolidine-2,5-dione (1 g, 3.54 mmol) was dissolved in EtOH (125 mL) and water (10 mL) and the solution cooled in an ice-bath. NaBH$_4$ (805 mg, 21.3 mmol) was added and the mixture stirred. HCl (aq) (6M) was added dropwise at 10 min intervals so as to keep the pH value at 8-10 (1-2 drops every 10-20 min). After 2.25 hrs the pH value was adjusted to 4 with 6M (aq) HCl and the mixture poured into water (300 mL). This was extracted with DCM and the combined organics dried over MgSO$_4$, filtered and concentrated in vacuo to afford the title compound (972 mg, 87%) as a white solid.

[M+H]$^+$=284.0/286.0

9-Bromo-2,5,6,10b-tetrahydro-1H-pyrrolo[2,1-a]isoquinolin-3-one

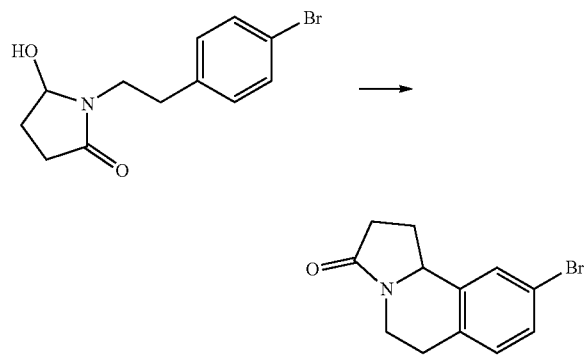

1-[2-(4-Bromophenyl)ethyl]-5-hydroxy-pyrrolidin-2-one (1010 mg, 3.54 mmol) was suspended in DCM (6 mL) and cooled in an ice-bath. Trifluoromethanesulfonic acid (0.63 mL, 7.08 mmol) was added and the mixture stirred at rt overnight. The mixture was diluted with DCM (25 mL) and partitioned over saturated NaHCO$_3$(aq) (30 mL). The aqueous layer was extracted with further DCM and the combined organics dried over Na$_2$SO$_4$ and concentrated in vacuo to afford a clear oil. Flash chromatography (40-100% EtOAc/Iso-Hexanes) afforded the title compound (790 mg, 83%) as a clear oil which crystallized on standing.

[M+H]$^+$=266.1/268.1

$^1$H NMR (DMSO-d6) 1.69 (1H, ddt, J=12.2, 10.9, 9.2 Hz), 2.26 (1H, ddd, J=16.4, 9.4, 1.9 Hz), 2.40-2.48 (1H, m), 2.66-2.81 (3H, m), 2.99 (1H, dddd, J=12.6, 10.8, 4.9, 1.3 Hz), 4.02 (1H, ddd, J=12.9, 6.1, 2.7 Hz), 4.75 (1H, t, J=8.1 Hz), 7.15 (1H, d, J=8.2 Hz), 7.38 (1H, dd, J=8.2, 2.1 Hz), 7.43 (1H, d, J=2.1 Hz)

Methyl 3-oxo-2,5,6,10b-tetrahydro-1H-pyrrolo[2,1-a]isoquinoline-9-carboxylate

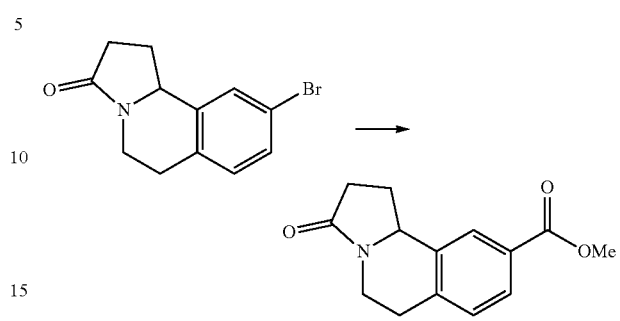

Methyl 3-oxo-2,5,6,10b-tetrahydro-1H-pyrrolo[2,1-a]isoquinoline-9-carboxylate was prepared from 9-bromo-2,5,6,10b-tetrahydro-1H-pyrrolo[2,1-a]isoquinolin-3-one according to procedure L1d.

$^1$H NMR (DMSO-d6) 1.70 (1H, ddt, J=12.2, 11.1, 9.3 Hz), 2.27 (1H, ddd, J=16.4, 9.4, 1.9 Hz),2.42-2.49 (1H, m), 2.73-2.78 (1H, m), 2.78-2.88 (2H, m), 3.04 (1H, dddd, J=12.6, 10.5, 5.0, 1.3 Hz), 3.85 (3H, s), 4.04 (1H, ddd, J=12.8, 6.0, 2.8 Hz), 4.81 (1H, t, J=8.1 Hz), 7.33 (1H, d, J=8.5 Hz), 7.73-7.81 (2H, m)

1,2,3,5,6,10b-Hexahydropyrrolo[2,1-a]isoquinolin-9-ylmethanol

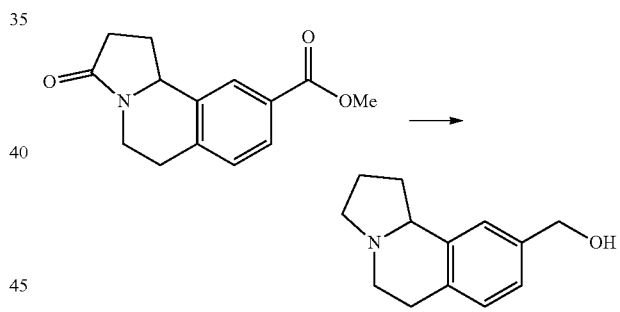

A solution of methyl 3-oxo-2,5,6,10b-tetrahydro-1H-pyrrolo[2,1-a]isoquinoline-9-carboxylate (200 mg, 0.69 mmol) in THF (4 mL) was cooled in an ice/water bath prior to the addition of a 1M THF solution of LiAlH$_4$ (3.2 mL, 3.2 mmol) dropwise. The mixture was warmed to rt for 1.5 hrs then cooled in an ice/water bath. A mixture of sodium sulfate decahydrate and Celite was added portion wise and the mixture stirred for 10 min. 1 to 2 drops of water were added cautiously followed by THF (10 mL) and further Celite mixture. This was stirred in an ice/water bath for 60 min then filtered washing with copious THF. Concentration in vacuo gave the title compound (167 mg, 98%) as a brown oil.

[M+H]$^+$=204.1

$^1$H NMR (DMSO-d6) 1.53 (1H, dtd, J=11.8, 10.3, 7.5 Hz), 1.72-1.83 (2H, m), 2.29 (1H, tdd, J=11.5, 5.5, 3.3 Hz), 2.37 (1H, q, J=8.6 Hz), 2.46 (1H, dt, J=10.7, 5.3 Hz), 2.66-2.76 (1H, m), 2.87-3.02 (2H, m), 3.08 (1H, ddd, J=11.1, 6.3, 2.9 Hz), 3.25 (1H, dd, J=9.8, 7.0 Hz), 4.43 (2H, d, J=5.7 Hz), 5.07 (1H, t, J=5.7 Hz), 6.98-7.08 (3H, m).

141

Tert-Butyl 7-(hydroxymethyl)-1,2,4,5-tetrahydro-3H-benzo[d]azepine-3-carboxylate

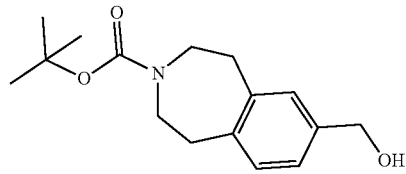 [SMILES: CC(C)(C)OC(=O)N1CCc2ccc(CO)cc2CC1]

Synthesis of tert-butyl 7-(hydroxymethyl)-1,2,4,5-tetrahydro-3H-benzo[d]azepine-3-carboxylate is reported in WO2017068412.

Methyl 3,4-bis(trimethylsilyl)benzoate

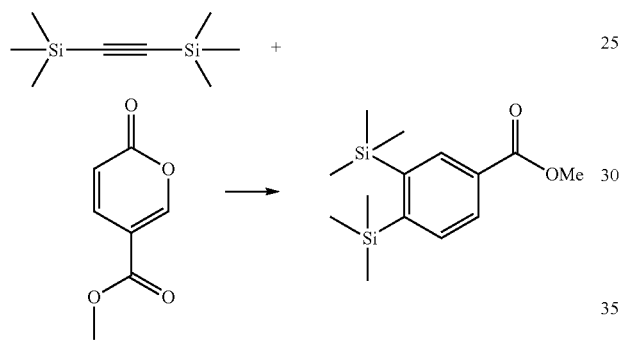

To a thick walled pressure vessel was added methyl 6-oxopyran-3-carboxylate (1 g, 6.49 mmol) and trimethyl(2-trimethylsilylethynyl)silane (3320 mg, 19.5 mmol). The vessel was sealed and the mixture heated to 200° C. overnight with stirring. The mixture was cooled and absorbed directly onto silica and purified by flash chromatography (0-30% EtOAc in hexane) to afford the title compound (1.76 g) as a colourless viscous oil.

[M+H]$^+$=281.1

$^1$H NMR (DMSO-d6) 0.37 (18H, t, J=1.7 Hz), 3.86 (3H, s), 7.80 (1H, d, J=7.8 Hz), 7.90 (1H, dd, J=7.9, 1.8 Hz), 8.20 (1H, d, J=1.8 Hz).

(4-Methoxycarbonyl-2-trimethylsilyl-phenyl)-phenyl-iodonium; trifluoromethanesulfonate

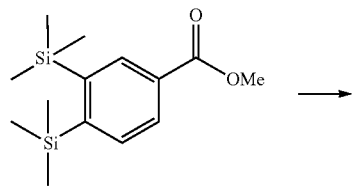

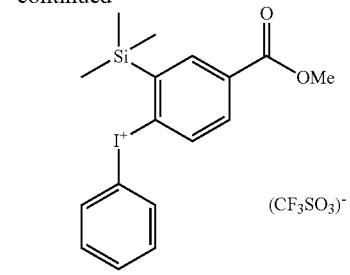

To phenyl-λ$^3$-iodanediyl diacetate (2.1 g, 6.52 mmol) dissolved in DCM (30 mL) in an ice/water bath was added trifluoromethanesulfonic acid (1.3 mL, 12.3 mmol) dropwise over 20 min. The mixture was stirred for 30 min and left to warm to rt. The mixture was again cooled in an ice/water bath and a solution of methyl 3,4-bis(trimethylsilyl)benzoate (1.76 g, 6.27 mmol) in DCM (3 mL) added. The mixture was left to warm to rt and stirred overnight. The volatiles were removed, and the residue triturated and sonicated with TBME (10 mL) to give the title compound (1.7 g1, 48%) as a white solid.

$^1$H NMR (DMSO-d6) 0.38 (9H, s), 3.93 (3H, s), 7.54 (2H, dd, J=8.4, 7.0 Hz), 7.60-7.66 (1H, m), 7.91 (1H, d, J=7.8 Hz), 7.93-7.98 (2H, m), 8.23 (1H, dd, J=7.7, 1.6 Hz), 9.08 (1H, d, J=1.6 Hz).

9-(tert-Butyl) 6-methyl-1,4-dihydro-1,4-epiminonaphthalene-6,9-dicarboxylate

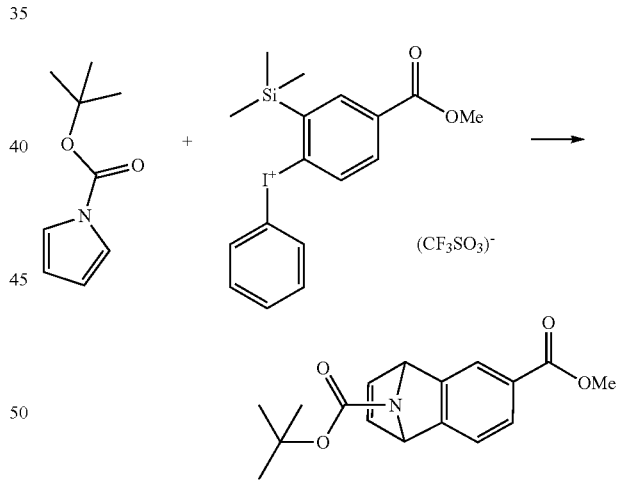

(4-Methoxycarbonyl-2-trimethylsilyl-phenyl)-phenyl-iodium; trifluoromethanesulfonate (1.7 g, 3.03 mmol) was dissolved in DCM (30 mL) and cooled in an ice/water bath. A solution of tert-butyl pyrrole-1-carboxylate (1.7 mL, 10.2 mmol) in THF (4 mL) was added dropwise over 10 min, followed by the addition of tetra-n-butylammonium fluoride solution (1M in THF, 4 mL, 4 mmol). The mixture was stirred for a further 20 min. The mixture was partitioned between water (20 mL) and DCM (20 mL). The aqueous layer extracted with further DCM and the combined organic layers dried over MgSO$_4$. Flash chromatography (dry loaded, 0-10% EtOAc in hexane) afforded the title compound (852 mg, 44%) as a mixture of enantiomers.

¹H NMR (DMSO-d6) 1.31 (9H, s), 3.82 (3H, s), 5.55 (2H, dd, J=11.4, 1.9 Hz), 7.07 (2H, s), 7.46 (1H, d, J=7.5 Hz), 7.66 (1H, dd, J=7.5, 1.5 Hz), 7.83-7.89 (1H, m)

9-(tert-Butyl) 6-methyl-1,2,3,4-tetrahydro-1,4-epiminonaphthalene-6,9-dicarboxylate (Racemic)

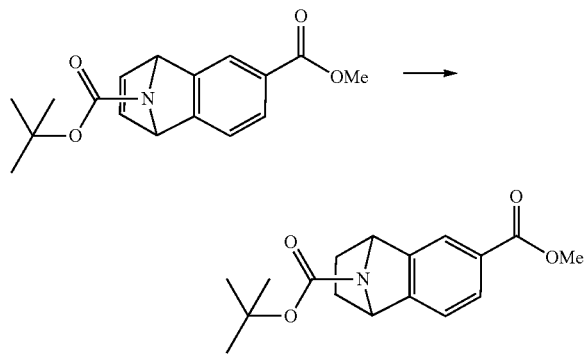

9-(tert-Butyl) 6-methyl-1,4-dihydro-1,4-epiminonaphthalene-6,9-dicarboxylate (852 mg, 1.34 mmol) was dissolved in EtOH (10 mL) before addition of Pd/C (120 mg, 1.13 mmol). The hydrogenation vessel was sealed and placed under a H₂ gas atmosphere and pressure of 55 psi. The mixture was stirred overnight at rt, filtered through Celite and the filtrate concentrated in vacuo to afford the title compound (687 mg, 79%).

[(M-Boc)+H]⁺=204.1

¹H NMR (DMSO-d6) 1.15-1.25 (2H, m), 1.33 (9H, s), 2.04 (2H, dd, J=9.7, 3.0 Hz), 3.84 (3H, s), 5.14 (2H, dd, J=12.2, 3.5 Hz), 7.47 (1H, d, J=7.7 Hz), 7.82 (1H, dd, J=7.6, 1.5 Hz), 7.90 (1H, d, J=1.5 Hz)

Tert-Butyl 6-(hydroxymethyl)-1,2,3,4-tetrahydro-1,4-epiminonaphthalene-9-carboxylate

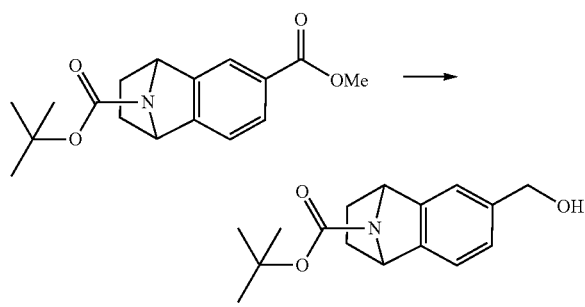

tert-Butyl 6-(hydroxymethyl)-1,2,3,4-tetrahydro-1,4-epiminonaphthalene-9-carboxylate was prepared from 9-(tert-butyl) 6-methyl-1,2,3,4-tetrahydro-1,4-epiminonaphthalene-6,9-dicarboxylate according to procedure L2d.

[(M-Boc)+H]⁺=176.1

5-Bromo-2,3,3-trimethyl-isoindolin-1-one

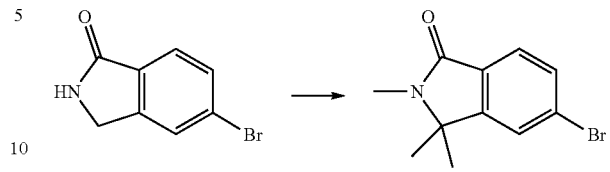

A suspension of sodium hydride (128 mg, 3.2 mmol) and tetrabutylammonium iodide (250 mg, 0.68 mmol) in THF (20 mL) was stirred at rt and a fine suspension of 5-bromoisoindolin-1-one (675 mg, 3.18 mmol) in a mixture of THF (20 mL) and DMF (4 mL) was added. The mixture was left at rt for 15 min, iodomethane (0.198 mL, 3.18 mmol) added and stirring continued for 30 min. Sodium hydride (637 mg, 15.9 mmol) was added portion wise and the mixture stirred for 25 min. Iodomethane (1.19 mL, 19.1 mmol) was added dropwise and stirred for 10 min, heated to reflux for 30 min and stirred at rt overnight. The mixture was cooled in an ice-bath and carefully quenched with saturated NH₄Cl(aq) (40 mL). The mixture was extracted with EtOAc and the combined organic layers washed with brine, dried over MgSO₄ and concentrated in vacuo. The residue was treated with iso-hexanes and decanted (×3) Flash chromatography (0 to 60% EtOAc/Iso-Hexanes) afforded the title compound (224 mg, 27%).

[M+H]⁺=254.0/256.0

¹H NMR (DMSO-d6) 1.43 (6H, s), 2.90 (3H, s), 7.58 (1H, d, J=8.0 Hz), 7.65 (1H, dd, J=8.0, 1.7 Hz), 8.03 (1H, d, J=1.7 Hz)

Methyl 2,3,3-trimethyl-1-oxo-isoindoline-5-carboxylate

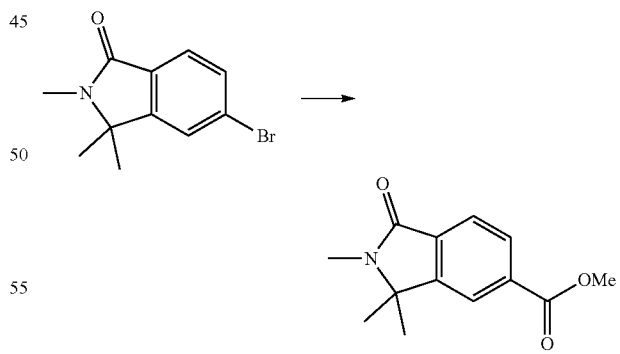

Methyl 2,3,3-trimethyl-1-oxo-isoindoline-5-carboxylate was prepared from 5-bromo-2,3,3-trimethyl-isoindolin-1-one according to procedure L1d.

[M+H]⁺=234.2

¹H NMR (DMSO-d6) 1.47 (6H, s), 2.95 (3H, s), 3.90 (3H, s), 7.78 (1H, dd, J=7.9, 0.7 Hz), 8.05 (1H, dd, J=7.9, 1.4 Hz), 8.27 (1H, dd, J=1.5, 0.7 Hz).

(2,3,3-Trimethylisoindolin-5-yl)methanol

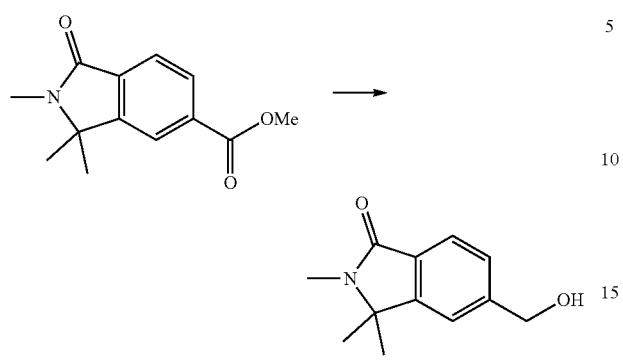

A solution of methyl 2,3,3-trimethyl-1-oxo-isoindoline-5-carboxylate (161 mg, 0.69 mmol) in THF (4 mL) was cooled in an ice-bath. A 1M THF solution of LiAlH$_4$ (3.2 mL, 3.2 mmol) was added dropwise. The mixture was warmed to rt for 1.5 hrs and cooled in an ice bath. A mixture of sodium sulfate decahydrate and Celite was added portion wise and the mixture stirred for 10 min. 1 to 2 drops of water were added cautiously and the mixture was diluted with THF (10 mL) and stirred for 60 min. The mixture was filtered, washing with copious THF and concentrated in vacuo. Flash chromatography (1-12% MeOH (1% NH$_3$)/DCM) afforded the title compound (72 mg, 53%) as a pale pink oil.

[M+H]$^+$=192.2

$^1$H NMR (DMSO-d6) 1.17 (6H, s), 2.35 (3H, s), 3.79 (2H, s), 4.47 (2H, d, J=5.8 Hz), 5.11 (1H, t, J=5.7 Hz), 7.07-7.16 (3H, m)

N-[[1-(4-Bromophenyl)cyclopropyl]methyl]-2,2,2-trifluoro-acetamide

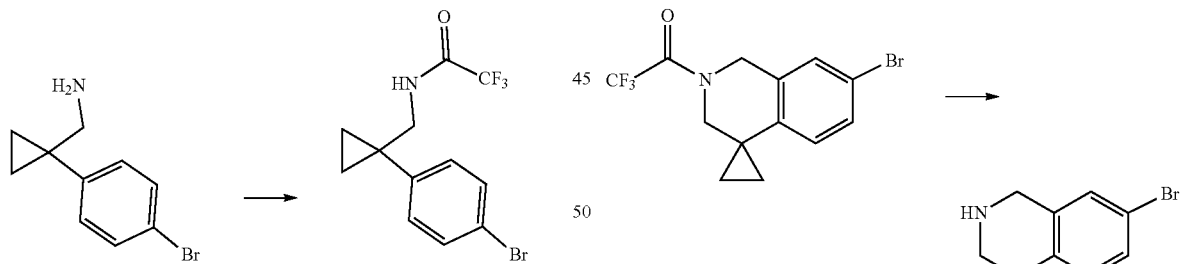

To a stirred solution of [1-(4-bromophenyl)cyclopropyl]methanamine (1.07 g, 4.73 mmol) in DCM (8 mL) was added TEA (0.79 mL, 5.68 mmol). The mixture was cooled in an ice/water bath and treated dropwise with trifluoroacetic anhydride (0.80 mL, 5.68 mmol). The mixture was warmed to rt and stirred for 2 hrs then left in at −20° C. for 48 hrs. The mixture was diluted with DCM (20 mL) and washed with saturated NaHCO$_3$(aq), saturated NH$_4$Cl(aq) and brine, dried over Na$_2$SO$_4$ and concentrated in vacuo to afford the title compound (1.35 g, 88%) as a white solid.

[M+H]$^+$=320.0/322.0

$^1$H NMR (DMSO-d6) 0.72-0.82 (2H, m), 0.89-0.98 (2H, m), 3.40 (2H, d, J=5.6 Hz), 7.22 (2H, d, J=8.5 Hz), 7.46 (2H, d, J=8.5 Hz), 9.44 (1H, t, J=5.1 Hz)

1-(7-Bromospiro[1,3-dihydroisoquinoline-4,1'-cyclopropane]-2-yl)-2,2,2-trifluoro-ethanone

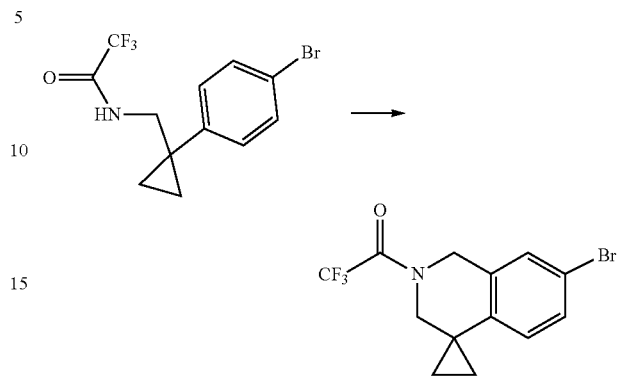

Paraformaldehyde (220 mg, 7.33 mmol) was added to a solution of N-[[1-(4-bromophenyl) cyclopropyl]methyl]-2,2,2-trifluoro-acetamide (1.34 g, 4.16 mmol) in acetic acid (9 mL). Sulfuric acid (5.2 mL, 97.6 mmol) was added dropwise and the mixture was heated at 50° C. for 5 h and stirred at rt overnight. The mixture was poured into a mixture of EtOAc (50 mL) and water (40 mL). The aqueous layer was extracted with EtOAc and the combined organics washed with brine (50 mL), dried over MgSO$_4$ and concentrated in vacuo. Flash chromatography (0 to 30% EtOAc/Iso-Hexanes) afforded the title compound (436 mg, 31%) as a clear oil which crystallized on standing.

[M+H]$^+$=334.0/336.0

$^1$H NMR (DMSO-d6) 0.99-1.09 (4H, m), 3.67 (2H, d, J=12.4 Hz), 4.89 (2H, d, J=13.9 Hz), 6.83 (1H, dd, J=8.5, 2.5 Hz), 7.38 (1H, ddd, J=8.3, 5.8, 2.2 Hz), 7.49-7.60 (1H, m)

7'-Bromo-2',3'-dihydro-1'H-spiro[cyclopropane-1,4'-isoquinoline]

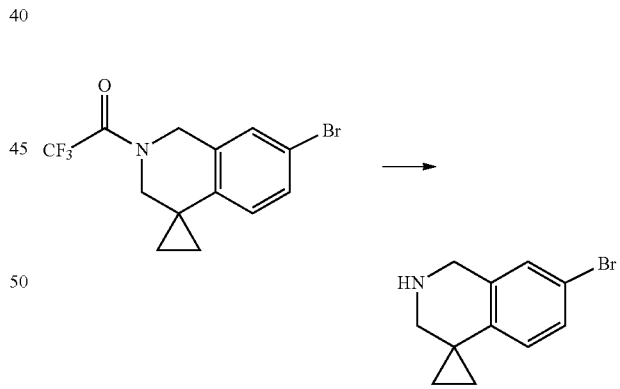

A suspension of 1-(7-bromospiro[1,3-dihydroisoquinoline-4,1'-cyclopropane]-2-yl)-2,2,2-trifluoro-ethanone (432 mg, 1.29 mmol) and Na$_2$CO$_3$ (165 mg, 1.56 mmol) in a mixture of MeOH (2 mL) and water (1 mL) was heated at 40° C. for 6 hrs. Heating was discontinued and the mixture left at rt overnight. MeOH was removed in vacuo. The residue was partitioned between EtOAc (10 mL) and water (10 mL). The aqueous layer was extracted with EtOAc and the combined organics washed with brine, dried over MgSO$_4$ and concentrated in vacuo to afford the title compound (271 mg, 87%) as a clear oil which solidified on standing.

[M+H]⁺=238.0/240.0

¹H NMR (DMSO-d6) 0.79-0.83 (2H, m), 0.87-0.92 (2H, m), 2.63 (1H, s), 2.72 (2H, s), 3.91 (2H, s), 6.67 (1H, d, J=8.4 Hz), 7.19 (1H, d, J=2.2 Hz), 7.22 (1H, dd, J=8.4, 2.2 Hz)

Tert-Butyl 7'-bromo-1'H-spiro[cyclopropane-1,4'-isoquinoline]-2'(3'H)-carboxylate

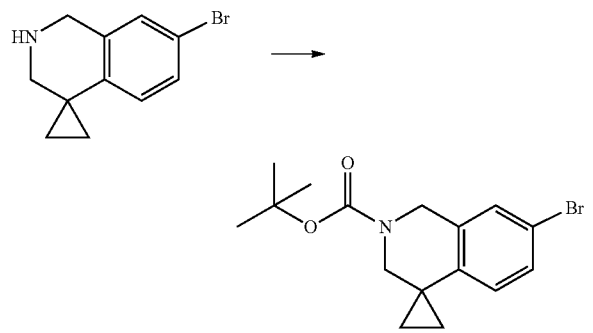

tert-Butyl 7'-bromo-1'H-spiro[cyclopropane-1,4'-isoquinoline]-2'(3'H)-carboxylate was prepared from 7'-bromo-2',3'-dihydro-1'H-spiro[cyclopropane-1,4'-isoquinoline] according to procedure L1e.

[(M-Boc)+H]⁺=238.0/240.0

¹H NMR (DMSO-d6) 0.95 (4H, dd, J=6.6, 2.0 Hz), 1.41 (9H, s), 3.39 (2H, s), 4.61 (2H, s), 6.77 (1H, d, J=8.4 Hz), 7.30 (1H, dd, J=8.4, 2.2 Hz), 7.39 (1H, d, J=2.2 Hz).

2'-(tert-Butyl) 7'-methyl 1'H-spiro[cyclopropane-1,4'-isoquinoline]-2',7'(3'H)-dicarboxylate

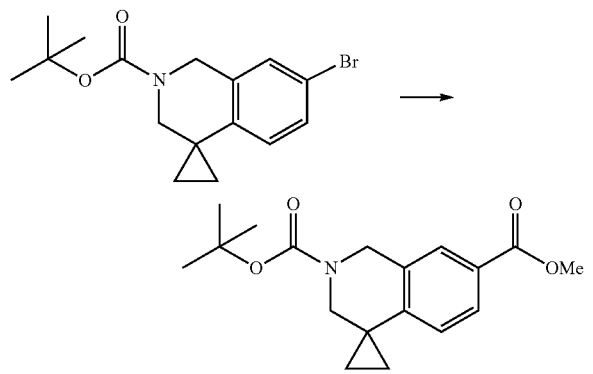

2'-(tert-Butyl) 7'-methyl 1'H-spiro[cyclopropane-1,4'-isoquinoline]-2',7'(3'H)-dicarboxylate was prepared from tert-butyl 7'-bromo-1'H-spiro[cyclopropane-1,4'-isoquinoline]-2'(3'H)-carboxylate according to procedure L1d.

[(M-Boc)+H]⁺=218.2

¹H NMR (DMSO-d6) 0.96-1.09 (4H, m), 1.41 (9H, s), 3.43 (2H, s), 3.83 (3H, s), 4.68 (2H, s), 6.95 (1H, d, J=8.2 Hz), 7.71 (1H, dd, J=8.2, 1.9 Hz), 7.74 (1H, d, J=1.7 Hz).

Tert-Butyl 7'-(hydroxymethyl)-1'H-spiro[cyclopropane-1,4'-isoquinoline]-2'(3'H)-carboxylate

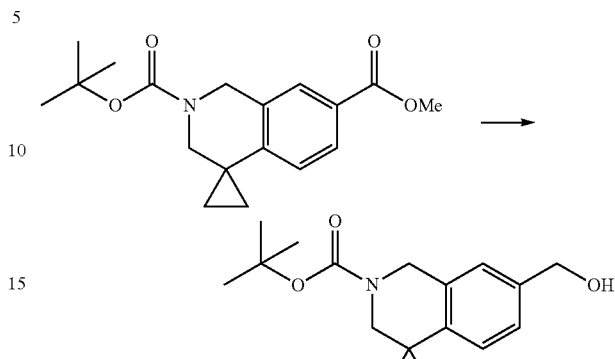

tert-Butyl 7'-(hydroxymethyl)-1'H-spiro[cyclopropane-1,4'-isoquinoline]-2'(3'H)-carboxylate was prepared from 2'-(tert-butyl) 7'-methyl 1'H-spiro[cyclopropane-1,4'-isoquinoline]-2',7'(3'H)-dicarboxylate according to procedure L2d.

[(M-tBu-OH)+H]⁺=216.1

¹H NMR (DMSO-d6) 0.86-0.98 (4H, m), 1.41 (9H, s), 3.39 (2H, s), 4.42 (2H, d, J=5.7 Hz), 4.59 (2H, s), 5.09 (1H, t, J=5.7 Hz), 6.76 (1H, d, J=8.0 Hz), 7.01-7.12 (2H, m)

Rac-9-Bromo-10b-methyl-5,6-dihydrooxazolo[2,3-a]isoquinoline-2,3-dione

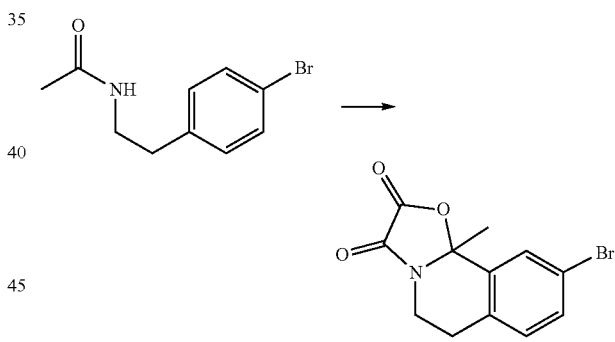

To a 100 mL flask was added N-[2-(4-bromophenyl)ethyl]acetamide (1.25 g, 5.16 mmol) and DCM (20 mL) and cooled in an ice/water bath. Oxalyl chloride solution (2.0 M in DCM, 2.81 mL, 5.62 mmol) was added dropwise and the mixture allowed to warm to rt overnight. The mixture was briefly flushed with N₂ before the addition (in one portion) of ferric chloride (1 g, 6.17 mmol). This caused gas evolution and a mild exotherm which was controlled using an ice/water bath for 5 min. The mixture was warmed to rt and stirred for 4 hrs then water (20 mL) was added with vigorous stirring. After 5 min the layers were separated and the aqueous extracted with DCM. The combined organics were washed with brine, dried over Na₂SO₄ and concentrated in vacuo to afford the title compound (1.39 g, 86%) as a coloured solid.

[M+H]⁺=296.0/298.0

¹H NMR (DMSO-d6) 1.98 (3H, s), 2.87 (1H, ddd, J=17.0, 5.5, 1.9 Hz), 2.98 (1H, ddd, J=17.6, 10.9, 6.9 Hz), 3.66 (1H, ddd, J=13.6, 11.0, 5.4 Hz), 4.28 (1H, ddd, J=13.6, 6.9, 2.0 Hz), 7.21 (1H, d, J=8.3 Hz), 7.55 (1H, dd, J=8.3, 2.1 Hz), 7.75 (1H, d, J=2.1 Hz)

7-Bromo-1-methyl-3,4-dihydroisoquinoline

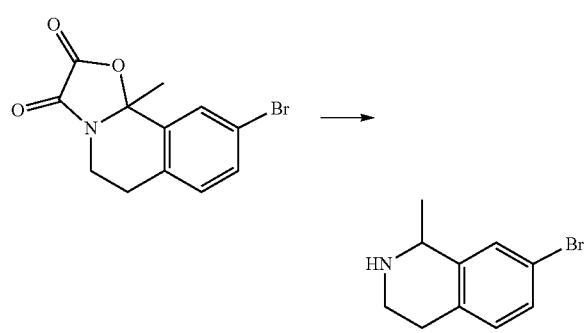

A suspension of rac-9-bromo-10b-methyl-5,6-dihydrooxazolo[2,3-a]isoquinoline-2,3-dione (1.39 g, 3.76 mmol) in a mixture of EtOH (30 mL) and H$_2$SO$_4$ (1 mL) was heated at 65° C. for 2 days. The mixture was cooled in an ice/water bath before the addition of 30% aqueous NH$_3$ to basic pH (~8-9). Solvents were removed in vacuo and the residue diluted with water and 2N NaOH(aq) to pH 10-12, extracted with EtOAc and the combined organics dried over MgSO$_4$ and concentrated in vacuo. Flash chromatography (0 to 100% EtOAc/Iso-Hexanes) afforded the title compound (835 mg 78%) as a pale yellow semi-solid.

[M+H]$^+$=224.0/226.1

$^1$H NMR (DMSO-d6) 2.30 (3H, s), 2.57-2.62 (2H, m), 3.52 (2H, ddd, J=9.1, 5.8, 1.7 Hz), 7.22 (1H, d, J=8.0 Hz), 7.58 (1H, dd, J=8.0, 2.1 Hz), 7.70 (1H, d, J=2.1 Hz)

2-Benzyl-7-bromo-1-methyl-3,4-dihydroisoquinolin-2-ium bromide

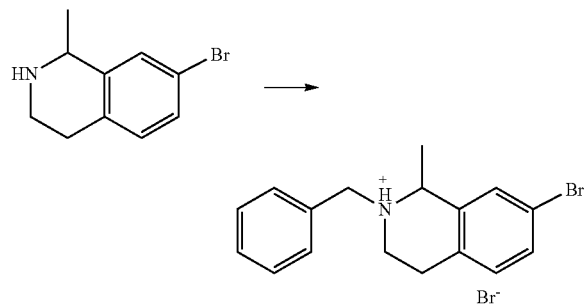

A suspension of 7-bromo-1-methyl-3,4-dihydroisoquinoline (0.835 g, 3.35 mmol) in acetonitrile (20 mL) was treated with bromomethylbenzene (0.57 mL, 4.7 mmol) and the mixture heated at 70° C. for 3 hrs. The mixture was cooled to rt and stirred overnight. The mixture was concentrated in vacuo and the residue purified by flash chromatography (0 to 7% MeOH/DCM) to afford the title compound (722 mg, 54%) as a pale yellow solid.

[M]$^+$=314.2/316.2

$^1$H NMR (DMSO-d6) 3.01 (3H, s), 3.07 (2H, t, J=7.5 Hz), 3.96 (2H, t, J=7.8 Hz), 5.40 (2H, s), 7.40-7.53 (6H, m), 7.98 (1H, dd, J=8.1, 2.0 Hz), 8.35 (1H, d, J=2.0 Hz)

2-Benzyl-7-bromo-1,1-dimethyl-3,4-dihydroisoquinoline

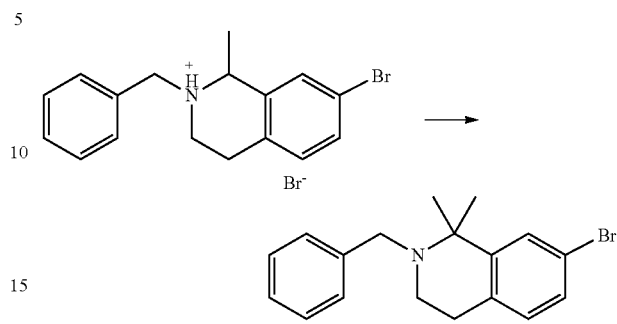

A suspension of 2-benzyl-7-bromo-1-methyl-3,4-dihydroisoquinolin-2-ium bromide (834 mg, 2.11 mmol) in THF (7 mL) was treated dropwise with a 3M solution of methyl magnesium bromide in Et$_2$O (21 mL, 63 mmol). The mixture was heated to reflux for 1.5 hrs and left at rt overnight. The mixture was quenched carefully into saturated NH$_4$Cl (aq) (100 mL) and extracted with EtOAc. The combined organics were washed with brine, dried over MgSO$_4$ and concentrated in vacuo. Flash chromatography (0 to 60% TBME/Iso-Hexanes) afforded the title compound (448 mg, 58%) as a pale yellow oil which crystallized on standing.

[M+H]$^+$=330.1/332.1

Methyl 2-benzyl-1,1-dimethyl-3,4-dihydroisoquinoline-7-carboxylate

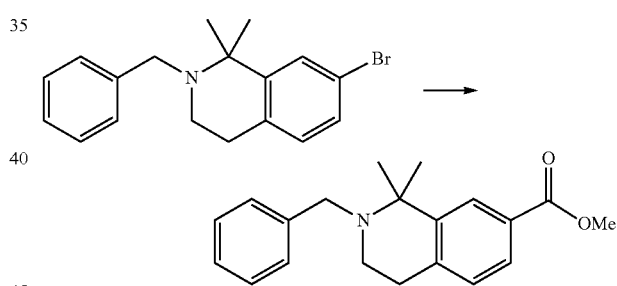

Methyl 2-benzyl-1,1-dimethyl-3,4-dihydroisoquinoline-7-carboxylate was prepared from 2-benzyl-7-bromo-1,1-dimethyl-3,4-dihydroisoquinoline according to procedure L1d.

[M+H]$^+$=310.3

$^1$H NMR (DMSO-d6) 1.47 (6H, s), 2.63 (2H, t, J=5.6 Hz), 2.71 (2H, t, J=5.6 Hz), 3.70 (2H, s), 3.85 (3H, s), 7.18 (1H, d, J=8.0 Hz), 7.23 (1H, t, J=7.3 Hz), 7.32 (2H, t, J=7.6 Hz), 7.35-7.42 (2H, m), 7.69 (1H, dd, J=7.9, 1.7 Hz), 7.94 (1H, d, J=1.7 Hz)

Methyl 1,1-dimethyl-3,4-dihydro-2H-isoquinoline-7-carboxylate

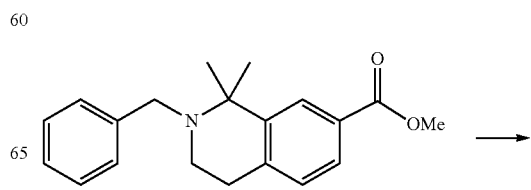

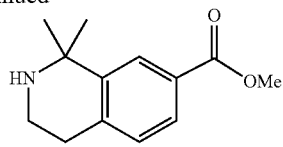

A solution of methyl 2-benzyl-1,1-dimethyl-3,4-dihydroisoquinoline-7-carboxylate (315 mg, 0.94 mmol) in MeOH (30 mL) was treated with 10% palladium on carbon (92 mg, 0.09 mmol), and placed in sealed hydrogenation apparatus. The vessel was purged with $N_2$ gas then placed under $H_2$ gas at 3 bar pressure at rt for 4 hrs. The mixture was filtered through Celite and concentrated in vacuo to afford the title compound (194 mg, 0.86 mmol, 92%).

$[M+H]^+=220.2$ $^1$H NMR (DMSO-d6) 1.36 (6H, s), 2.31 (1H, s), 2.73 (2H, t, J=5.8 Hz), 2.95 (2H, t, J=5.8 Hz), 3.83 (3H, s), 7.18 (1H, d, J=8.0 Hz), 7.65 (1H, dd, J=7.9, 1.8 Hz), 7.81 (1H, d, J=1.8 Hz)

2-(tert-Butyl) 7-methyl 1,1-dimethyl-3,4-dihydroisoquinoline-2,7(1H)-dicarboxylate

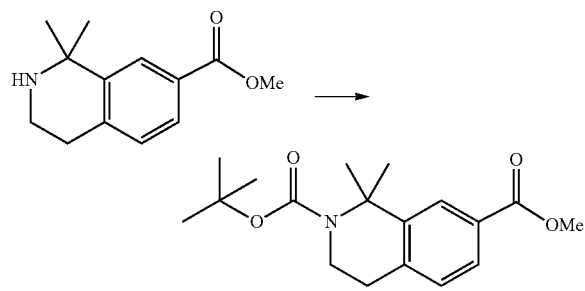

2-(tert-Butyl) 7-methyl 1,1-dimethyl-3,4-dihydroisoquinoline-2,7(1H)-dicarboxylate was prepared from methyl 1,1-dimethyl-3,4-dihydro-2H-isoquinoline-7-carboxylate according to procedure L1e.

$^1$H NMR (DMSO-d6) 1.46 (9H, s), 1.72 (6H, s), 2.80-2.85 (2H, m), 3.53-3.62 (2H, m), 3.85 (3H, s), 7.27 (1H, d, J=7.9 Hz), 7.72 (1H, dd, J=7.9, 1.7 Hz), 7.93 (1H, d, J=1.7 Hz)

tert-Butyl 7-(hydroxymethyl)-1,1-dimethyl-3,4-dihydroisoquinoline-2-carboxylate

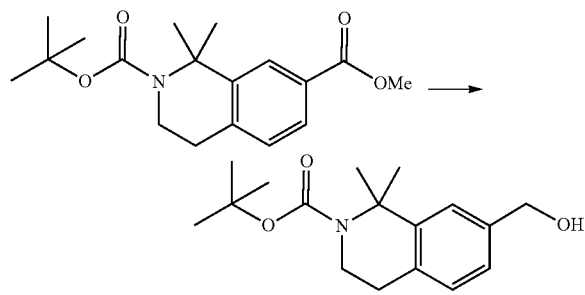

tert-Butyl 7-(hydroxymethyl)-1,1-dimethyl-3,4-dihydroisoquinoline-2-carboxylate was prepared from 2-(tert-butyl) 7-methyl 1,1-dimethyl-3,4-dihydroisoquinoline-2,7(1H)-dicarboxylate according to procedure L2d.

$[(M-tBu-OH)+H]^+=218.1$ $^1$H NMR (DMSO-d6) 1.45 (9H, s), 1.69 (6H, s), 2.71 (2H, t, J=5.4 Hz) 3.50-3.60 (2H, m), 4.46 (2H, d, J=5.7 Hz), 5.11 (1H, t, J=5.8 Hz), 7.00-7.09 (2H, m), 7.30 (1H, d, J=1.6 Hz)

2-(tert-Butyl) 7-methyl 4,4-dimethyl-3,4-dihydroisoquinoline-2,7(1H)-dicarboxylate

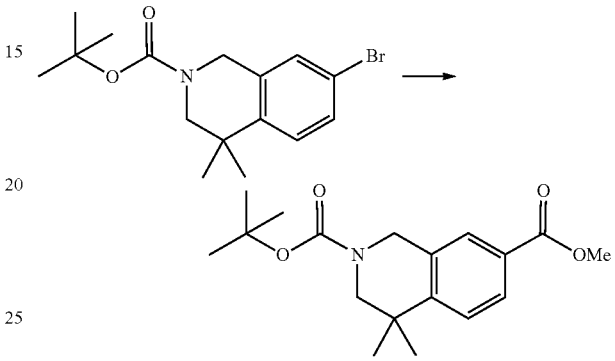

2-(tert-Butyl) 7-methyl 4,4-dimethyl-3,4-dihydroisoquinoline-2,7(1H)-dicarboxylate was prepared from tert-butyl 7-bromo-4,4-dimethyl-1,3-dihydroisoquinoline-2-carboxylate (reported in WO2000024717) according to procedure L1d.

$[(M-tBu)+H]^+=264.3$ $^1$H NMR (DMSO-d6) 1.22 (6H, s), 1.43 (9H, s), 3.39 (2H, s), 3.83 (3H, s), 4.62 (2H, s), 7.54 (1H, d, J=8.2 Hz), 7.73 (1H, d, J=1.8 Hz), 7.77 (1H, dd, J=8.2, 1.9 Hz).

tert-Butyl 7-(hydroxymethyl)-4,4-dimethyl-1,3-dihydroisoquinoline-2-carboxylate

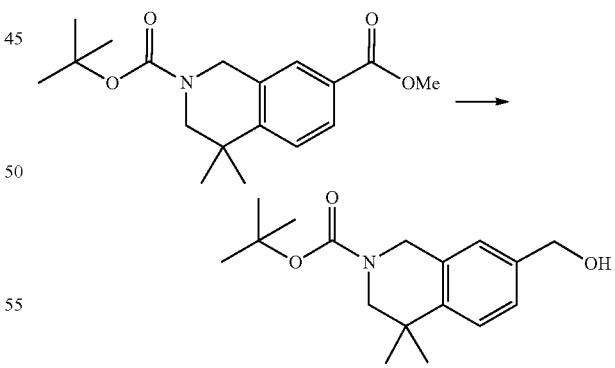

tert-Butyl 7-(hydroxymethyl)-4,4-dimethyl-1,3-dihydroisoquinoline-2-carboxylate was prepared from 2-(tert-butyl) 7-methyl 4,4-dimethyl-3,4-dihydroisoquinoline-2,7(1H)-dicarboxylate according to procedure L2d.

$[(M-tBu)+H]^+=236.2$ $^1$H NMR (DMSO-d6) 1.19 (6H, s), 1.42 (9H, s), 3.35 (2H, s), 4.42 (2H, d, J=5.8 Hz), 4.53 (2H, s), 5.08 (1H, t, J=5.7 Hz), 7.03 (1H, s), 7.09-7.16 (1H, m), 7.28-7.36 (1H, m).

153

7-(tert-Butyl) 2-methyl 5,8-dihydro-1,7-naphthyridine-2,7(6H)-dicarboxylate

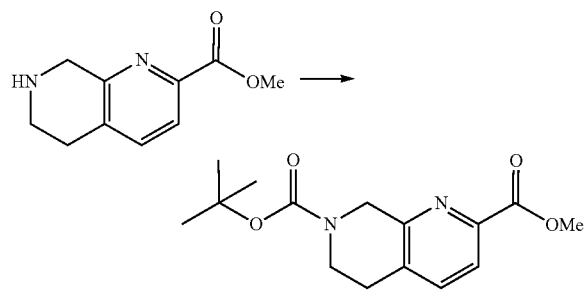

7-(tert-Butyl) 2-methyl 5,8-dihydro-1,7-naphthyridine-2,7(6H)-dicarboxylate was prepared from methyl 5,6,7,8-tetrahydro-1,7-naphthyridine-2-carboxylate dihydrochloride according to procedure L1e.

[M+H]$^+$=293.1 tert-Butyl 2-(hydroxymethyl)-6,8-dihydro-5H-1,7-naphthyridine-7-carboxylate

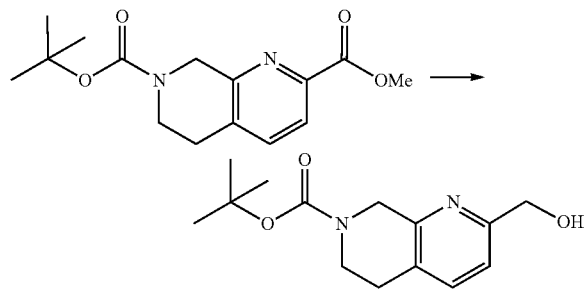

tert-Butyl 2-(hydroxymethyl)-6,8-dihydro-5H-1,7-naphthyridine-7-carboxylate was prepared from 7-(tert-butyl) 2-methyl 5,8-dihydro-1,7-naphthyridine-2,7(6H)-dicarboxylate according to procedure L2d.

[M+H]$^+$=265.1 tert-Butyl 3-(hydroxymethyl)-7,8-dihydro-5H-1,6-naphthyridine-6-carboxylate

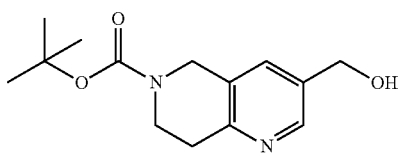 [SMILES: CC(C)(C)OC(=O)N1CCc2ncc(CO)cc2C1]

Synthesis of 6-(tert-butyl) 3-methyl 7,8-dihydro-1,6-naphthyridine-3,6(5H)-dicarboxylate is reported in WO2012027564.

154

6-(Hydroxymethyl)-2-methyl-3,4-dihydroisoquinolin-1(2H)-one

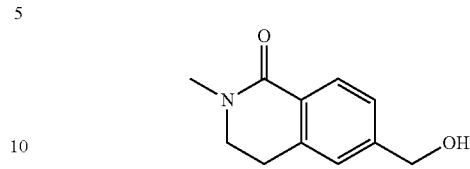

Synthesis of 6-(hydroxymethyl)-2-methyl-3,4-dihydroisoquinolin-1(2H)-one is reported in WO2012122340.

Specific Examples of the Present Invention

General Method A

N-{[2-Fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl] pyrazole-4-carboxamide (Example 2)

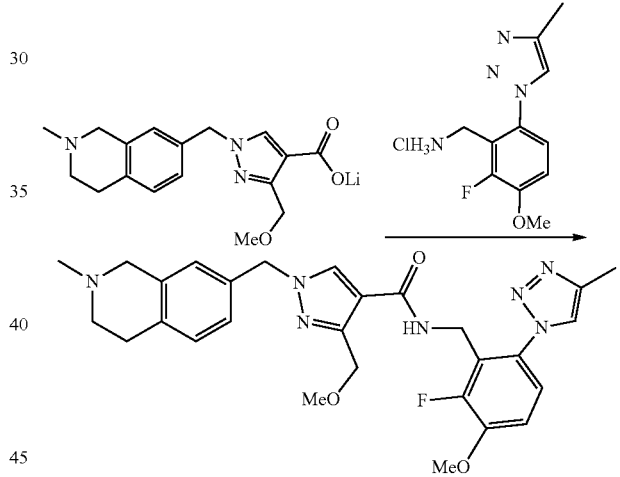

DIPEA (0.2 mL, 1.2 mmol) was added to a mixture of lithium 3-(methoxymethyl)-1-((2-methyl-1,2,3,4-tetrahydroisoquinolin-7-yl)methyl)-1H-pyrazole-4-carboxylate (70 mg, 0.22 mmol), (2-fluoro-3-methoxy-6-(4-methyl-1H-1,2,3-triazol-1-yl)phenyl)methanamine hydrochloride (65 mg, 0.24 mmol) and HATU (95 mg, 0.25 mmol) in DCM (2 mL) and NMP (0.4 mL) and stirred at rt overnight. The mixture was concentrated in vacuo and flash chromatography (0 to 10% MeOH (1% NH$_3$)/DCM) afforded the title compound (87 mg, 74%). Two minor components were identified as Examples 73 and 162.

Title Compound:

[M+H]$^+$=534.2

$^1$H NMR (d6 DMSO) 2.30 (3H, d, J=0.8 Hz), 2.32 (3H, s), 2.56 (2H, t, J=5.9 Hz), 2.78 (2H, t, J=5.9 Hz), 3.17 (3H, s), 3.44 (2H, s), 3.92 (3H, s), 4.26 (2H, d, J=5.2 Hz), 4.44 (2H, s), 5.20 (2H, s), 6.94 (1H, s), 6.97-7.03 (1H, m), 7.08 (1H, d, J=7.9 Hz), 7.25-7.35 (2H, m), 8.02 (1H, t, J=5.0 Hz), 8.12 (1H, s), 8.15 (1H, d, J=1.0 Hz)

N-{[2-Fluoro-3-methoxy-6-(4-methyl-1,2,3-triazol-1-yl)phenyl]methyl}-3-(methoxymethyl)-1-[(2-methyl-1-oxo-3,4-dihydroisoquinolin-7-yl)methyl]pyrazole-4-carboxamide (Example 73)

[M+H]$^+$=548.2
$^1$H NMR (Chloroform-d) 2.43 (3H, d, J=0.8 Hz), 2.98 (2H, t, J=6.6 Hz), 3.14 (3H, s), 3.37 (3H, d, J=1.8 Hz), 3.55 (2H, t, J=6.7 Hz), 3.93 (3H, s), 4.38 (2H, dd, J=5.7, 1.5 Hz), 4.56 (2H, d, J=3.5 Hz), 5.23 (2H, s), 6.98 (1H, t, J=8.7 Hz), 7.10-7.16 (2H, m), 7.18-7.23 (1H, m), 7.80 (1H, s), 7.93 (1H, d, J=1.0 Hz), 7.97 (1H, d, J=2.0 Hz), 8.34 (1H, t, J=6.0 Hz)

N-{[2-Fluoro-3-methoxy-6-(4-methyl-1,2,3-triazol-1-yl)phenyl]methyl}-1-[(1-hydroxy-2-methyl-3,4-dihydro-1H-isoquinolin-7-yl)methyl]-3-(methoxymethyl)pyrazole-4-carboxamide (Example 162)

[M+H]$^+$=550.2
$^1$H NMR (Chloroform-d) 2.43 (3H, d, J=0.8 Hz), 2.99 (1H, dd, J=17.4, 6.2 Hz), 3.35 (3H, s), 3.36 (3H, s), 3.46-3.56 (1H, m), 3.61 (1H, dt, J=11.7, 6.1 Hz), 3.64-3.75 (1H, m), 3.93 (3H, s), 4.36-4.41 (2H, m), 4.44-4.57 (2H, m), 4.55 (2H, s), 5.17 (2H, s), 6.90 (1H, s), 6.99 (1H, t, J=8.7 Hz), 7.13 (2H, dd, J=8.8, 1.7 Hz), 7.21 (1H, d, J=7.9 Hz), 7.84 (2H, d, J=13.6 Hz), 8.27-8.34 (1H, m)
General Method B N-{[2-Fluoro-3-methoxy-6-(4-methyl-1,2,3-triazol-1-yl)phenyl]methyl}-1-[(2-isopropyl-1,3-dihydroisoindol-5-yl)methyl]-3-(methoxymethyl)pyrazole-4-carboxamide (Example 55)

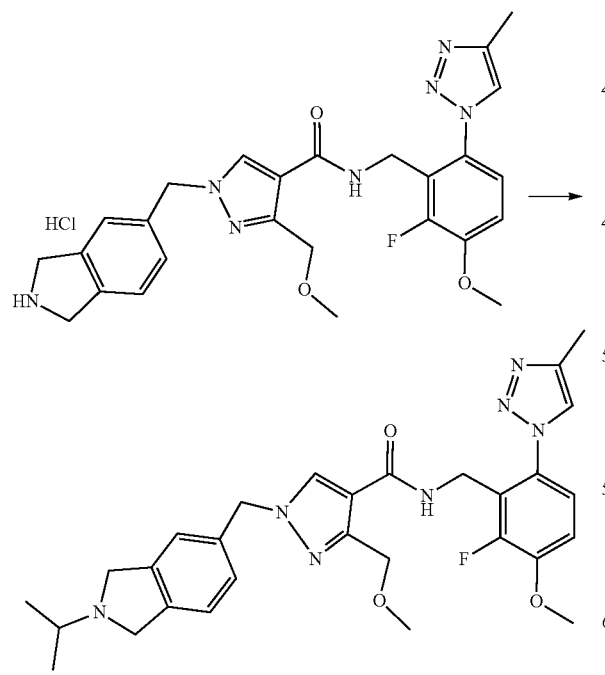

To a solution of N-(2-fluoro-3-methoxy-6-(4-methyl-1H-1,2,3-triazol-1-yl)benzyl)-1-(isoindolin-5-ylmethyl)-3-(methoxymethyl)-1H-pyrazole-4-carboxamide hydrochloride (350 mg, 0.65 mmol) in DCM (21 mL) was added acetone (12 mL, 160 mmol) and TEA (180 uL, 1.29 mmol). After 30 min sodium triacetoxyborohydride (342 mg, 1.61 mmol) was added and stirring continued for 60 min. The mixture was diluted with MeOH (150 mL) and SCX resin (sufficient to capture the product) was added. The resin was collected by filtration and washed with MeOH. The product was then released by eluting with 1% NH$_3$ in MeOH and the methanolic ammonia solution was concentrated in vacuo. Repeated flash chromatography (10% MeOH in EtOAc) then 0-10% (1% NH$_3$ in MeOH) in DCM afforded an oil which was triturated with Et$_2$O and dried to afford the title compound (84 mg, 23% yield) as an off-white solid.

[M+H]$^+$=548.4
$^1$H NMR (d6 DMSO) 1.08 (6H, d, J=6.3 Hz), 2.29 (3H, s), 2.67 (1H), 3.16 (3H, s), 3.82 (4H, s), 3.92 (3H, s), 4.25 (2H, d, J=5.0 Hz), 4.43 (2H, s), 5.24 (2H, s), 7.05-7.13 (2H, m), 7.17-7.22 (1H, m), 7.25-7.33 (2H, m), 8.02 (1H, t, J=5.1 Hz), 8.10-8.16 (2H, m).

TABLE 1

| Example number | R8 | R5 | B" | Free Base MW | [M + H]$^+$ |
|---|---|---|---|---|---|
| 1 | Me | CH$_2$OMe | (structure) | 569.6 | 570.2 |
| 2 | Me | CH$_2$OMe | (structure) | 533.6 | 534.2 |
| 3 | Me | H | (structure) | 489.5 | 490.2 |
| 4 | Me | CH$_2$OMe | (structure) | 533.6 | 534.0 |
| 5 | Me | CH$_2$OMe | (structure) | 533.6 | |

TABLE 1-continued

| Example number | R8 | R5 | B" | Free Base MW | [M + H]+ |
|---|---|---|---|---|---|
| 6 | Me | CH2OMe | ethyl-triazolyl | 547.6 | 547.9 |
| 7 | Me | CH2OMe | triazolyl | 519.6 | 520.0 |
| 8 | Me | CH2OMe | CF3-pyrazolyl | 586.6 | 586.9 |
| 9 | Me | CH2OMe | cyclopropyl-pyrazolyl | 558.6 | 559.0 |
| 10 | Me | CH2OMe | CN-pyrrolyl | 542.6 | |
| 11 | Me | CH2OMe | CN-pyrazolyl | 543.6 | 543.9 |
| 12 | Me | CH2OMe | methyl-triazolyl | 533.6 | 533.9 |
| 13 | Me | CH2OMe | CF3-triazolyl | 587.6 | 587.9 |
| 14 | cyclopropyl | CH2OMe | methyl-triazolyl | 559.6 | 560.5 |
| 15 | Me | CH2OMe | CHF2-triazolyl | 569.6 | 570.5 |
| 16 | Et | CH2OMe | methyl-triazolyl | 547.6 | 548.4 |
| 17 | iPr | CH2OMe | methyl-triazolyl | 561.7 | 562.5 |
| 18 | cyclobutyl | CH2OMe | methyl-triazolyl | 573.7 | 574.5 |
| 19 | cyclopropyl | CH2OMe | CHF2-triazolyl | 595.6 | 596.5 |

TABLE 1-continued

| Example number | R8 | R5 | B" | Free Base MW | [M + H]+ |
|---|---|---|---|---|---|
| 20 | cyclopropyl | CH₂OMe | 3-(CF₃)-1,2,4-triazol-1-yl | 613.3 | 614.4 |
| 21 | cyclopropyl | CH₂OMe | 3-cyano-pyrazol-1-yl | 569.6 | 570.5 |
| 22 | iPr | CH₂OMe | 3-(CF₃)-1,2,4-triazol-1-yl | 615.6 | 616.2 |
| 23 | iPr | CH₂OMe | 3-(CHF₂)-1,2,4-triazol-1-yl | 597.6 | 598.2 |
| 24 | iPr | CH₂OMe | 3-cyano-pyrazol-1-yl | 571.7 | 572.2 |
| 25 | Et | CH₂OMe | 3-(CF₃)-1,2,4-triazol-1-yl | 601.6 | 602.4 |
| 26 | Et | CH₂OMe | 3-(CHF₂)-1,2,4-triazol-1-yl | 583.6 | 584.5 |
| 27 | Et | CH₂OMe | 3-cyano-pyrazol-1-yl | 557.6 | 558.5 |
| 28 | iPr | CH₂OMe | 3,5-dimethyl-1,2,4-triazol-1-yl | 575.7 | 576.5 |
| 29 | Me | CH₂OMe | 3,5-dimethyl-1,2,4-triazol-1-yl | 547.6 | 548.4 |
| 30 | iPr | CH₂OMe | 3-cyano-pyrazol-1-yl | 571.6 | 572.4 |
| 31 | Me | H | 3-(CF₃)-1,2,4-triazol-1-yl | 543.5 | 544.3 |

TABLE 1-continued

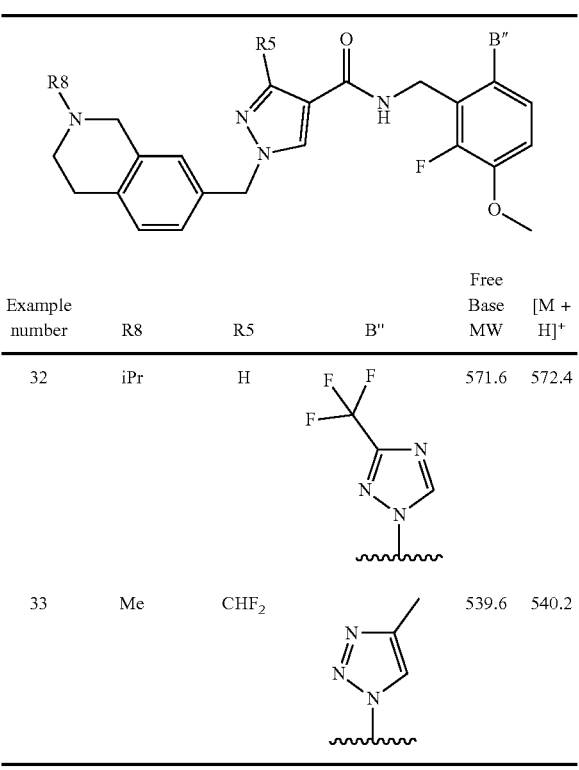

| Example number | R8 | R5 | B" | Free Base MW | [M + H]+ |
|---|---|---|---|---|---|
| 32 | iPr | H | 3-(trifluoromethyl)-1,2,4-triazol-1-yl | 571.6 | 572.4 |
| 33 | Me | CHF$_2$ | 4-methyl-1,2,3-triazol-1-yl | 539.6 | 540.2 |

TABLE 2

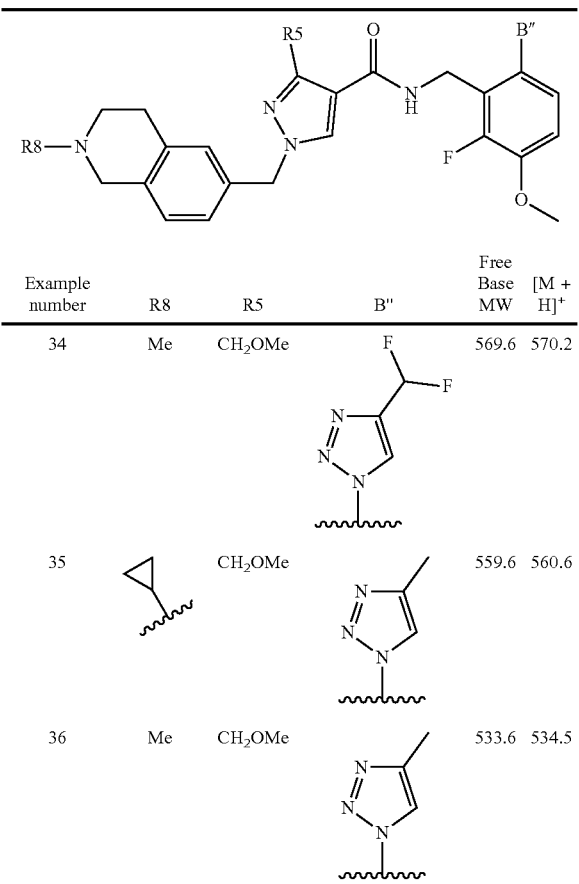

| Example number | R8 | R5 | B" | Free Base MW | [M + H]+ |
|---|---|---|---|---|---|
| 34 | Me | CH$_2$OMe | 4-(difluoromethyl)-1,2,3-triazol-1-yl | 569.6 | 570.2 |
| 35 | cyclopropyl | CH$_2$OMe | 4-methyl-1,2,3-triazol-1-yl | 559.6 | 560.6 |
| 36 | Me | CH$_2$OMe | 4-methyl-1,2,3-triazol-1-yl | 533.6 | 534.5 |

TABLE 2-continued

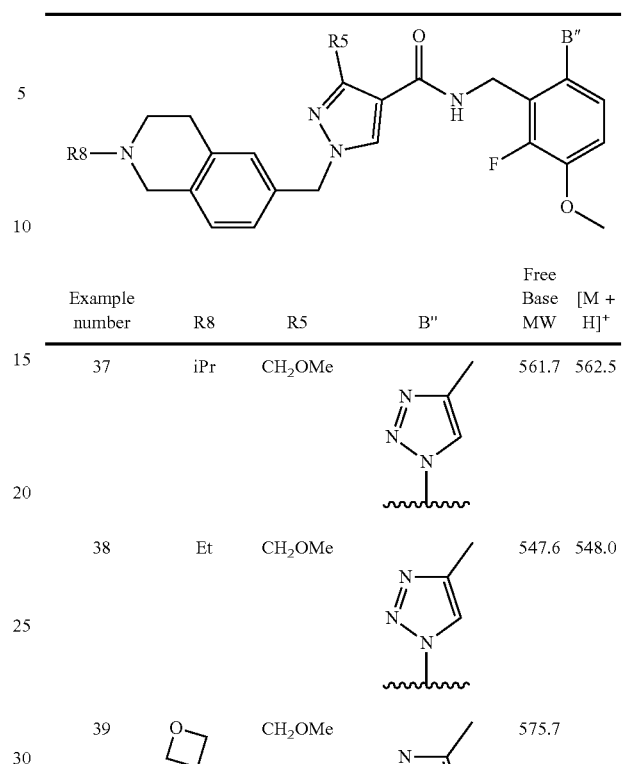

| Example number | R8 | R5 | B" | Free Base MW | [M + H]+ |
|---|---|---|---|---|---|
| 37 | iPr | CH$_2$OMe | 4-methyl-1,2,3-triazol-1-yl | 561.7 | 562.5 |
| 38 | Et | CH$_2$OMe | 4-methyl-1,2,3-triazol-1-yl | 547.6 | 548.0 |
| 39 | oxetan-3-yl | CH$_2$OMe | 4-methyl-1,2,3-triazol-1-yl | 575.7 | |
| 40 | cyclobutyl | CH$_2$OMe | 4-methyl-1,2,3-triazol-1-yl | 573.7 | 574.4 |
| 41 | Me | CH$_2$OMe | 3-(difluoromethyl)-1,2,4-triazol-1-yl | 569.6 | 570.3 |
| 42 | Me | CH$_2$OMe | 3-(trifluoromethyl)-1,2,4-triazol-1-yl | 587.6 | 588.3 |
| 43 | Me | CH$_2$OMe | 3-cyano-pyrazol-1-yl | 543.6 | 544.3 |

TABLE 2-continued

| Example number | R8 | R5 | B" | Free Base MW | [M + H]+ |
|---|---|---|---|---|---|
| 44 | iPr | CH$_2$OMe | 3-(difluoromethyl)-1,2,4-triazol-1-yl | 597.6 | 598.3 |
| 45 | iPr | CH$_2$OMe | 3-(trifluoromethyl)-1,2,4-triazol-1-yl | 615.6 | 616.3 |
| 46 | iPr | CH$_2$OMe | 3-cyano-pyrazol-1-yl | 571.6 | 572.4 |
| 47 | cyclopropyl | CH$_2$OMe | 3-(difluoromethyl)-1,2,4-triazol-1-yl | 595.6 | 596.4 |
| 48 | cyclopropyl | CH$_2$OMe | 3-(trifluoromethyl)-1,2,4-triazol-1-yl | 613.6 | 614.4 |
| 49 | cyclopropyl | CH$_2$OMe | 3-cyano-pyrazol-1-yl | 569.6 | 570.4 |
| 50 | Et | CH$_2$OMe | 3-(difluoromethyl)-1,2,4-triazol-1-yl | 583.6 | 584.4 |
| 51 | Et | CH$_2$OMe | 3-(trifluoromethyl)-1,2,4-triazol-1-yl | 601.6 | 602.4 |
| 52 | Et | CH$_2$OMe | 3-cyano-pyrazol-1-yl | 557.6 | 558.4 |

TABLE 3

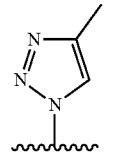 [SMILES: *n1cc(C)nn1]

| Example number | R8 | B" | Free Base MW | [M + H]+ |
|---|---|---|---|---|
| 53 | H | 4-methyl-1,2,3-triazol-1-yl | 505.5 | 506.2 |

TABLE 3-continued
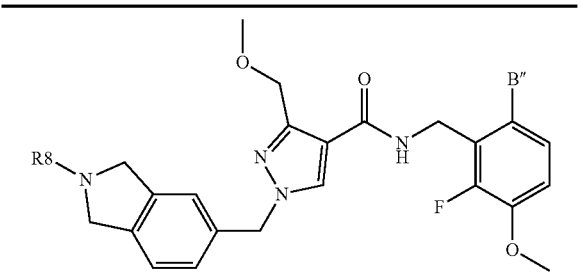
| Example number | R8 | B" | Free Base MW | [M + H]+ |
|---|---|---|---|---|
| 54 | Me | 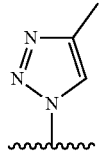 [SMILES: *n1cc(C)nn1] | 519.6 | 520.2 |
| 55 | iPr | 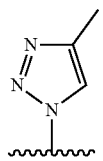 | 547.6 | 548.2 |
| 56 | Et | 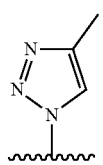 [SMILES: *n1cc(C)nn1] | 533.6 | 534.4 |
| 57 | Me |  | 555.6 | 556.4 |
TABLE 3-continued
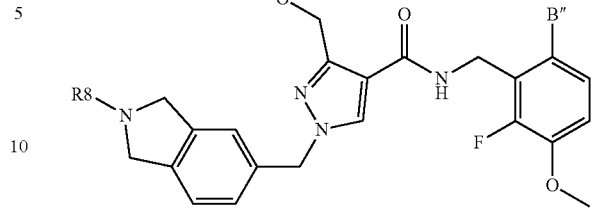
| Example number | R8 | B" | Free Base MW | [M + H]+ |
|---|---|---|---|---|
| 58 | Me | 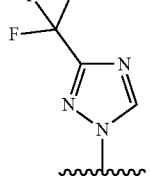 | 573.5 | 574.3 |
| 59 | iPr |  | 583.6 | 584.2 |
| 60 | iPr | 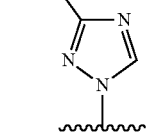 | 601.6 | 602.2 |
TABLE 4
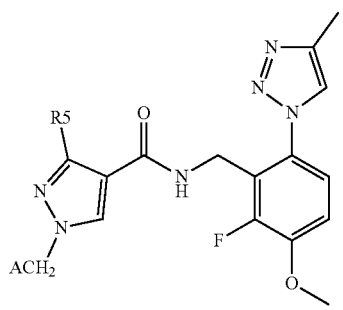
| Example number | ACH2 | R5 | Free Base MW | [M + H]+ |
|---|---|---|---|---|
| 61 | 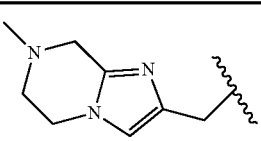 | CF3 | 547.5 | 548.4 |

TABLE 4-continued

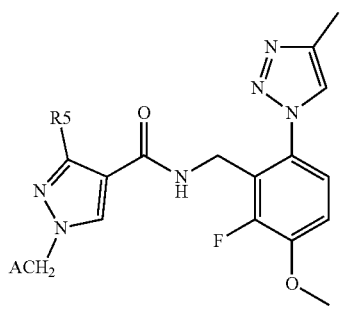

| Example number | ACH$_2$ | R5 | Free Base MW | [M + H]$^+$ |
|---|---|---|---|---|
| 62 | (1-methyl-5,6,7,8-tetrahydro-[1,2,4]triazolo[1,5-a]pyrazin-2-yl)methyl | CF$_3$ | 548.5 | |
| 63 | (7-methyl-5,6,7,8-tetrahydropyrido[3,4-d]pyrimidin-2-yl)methyl | CF$_3$ | 559.5 | 560.4 |
| 64 | (4-chloro-7-methyl-5,6,7,8-tetrahydro-1,7-naphthyridin-3-yl)methyl | CH$_2$OMe | 569.0 | 569.4 |
| 65 | (1-oxo-1,2,3,4-tetrahydroisoquinolin-6-yl)methyl | CH$_2$OMe | 533.6 | |
| 66 | (6-methyl-2-oxo-1,2,5,6,7,8-hexahydro-1,6-naphthyridin-3-yl)methyl | CF$_3$ | 574.5 | |
| 67 | (4-chloro-7-methyl-5,6,7,8-tetrahydro-1,8-naphthyridin-2-yl)methyl | CH$_2$OMe | 569.0 | |
| 68 | (isochroman-7-yl)methyl | CH$_2$OMe | 520.6 | 521.4 |

TABLE 4-continued
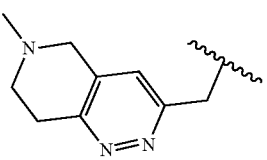 [SMILES: *Cc1cc2c(nn1)CCN(C)C2]
| Example number | ACH₂ | R5 | Free Base MW | [M + H]⁺ |
|---|---|---|---|---|
| 69 | 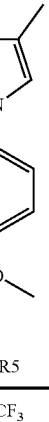 | CF₃ | 559.5 | |
| 70 | 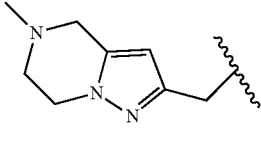 [SMILES: *Cc1cc2n(n1)CCN(C)C2] | CH₂OMe | 523.6 | 524.5 |
| 71 | 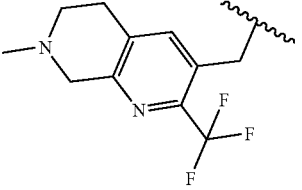 [SMILES: *Cc1cc2c(nc1C(F)(F)F)CN(C)CC2] | CH₂OH | 588.6 | |
| 72 | 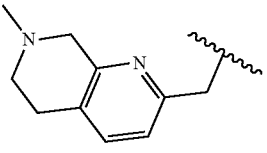 [SMILES: *Cc1ccc2c(n1)CN(C)CC2] | CHF₂ | 540.5 | |
| 73 | 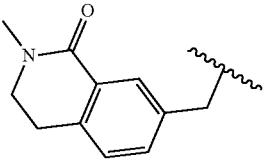 [SMILES: *Cc1ccc2c(c1)C(=O)N(C)CC2] | CH₂OMe | 547.6 | 548.2 |
| 74 | 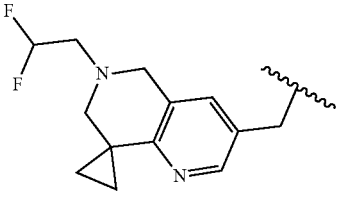 [SMILES: *Cc1cnc2c(c1)CN(CC(F)F)CC21CC1] | CH₂OH | 596.6 | |
| 75 | 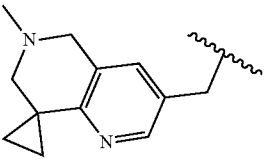 [SMILES: *Cc1cnc2c(c1)CN(C)CC21CC1] | CH₂OMe | 560.6 | |

TABLE 4-continued
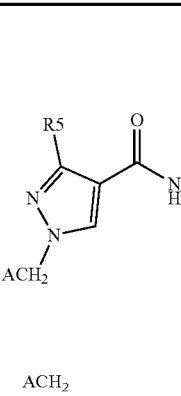
| Example number | ACH$_2$ | R5 | Free Base MW | [M + H]$^+$ |
|---|---|---|---|---|
| 76 | 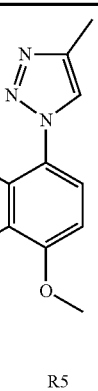 | 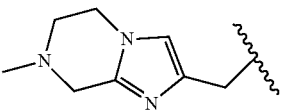 [SMILES: *Cc1cn2c(n1)CN(C)CC2] | 549.6 | |
| 77 | 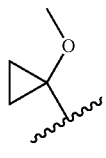 [SMILES: *C1(OC)CC1] | 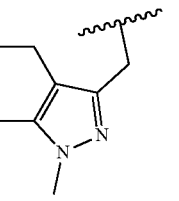 | 549.6 | |
| 78 | 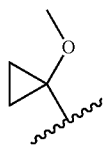 [SMILES: *C1(OC)CC1] | 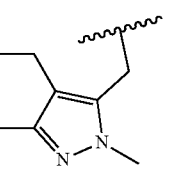 | 563.6 | |
| 79 | 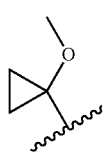 [SMILES: *C1(OC)CC1] | 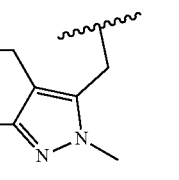 | 563.6 | |
| 80 | 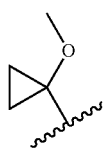 [SMILES: *C1(OC)CC1] | 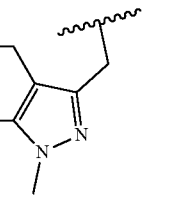 | 563.6 | |
| 81 | 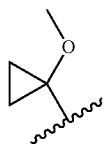 [SMILES: *C1(OC)CC1] | 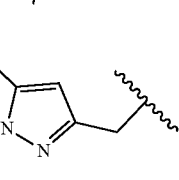 | 563.6 | |
| 82 |  | CHF$_2$ | 555.6 | 556.6 |

TABLE 4-continued
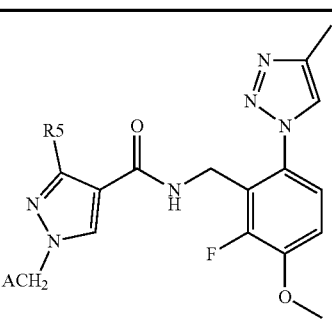
| Example number | ACH$_2$ | R5 | Free Base MW [M + H]$^+$ |
|---|---|---|---|
| 83 |  | 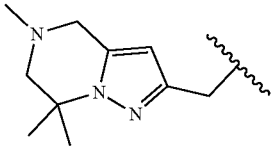 [SMILES: *Cc1cc2n(n1)C(C)(C)CN(C)C2] | 561.6 |
| 84 | 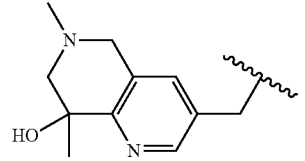 [SMILES: *Cc1cnc2c(c1)CN(C)CC2(C)O] | CH$_2$OMe | 551.6 |
| 85 | 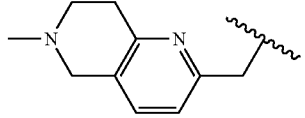 [SMILES: *Cc1ccc2c(n1)CCN(C)C2] | CH$_2$OMe | 564.6 |
| 86 | 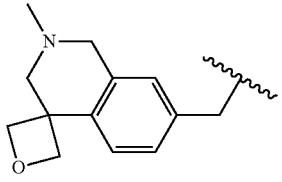 [SMILES: *Cc1ccc2c(c1)CN(C)CC21COC1] | CHF$_2$ | 540.5 |
| 87 | 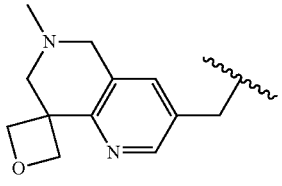 [SMILES: *Cc1cnc2c(c1)CN(C)CC21COC1] | CH$_2$OMe | 575.6 |
| 88 | 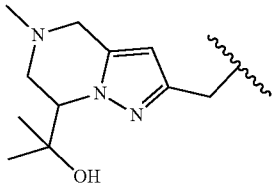 [SMILES: *Cc1cc2n(n1)C(C(C)(C)O)CN(C)C2] | CH$_2$OMe | 576.6 |
| 89 |  | CH$_2$OMe | 581.6 |

TABLE 4-continued
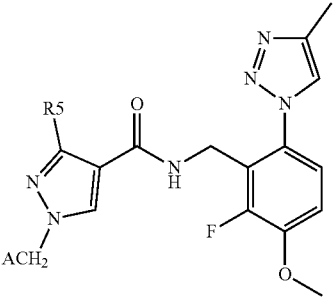
| Example number | ACH₂ | R5 | Free Base MW [M + H]⁺ |
|---|---|---|---|
| 90 |  | CHF₂ | 587.6 |
| 91 | 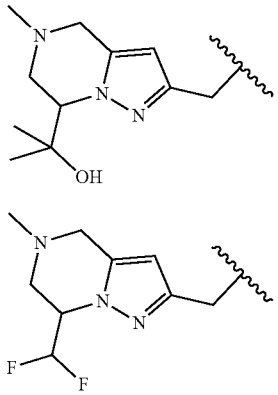 | CH₂OMe | 573.6 |
| 92 | 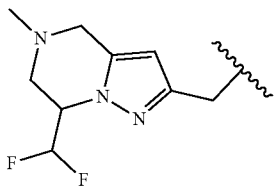 [SMILES: *Cc1cc2n(n1)C(C(F)F)CN(C)C2] | 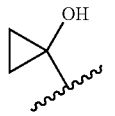 | 585.6 |
| 93 | 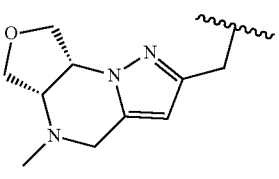 [SMILES: *Cc1cc2n(n1)[C@H]1COC[C@H]1N(C)C2] | CHF₂ | 571.6 |
| 94 |  | CHF₂ | 557.5 |
| 95 | 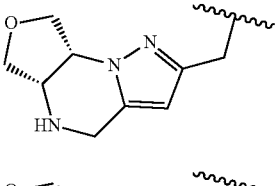 | CH₂OMe | 565.6 |
| 96 |  | 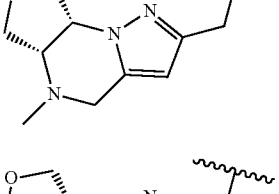 | 577.6 |

TABLE 4-continued

| Example number | ACH₂ | R5 | Free Base MW | [M + H]⁺ |
|---|---|---|---|---|
| 97 | (5-methyl-4,5,6,7-tetrahydropyrazolo[1,5-a]pyrazinyl with CH₂OH) | CHF₂ | 559.5 | |
| 98 | (5-methyl-4,5,6,7-tetrahydropyrazolo[1,5-a]pyrazinyl with CH₂OH) | (1-methoxycyclopropyl) | 579.6 | |
| 99 | (5-methyl-4,5,6,7-tetrahydropyrazolo[1,5-a]pyrazinyl with CH₃) | CHF₂ | 543.5 | |
| 100 | (5-methyl-4,5,6,7-tetrahydropyrazolo[1,5-a]pyrazinyl with CH₃) | CH₂OMe | 537.6 | |
| 101 | (5-methyl-4,5,6,7-tetrahydropyrazolo[1,5-a]pyrazinyl with CH₃) | (1-hydroxycyclopropyl) | 549.6 | |
| 102 | (7-methyl-5,6,7,8-tetrahydro-1,7-naphthyridinyl) | CH₂OMe | 534.6 | 535.2 |
| 103 | (2-methyl-7-fluoro-1,2,3,4-tetrahydroisoquinolinyl) | CH₂OMe | 551.6 | 552.0 |

TABLE 4-continued
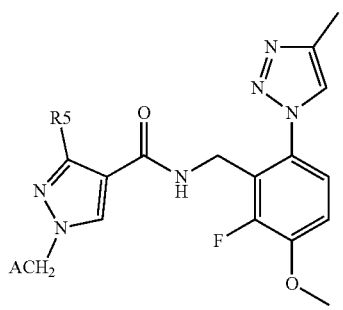
| Example number | ACH₂ | R5 | Free Base MW | [M + H]⁺ |
|---|---|---|---|---|
| 104 | (N-methyl tetrahydroisoquinoline with Cl) | CH₂OMe | 568.0 | 567.9 |
| 105 | (N-methyl 4,4-difluoro tetrahydroisoquinoline) | CH₂OMe | 569.6 | 569.9 |
| 106 | (N-methyl 4,4-difluoro tetrahydroisoquinoline) | CH₂OMe | 569.6 | 570.5 |
| 107 | (N-methyl tetrahydroisoquinoline with F) | CH₂OMe | 551.6 | 552.3 |
| 108 | (N-methyl benzoxazepine) | CH₂OMe | 549.6 | 550.7 |
| 109 | (N-methyl tetrahydrothiazolopyridine) | CH₂OMe | 540.6 | 541.5 |
| 110 | (benzoxazepine NH) | CH₂OMe | 535.6 | 536.5 |

TABLE 4-continued

| Example number | ACH₂ | R5 | Free Base MW | [M + H]⁺ |
|---|---|---|---|---|
| 111 | (4-methyl-benzothiazepine) | CH₂OMe | 565.7 | |
| 112 | (4-methyl-benzothiazepine S-oxide) | CH₂OMe | 581.7 | |
| 113 | (4-methyl-benzothiazepine S,S-dioxide) | CH₂OMe | 597.7 | |
| 114 | (N-methyl-fluoro-tetrahydroisoquinoline) | CH₂OMe | 551.6 | 552.2 |
| 115 | (N-difluoroethyl-tetrahydronaphthyridine) | CH₂OMe | 584.6 | 585.5 |
| 116 | (N-methyl-fluoro-tetrahydroisoquinoline) | CH₂OMe | 551.6 | 552.5 |
| 117 | (N-isopropyl-tetrahydronaphthyridine) | CH₂OMe | 562.6 | 563.4 |

TABLE 4-continued
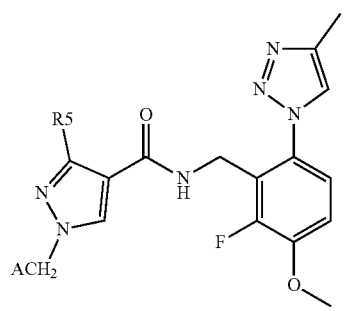
| Example number | ACH₂ | R5 | Free Base MW | [M + H]⁺ |
|---|---|---|---|---|
| 118 | (N-methyl-tetrahydroisoquinoline with F) | CH₂OMe | 551.6 | 552.4 |
| 119 | (CD₃-tetrahydroisoquinoline) | CH₂OMe | 536.6 | 537.2 |
| 120 | (pyrrolo-fused tetrahydroisoquinoline) | CH₂OMe | 559.6 | 560.4 |
| 121 | (N-methyl-benzazepine) | CH₂OMe | 547.6 | 548.4 |
| 122 | (N-isopropyl-benzazepine) | CH₂OMe | 575.7 | 576.4 |
| 123 | (N-isopropyl bridged bicyclic amine) | CH₂OMe | 573.7 | 574.2 |

TABLE 4-continued

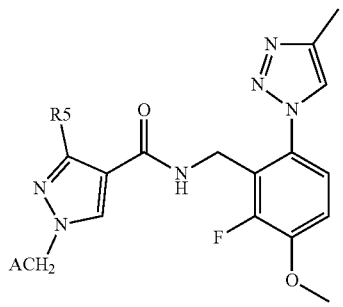

| Example number | ACH$_2$ | R5 | Free Base MW | [M + H]$^+$ |
|---|---|---|---|---|
| 124 | (2,1,1-trimethyl-2,3-dihydro-1H-isoindol-5-yl) | CH$_2$OMe | 547.6 | 548.4 |
| 125 | (5-methyl-4,5,6,7-tetrahydropyrazolo[1,5-a]pyrazin-2-yl) | CF$_3$ | 547.5 | 548.3 |
| 126 | (2'-methyl-2',3'-dihydro-1'H-spiro[cyclopropane-1,4'-isoquinolin]-7'-yl) | CH$_2$OMe | 559.6 | 560.4 |
| 127 | (2',3'-dihydro-1'H-spiro[cyclopropane-1,4'-isoquinolin]-7'-yl) | CH$_2$OMe | 545.6 | 546.4 |
| 128 | (1,1-dimethyl-1,2,3,4-tetrahydroisoquinolin-7-yl) | CH$_2$OMe | 547.6 | 548.3 |
| 129 | (1,1,2-trimethyl-1,2,3,4-tetrahydroisoquinolin-7-yl) | CH$_2$OMe | 561.7 | 562.5 |
| 130 | (4,4-dimethyl-1,2,3,4-tetrahydroisoquinolin-7-yl) | CH$_2$OMe | 547.6 | 548.4 |
| 131 | (7-methyl-5,6,7,8-tetrahydro-1,7-naphthyridin-3-yl) | CF$_3$ | 558.5 | 559.4 |

TABLE 4-continued
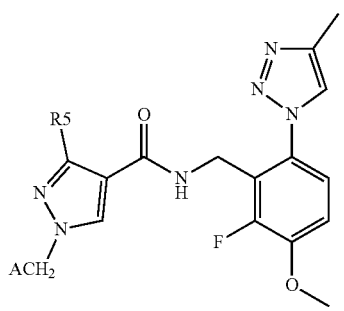
| Example number | ACH₂ | R5 | Free Base MW | [M + H]⁺ |
|---|---|---|---|---|
| 132 | (isopropyl-tetrahydro-1,6-naphthyridinyl) | CH₂OMe | 562.6 | 563.5 |
| 133 | (isochromanyl) | CH₂OMe | 520.6 | 521.5 |
| 134 | (2,4,4-trimethyl-tetrahydroisoquinolinyl) | CH₂OMe | 561.7 | 562.5 |
| 135 | (methyl-oxo-tetrahydroisoquinolinyl) | CH₂OMe | 547.6 | 548.3 |
| 136 | (methyl-tetrahydropyrazolopyrazinyl) | CHF₂ | 529.5 | 530.5 |
| 137 | (methyl-tetrahydro-2,7-naphthyridinyl) | CHF₂ | 540.5 | 541.4 |
| 138 | (methyl-tetrahydro-1,6-naphthyridinyl) | CF₃ | 558.5 | 559.2 |

TABLE 5

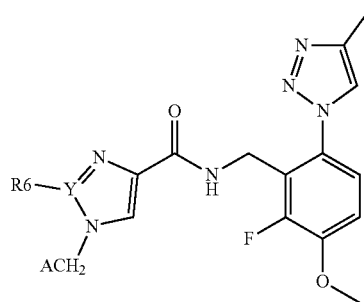

| Example number | ACH₂ | Y—R6 | Free Base MW [M + H]⁺ |
|---|---|---|---|
| 139 | [2,2-difluoroethyl-substituted spiro cyclopropane naphthyridine] | CCH₂OH | 596.6 |
| 140 | [methyl-substituted spiro cyclopropane naphthyridine] | CCH₃ | 530.6 |
| 141 | [methyl-substituted spiro cyclopropane naphthyridine] | CCH₂OMe | 560.6 |
| 142 | [methyl-substituted spiro cyclopropane pyrazolopyrazine] | CCH₃ | 519.6 |
| 143 | [methyl-substituted spiro cyclopropane pyrazolopyrazine] | CCH₂OMe | 549.6 |
| 144 | [methyl-substituted dimethyl pyrazolopyrazine] | CCH₃ | 521.6 |
| 145 | [methyl-substituted dimethyl pyrazolopyrazine] | CCH₂OMe | 551.6 |

TABLE 5-continued

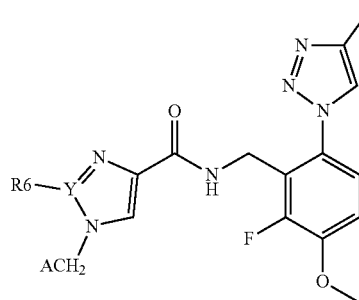

| Example number | ACH₂ | Y—R6 | Free Base MW | [M + H]⁺ |
|---|---|---|---|---|
| 146 | 5-methyl-4,5,6,7-tetrahydropyrazolo[1,5-a]pyrazine with 2-hydroxypropan-2-yl substituent | CCH₂OMe | 581.6 | |
| 147 | 2-isopropyl isoindoline | CCH₂OMe | 547.6 | 548.2 |
| 148 | 2-methyl tetrahydroisoquinoline | CCH₂OMe | 533.6 | 534.2 |
| 149 | 2-methyl tetrahydroisoquinoline | C—cyclopropyl | 529.6 | 530.2 |
| 150 | 2-isopropyl isoindoline | C—cyclopropyl | 543.6 | 544.3 |
| 151 | 2-methyl tetrahydroisoquinoline | CCH₃ | 503.6 | 504.2 |
| 152 | 2-methyl tetrahydroisoquinoline | N | 490.5 | 491.2 |

TABLE 5-continued

| Example number | ACH₂ | Y—R6 | Free Base MW | [M + H]⁺ |
|---|---|---|---|---|
| 153 | (2-isopropyl-isoindoline-5-ylmethyl) | N | 504.6 | 505.2 |

TABLE 6

| Example number | R9 | R10 | Free Base MW | [M + H]⁺ |
|---|---|---|---|---|
| 154 | F | OCH(cyclopropyl) | 549.6 | |
| 155 | F | Cl | 574.0 | 574.3 |
| 156 | Cl | OMe | 586.0 | 586.3 |
| 157 | F | C(CH₃)(F)₂ | 603.6 | 604.4 |

Example 158

| Example number | Free Base MW | [M + H]⁺ |
|---|---|---|
| 158 | 601.6 | 602.3 |

Example 159

| Example number | Free Base MW | [M + H]⁺ |
|---|---|---|
| 159 | 516.6 | 517.5 |

Example 160
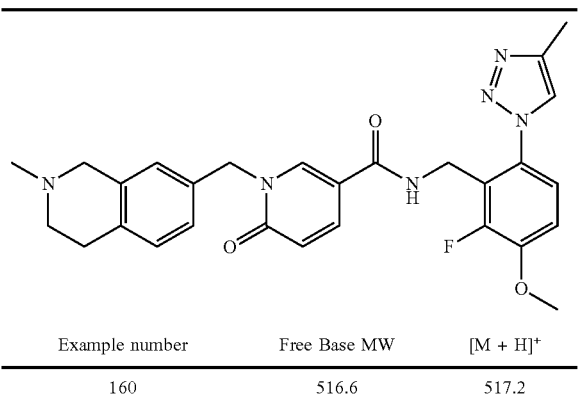
| Example number | Free Base MW | [M + H]+ |
|---|---|---|
| 160 | 516.6 | 517.2 |
Example 162
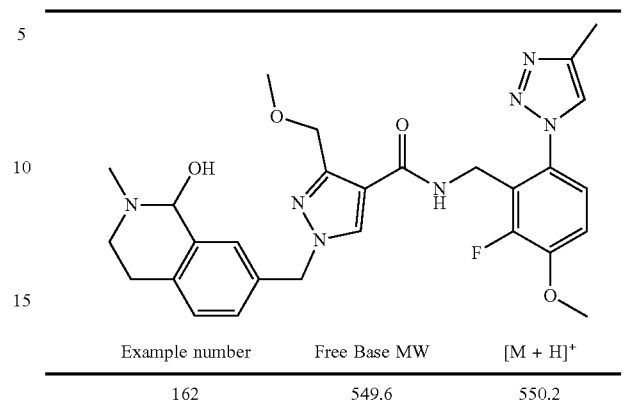
| Example number | Free Base MW | [M + H]+ |
|---|---|---|
| 162 | 549.6 | 550.2 |
Example 161
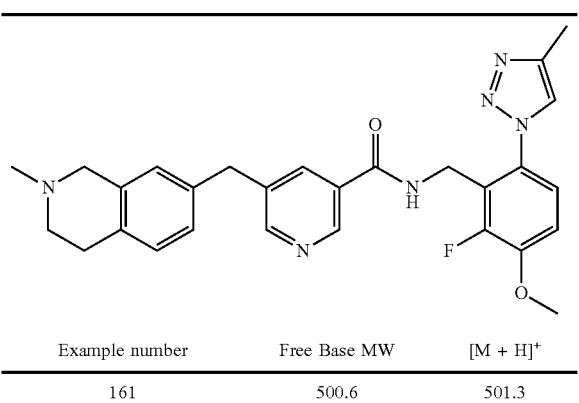
| Example number | Free Base MW | [M + H]+ |
|---|---|---|
| 161 | 500.6 | 501.3 |
Example 163
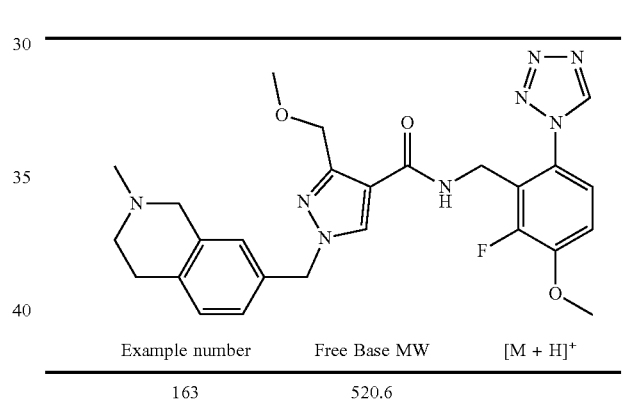
| Example number | Free Base MW | [M + H]+ |
|---|---|---|
| 163 | 520.6 | |
TABLE 7
| Example number | Structure | Free Base MW | [M + H]+ |
|---|---|---|---|
| 164 | 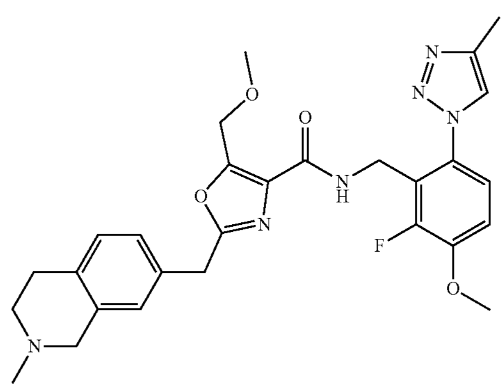 [SMILES: COCc1oc(Cc2ccc3c(c2)CN(C)CC3)nc1C(=O)NCc1c(-n2cc(C)nn2)ccc(OC)c1F] | 534.6 | |

TABLE 7-continued
| Example number | Structure | Free Base MW | [M + H]⁺ |
|---|---|---|---|
| 165 | 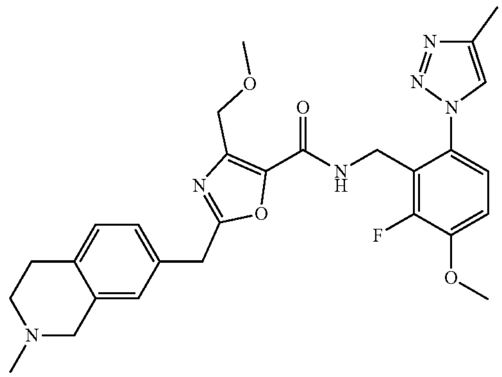 [SMILES: COCc1nc(Cc2ccc3c(c2)CN(C)CC3)oc1C(=O)NCc1c(-n2cc(C)nn2)ccc(OC)c1F] | 534.6 | |
| 166 | 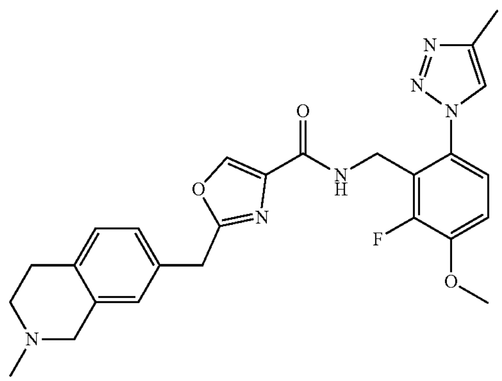 [SMILES: COc1ccc(-n2cc(C)nn2)c(CNC(=O)c2coc(Cc3ccc4c(c3)CN(C)CC4)n2)c1F] | 490.5 | |
| 167 | 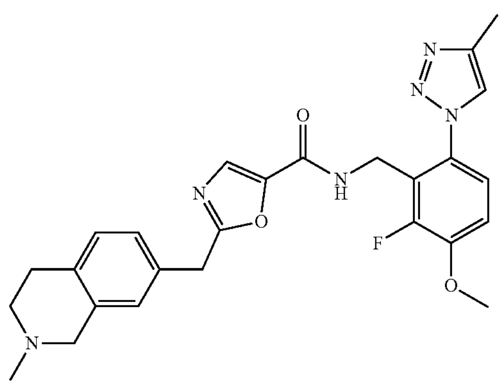 [SMILES: COc1ccc(-n2cc(C)nn2)c(CNC(=O)c2cnc(Cc3ccc4c(c3)CN(C)CC4)o2)c1F] | 490.5 | |
REFERENCE COMPOUNDS
Reference Compounds RC1, RC2 and RC3 were prepared according to procedures described herein.
Reference Compound RC4 is described in WO2017207983.
Reference Compounds RC5, RC6 and RC7 are described below:
Reference Compound 5
(2-Fluoro-3-methoxy-6-(4-(trimethylsilyl)-1H-1,2,3-triazol-1-yl)phenyl)methanol
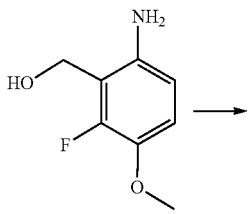

-continued

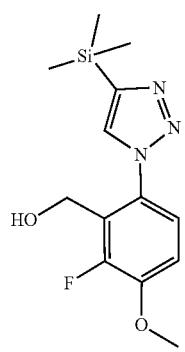

(6-Amino-2-fluoro-3-methoxyphenyl)methanol (described in WO2017207983) (350 mg, 2.05 mmol) was stirred in MeCN (15 mL) and cooled in an ice/water bath. 3-Methylbutyl nitrite (412 μL, 3.07 mmol) was added. Trimethylsilyl azide (407 μL, 3.067 mmol) was added dropwise and after 10 min the ice bath was removed and the mixture was warmed to rt. After 60 min further charges of 3-methylbutyl nitrite (69 μL, 0.51 mmol) and trimethylsilyl azide (68 μL, 0.51 mmol) were made and the mixture stirred for 60 min. The mixture was concentrated in vacuo to low volume and 1,4-dioxane (25 mL) was added, the flask was covered in tin foil and ethynyltrimethylsilane (2.5 mL, 18.40 mmol), CuI (58.4 mg, 0.31 mmol) and sodium ascorbate (243 mg, 1.23 mmol) were added and the mixture heated to 80° C. On completion of the reaction the mixture was cooled and partitioned between EtOAc (50 mL) and saturated NH₄Cl(aq) (40 mL) and the layers separated. The organic layer was washed with saturated NaHCO₃(aq), brine, dried over Na₂SO₄ and concentrated in vacuo. Flash chromatography afforded the title compound (150 mg, 25%) as a yellow solid.

[M+H]⁺=296.2

¹H NMR 0.39 (9H, s), 3.64 (1H, t, J=7.1 Hz), 3.96 (3H, s), 4.50 (2H, dd, J=7.3, 2.5 Hz), 7.02 (1H, t, J=8.7 Hz), 7.15 (1H, dd, J=8.8, 1.8 Hz), 7.85 (1H, s)

(2-Fluoro-3-methoxy-6-(1H-1,2,3-triazol-1-yl)phenyl)methanol

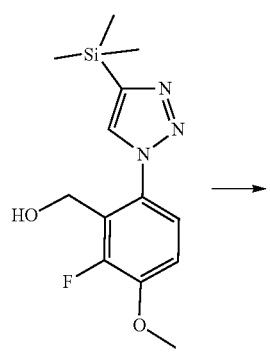

To a vial was added (2-fluoro-3-methoxy-6-(4-(trimethylsilyl)-1H-1,2,3-triazol-1-yl)phenyl)methanol (55 mg, 0.186 mmol) in THF (5 mL). A 1M solution of tetra-n-butylammonium fluoride in THF (1.9 mL) was added. The mixture was stirred at rt for 18 hrs, diluted with EtOAc (50 mL) and washed with water, brine, dried over MgSO₄ and concentrated in vacuo. Flash chromatography (10-100% EtOAC in Pet. Ether) afforded the title compound (36 mg, 87%) as a white solid.

[M+H]⁺=224.2

¹H NMR (CDCl₃) 3.38 (1H, t, J=7.1 Hz), 3.97 (3H, s), 4.51 (2H, dd, J=7.1, 2.5 Hz), 7.04 (1H, t, J=8.7 Hz), 7.18 (1H, dd, J=8.8, 1.8 Hz), 7.88 (1H, d, J=0.8 Hz), 7.95 (1H, d, J=0.9 Hz)

1-(2-(Bromomethyl)-3-fluoro-4-methoxyphenyl)-1H-1,2,3-triazole

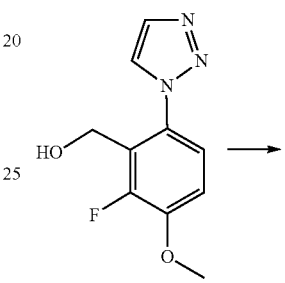

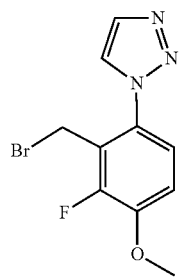

(2-Fluoro-3-methoxy-6-(1H-1,2,3-triazol-1-yl)phenyl)methanol (117 mg, 0.52 mmol) was dissolved in THF (15 mL) and PBr₃ (170 mg, 0.63 mmol) was added and the mixture stirred at rt for 2 hrs. Dilute NaHCO₃(aq) was added followed by DCM. The organic layer was separated and washed with water, brine, dried over MgSO₄ and concentrated in vacuo. Flash chromatography (10-60% EtOAc in Pet. Ether) afforded the title compound (80 mg, 53%) as an off white solid.

[M+H]⁺=285.6

2-(2-Fluoro-3-methoxy-6-(1H-1,2,3-triazol-1-yl)benzyl)isoindoline-1,3-dione

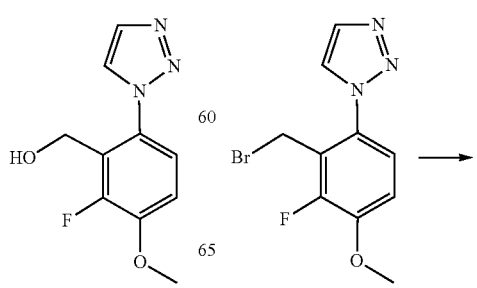

201
-continued

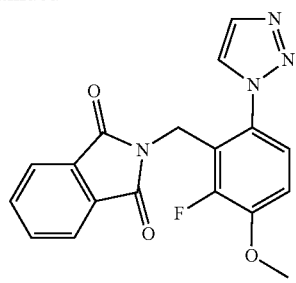

To 1-(2-(bromomethyl)-3-fluoro-4-methoxyphenyl)-1H-1,2,3-triazole (258 mg, 0.90 mmol) in DMF (4 mL) was added potassium phthalimide (159 mg, 0.86 mmol) and stirred at rt. After 5 min K$_2$CO$_3$ (237 mg, 1.72 mmol) was added and the mixture heated to 85° C. overnight. The mixture was concentrated in vacuo and azeotroped with toluene. Flash chromatography (0-10% DCM/MeOH) afforded the title compound (205 mg, 68%) as a white solid.

[M+H]$^+$=353.1

(2-Fluoro-3-methoxy-6-(1H-1,2,3-triazol-1-yl)phenyl)methanamine

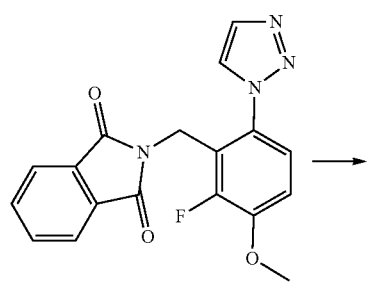

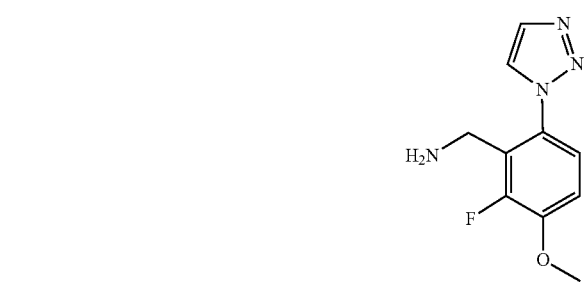

To a solution of 2-(2-fluoro-3-methoxy-6-(1H-1,2,3-triazol-1-yl)benzyl)isoindoline-1,3-dione (205 mg, 0.58 mmol) in MeOH (10 mL) was added hydrazine hydrate (50-60%, 339 µL) and the mixture stirred at 80° C. for 2 hrs. The mixture was cooled to rt and concentrated in vacuo and azeotroped with toluene. Flash chromatography (0-10% MeOH in DCM) afforded the title compound (129 mg, quantitative) as a white solid.

[M+H]$^+$=223.1

202
N-{[2-Fluoro-3-methoxy-6-(1,2,3-triazol-1-yl)phenyl]methyl}-3-(methoxymethyl)-1-{[2-(pyrrolidin-1-yl) pyrimidin-5-yl]methyl}pyrazole-4-carboxamide

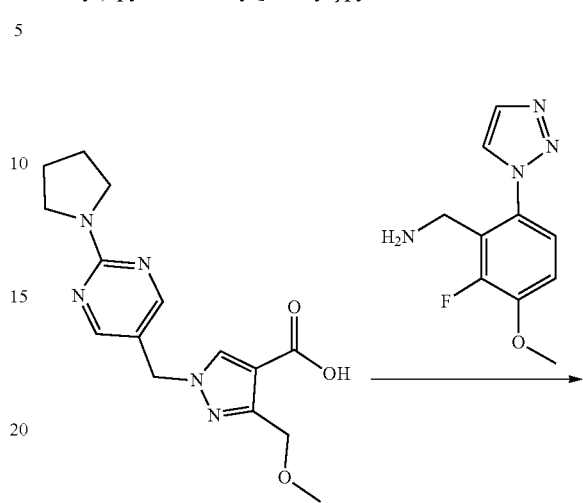

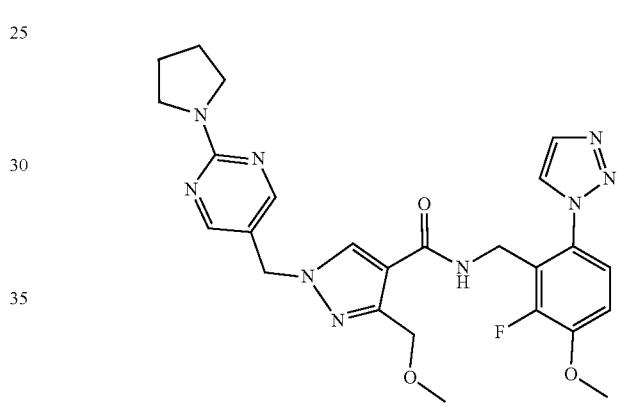

3-Methoxymethyl-1-(2-pyrrolidin-1-yl-pyrimidin-5-ylmethyl)-1H-pyrazole-4-carboxylic acid (described in WO 2016083816) (134 mg, 0.43 mmol) and (2-fluoro-3-methoxy-6-(1H-1,2,3-triazol-1-yl)phenyl)methanamine (95 mg, 0.43 mmol) were combined and taken up in DCM (10 mL) in an ice/water bath. The mixture was treated with HOBt (69 mg, 0.51 mmol), TEA (296 µL, 2.13 mmol) and 1-ethyl-3-(3-dimethylaminopropyl)carbodiimide (114 mg, 0.60 mmol). The mixture was warmed to rt and stirred for 18 hrs. The mixture was diluted with CHCl$_3$ (50 mL) and saturated NaHCO$_3$(aq) (10 mL) was added. The organic layer was separated and washed with water and brine, dried over MgSO$_4$ and concentrated in vacuo. Flash chromatography (1-3% MeOH in DCM) afforded the title compound (138 mg, 62%) as a white solid.

[M+H]$^+$=522.2

$^1$H NMR (d6-DMSO) 1.89-1.92 (4H, m), 3.17 (3H, s), 3.43-3.46 (4H, m), 3.92 (3H, s), 4.22 (2H, d, J=4.4 Hz), 4.42 (2H, s), 5.10 (2H, s), 7.29-7.35 (2H, m), 7.92 (1H, d, J=0.8 Hz), 8.04 (1H, t, J=5.0 Hz), 8.09 (1H, s), 8.34 (2H, s), 8.45 (1H, d, J=0.9 Hz)

203

Reference Compound 6

N-{[2-Fluoro-3-methoxy-6-(4-methyl-1,2,3-triazol-1-yl)phenyl]methyl}-3-(methoxymethyl)-1-{[2-(pyrrolidin-1-yl)pyrimidin-5-yl]methyl}pyrazole-4-carboxamide

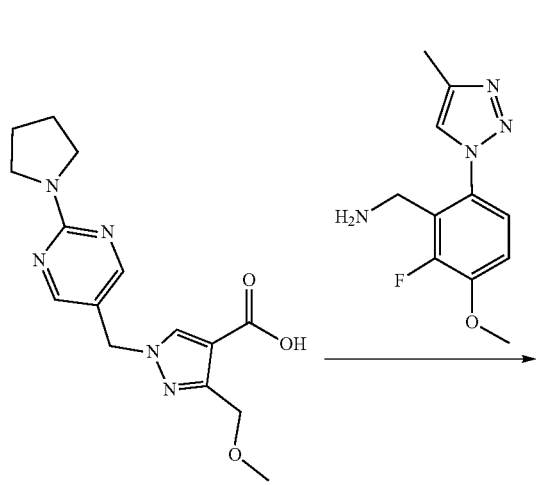

3-Methoxymethyl-1-(2-pyrrolidin-1-yl-pyrimidin-5-ylmethyl)-1H-pyrazole-4-carboxylic acid (150 mg, 0.47 mmol) was dissolved in DCM (30 mL). To the solution was added HBTU (215 mg, 0.57 mmol) and DIPEA (122 mg, 0.95 mmol) and stirred at rt. After 20 min, (2-fluoro-3-methoxy-6-(4-methyl-1H-1,2,3-triazol-1-yl)phenyl)methanamine (117 mg, 0.50 mmol) was added and the mixture stirred at rt for 40 hrs. The mixture was diluted with $CHCl_3$ (50 mL), washed with saturated $NaHCO_3$(aq), water, brine, dried over $Na_2SO_4$ and concentrated in vacuo. Flash chromatography (5% MeOH, 95% $CHCl_3$) afforded the title compound (143 mg, 56%) as a white solid.

[M+H]1=536.3

$^1$H NMR (d6-DMSO) 1.89-1.92 (4H, m), 2.28 (3H, s), 3.17 (3H, s), 3.45 (4H, t, J=6.6 Hz), 3.92 (3H, s), 4.24 (2H, d, J=4.6 Hz), 4.42 (2H, s), 5.11 (2H, s), 7.25-7.32 (2H, m), 8.00 (1H, t, J=5.0 Hz), 8.09 (1H, s), 8.13 (1H, s), 8.34 (2H, s)

204

Reference Compound 7

N-({6-[4-(Difluoromethyl)-1,2,3-triazol-1-yl]-2-fluoro-3-methoxyphenyl}methyl)-3-(methoxymethyl)-1-{[2-(pyrrolidin-1-yl)pyrimidin-5-yl]methyl}pyrazole-4-carboxamide

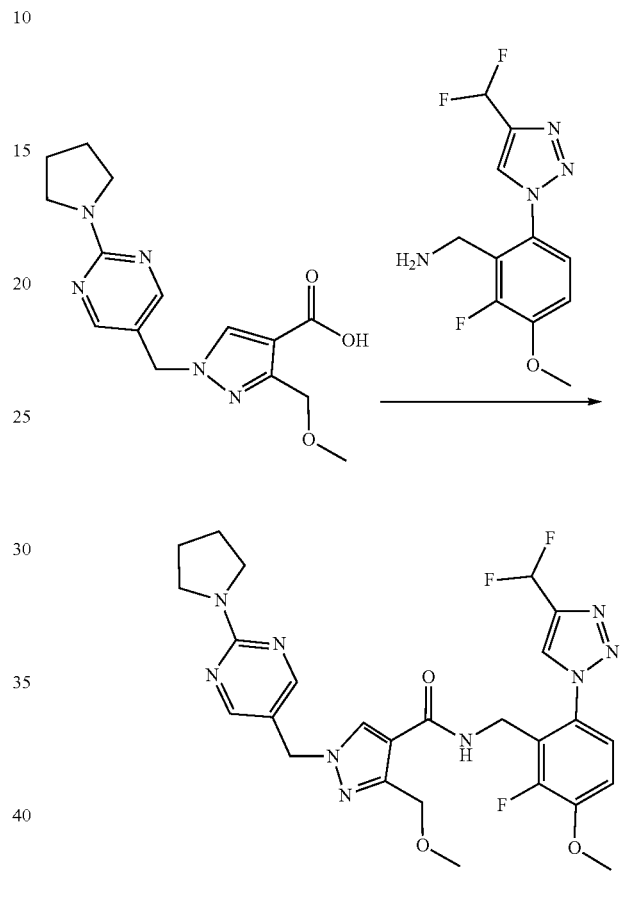

3-Methoxymethyl-1-(2-pyrrolidin-1-yl-pyrimidin-5-ylmethyl)-1H-pyrazole-4-carboxylic acid (94 mg, 0.30 mmol) and (6-(4-(difluoromethyl)-1H-1,2,3-triazol-1-yl)-2-fluoro-3-methoxyphenyl) methanamine (135 mg, 0.30 mmol) were taken up in DCM (10 mL) while cooling in an ice/water bath. The mixture was treated with HOBt (48 mg, 0.36 mmol), TEA (207 µL, 1.49 mmol) and 1-ethyl-3-(3-dimethylaminopropyl)carbodiimide (80 mg, 0.42 mmol). The mixture was warmed to rt and stirred for 18 hrs. The mixture was diluted with $CHCl_3$ (50 mL) and saturated $NaHCO_3$(aq) (10 mL) added. The organic layer was separated and washed with water and brine, dried over $MgSO_4$ and concentrated in vacuo. Flash chromatography (1-3% MeOH in DCM) afforded the title compound (117 mg, 68%) as a white solid.

[M+H]$^+$=572.2

$^1$H NMR (d6-DMSO) 1.89-1.92 (4H, m), 3.17 (3H, s), 3.43-3.46 (4H, m), 3.93 (3H, s), 4.25 (2H, d, J=4.8 Hz), 4.42 (2H, s), 5.10 (2H, s), 7.28 (1H, t, J=54.1 Hz), 7.31-7.38 (2H, m), 8.08 (1H, s), 8.09 (1H, t, J=5.1 Hz), 8.33 (2H, s), 8.89 (1H, t, J=1.4 Hz)

TABLE 8

Reference compounds

| Example number | ACH₂ | R5 | B" | Free Base MW | [M + H]⁺ |
|---|---|---|---|---|---|
| RC1 | isoquinoline-7-ylmethyl | CH₂OMe | 4-methyl-1,2,3-triazol-1-yl | 515.5 | 516.4 |
| RC2 | (2-methylquinolin-6-yl)methyl | CH₂OMe | tetrazol-1-yl | 516.5 | 517.3 |
| RC3 | quinolin-6-ylmethyl | CH₂OMe | tetrazol-1-yl | 502.5 | 503.2 |

TABLE 9

Reference compounds

| Example number | B" | Free Base MW | [M + H]⁺ |
|---|---|---|---|
| RC4 | tetrazol-1-yl | n/a | n/a |
| RC5 | triazol-1-yl | 521.6 | 522.2 |
| RC6 | 4-methyl-triazol-1-yl | 535.6 | 536.3 |
| RC7 | 4-(difluoromethyl)-triazol-1-yl | 571.6 | 572.2 |

TABLE 10

Compound Names

| Example Number | Name |
|---|---|
| 1 | N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide |
| 2 | N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide |
| 3 | N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]pyrazole-4-carboxamide |
| 4 | N-{[2-fluoro-3-methoxy-6-(3-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide |
| 5 | N-(2-fluoro-3-methoxy-6-(4-methyl-2H-1,2,3-triazol-2-yl)benzyl)-3-(methoxymethyl)-1-((2-methyl-1,2,3,4-tetrahydroisoquinolin-7-yl)methyl)-1H-pyrazole-4-carboxamide |
| 6 | N-{[6-(3-ethyl-1,2,4-triazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide |
| 7 | N-{[2-fluoro-3-methoxy-6-(1,2,4-triazol-1-yl)phenyl]methyl}-3-(methoxymethyl)-1-[(2-methyl-3,4-dihydro-1H-isoquinolin-7-yl)methyl]pyrazole-4-carboxamide |
| 8 | N-({2-fluoro-3-methoxy-6-[3-(trifluoromethyl)pyrazol-1-yl]phenyl}methyl)-3-(methoxymethyl)-1-[(2-methyl-3,4-dihydro-1H-isoquinolin-7-yl)methyl]pyrazole-4-carboxamide |
| 9 | N-{[6-(3-cyclopropylpyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide |
| 10 | N-(6-(3-cyano-1H-pyrrol-1-yl)-2-fluoro-3-methoxybenzyl)-3-(methoxymethyl)-1-((2-methyl-1,2,3,4-tetrahydroisoquinolin-7-yl)methyl)-1H-pyrazole-4-carboxamide |
| 11 | N-{[6-(3-cyanopyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide |
| 12 | N-{[2-fluoro-3-methoxy-6-(5-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide |
| 13 | N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-7-yl)methyl]pyrazole-4-carboxamide |
| 14 | 1-[(2-cyclopropyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide |
| 15 | N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide |
| 16 | 1-[(2-ethyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide |
| 17 | N-{[2-fluoro-3-methoxy-6-(4-methyl-1,2,3-triazol-1-yl)phenyl]methyl}-1-[(2-isopropyl-3,4-dihydro-1H-isoquinolin-7-yl)methyl]-3-(methoxymethyl)pyrazole-4-carboxamide |
| 18 | 1-((2-cyclobutyl-1,2,3,4-tetrahydroisoquinolin-7-yl)methyl)-N-(2-fluoro-3-methoxy-6-(4-methyl-1H-1,2,3-triazol-1-yl)benzyl)-3-(methoxymethyl)-1H-pyrazole-4-carboxamide |
| 19 | 1-[(2-cyclopropyl-3,4-dihydro-1H-isoquinolin-7-yl)methyl]-N-({6-[3-(difluoromethyl)-1,2,4-triazol-1-yl]-2-fluoro-3-methoxyphenyl}methyl)-3-(methoxymethyl)pyrazole-4-carboxamide |
| 20 | 1-[(2-cyclopropyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide |
| 21 | N-{[6-(3-cyanopyrazol-1-yl)-2-fluoro-3-methoxyphenyl]methyl}-1-[(2-cyclopropyl-3,4-dihydro-1H-isoquinolin-7-yl)methyl]-3-(methoxymethyl)pyrazole-4-carboxamide |
| 22 | N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]-3-(methoxymethyl)pyrazole-4-carboxamide |
| 23 | N-({6-[3-(difluoromethyl)-1,2,4-triazol-1-yl]-2-fluoro-3-methoxyphenyl}methyl)-1-[(2-isopropyl-3,4-dihydro-1H-isoquinolin-7-yl)methyl]-3-(methoxymethyl)pyrazole-4-carboxamide |
| 24 | N-{[6-(3-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide |
| 25 | 1-[(2-ethyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide |
| 26 | N-({6-[3-(difluoromethyl)-1,2,4-triazol-1-yl]-2-fluoro-3-methoxyphenyl}methyl)-1-[(2-ethyl-3,4-dihydro-1H-isoquinolin-7-yl)methyl]-3-(methoxymethyl)pyrazole-4-carboxamide |
| 27 | N-{[6-(3-cyanopyrazol-1-yl)-2-fluoro-3-methoxyphenyl]methyl}-1-[(2-ethyl-3,4-dihydro-1H-isoquinolin-7-yl)methyl]-3-(methoxymethyl)pyrazole-4-carboxamide |
| 28 | N-{[6-(dimethyl-1,2,4-triazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide |

TABLE 10-continued

Compound Names

| Example Number | Name |
|---|---|
| 29 | N-{[6-(dimethyl-1,2,4-triazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide |
| 30 | N-{[6-(4-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide |
| 31 | N-({2-fluoro-3-methoxy-6-[3-(trifluoromethyl)-1,2,4-triazol-1-yl]phenyl}methyl)-1-[(2-methyl-3,4-dihydro-1H-isoquinolin-7-yl)methyl]pyrazole-4-carboxamide |
| 32 | N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]pyrazole-4-carboxamide |
| 33 | 3-(difluoromethyl)-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]pyrazole-4-carboxamide |
| 34 | N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide |
| 35 | 1-[(2-cyclopropyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide |
| 36 | N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-6-yl)methyl]pyrazole-4-carboxamide |
| 37 | N-{[2-fluoro-3-methoxy-6-(4-methyl-1,2,3-triazol-1-yl)phenyl]methyl}-1-[(2-isopropyl-3,4-dihydro-1H-isoquinolin-6-yl)methyl]-3-(methoxymethyl)pyrazole-4-carboxamide |
| 38 | 1-[(2-ethyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide |
| 39 | N-(2-fluoro-3-methoxy-6-(4-methyl-1H-1,2,3-triazol-1-yl)benzyl)-3-(methoxymethyl)-1-((2-(oxetan-3-yl)-1,2,3,4-tetrahydroisoquinolin-7-yl)methyl)-1H-pyrazole-4-carboxamide |
| 40 | 1-[(2-cyclobutyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide |
| 41 | N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide |
| 42 | N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-6-yl)methyl]pyrazole-4-carboxamide |
| 43 | N-{[6-(3-cyanopyrazol-1-yl)-2-fluoro-3-methoxyphenyl]methyl}-3-(methoxymethyl)-1-[(2-methyl-3,4-dihydro-1H-isoquinolin-6-yl)methyl]pyrazole-4-carboxamide |
| 44 | N-({6-[3-(difluoromethyl)-1,2,4-triazol-1-yl]-2-fluoro-3-methoxyphenyl}methyl)-1-[(2-isopropyl-3,4-dihydro-1H-isoquinolin-6-yl)methyl]-3-(methoxymethyl)pyrazole-4-carboxamide |
| 45 | N-({2-fluoro-3-methoxy-6-[3-(trifluoromethyl)-1,2,4-triazol-1-yl]phenyl}methyl)-1-[(2-isopropyl-3,4-dihydro-1H-isoquinolin-6-yl)methyl]-3-(methoxymethyl)pyrazole-4-carboxamide |
| 46 | N-{[6-(3-cyanopyrazol-1-yl)-2-fluoro-3-methoxyphenyl]methyl}-1-[(2-isopropyl-3,4-dihydro-1H-isoquinolin-6-yl)methyl]-3-(methoxymethyl)pyrazole-4-carboxamide |
| 47 | 1-[(2-cyclopropyl-3,4-dihydro-1H-isoquinolin-6-yl)methyl]-N-({6-[3-(difluoromethyl)-1,2,4-triazol-1-yl]-2-fluoro-3-methoxyphenyl}methyl)-3-(methoxymethyl)pyrazole-4-carboxamide |
| 48 | 1-[(2-cyclopropyl-3,4-dihydro-1H-isoquinolin-6-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide |
| 49 | N-{[6-(3-cyanopyrazol-1-yl)-2-fluoro-3-methoxyphenyl]methyl}-1-[(2-cyclopropyl-3,4-dihydro-1H-isoquinolin-6-yl)methyl]-3-(methoxymethyl)pyrazole-4-carboxamide |
| 50 | N-({6-[3-(difluoromethyl)-1,2,4-triazol-1-yl]-2-fluoro-3-methoxyphenyl}methyl)-1-[(2-ethyl-3,4-dihydro-1H-isoquinolin-6-yl)methyl]-3-(methoxymethyl)pyrazole-4-carboxamide |
| 51 | 1-[(2-ethyl-3,4-dihydro-1H-isoquinolin-6-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide |
| 52 | N-{[6-(3-cyanopyrazol-1-yl)-2-fluoro-3-methoxyphenyl]methyl}-1-[(2-ethyl-3,4-dihydro-1H-isoquinolin-6-yl)methyl]-3-(methoxymethyl)pyrazole-4-carboxamide |
| 53 | 1-(2,3-dihydro-1H-isoindol-5-ylmethyl)-N-{[2-fluoro-3-methoxy-6-(4-methyl-1,2,3-triazol-1-yl)phenyl]methyl}-3-(methoxymethyl)pyrazole-4-carboxamide |
| 54 | N-{[2-fluoro-3-methoxy-6-(4-methyl-1,2,3-triazol-1-yl)phenyl]methyl}-3-(methoxymethyl)-1-[(2-methyl-1,3-dihydroisoindol-5-yl)methyl]pyrazole-4-carboxamide |
| 55 | N-{[2-fluoro-3-methoxy-6-(4-methyl-1,2,3-triazol-1-yl)phenyl]methyl}-1-[(2-isopropyl-1,3-dihydroisoindol-5-yl)methyl]-3-(methoxymethyl)pyrazole-4-carboxamide |
| 56 | 1-[(2-ethyl-1,3-dihydroisoindol-5-yl)methyl]-N-{[2-fluoro-3-methoxy-6-(4-methyl-1,2,3-triazol-1-yl)phenyl]methyl}-3-(methoxymethyl)pyrazole-4-carboxamide |

TABLE 10-continued

Compound Names

| Example Number | Name |
|---|---|
| 57 | N-({6-[3-(difluoromethyl)-1,2,4-triazol-1-yl]-2-fluoro-3-methoxyphenyl}methyl)-3-(methoxymethyl)-1-[(2-methyl-1,3-dihydroisoindol-5-yl)methyl]pyrazole-4-carboxamide |
| 58 | N-({2-fluoro-3-methoxy-6-[3-(trifluoromethyl)-1,2,4-triazol-1-yl]phenyl}methyl)-3-(methoxymethyl)-1-[(2-methyl-1,3-dihydroisoindol-5-yl)methyl]pyrazole-4-carboxamide |
| 59 | N-({6-[3-(difluoromethyl)-1,2,4-triazol-1-yl]-2-fluoro-3-methoxyphenyl}methyl)-1-[(2-isopropyl-1,3-dihydroisoindol-5-yl)methyl]-3-(methoxymethyl)pyrazole-4-carboxamide |
| 60 | N-({2-fluoro-3-methoxy-6-[3-(trifluoromethyl)-1,2,4-triazol-1-yl]phenyl}methyl)-1-[(2-isopropyl-1,3-dihydroisoindol-5-yl)methyl]-3-(methoxymethyl)pyrazole-4-carboxamide |
| 61 | N-{[2-fluoro-3-methoxy-6-(4-methyl-1,2,3-triazol-1-yl)phenyl]methyl}-1-({7-methyl-5H,6H,8H-imidazo[1,2-a]pyrazin-2-yl}methyl)-3-(trifluoromethyl)pyrazole-4-carboxamide |
| 62 | N-{[2-fluoro-3-methoxy-6-(4-methyl-1,2,3-triazol-1-yl)phenyl]methyl}-1-({7-methyl-4H,6H,7H-[1,2,4]triazolo[1,5-a]pyrazin-2-yl}methyl)-3-(trifluoromethyl)pyrazole-4-carboxamide |
| 63 | N-{[2-fluoro-3-methoxy-6-(4-methyl-1,2,3-triazol-1-yl)phenyl]methyl}-1-({7-methyl-5H,6H,8H-pyrido[3,4-d]pyrimidin-2-yl}methyl)-3-(trifluoromethyl)pyrazole-4-carboxamide |
| 64 | 1-[(4-chloro-7-methyl-6,8-dihydro-5H-1,7-naphthyridin-3-yl)methyl]-N-{[2-fluoro-3-methoxy-6-(4-methyl-1,2,3-triazol-1-yl)phenyl]methyl}-3-(methoxymethyl)pyrazole-4-carboxamide |
| 65 | N-{[2-fluoro-3-methoxy-6-(4-methyl-1,2,3-triazol-1-yl)phenyl]methyl}-3-(methoxymethyl)-1-[(1-oxo-3,4-dihydro-2H-isoquinolin-6-yl)methyl]pyrazole-4-carboxamide |
| 66 | N-{[2-fluoro-3-methoxy-6-(4-methyl-1,2,3-triazol-1-yl)phenyl]methyl}-1-[(6-methyl-2-oxo-1,5,7,8-tetrahydro-1,6-naphthyridin-3-yl)methyl]-3-(trifluoromethyl)pyrazole-4-carboxamide |
| 67 | 1-[(4-chloro-7-methyl-6,8-dihydro-5H-1,7-naphthyridin-2-yl)methyl]-N-{[2-fluoro-3-methoxy-6-(4-methyl-1,2,3-triazol-1-yl)phenyl]methyl}-3-(methoxymethyl)pyrazole-4-carboxamide |
| 68 | 1-(3,4-dihydro-1H-2-benzopyran-6-ylmethyl)-N-{[2-fluoro-3-methoxy-6-(4-methyl-1,2,3-triazol-1-yl)phenyl]methyl}-3-(methoxymethyl)pyrazole-4-carboxamide |
| 69 | N-{[2-fluoro-3-methoxy-6-(4-methyl-1,2,3-triazol-1-yl)phenyl]methyl}-1-({6-methyl-5H,7H,8H-pyrido[4,3-c]pyridazin-3-yl}methyl)-3-(trifluoromethyl)pyrazole-4-carboxamide |
| 70 | N-{[2-fluoro-3-methoxy-6-(4-methyl-1,2,3-triazol-1-yl)phenyl]methyl}-3-(methoxymethyl)-1-({5-methyl-4H,6H,7H-pyrazolo[1,5-a]pyrazin-2-yl}methyl)pyrazole-4-carboxamide |
| 71 | N-{[2-fluoro-3-methoxy-6-(4-methyl-1,2,3-triazol-1-yl)phenyl]methyl}-3-(hydroxymethyl)-1-{[7-methyl-2-(trifluoromethyl)-6,8-dihydro-5H-1,7-naphthyridin-3-yl]methyl}pyrazole-4-carboxamide |
| 72 | 3-(difluoromethyl)-N-{[2-fluoro-3-methoxy-6-(4-methyl-1,2,3-triazol-1-yl)phenyl]methyl}-1-[(7-methyl-6,8-dihydro-5H-1,7-naphthyridin-2-yl)methyl]pyrazole-4-carboxamide |
| 73 | N-{[2-fluoro-3-methoxy-6-(4-methyl-1,2,3-triazol-1-yl)phenyl]methyl}-3-(methoxymethyl)-1-[(2-methyl-1-oxo-3,4-dihydroisoquinolin-7-yl)methyl]pyrazole-4-carboxamide |
| 74 | 1-[6-(2,2-difluoroethyl)-5,7-dihydrospiro[1,6-naphthyridine-8,1'-cyclopropane]-3-ylmethyl]-N-{[2-fluoro-3-methoxy-6-(4-methyl-1,2,3-triazol-1-yl)phenyl]methyl}-3-(hydroxymethyl)pyrazole-4-carboxamide |
| 75 | N-{[2-fluoro-3-methoxy-6-(4-methyl-1,2,3-triazol-1-yl)phenyl]methyl}-3-(methoxymethyl)-1-{6-methyl-5,7-dihydrospiro[1,6-naphthyridine-8,1'-cyclopropane]-3-ylmethyl}pyrazole-4-carboxamide |
| 76 | N-{[2-fluoro-3-methoxy-6-(4-methyl-1,2,3-triazol-1-yl)phenyl]methyl}-3-(1-methoxycyclopropyl)-1-({5-methyl-4H,6H,7H-pyrazolo[1,5-a]pyrazin-2-yl}methyl)pyrazole-4-carboxamide |
| 77 | N-{[2-fluoro-3-methoxy-6-(4-methyl-1,2,3-triazol-1-yl)phenyl]methyl}-3-(1-methoxycyclopropyl)-1-({7-methyl-5H,6H,8H-imidazo[1,2-a]pyrazin-2-yl}methyl)pyrazole-4-carboxamide |
| 78 | 1-({1,6-dimethyl-4H,5H,7H-pyrazolo[3,4-c]pyridin-3-yl}methyl)-N-{[2-fluoro-3-methoxy-6-(4-methyl-1,2,3-triazol-1-yl)phenyl]methyl}-3-(1-methoxycyclopropyl)pyrazole-4-carboxamide |
| 79 | 1-({2,6-dimethyl-4H,5H,7H-pyrazolo[3,4-c]pyridin-3-yl}methyl)-N-{[2-fluoro-3-methoxy-6-(4-methyl-1,2,3-triazol-1-yl)phenyl]methyl}-3-(1-methoxycyclopropyl)pyrazole-4-carboxamide |
| 80 | 1-({2,5-dimethyl-4H,6H,7H-pyrazolo[4,3-c]pyridin-3-yl}methyl)-N-{[2-fluoro-3-methoxy-6-(4-methyl-1,2,3-triazol-1-yl)phenyl]methyl}-3-(1-methoxycyclopropyl)pyrazole-4-carboxamide |
| 81 | 1-({1,5-dimethyl-4H,6H,7H-pyrazolo[4,3-c]pyridin-3-yl}methyl)-N-{[2-fluoro-3-methoxy-6-(4-methyl-1,2,3-triazol-1-yl)phenyl]methyl}-3-(1-methoxycyclopropyl)pyrazole-4-carboxamide |

TABLE 10-continued

Compound Names

| Example Number | Name |
|---|---|
| 82 | 3-(difluoromethyl)-N-(2-fluoro-3-methoxy-6-(4-methyl-1H-1,2,3-triazol-1-yl)benzyl)-1-((5'-methyl-5',6'-dihydro-4'H-spiro[cyclopropane-1,7'-pyrazolo[1,5-a]pyrazin[-2'-yl]methyl)-1H-pyrazole-4-carboxamide |
| 83 | N-(2-fluoro-3-methoxy-6-(4-methyl-1H-1,2,3-triazol-1-yl)benzyl)-3-(1-hydroxycyclopropyl)-1-((5'-methyl-5',6'-dihydro-4'H-spiro[cyclopropane-1,7'-pyrazolo[1,5-a]pyrazin]-2'-yl)methyl)-1H-pyrazole-4-carboxamide |
| 84 | N-{[2-fluoro-3-methoxy-6-(4-methyl-1,2,3-triazol-1-yl)phenyl]methyl}-3-(methoxymethyl)-1-({5,7,7-trimethyl-4H,6H-pyrazolo[1,5-a]pyrazin-2-yl}methyl)pyrazole-4-carboxamide |
| 85 | N-{[2-fluoro-3-methoxy-6-(4-methyl-1,2,3-triazol-1-yl)phenyl]methyl}-1-[(8-hydroxy-6,8-dimethyl-5,7-dihydro-1,6-naphthyridin-3-yl)methyl]-3-(methoxymethyl)pyrazole-4-carboxamide |
| 86 | 3-(difluoromethyl)-N-{[2-fluoro-3-methoxy-6-(4-methyl-1,2,3-triazol-1-yl)phenyl]methyl}-1-[(6-methyl-7,8-dihydro-5H-1,6-naphthyridin-2-yl)methyl]pyrazole-4-carboxamide |
| 87 | N-{[2-fluoro-3-methoxy-6-(4-methyl-1,2,3-triazol-1-yl)phenyl]methyl}-3-(methoxymethyl)-1-{2-methyl-1,3-dihydrospiro[isoquinoline-4,3'-oxetane]-7-ylmethyl}pyrazole-4-carboxamide |
| 88 | N-{[2-fluoro-3-methoxy-6-(4-methyl-1,2,3-triazol-1-yl)phenyl]methyl}-3-(methoxymethyl)-1-{6-methyl-5,7-dihydrospiro[1,6-naphthyridine-8,3'-oxetane]-3-ylmethyl}pyrazole-4-carboxamide |
| 89 | N-{[2-fluoro-3-methoxy-6-(4-methyl-1,2,3-triazol-1-yl)phenyl]methyl}-1-{[7-(2-hydroxypropan-2-yl)-5-methyl-4H,6H,7H-pyrazolo[1,5-a]pyrazin-2-yl]methyl}-3-(methoxymethyl)pyrazole-4-carboxamide |
| 90 | 3-(difluoromethyl)-N-{[2-fluoro-3-methoxy-6-(4-methyl-1,2,3-triazol-1-yl)phenyl]methyl}-1-{[7-(2-hydroxypropan-2-yl)-5-methyl-4H,6H,7H-pyrazolo[1,5-a]pyrazin-2-yl]methyl}pyrazole-4-carboxamide |
| 91 | 1-{[7-(difluoromethyl)-5-methyl-4H,6H,7H-pyrazolo[1,5-a]pyrazin-2-yl]methyl}-N-{[2-fluoro-3-methoxy-6-(4-methyl-1,2,3-triazol-1-yl)phenyl]methyl}-3-(methoxymethyl)pyrazole-4-carboxamide |
| 92 | 1-{[7-(difluoromethyl)-5-methyl-4H,6H,7H-pyrazolo[1,5-a]pyrazin-2-yl]methyl}-N-{[2-fluoro-3-methoxy-6-(4-methyl-1,2,3-triazol-1-yl)phenyl]methyl}-3-(1-hydroxycyclopropyl)pyrazole-4-carboxamide |
| 93 | 3-(difluoromethyl)-N-{[2-fluoro-3-methoxy-6-(4-methyl-1,2,3-triazol-1-yl)phenyl]methyl}-1-{[(2R,6S)-7-methyl-4-oxa-1,7,12-triazatricyclo[7.3.0.0^{2,6}]dodeca-9,11-dien-11-yl]methyl}pyrazole-4-carboxamide |
| 94 | 3-(difluoromethyl)-N-{[2-fluoro-3-methoxy-6-(4-methyl-1,2,3-triazol-1-yl)phenyl]methyl}-1-[(2R,6S)-4-oxa-1,7,12-triazatricyclo[7.3.0.0^{2,6}]dodeca-9,11-dien-11-ylmethyl]pyrazole-4-carboxamide |
| 95 | N-{[2-fluoro-3-methoxy-6-(4-methyl-1,2,3-triazol-1-yl)phenyl]methyl}-3-(methoxymethyl)-1-{[(2R,6S)-7-methyl-4-oxa-1,7,12-triazatricyclo[7.3.0.0^{2,6}]dodeca-9,11-dien-11-yl]methyl}pyrazole-4-carboxamide |
| 96 | N-{[2-fluoro-3-methoxy-6-(4-methyl-1,2,3-triazol-1-yl)phenyl]methyl}-3-(1-hydroxycyclopropyl)-1-{[(2R,6S)-7-methyl-4-oxa-1,7,12-triazatricyclo[7.3.0.0^{2,6}]dodeca-9,11-dien-11-yl]methyl}pyrazole-4-carboxamide |
| 97 | 3-(difluoromethyl)-N-{[2-fluoro-3-methoxy-6-(4-methyl-1,2,3-triazol-1-yl)phenyl]methyl}-1-{[7-(hydroxymethyl)-5-methyl-4H,6H,7H-pyrazolo[1,5-a]pyrazin-2-yl]methyl}pyrazole-4-carboxamide |
| 98 | N-{[2-fluoro-3-methoxy-6-(4-methyl-1,2,3-triazol-1-yl)phenyl]methyl}-1-{[7-(hydroxymethyl)-5-methyl-4H,6H,7H-pyrazolo[1,5-a]pyrazin-2-yl]methyl}-3-(1-methoxycyclopropyl)pyrazole-4-carboxamide |
| 99 | 3-(difluoromethyl)-1-({5,7-dimethyl-4H,6H,7H-pyrazolo[1,5-a]pyrazin-2-yl}methyl)-N-{[2-fluoro-3-methoxy-6-(4-methyl-1,2,3-triazol-1-yl)phenyl]methyl}pyrazole-4-carboxamide |
| 100 | 1-({5,7-dimethyl-4H,6H,7H-pyrazolo[1,5-a]pyrazin-2-yl}methyl)-N-{[2-fluoro-3-methoxy-6-(4-methyl-1,2,3-triazol-1-yl)phenyl]methyl}-3-(methoxymethyl)pyrazole-4-carboxamide |
| 101 | 1-({5,7-dimethyl-4H,6H,7H-pyrazolo[1,5-a]pyrazin-2-yl}methyl)-N-{[2-fluoro-3-methoxy-6-(4-methyl-1,2,3-triazol-1-yl)phenyl]methyl}-3-(1-hydroxycyclopropyl)pyrazole-4-carboxamide |
| 102 | N-{[2-fluoro-3-methoxy-6-(4-methyl-1,2,3-triazol-1-yl)phenyl]methyl}-3-(methoxymethyl)-1-[(7-methyl-6,8-dihydro-5H-1,7-naphthyridin-3-yl)methyl]pyrazole-4-carboxamide |
| 103 | 1-[(7-fluoro-2-methyl-3,4-dihydro-1H-isoquinolin-5-yl)methyl]-N-{[2-fluoro-3-methoxy-6-(4-methyl-1,2,3-triazol-1-yl)phenyl]methyl}-3-(methoxymethyl)pyrazole-4-carboxamide |
| 104 | 1-[(5-chloro-2-methyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide |
| 105 | 1-[(4,4-difluoro-2-methyl-1,3-dihydroisoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide |
| 106 | 1-[(4,4-difluoro-2-methyl-1,3-dihydroisoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide |

TABLE 10-continued

Compound Names

| Example Number | Name |
|---|---|
| 107 | 1-[(8-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide |
| 108 | N-{[2-fluoro-3-methoxy-6-(4-methyl-1,2,3-triazol-1-yl)phenyl]methyl}-3-(methoxymethyl)-1-[(4-methyl-3,5-dihydro-2H-1,4-benzoxazepin-7-yl)methyl]pyrazole-4-carboxamide |
| 109 | N-{[2-fluoro-3-methoxy-6-(4-methyl-1,2,3-triazol-1-yl)phenyl]methyl}-3-(methoxymethyl)-1-({5-methyl-4H,6H,7H-[1,3]thiazolo[5,4-c]pyridin-2-yl}methyl)pyrazole-4-carboxamide |
| 110 | N-{[2-fluoro-3-methoxy-6-(4-methyl-1,2,3-triazol-1-yl)phenyl]methyl}-3-(methoxymethyl)-1-(2,3,4,5-tetrahydro-1,4-benzoxazepin-7-ylmethyl)pyrazole-4-carboxamide |
| 111 | N-(2-fluoro-3-methoxy-6-(4-methyl-1H-1,2,3-triazol-1-yl)benzyl)-3-(methoxymethyl)-1-((4-methyl-2,3,4,5-tetrahydrobenzo[f][1,4]thiazepin-8-yl)methyl)-1H-pyrazole-4-carboxamide |
| 112 | N-(2-fluoro-3-methoxy-6-(4-methyl-1H-1,2,3-triazol-1-yl)benzyl)-3-(methoxymethyl)-1-((4-methyl-1-oxido-2,3,4,5-tetrahydrobenzo[f][1,4]thiazepin-8-yl)methyl)-1H-pyrazole-4-carboxamide |
| 113 | N-(2-fluoro-3-methoxy-6-(4-methyl-1H-1,2,3-triazol-1-yl)benzyl)-3-(methoxymethyl)-1-((4-methyl-1,1-dioxido-2,3,4,5-tetrahydrobenzo[f][1,4]thiazepin-8-yl)methyl)-1H-pyrazole-4-carboxamide |
| 114 | 1-[(5-fluoro-2-methyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide |
| 115 | 1-{[7-(2,2-difluoroethyl)-6,8-dihydro-5H-1,7-naphthyridin-3-yl]methyl}-N-{[2-fluoro-3-methoxy-6-(4-methyl-1,2,3-triazol-1-yl)phenyl]methyl}-3-(methoxymethyl)pyrazole-4-carboxamide |
| 116 | 1-[(8-fluoro-2-methyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide |
| 117 | N-{[2-fluoro-3-methoxy-6-(4-methyl-1,2,3-triazol-1-yl)phenyl]methyl}-1-[(7-isopropyl-6,8-dihydro-5H-1,7-naphthyridin-3-yl)methyl]-3-(methoxymethyl)pyrazole-4-carboxamide |
| 118 | 1-[(6-fluoro-2-methyl-3,4-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide |
| 119 | N-{[2-fluoro-3-methoxy-6-(4-methyl-1,2,3-triazol-1-yl)phenyl]methyl}-3-(methoxymethyl)-1-{[2-($^2$H$_3$)methyl-3,4-dihydro-1H-isoquinolin-7-yl]methyl}pyrazole-4-carboxamide |
| 120 | 1-{1H,2H,3H,5H,6H,10bH-pyrrolo[2,1-a]isoquinolin-9-ylmethyl}-N-{[2-fluoro-3-methoxy-6-(4-methyl-1,2,3-triazol-1-yl)phenyl]methyl}-3-(methoxymethyl)pyrazole-4-carboxamide |
| 121 | N-{[2-fluoro-3-methoxy-6-(4-methyl-1,2,3-triazol-1-yl)phenyl]methyl}-3-(methoxymethyl)-1-[(3-methyl-1,2,4,5-tetrahydro-3-benzazepin-7-yl)methyl]pyrazole-4-carboxamide |
| 122 | N-{[2-fluoro-3-methoxy-6-(4-methyl-1,2,3-triazol-1-yl)phenyl]methyl}-1-[(3-isopropyl-1,2,4,5-tetrahydro-3-benzazepin-7-yl)methyl]-3-(methoxymethyl)pyrazole-4-carboxamide |
| 123 | N-{[2-fluoro-3-methoxy-6-(4-methyl-1,2,3-triazol-1-yl)phenyl]methyl}-1-({11-isopropyl-11-azatricyclo[6.2.1.0^{2,7}]undeca-2(7),3,5-trien-4-yl}methyl)-3-(methoxymethyl)pyrazole-4-carboxamide |
| 124 | N-{[2-fluoro-3-methoxy-6-(4-methyl-1,2,3-triazol-1-yl)phenyl]methyl}-3-(methoxymethyl)-1-[(2,3,3-trimethyl-1H-isoindol-5-yl)methyl]pyrazole-4-carboxamide |
| 125 | N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)-3-(trifluoromethyl)pyrazole-4-carboxamide |
| 126 | N-{[2-fluoro-3-methoxy-6-(4-methyl-1,2,3-triazol-1-yl)phenyl]methyl}-3-(methoxymethyl)-1-{2'-methyl-1',3'-dihydrospiro[cyclopropane-1,4'-isoquinoline]-7'-ylmethyl}pyrazole-4-carboxamide |
| 127 | 1-{2',3'-dihydro-1'H-spiro[cyclopropane-1,4'-isoquinoline]-7'-ylmethyl}-N-{[2-fluoro-3-methoxy-6-(4-methyl-1,2,3-triazol-1-yl)phenyl]methyl}-3-(methoxymethyl)pyrazole-4-carboxamide |
| 128 | 1-[(1,1-dimethyl-3,4-dihydro-2H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide |
| 129 | N-{[2-fluoro-3-methoxy-6-(4-methyl-1,2,3-triazol-1-yl)phenyl]methyl}-3-(methoxymethyl)-1-[(1,1,2-trimethyl-3,4-dihydroisoquinolin-7-yl)methyl]pyrazole-4-carboxamide |
| 130 | 1-[(4,4-dimethyl-2,3-dihydro-1H-isoquinolin-7-yl)methyl]-N-{[2-fluoro-3-methoxy-6-(4-methyl-1,2,3-triazol-1-yl)phenyl]methyl}-3-(methoxymethyl)pyrazole-4-carboxamide |
| 131 | N-{[2-fluoro-3-methoxy-6-(4-methyl-1H-1,2,3-triazol-1-yl)phenyl]methyl}-1-[(7-methyl-5,6,7,8-tetrahydro-1,7-naphthyridin-2-yl)methyl]-3-(trifluoromethyl)-1H-pyrazole-4-carboxamide |

TABLE 10-continued

Compound Names

| Example Number | Name |
|---|---|
| 132 | N-{[2-fluoro-3-methoxy-6-(4-methyl-1H-1,2,3-triazol-1-yl)phenyl]methyl}-3-(methoxymethyl)-1-{[6-(propan-2-yl)-5,6,7,8-tetrahydro-1,6-naphthyridin-3-yl]methyl}-1H-pyrazole-4-carboxamide |
| 133 | 1-(3,4-dihydro-1H-2-benzopyran-7-ylmethyl)-N-{[2-fluoro-3-methoxy-6-(4-methyl-1,2,3-triazol-1-yl)phenyl]methyl}-3-(methoxymethyl)pyrazole-4-carboxamide |
| 134 | N-{[2-fluoro-3-methoxy-6-(4-methyl-1,2,3-triazol-1-yl)phenyl]methyl}-3-(methoxymethyl)-1-[(2,4,4-trimethyl-1,3-dihydroisoquinolin-7-yl)methyl]pyrazole-4-carboxamide |
| 135 | N-{[2-fluoro-3-methoxy-6-(4-methyl-1,2,3-triazol-1-yl)phenyl]methyl}-3-(methoxymethyl)-1-[(2-methyl-1-oxo-3,4-dihydroisoquinolin-6-yl)methyl]pyrazole-4-carboxamide |
| 136 | 3-(difluoromethyl)-N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)pyrazole-4-carboxamide |
| 137 | 3-(difluoromethyl)-N-{[2-fluoro-3-methoxy-6-(4-methyl-1,2,3-triazol-1-yl)phenyl]methyl}-1-[(7-methyl-6,8-dihydro-5H-1,7-naphthyridin-3-yl)methyl]pyrazole-4-carboxamide |
| 138 | N-{[2-fluoro-3-methoxy-6-(4-methyl-1,2,3-triazol-1-yl)phenyl]methyl}-1-[(6-methyl-7,8-dihydro-5H-1,6-naphthyridin-2-yl)methyl]-3-(trifluoromethyl)pyrazole-4-carboxamide |
| 139 | 1-[6-(2,2-difluoroethyl)-5,7-dihydrospiro[1,6-naphthyridine-8,1'-cyclopropane]-3-ylmethyl]-N-{[2-fluoro-3-methoxy-6-(4-methyl-1,2,3-triazol-1-yl)phenyl]methyl}-2-(hydroxymethyl)imidazole-4-carboxamide |
| 140 | N-{[2-fluoro-3-methoxy-6-(4-methyl-1,2,3-triazol-1-yl)phenyl]methyl}-2-methyl-1-{6-methyl-5,7-dihydrospiro[1,6-naphthyridine-8,1'-cyclopropane]-3-ylmethyl}imidazole-4-carboxamide |
| 141 | N-{[2-fluoro-3-methoxy-6-(4-methyl-1,2,3-triazol-1-yl)phenyl]methyl}-2-(methoxymethyl)-1-{6-methyl-5,7-dihydrospiro[1,6-naphthyridine-8,1'-cyclopropane]-3-ylmethyl}imidazole-4-carboxamide |
| 142 | N-(2-fluoro-3-methoxy-6-(4-methyl-1H-1,2,3-triazol-1-yl)benzyl)-2-methyl-1-((5'-methyl-5',6'-dihydro-4'H-spiro[cyclopropane-1,7'-pyrazolo[1,5-a]pyrazin]-2'-yl)methyl)-1H-imidazole-4-carboxamide |
| 143 | N-(2-fluoro-3-methoxy-6-(4-methyl-1H-1,2,3-triazol-1-yl)benzyl)-2-(methoxymethyl)-1-((5'-methyl-5',6'-dihydro-4'H-spiro[cyclopropane-1,7'-pyrazolo[1,5-a]pyrazin]-2'-yl)methyl)-1H-imidazole-4-carboxamide |
| 144 | N-{[2-fluoro-3-methoxy-6-(4-methyl-1,2,3-triazol-1-yl)phenyl]methyl}-2-methyl-1-({5,7,7-trimethyl-4H,6H-pyrazolo[1,5-a]pyrazin-2-yl}methyl)imidazole-4-carboxamide |
| 145 | N-{[2-fluoro-3-methoxy-6-(4-methyl-1,2,3-triazol-1-yl)phenyl]methyl}-2-(methoxymethyl)-1-({5,7,7-trimethyl-4H,6H-pyrazolo[1,5-a]pyrazin-2-yl}methyl)imidazole-4-carboxamide |
| 146 | N-{[2-fluoro-3-methoxy-6-(4-methyl-1,2,3-triazol-1-yl)phenyl]methyl}-1-{[7-(2-hydroxypropan-2-yl)-5-methyl-4H,6H,7H-pyrazolo[1,5-a]pyrazin-2-yl]methyl}-2-(methoxymethyl)imidazole-4-carboxamide |
| 147 | N-{[2-fluoro-3-methoxy-6-(4-methyl-1,2,3-triazol-1-yl)phenyl]methyl}-1-[(2-isopropyl-1,3-dihydroisoindol-5-yl)methyl]-2-(methoxymethyl)imidazole-4-carboxamide |
| 148 | N-{[2-fluoro-3-methoxy-6-(4-methyl-1,2,3-triazol-1-yl)phenyl]methyl}-2-(methoxymethyl)-1-[(2-methyl-3,4-dihydro-1H-isoquinolin-7-yl)methyl]imidazole-4-carboxamide |
| 149 | 2-cyclopropyl-N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]imidazole-4-carboxamide |
| 150 | 2-cyclopropyl-N-{[2-fluoro-3-methoxy-6-(4-methyl-1,2,3-triazol-1-yl)phenyl]methyl}-1-[(2-isopropyl-1,3-dihydroisoindol-5-yl)methyl]imidazole-4-carboxamide |
| 151 | N-{[2-fluoro-3-methoxy-6-(4-methyl-1,2,3-triazol-1-yl)phenyl]methyl}-2-methyl-1-[(2-methyl-3,4-dihydro-1H-isoquinolin-7-yl)methyl]imidazole-4-carboxamide |
| 152 | N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-1,2,3-triazole-4-carboxamide |
| 153 | N-{[2-fluoro-3-methoxy-6-(4-methyl-1,2,3-triazol-1-yl)phenyl]methyl}-1-[(2-isopropyl-1,3-dihydroisoindol-5-yl)methyl]-1,2,3-triazole-4-carboxamide |
| 154 | N-{[3-cyclopropoxy-2-fluoro-6-(4-methyl-1,2,3-triazol-1-yl)phenyl]methyl}-3-(methoxymethyl)-1-({5-methyl-4H,6H,7H-pyrazolo[1,5-a]pyrazin-2-yl}methyl)pyrazole-4-carboxamide |
| 155 | N-({3-chloro-6-[3-(difluoromethyl)-1,2,4-triazol-1-yl]-2-fluorophenyl}methyl)-3-(methoxymethyl)-1-[(2-methyl-3,4-dihydro-1H-isoquinolin-7-yl)methyl]pyrazole-4-carboxamide |
| 156 | N-({2-chloro-6-[3-(difluoromethyl)-1,2,4-triazol-1-yl]-3-methoxyphenyl}methyl)-3-(methoxymethyl)-1-[(2-methyl-3,4-dihydro-1H-isoquinolin-7-yl)methyl]pyrazole-4-carboxamide |
| 157 | N-{[3-(1,1-difluoroethyl)-6-[3-(difluoromethyl)-1,2,4-triazol-1-yl]-2-fluorophenyl]methyl}-3-(methoxymethyl)-1-[(2-methyl-3,4-dihydro-1H-isoquinolin-7-yl)methyl]pyrazole-4-carboxamide |
| 158 | N-({2-fluoro-3-methoxy-6-[3-(trifluoromethyl)-1,2,4-triazol-1-yl]phenyl}methyl)-3-(methoxymethyl)-1-[(3-methyl-1,2,4,5-tetrahydro-3-benzazepin-7-yl)methyl]pyrazole-4-carboxamide |

TABLE 10-continued

Compound Names

| Example Number | Name |
|---|---|
| 159 | N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-2-oxopyridine-4-carboxamide |
| 160 | N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-6-oxopyridine-3-carboxamide |
| 161 | N-{[2-fluoro-3-methoxy-6-(4-methyl-1,2,3-triazol-1-yl)phenyl]methyl}-5-[(2-methyl-3,4-dihydro-1H-isoquinolin-7-yl)methyl]pyridine-3-carboxamide |
| 162 | N-{[2-fluoro-3-methoxy-6-(4-methyl-1,2,3-triazol-1-yl)phenyl]methyl}-1-[(1-hydroxy-2-methyl-3,4-dihydro-1H-isoquinolin-7-yl)methyl]-3-(methoxymethyl)pyrazole-4-carboxamide |
| 163 | N-{[2-fluoro-3-methoxy-6-(1H-(1,2,3,4-tetrazol-1-yl)phenyl]methyl}-3-(methoxymethyl)-1-[(2-methyl-1,2,3,4-tetrahydroisoquinolin-7-yl)methyl]-1H-pyrazole-4-carboxamide |
| 164 | N-{[2-fluoro-3-methoxy-6-(4-methyl-1H-1,2,3-triazol-1-yl)phenyl]methyl}-5-(methoxymethyl)-2-[(2-methyl-1,2,3,4-tetrahydroisoquinolin-7-yl)methyl]-1,3-oxazole-4-carboxamide |
| 165 | N-{[2-fluoro-3-methoxy-6-(4-methyl-1H-1,2,3-triazol-1-yl)phenyl]methyl}-4-(methoxymethyl)-2-[(2-methyl-1,2,3,4-tetrahydroisoquinolin-7-yl)methyl]-1,3-oxazole-5-carboxamide |
| 166 | N-{[2-fluoro-3-methoxy-6-(4-methyl-1H-1,2,3-triazol-1-yl)phenyl]methyl}-2-[(2-methyl-1,2,3,4-tetrahydroisoquinolin-7-yl)methyl]-1,3-oxazole-4-carboxamide |
| 167 | N-{[2-fluoro-3-methoxy-6-(4-methyl-1H-1,2,3-triazol-1-yl)phenyl]methyl}-2-[(2-methyl-1,2,3,4-tetrahydroisoquinolin-7-yl)methyl]-1,3-oxazole-5-carboxamide |
| RC1 | N-{[2-fluoro-3-methoxy-6-(4-methyl-1,2,3-triazol-1-yl)phenyl]methyl}-1-(isoquinolin-7-ylmethyl)-3-(methoxymethyl)pyrazole-4-carboxamide |
| RC2 | N-{[2-fluoro-3-methoxy-6-(1,2,3,4-tetrazol-1-yl)phenyl]methyl}-3-(methoxymethyl)-1-[(2-methylquinolin-6-yl)methyl]pyrazole-4-carboxamide |
| RC3 | N-{[2-fluoro-3-methoxy-6-(1,2,3,4-tetrazol-1-yl)phenyl]methyl}-3-(methoxymethyl)-1-(quinolin-6-ylmethyl)pyrazole-4-carboxamide |
| RC4 | N-{[2-fluoro-3-methoxy-6-(1,2,3,4-tetrazol-1-yl)phenyl]methyl}-3-(methoxymethyl)-1-{[2-(pyrrolidin-1-yl)pyrimidin-5-yl]methyl}pyrazole-4-carboxamide |
| RC5 | N-{[2-fluoro-3-methoxy-6-(1,2,3-triazol-1-yl)phenyl]methyl}-3-(methoxymethyl)-1-{[2-(pyrrolidin-1-yl)pyrimidin-5-yl]methyl}pyrazole-4-carboxamide |
| RC6 | N-{[2-fluoro-3-methoxy-6-(4-methyl-1,2,3-triazol-1-yl)phenyl]methyl}-3-(methoxymethyl)-1-{[2-(pyrrolidin-1-yl)pyrimidin-5-yl]methyl}pyrazole-4-carboxamide |
| RC7 | N-({6-[4-(difluoromethyl)-1,2,3-triazol-1-yl]-2-fluoro-3-methoxyphenyl}methyl)-3-(methoxymethyl)-1-{[2-(pyrrolidin-1-yl)pyrimidin-5-yl]methyl}pyrazole-4-carboxamide |

TABLE 11

$^1$H NMR data of examples (solvent d6 DMSO unless otherwise indicated)

| Example Number | Chemical shift |
|---|---|
| 1 | 2.30 (3H, s), 2.55 (2H, t, J = 5.9 Hz), 2.76 (2H, t, J = 5.9 Hz), 3.17 (3H, s), 3.42 (2H, s), 3.93 (3H, s), 4.26 (2H, d, J = 4.9 Hz), 4.43 (2H, s), 5.18 (2H, s), 6.92 (1H, s), 6.98 (1H, dd, J = 7.8, 1.8 Hz), 7.06 (1H, d, J = 7.8 Hz), 7.28 (1H, t, J = 54.1 Hz), 7.31-7.39 (2H, m), 8.10 (2H, d, J = 5.9 Hz), 8.89 (1H, t, J = 1.5 Hz) |
| 2 | 2.30 (3H, d, J = 0.8 Hz), 2.32 (3H, s), 2.56 (2H, t, J = 5.9 Hz), 2.78 (2H, t, J = 5.9 Hz), 3.17 (3H, s), 3.44 (2H, s), 3.92 (3H, s), 4.26 (2H, d, J = 5.2 Hz), 4.44 (2H, s), 5.20 (2H, s), 6.94 (1H, s), 6.97-7.03 (1H, m), 7.08 (1H, d, J = 7.9 Hz), 7.25-7.35 (2H, m), 8.02 (1H, t, J = 5.0 Hz), 8.12 (1H, s), 8.15 (1H, d, J = 1.0 Hz) |
| 3 | 2.27 (3H, s), 2.31 (3H, s), 2.55 (2H, t, J = 6.0 Hz), 2.77 (2H, t, J = 6.0 Hz), 3.43 (2H, s), 3.91 (3H, s), 4.22 (2H, d, J = 5.0 Hz), 5.22 (2H, s), 6.90-7.10 (3H, m), 7.22-7.33 (2H, m), 7.77 (1H, s), 8.07-8.15 (2H, m), 8.20 (1H, t, J = 5.0 Hz) |
| 4 | 2.31 (6H, d, J = 3.0 Hz), 2.56 (2H, d, J = 5.9 Hz), 2.77 (2H, t, J = 5.9 Hz), 3.17 (3H, s), 3.43 (2H, s), 3.91 (3H, s), 4.32 (2H, d, J = 5.3 Hz), 4.44 (2H, s), 5.20 (2H, s), 6.94 (1H, s), 6.98-7.02 (1H, m), 7.07 (1H, d, J = 7.8 Hz), 7.23-7.31 (2H, m), 8.02 (1H, t, J = 5.2 Hz), 8.12 (1H, s), 8.64 (1H, s) |
| 6 | 1.20 (3H, t, J = 7.6 Hz), 2.31 (3H, s), 2.56 (2H, t, J = 5.9 Hz), 2.65-2.69 (2H, m), 2.77 (2H, t, J = 6.0 Hz), 3.15 (3H, s), 3.43 (2H, s), 3.91 (3H, s), 4.32 (2H, d, J = 5.2 Hz), 4.44 (2H, s), 5.20 (2H, s), 6.93 (1H, s), 6.99 (1H, d, J = 8.1 Hz), 7.07 (1H, d, J = 7.8 Hz), 7.27 (2H, d, J = 6.1 Hz), 8.00 (1H, t, J = 5.3 Hz), 8.11 (1H, s), 8.64 (1H, s) |

TABLE 11-continued $^1$H NMR data of examples (solvent d6 DMSO unless otherwise indicated)

| Example Number | Chemical shift |
|---|---|
| 7 | 2.30 (3H, s), 2.55 (2H, t, J = 5.9 Hz), 2.77 (2H, t, J = 5.9 Hz), 3.16 (3H, s), 3.42 (2H, s), 3.91 (3H, s), 4.29 (2H, d, J = 5.0 Hz), 4.42 (2H, s), 5.19 (2H, s), 6.93 (1H, d, J = 1.7 Hz), 6.99 (1H, dd, J = 7.8, 1.8 Hz), 7.06 (1H, d, J = 7.8 Hz), 7.25-7.33 (2H, m), 8.03 (1H, t, J = 5.2 Hz), 8.11 (1H, s), 8.20 (1H, s), 8.81 (1H, s) |
| 8 | 2.30 (3H, s), 2.55 (2H, t, J = 5.9 Hz), 2.77 (2H, t, J = 6.0 Hz), 3.15 (3H, s), 3.42 (2H, s), 3.91 (3H, s), 4.22-4.33 (2H, m), 4.43 (2H, s), 5.19 (2H, s), 6.92 (1H, d, J = 1.7 Hz), 6.95 (1H, d, J = 2.5 Hz), 6.98 (1H, dd, J = 7.8, 1.8 Hz), 7.06 (1H, d, J = 7.8 Hz), 7.24-7.36 (2H, m), 8.03 (1H, t, J = 5.1 Hz), 8.10 (1H, s), 8.23-8.29 (1H, m) |
| 9 | 0.62-0.70 (2H, m), 0.80-0.88 (2H, m), 1.84-1.93 (1H, m), 2.30 (3H, s), 2.55 (2H, t, J = 5.9 Hz), 2.77 (2H, t, J = 5.9 Hz), 3.13 (3H, s), 3.42 (2H, s), 3.88 (3H, s), 4.31 (2H, dd, J = 5.0, 1.6 Hz), 4.43 (2H, s), 5.20 (2H, s), 6.18 (1H, d, J = 2.3 Hz), 6.93 (1H, d, J = 1.8 Hz), 6.99 (1H, dd, J = 7.9, 1.8 Hz), 7.06 (1H, d, J = 7.9 Hz), 7.16-7.26 (2H, m), 7.85 (1H, d, J = 2.4 Hz), 7.94 (1H, t, J = 4.9 Hz), 8.14 (1H, s) |
| 11 | 2.31 (3H, s), 2.55 (2H, t, J = 5.9 Hz), 2.77 (2H, t, J = 6.0 Hz), 3.17 (3H, s), 3.42 (2H, s), 3.91 (3H, s), 4.30 (2H, d, J = 5.1 Hz), 4.43 (2H, s), 5.19 (2H, s), 6.93 (1H, s), 6.99 (1H, d, J = 7.8 Hz), 7.07 (1H, d, J = 7.8 Hz), 7.17 (1H, d, J = 2.5 Hz), 7.25-7.34 (2H, m), 8.02 (1H, t, J = 5.1 Hz), 8.08 (1H, s), 8.31 (1H, d, J = 2.5 Hz) |
| 12 | 2.23 (3H, s), 2.32 (3H, s), 2.57 (2H, d, J = 5.8 Hz), 2.78 (2H, t, J = 6.0 Hz), 3.18 (3H, s), 3.43 (2H, s), 3.92 (3H, s), 4.14 (2H, d, J = 5.2 Hz), 4.43 (2H, s), 5.20 (2H, s), 6.93 (1H, s), 6.99 (1H, d, J = 7.8 Hz), 7.08 (1H, d, J = 7.8 Hz), 7.28 (2H, d, J = 6.6 Hz), 7.99 (1H, s), 8.02 (1H, t, J = 5.2 Hz), 8.10 (1H, s) |
| 13 | 2.31 (3H, s), 2.55 (2H, d, J = 6.0 Hz), 2.77 (2H, t, J = 6.0 Hz), 3.17 (3H, s), 3.42 (2H, s), 3.93 (3H, s), 4.32 (2H, d, J = 5.3 Hz), 4.43 (2H, s), 5.19 (2H, s), 6.91 (1H, s), 6.98 (1H, d, J = 7.8 Hz), 7.07 (1H, d, J = 7.8 Hz), 7.33 (1H, d, J = 8.8 Hz), 7.42 (1H, d, J = 8.8 Hz), 8.09 (1H, s), 8.13 (1H, d, J = 5.4 Hz), 9.12 (1H, s) |
| 14 | 0.35-0.41 (2H, m), 0.43-0.54 (2H, m), 1.73-1.82 (1H, m), 2.30 (3H, s), 2.73 (2H, t, J = 5.8 Hz), 2.81 (2H, t, J = 5.8 Hz), 3.17 (3H, s), 3.66 (2H, s), 3.92 (3H, s), 4.26 (2H, d, J = 5.0 Hz), 4.44 (2H, s), 5.19 (2H, s), 6.93-7.03 (2H, m), 7.06 (1H, d, J = 7.8 Hz), 7.25-7.34 (2H, m), 8.03 (1H, d, J = 5.0 Hz), 8.12 (1H, s), 8.16 (1H, s) |
| 15 | 2.31 (3H, s), 2.55 (2H, t, J = 5.9 Hz), 2.77 (2H, t, J = 5.9 Hz), 3.17 (3H, s), 3.42 (2H, s), 3.92 (3H, s), 4.30 (2H, d, J = 5.3 Hz), 4.43 (2H, s), 5.19 (2H, s), 6.90-6.94 (1H, m), 6.96-7.01 (1H, m), 7.01-7.26 (2H, m), 7.27-7.34 (1H, m), 7.34-7.40 (1H, m), 8.04-8.14 (2H, m), 8.98 (1H, s) |
| 16 | 1.06 (3H, t, J = 7.2 Hz), 2.29 (3H, s), 2.44-2.48 (2H, m), 2.60 (2H, t, J = 5.8 Hz), 2.76 (2H, t, J = 5.8 Hz), 3.17 (3H, s), 3.48 (2H, s), 3.92 (3H, s), 4.25 (2H, d, J = 4.8 Hz), 4.43 (2H, s), 5.19 (2H, s), 6.94 (1H, s), 6.97-7.01 (1H, m), 7.06 (1H, d, J = 7.9 Hz), 7.24-7.33 (2H, m), 8.02 (1H, t, J = 5.0 Hz), 8.11 (1H, s), 8.13-8.15 (1H, m) |
| 17 | 1.03 (6H, d, J = 6.5 Hz), 2.29 (3H, s), 2.61-2.69 (2H, m), 2.70-2.78 (2H, m), 2.79-2.88 (1H, m), 3.17 (3H, s), 3.54-3.62 (2H, m), 3.92 (3H, s), 4.25 (2H, d, J = 5.1 Hz), 4.43 (2H, s), 5.19 (2H, s), 6.93-6.95 (1H, m), 6.98 (1H, d, J = 7.9 Hz), 7.05 (1H, d, J = 7.8 Hz), 7.25-7.34 (2H, m), 8.02 (1H, t, J = 5.1 Hz), 8.11 (1H, s), 8.13-8.17 (1H, m) |
| 18 | 1.61-1.70 (2H, m), 1.78-1.89 (2H, m), 1.99-2.09 (2H, m), 2.29 (3H, s), 2.46-2.50 (2H, m), 2.71-2.78 (2H, m), 2.79-2.89 (1H, m), 3.16 (3H, s), 3.34-3.41 (2H, m), 3.92 (3H, s), 4.22-4.28 (2H, m), 4.43 (2H, s), 5.19 (2H, s), 6.94 (1H, s), 6.99 (1H, d, J = 7.9 Hz), 7.06 (1H, d, J = 7.9 Hz), 7.24-7.33 (2H, m), 8.01 (1H, t, J = 5.0 Hz), 8.11 (1H, s), 8.13-8.16 (1H, m) |
| 19 | 0.34-0.42 (2H, m), 0.42-0.50 (2H, m), 1.72-1.79 (1H, m), 2.72 (2H, t, J = 5.9 Hz), 2.80 (2H, t, J = 5.8 Hz), 3.17 (3H, s), 3.65 (2H, s), 3.92 (3H, s), 4.30 (2H, d, J = 5.1 Hz), 4.43 (2H, s), 5.18 (2H, s), 6.92-7.00 (2H, m), 7.04 (1H, d, J = 7.9 Hz), 7.18 (1H, t, J = 53.0 Hz), 7.31 (1H, t, J = 8.8 Hz), 7.37 (1H, dd, J = 8.9, 1.3 Hz), 8.05-8.13 (2H, m), 8.98 (1H, s) |
| 20 | 0.33-0.42 (2H, m), 0.42-0.49 (2H, m), 1.72-1.79 (1H, m), 2.72 (2H, t, J = 5.9 Hz), 2.80 (2H, t, J = 5.8 Hz), 3.17 (3H, s), 3.65 (2H, s), 3.93 (3H, s), 4.31 (2H, d, J = 5.1 Hz), 4.42 (2H, s), 5.18 (2H, s), 6.93 (1H, s), 6.97 (1H, dd, J = 7.8, 1.8 Hz), 7.04 (1H, d, J = 7.8 Hz), 7.32 (1H, t, J = 8.8 Hz), 7.41 (1H, dd, J = 8.8, 1.4 Hz), 8.08 (1H, s), 8.11 (1H, t, J = 5.3 Hz), 9.11 (1H, s) |
| 21 | 0.34-0.41 (2H, m), 0.42-0.50 (2H, m), 1.72-1.80 (1H, m), 2.73 (2H, t, J = 5.9 Hz), 2.80 (2H, t, J = 5.8 Hz), 3.17 (3H, s), 3.65 (2H, s), 3.91 (3H, s), 4.30 (2H, d, J = 4.7 Hz), 4.43 (2H, s), 5.18 (2H, s), 6.96 (1H, s), 6.98 (1H, dd, J = 7.8, 1.8 Hz), 7.05 (1H, d, J = 7.8 Hz), 7.17 (1H, d, J = 2.5 Hz), 7.25-7.35 (2H, m), 8.01 (1H, t, J = 5.2 Hz), 8.08 (1H, s), 8.31 (1H, d, J = 2.5 Hz) |

TABLE 11-continued

<sup>1</sup>H NMR data of examples (solvent d6 DMSO unless otherwise indicated)

| Example Number | Chemical shift |
|---|---|
| 22 | 1.03 (6H, d, J = 6.5 Hz), 2.62-2.69 (2H, m), 2.70-2.77 (2H, m), 2.79-2.86 (1H, m), 3.17 (3H, s), 3.30 (1H, s), 3.57 (2H, s), 3.93 (3H, s), 4.32 (2H, d, J = 5.3 Hz), 4.43 (2H, s), 5.18 (2H, s), 6.92 (1H, s), 6.98 (1H, d, J = 7.8 Hz), 7.05 (1H, d, J = 7.8 Hz), 7.33 (1H, t, J = 8.9 Hz), 7.42 (1H, d, J = 8.9 Hz), 8.08 (1H, s), 8.12 (1H, t, J = 5.3 Hz), 9.12 (1H, s) |
| 23 | 1.04 (6H, d, J = 6.5 Hz), 2.62-2.71 (2H, m), 2.71-2.78 (2H, m), 2.78-2.90 (1H, m), 3.17 (3H, s), 3.30 (1H, s), 3.58 (2H, s), 3.93 (3H, s), 4.30 (2H, d, J = 5.8 Hz), 4.44 (2H, s), 5.19 (2H, s), 6.94 (1H, s), 6.98 (1H, d, J = 7.9 Hz), 7.02-7.08 (1H, m), 7.19 (1H, d, J = 53.0 Hz), 7.31 (1H, d, J = 8.8 Hz), 7.38 (1H, d, J = 8.8 Hz), 8.08-8.14 (2H, m), 8.99 (1H, s) |
| 24 | 1.04 (6H, d, J = 6.5 Hz), 2.62-2.69 (2H, m), 2.71-2.77 (2H, m), 2.79-2.88 (1H, m), 3.18 (3H, s), 3.30 (1H, s), 3.58 (2H, s), 3.92 (2H, s), 4.31 (2H, d, J = 5.1 Hz), 4.44 (2H, s), 5.19 (2H, s), 6.94 (1H, s), 6.99 (1H, d, J = 7.9 Hz), 7.06 (1H, d, J = 7.9 Hz), 7.18 (1H, d, J = 2.5 Hz), 7.26-7.35 (2H, m), 8.02 (1H, t, J = 5.2 Hz), 8.08 (1H, s), 8.32 (1H, d, J = 2.6 Hz) |
| 25 | 1.06 (3H, t, J = 7.2 Hz), 2.46 (2H, q, J = 7.1 Hz), 2.60 (2H, t, J = 5.9 Hz), 2.76 (2H, t, J = 5.9 Hz), 3.17 (3H, s), 3.47 (2H, s), 3.93 (3H, s), 4.31 (2H, d, J = 5.3 Hz), 4.42 (2H, s), 5.18 (2H, s), 6.92 (1H, s), 6.98 (1H, d, J = 7.8 Hz), 7.06 (1H, d, J = 7.8 Hz), 7.32 (1H, t, J = 8.7 Hz), 7.41 (1H, dd, J = 8.9, 1.4 Hz), 8.08 (1H, s), 8.11 (1H, t, J = 5.4 Hz), 9.11 (1H, s) |
| 26 | 1.06 (3H, t, J = 7.1 Hz), 2.46 (2H, q, J = 7.2 Hz), 2.60 (2H, t, J = 5.9 Hz), 2.76 (2H, t, J = 5.9 Hz), 3.17 (3H, s), 3.48 (2H, s), 3.92 (3H, s), 4.30 (2H, d, J = 5.1 Hz), 4.43 (2H, s), 5.18 (2H, s), 6.93 (1H, s), 6.99 (1H, dd, J = 7.7, 1.9 Hz), 7.06 (1H, d, J = 7.9 Hz), 7.18 (1H, t, J = 53.0 Hz), 7.31 (1H, t, J = 8.8 Hz), 7.37 (1H, dd, J = 8.8, 1.3 Hz), 8.05-8.14 (2H, m), 8.98 (1H, s) |
| 27 | 1.07 (3H, t, J = 7.1 Hz), 2.43-2.49 (2H, m), 2.54-2.68 (2H, m), 2.72-2.81 (2H, m), 3.17 (3H, s), 3.49 (2H, s), 3.91 (3H, s), 4.30 (2H, d, J = 4.7 Hz), 4.43 (2H, s), 5.19 (2H, s), 6.94 (1H, s), 6.99 (1H, d, J = 7.6 Hz), 7.06 (1H, d, J = 7.9 Hz), 7.17 (1H, d, J = 2.5 Hz), 7.24-7.35 (2H, m), 8.02 (1H, t, J = 5.1 Hz), 8.08 (1H, s), 8.31 (1H, d, J = 2.5 Hz) |
| 28 | 0.91-1.14 (6H, m), 2.16 (3H, s), 2.20 (3H, s), 2.54-2.93 (5H, m), 3.17 (3H, s), 3.42-3.71 (2H, m), 3.91 (3H, s), 4.17 (2H, d, J = 5.1 Hz), 4.44 (2H, s), 5.13-5.26 (2H, m), 6.89-7.11 (3H, m), 7.19-7.28 (2H, m), 7.96-8.05 (1H, m), 8.10 (1H, s) |
| 29 | 2.16 (3H, s), 2.20 (3H, s), 2.31 (3H, s), 2.55 (2H, t, J = 5.9 Hz), 2.77 (2H, t, J = 5.9 Hz), 3.17 (3H, s), 3.42 (2H, s), 3.91 (3H, s), 4.16 (2H, d, J = 5.1 Hz), 4.44 (2H, s), 5.19 (2H, s), 6.89-6.95 (1H, m), 6.97-7.01 (1H, m), 7.04-7.08 (1H, m), 7.21-7.26 (2H, m), 7.96-8.04 (1H, m), 8.09 (1H, s) |
| 30 | 1.03 (6H, d, J = 6.5 Hz), 2.60-2.69 (2H, m), 2.69-2.77 (2H, m), 2.82 (1H, hept, J = 6.5 Hz), 3.17 (3H, s), 3.57 (2H, s), 3.91 (3H, s), 4.31 (2H, d, J = 5.2 Hz), 4.43 (2H, s), 5.18 (2H, s), 6.94 (1H, s), 6.96-7.02 (1H, m), 7.05 (1H, d, J = 7.8 Hz), 7.24-7.33 (2H, m), 8.01 (1H, t, J = 5.2 Hz), 8.10 (1H, s), 8.29 (1H, s), 8.87 (1H, s) |
| 31 | 2.30 (3H, s), 2.55 (2H, t, J = 5.9 Hz), 2.76 (2H, t, J = 5.9 Hz), 3.41 (2H, s), 3.92 (3H, s), 4.29 (2H, d, J = 4.8 Hz), 5.21 (2H, s), 6.88-6.91 (1H, m), 6.97 (1H, dd, J = 7.8, 1.8 Hz), 7.06 (1H, d, J = 7.8 Hz), 7.31 (1H, dd, J = 8.8 Hz), 7.37-7.41 (1H, m), 7.71-7.74 (1H, m), 8.06-8.09 (1H, m), 8.29 (1H, t, J = 5.2 Hz), 9.08-9.10 (1H, m) |
| 32 | 1.03 (6H, d, J = 6.5 Hz), 2.60-2.69 (2H, m), 2.70-2.77 (2H, m), 2.78-2.87 (1H, m), 3.51-3.60 (2H, m), 3.92 (3H, s), 4.29 (2H, d, J = 5.1 Hz), 5.21 (2H, s), 6.88-6.91 (1H, m), 6.95-6.99 (1H, m), 7.04 (1H, d, J = 7.8 Hz), 7.31 (1H, dd, J = 8.8 Hz), 7.39 (1H, dd, J = 8.8, 1.4 Hz), 7.73 (1H, s), 8.07 (1H, s), 8.29 (1H, t, J = 5.2 Hz), 9.07-9.10 (1H, m) |
| 33 | 2.27 (3H, s), 2.32 (3H, s), 2.57 (2H, t, J = 5.9 Hz), 2.79 (2H, t, J = 5.9 Hz), 3.45 (2H, s), 3.92 (3H, s), 4.25 (2H, d, J = 4.7 Hz), 5.30 (2H, s), 6.99 (1H, s), 7.04 (1H, dd, J = 7.7, 1.8 Hz), 7.10-7.14 (1H, m), 7.22-7.37 (3H, m), 8.09 (1H, s), 8.21 (1H, s), 8.35 (1H, t, J = 4.8 Hz) |
| 34 | 2.33 (3H, s), 2.58 (2H, s), 2.78 (2H, t, J = 5.9 Hz), 3.18 (3H, s), 3.46 (2H, s), 3.94 (3H, s), 4.27 (2H, d, J = 5.2 Hz), 4.43 (2H, s), 5.19 (2H, s), 7.00 (3H, d, J = 6.8 Hz), 7.17-7.41 (3H, m), 8.11 (2H, s), 8.90 (1H, d, J = 1.8 Hz) |
| 35 | 0.35-0.39 (2H, m), 0.47 (2H, dt, J = 6.2, 3.0 Hz), 1.77 (1H, tt, J = 6.6, 3.5 Hz), 2.30 (3H, s), 2.73 (2H, t, J = 6.0 Hz), 2.80 (2H, t, J = 5.8 Hz), 3.17 (3H, s), 3.67 (2H, s), 3.92 (3H, s), 4.26 (2H, d, J = 5.0 Hz), 4.43 (2H, s), 5.19 (2H, s), 6.96-7.01 (2H, m), 7.01-7.06 (1H, m), 7.26-7.34 (2H, m), 8.02 (1H, t, J = 5.1 Hz), 8.11 (1H, s), 8.15 (1H, s) |
| 36 | 2.30 (3H, s), 2.32 (3H, s), 2.57 (2H, s), 2.78 (2H, t, J = 6.0 Hz), 3.17 (3H, s), 3.45 (2H, s), 3.92 (3H, s), 4.26 (2H, d, J = 5.0 Hz), 4.44 (2H, s), 5.20 (2H, s), 7.01 (3H, d, J = 5.2 Hz), 7.25-7.34 (2H, m), 8.02 (1H, t, J = 5.1 Hz), 8.13 (1H, s), 8.15 (1H, s) |
| 37 | 1.04 (6H, d, J = 6.5 Hz), 2.30 (3H, s), 2.66 (2H, d, J = 5.6 Hz), 2.74 (2H, t, J = 5.8 Hz), 2.83 (1H, p, J = 6.4 Hz), 3.17 (3H, s), 3.59 (2H, s), 3.92 (3H, s), 4.26 (2H, d, J = 4.9 Hz), 4.44 (2H, s), 5.19 (2H, s), 6.98 (2H, d, J = 6.4 Hz), 7.03 (1H, d, J = 8.3 Hz), 7.26-7.33 (2H, m), 8.02 (1H, t, J = 5.1 Hz), 8.12 (1H, s), 8.15 (1H, s) |

TABLE 11-continued

1H NMR data of examples (solvent d6 DMSO unless otherwise indicated)

| Example Number | Chemical shift |
|---|---|
| 38 | 1.07 (3H, t, J = 7.2 Hz), 2.30 (3H, d, J = 0.8 Hz), 2.47 (2H, t, J = 7.2 Hz), 2.61, (2H, t, J = 5.9 Hz), 2.76 (2H, t, J = 5.9 Hz), 3.17 (3H, s), 3.49 (2H, s), 3.92 (3H, s), 4.23-4.28 (2H, m), 4.44 (2H, s), 5.20 (2H, s), 6.96-7.06 (3H, m), 7.25-7.35 (2H, m), 8.03 (1H, t, J = 5.1 Hz), 8.10-8.17 (2H, m) |
| 40 | 1.60-1.71 (2H, m), 1.80-1.90 (2H, m), 2.00-2.06 (2H, m), 2.30 (3H, s), 2.46-2.49 (4H, m), 2.74 (2H, t, J = 6.0 Hz), 2.83 (1H, quin, J = 7.8 Hz), 3.17 (3H, s), 3.92 (3H, s), 4.26 (2H, d, J = 5.1 Hz), 4.44 (2H, s), 5.20 (2H, s), 6.98 (2H, d, J = 7.7 Hz), 7.03 (1H, d, J = 7.8 Hz), 7.25-7.35 (2H, m), 8.02 (1H, t, J = 5.1 Hz), 8.10-8.17 (2H, m) |
| 41 | 2.30 (3H, s), 2.54 (2H, t, J = 5.9 Hz), 2.76 (2H, t, J = 6.0 Hz), 3.17 (3H, s), 3.43 (2H, s), 3.92 (3H, s), 4.30 (2H, d, J = 5.2 Hz), 4.43 (2H, s), 5.19 (2H, s), 6.95-7.02 (3H, m), 7.13 (1H, t, J = 53.0 Hz), 7.31 (1H, t, J = 8.8 Hz), 7.37 (1H, dd, J = 8.8, 1.3 Hz), 8.07-8.13 (2H, m), 8.98 (1H, s) |
| 42 | 2.30 (3H, s), 2.54 (2H, t, J = 5.9 Hz), 2.76 (2H, t, J = 5.9 Hz), 3.17 (3H, s), 3.43 (2H, s), 3.93 (3H, s), 4.31 (2H, d, J = 5.0 Hz), 4.42 (2H, s), 5.18 (2H, s), 6.93-7.03 (3H, m), 7.32 (1H, t, J = 8.8 Hz), 7.41 (1H, dd, J = 8.9, 1.4 Hz), 8.09 (1H, s), 8.12 (1H, t, J = 5.3 Hz), 9.11 (1H, s) |
| 43 | 2.30 (3H, s), 2.54 (2H, t, J = 5.9 Hz), 2.76 (2H, t, J = 5.9 Hz), 3.17 (3H, s), 3.43 (2H, s), 3.91 (3H, s), 4.30 (2H, d, J = 5.0 Hz), 4.43 (2H, s), 5.19 (2H, s), 6.95-7.03 (3H, m), 7.17 (1H, d, J = 2.5 Hz), 7.25-7.34 (2H, m), 8.02 (1H, t, J = 5.2 Hz), 8.09 (1H, s), 8.31 (1H, d, J = 2.5 Hz) |
| 44 | 1.03 (6H, d, J = 6.5 Hz), 2.64 (2H, t, J = 5.7 Hz), 2.73 (2H, t, J = 5.8 Hz), 2.81 (1H, h, J = 6.5 Hz), 3.17 (3H, s), 3.58 (2H, s), 3.92 (3H, s), 4.30 (2H, d, J = 5.2 Hz), 4.43 (2H, s), 5.18 (2H, s), 6.94-6.99 (2H, m), 6.99-7.04 (1H, m), 7.18 (1H, t, J = 53.0 Hz), 7.31 (1H, t, J = 8.8 Hz), 7.37 (1H, dd, J = 8.9, 1.3 Hz), 8.05-8.14 (2H, m), 8.98 (1H, s) |
| 45 | 1.03 (6H, d, J = 6.5 Hz), 2.60-2.68 (2H, m), 2.68-2.77 (2H, m), 2.77-2.88 (1H, m), 3.17 (3H, s), 3.59 (2H, s), 3.93 (3H, s), 4.31 (2H, d, J = 5.2 Hz), 4.42 (2H, s), 5.18 (2H, s), 6.91-6.99 (2H, m), 6.99-7.05 (1H, m), 7.32 (1H, t, J = 8.8 Hz), 7.41 (1H, dd, J = 8.9, 1.4 Hz), 8.08 (1H, s), 8.12 (1H, t, J = 5.4 Hz), 9.11 (1H, s) |
| 46 | 1.03 (6H, d, J = 6.5 Hz), 2.58-2.69 (2H, m), 2.69-2.77 (2H, m), 2.77-2.87 (1H, m), 3.17 (3H, s), 3.59 (2H, s), 3.91 (3H, s), 4.30 (2H, d, J = 5.0 Hz), 4.43 (2H, s), 5.19 (2H, s), 6.93-7.00 (2H, m), 7.00-7.05 (1H, m), 7.17 (1H, d, J = 2.5 Hz), 7.25-7.34 (2H, m), 8.02 (1H, t, J = 5.2 Hz), 8.08 (1H, s), 8.31 (1H, d, J = 2.5 Hz) |
| 47 | 0.32-0.39 (2H, m), 0.44-0.50 (2H, m), 1.72-1.79 (1H, m), 2.72 (2H, t, J = 5.9 Hz), 2.79 (2H, t, J = 5.8 Hz), 3.16 (3H, s), 3.66 (2H, s), 3.92 (3H, s), 4.29 (2H, d, J = 5.2 Hz), 4.43 (2H, s), 5.18 (2H, s), 6.94-7.00 (2H, m), 7.02 (1H, s), 7.13 (1H, t, J = 53.0 Hz), 7.31 (1H, t, J = 8.8 Hz), 7.37 (1H, d, J = 9.1 Hz), 8.05-8.14 (2H, m), 8.98 (1H, s) |
| 48 | 0.43-0.50 (2H, m), 1.71-1.80 (1H, m), 2.72 (2H, t, J = 5.7 Hz), 2.79 (2H, t, J = 5.8 Hz), 3.16 (3H, s), 3.66 (2H, s), 3.93 (3H, s), 4.31 (2H, d, J = 5.3 Hz), 4.42 (2H, s), 5.18 (2H, s), 6.92-7.00 (2H, m), 7.03 (1H, d, J = 7.8 Hz), 7.32 (1H, t, J = 8.8 Hz), 7.41 (1H, dd, J = 8.8, 1.4 Hz), 8.07 (1H, s), 8.12 (1H, t, J = 5.3 Hz), 9.11 (1H, s) |
| 49 | 0.32-0.40 (2H, m), 0.42-0.50 (2H, m), 1.72-1.79 (1H, m), 2.72 (2H, t, J = 6.0 Hz), 2.80 (2H, t, J = 5.8 Hz), 3.17 (3H, s), 3.66 (2H, s), 3.91 (3H, s), 4.30 (2H, d, J = 5.0 Hz), 4.43 (2H, s), 5.18 (2H, s), 6.95-7.01 (2H, m), 7.03 (1H, d, J = 8.3 Hz), 7.17 (1H, d, J = 2.5 Hz), 7.24-7.35 (2H, m), 8.01 (1H, t, J = 5.2 Hz), 8.07 (1H, s), 8.31 (1H, d, J = 2.5 Hz) |
| 50 | 1.07 (3H, t, J = 7.1 Hz), 2.43-2.49 (2H, m), 2.61 (2H, t, J = 5.8 Hz), 2.75 (2H, t, J = 5.9 Hz), 3.17 (3H, s), 3.49 (2H, s), 3.92 (3H, s), 4.30 (2H, d, J = 5.2 Hz), 4.43 (2H, s), 5.19 (2H, s), 6.95-7.00 (2H, m), 7.00-7.04 (1H, m), 7.18 (1H, t, J = 53.0 Hz), 7.31 (1H, t, J = 8.8 Hz), 7.37 (1H, d, J = 8.9 Hz), 8.07-8.13 (2H, m), 8.98 (1H, s) |
| 51 | 1.07 (3H, t, J = 7.1 Hz), 2.47 (2H, q, J = 7.4 Hz), 2.60 (2H, t, J = 5.9 Hz), 2.75 (2H, t, J = 5.9 Hz), 3.17 (3H, s), 3.49 (2H, s), 3.93 (3H, s), 4.31 (2H, d, J = 5.1 Hz), 4.42 (2H, s), 5.18 (2H, s), 6.92-6.99 (2H, m), 6.99-7.05 (1H, m), 7.32 (1H, t, J = 8.8 Hz), 7.41 (1H, d, J = 8.9 Hz), 8.09 (1H, s), 8.12 (1H, t, J = 5.3 Hz), 9.11 (1H, s) |
| 52 | 1.07 (3H, t, J = 7.1 Hz), 2.47 (2H, q, J = 7.4 Hz), 2.60 (2H, t, J = 5.9 Hz), 2.75 (2H, t, J = 5.9 Hz), 3.17 (3H, s), 3.49 (2H, s), 3.91 (3H, s), 4.30 (2H, d, J = 5.1 Hz), 4.43 (2H, s), 5.19 (2H, s), 6.96-7.00 (2H, m), 7.03 (1H, d, J = 8.4 Hz), 7.17 (1H, d, J = 2.5 Hz), 7.25-7.35 (2H, m), 8.02 (1H, t, J = 5.1 Hz), 8.09 (1H, s), 8.31 (1H, d, J = 2.5 Hz) |
| 53 | 2.30 (3H, s), 3.16 (3H, s), 3.92 (3H, s), 4.25 (2H, d, J = 4.9 Hz), 4.42 (2H, s), 4.46 (4H, t, J = 5.6 Hz), 5.31 (2H, s), 7.24-7.33 (4H, m), 7.37 (1H, d, J = 7.9 Hz), 8.04 (1H, t, J = 5.1 Hz), 8.17 (1H, d, J = 1.0 Hz), 8.19 (1H, s), 9.75 (2H, s) |
| 54 | 2.31 (3H, s), 2.98 (3H, s), 3.17 (3H, s), 3.93 (3H, s), 4.27 (2H, d, J = 5.0 Hz), 4.43 (6H, s), 5.32 (2H, s), 7.24-7.34 (4H, m), 7.39 (1H, d, J = 7.7 Hz), 8.04 (1H, t, J = 5.1 Hz), 8.18 (1H, s), 8.20 (1H, s), 11.19 (1H, s) |

TABLE 11-continued

<sup>1</sup>H NMR data of examples (solvent d6 DMSO unless otherwise indicated)

| Example Number | Chemical shift |
|---|---|
| 55 | 1.33 (6H, d, J = 6.5, 2.0 Hz), 2.30 (3H, s), 3.16 (3H, s), 3.61-3.65 (1H, m), 3.92 (3H, s), 4.26 (2H, d, J = 4.2 Hz), 4.42 (2H, s), 4.46-4.54 (2H, m), 4.69 (2H, dd, J = 14.7, 6.1 Hz), 5.32 (2H, s), 7.22 (1H, s), 7.25-(3H, m), 7.36 (1H, d, J = 7.8 Hz), 8.04 (1H, t, J = 5.1 Hz), 8.17 (1H, d, J = 0.9 Hz), 8.20 (1H, s), 11.35 (1H, s) |
| 56 | 1.08 (3H, t, J = 7.2 Hz), 2.29 (3H, s), 2.65 (2H, q, J = 7.2 Hz), 3.16 (3H, s), 3.78 (4H, s), 3.92 (3H, s), 4.25 (2H, d, J = 5.0 Hz), 4.43 (2H, s), 5.24 (2H, s), 7.04-7.13 (2H, m), 7.19 (1H, d, J = 7.6 Hz), 7.24-7.34 (2H, m), 7.99-8.05 (1H, m), 8.10-8.17 (2H, m) |
| 57 | 2.44 (3H, s), 3.17 (3H, s), 3.75 (4H, s), 3.92 (3H, s), 4.27-4.33 (2H, m), 4.43 (2H, s), 5.23 (2H, s), 6.99-7.25 (4H, m), 7.28-7.34 (1H, m), 7.34-7.40 (1H, m), 8.06-8.14 (2H, m), 8.98 (1H, s) |
| 58 | 2.44 (3H, s), 3.17 (3H, s), 3.75 (4H, s), 3.93 (3H, s), 4.31 (2H, d, J = 5.2 Hz), 4.42 (2H, s), 5.23 (2H, s), 7.02-7.11 (2H, m), 7.15-7.21 (1H, m), 7.29-7.36 (1H, m), 7.38-7.44 (1H, m), 8.08-8.15 (2H, m), 9.11 (1H, s) |
| 59 | 1.32 (6H, d, J = 6.4 Hz), 3.17 (3H, s), 3.66 (1H, s), 3.93 (3H, s), 4.31 (2H, d, J = 5.2 Hz), 4.43 (2H, s), 4.52 (2H, s), 4.71 (2H, d, J = 14.9 Hz), 5.32 (2H, s), 7.15 (1H, t, J = 53.0 Hz), 7.23 (1H, s), 7.28 (1H, d, J = 7.9 Hz), 7.32 (1H, t, J = 8.7 Hz), 7.38 (2H, t, J = 8.8 Hz), 8.12 (1H, s), 8.18 (1H, s), 9.00 (1H, s) |
| 60 | 1.32 (6H, d, J = 6.4 Hz), 3.17 (3H, s), 3.67 (1H, s), 3.94 (3H, s), 4.33 (2H, d, J = 5.2 Hz), 4.42 (2H, s), 4.53 (2H, s), 4.70 (2H, s), 5.32 (2H, s), 7.22 (1H, s), 7.27 (1H, d, J = 7.9 Hz), 7.35 (2H, q, J = 8.8 Hz), 7.43 (1H, d, J = 8.9 Hz), 8.15 (1H, t, J = 5.3 Hz), 8.17 (1H, s), 9.13 (1H, s) |
| 61 | 2.28 (3H, s), 2.35 (3H, s), 2.69-2.76 (2H, m), 3.46 (2H, s), 3.89-3.97 (5H, m), 4.22 (2H, d, J = 4.7 Hz), 5.18 (2H, s), 7.13 (1H, s), 7.26-7.34 (2H, m), 8.08 (1H, s), 8.23 (1H, s), 8.38 (1H, t, J = 4.8 Hz) |
| 63 | 2.31 (3H, s), 2.94 (3H, s), 3.10 (2H, t, J = 21.0 Hz), 3.34 (1H, s), 3.71 (1H, s), 3.94 (3H, s), 4.25 (2H, d, J = 4.6 Hz), 4.37 (1H, d, J = 8.0 Hz), 4.49 (1H, d, J = 17.2 Hz), 5.66 (2H, s), 7.25-7.39 (2H, m), 8.14 (1H, s), 8.44 (1H, s), 8.49 (1H, t, J = 4.8 Hz), 8.74 (1H, s), 10.89 (1H, s) |
| 64 | 2.30 (3H, s), 2.93 (3H, d, J = 4.1 Hz), 3.07-3.13 (2H, m), 3.16 (3H, s), 3.30-3.40 (1H, m), 3.68-3.76 (1H, m), 3.92 (3H, s), 4.26 (2H, d, J = 4.9 Hz), 4.32-4.40 (1H, m), 4.41 (2H, s), 4.46-4.52 (1H, m), 5.47 (2H, s), 7.26-7.34 (2H, m), 8.07 (1H, t, J = 5.1 Hz), 8.17 (1H, s), 8.23 (1H, s), 8.40 (1H, s), 11.33 (1H, br s) |
| 68 | 2.30 (3H, d, J = 0.8 Hz), 2.74 (2H, t, J = 5.7 Hz), 3.18 (3H, s,), 3.85 (2H, t, J = 5.7 Hz), 3.92 (3H, s), 4.26 (2H, d, J = 5.0 Hz), 4.44 (2H, s), 4.65 (2H, s), 5.22 (2H, s), 7.00-7.05 (3H, m),7.23-7.35 (2H, m), 8.03 (1H, t, J = 5.0 Hz), 8.10-8.18 (2H, m) |
| 70 | 2.30 (3H, s), 2.34 (3H, s), 2.79 (2H, t, J = 5.6 Hz), 3.18 (3H, s), 3.50 (2H, s), 3.92 (3H, s), 4.02 (2H, t, J = 5.6 Hz), 4.25 (2H, d, J = 5.0 Hz), 4.43 (2H, s), 5.16 (2H, s), 5.91 (1H, s), 7.21-7.35 (2H, m), 8.02 (1H, t, J = 5.0 Hz), 8.06 (1H, s), 8.14 (1H, d, J = 0.9 Hz) |
| 73 | (Chloroform-d) 2.43 (3H, d, J = 0.8 Hz), 2.98 (2H, t, J = 6.6 Hz), 3.14 (3H, s), 3.37 (3H, d, J = 1.8 Hz), 3.55 (2H, t, J = 6.7 Hz), 3.93 (3H, s), 4.38 (2H, dd, J = 5.7, 1.5 Hz), 4.56 (2H, d, J = 3.5 Hz), 5.23 (2H, s), 6.98 (1H, t, J = 8.7 Hz), 7.10-7.16 (2H, m), 7.18-7.23 (1H, m), 7.80 (1H, s), 7.93 (1H, d, J = 1.0 Hz), 7.97 (1H, d, J = 2.0 Hz), 8.34 (1H, t, J = 6.0 Hz) |
| 82 | 0.87-0.92 (2H, m), 1.27-1.33 (2H, m), 2.26 (3H, s), 2.35 (3H, s), 2.79 (2H, s), 3.64 (2H, s), 3.92 (3H, s), 4.24 (2H, d, J = 4.8 Hz), 5.24 (2H, s), 5.96 (1H, s), 7.12-7.35 (3H, m), 8.08 (1H, s), 8.17 (1H, s), 8.36 (1H, t, J = 4.9 Hz) |
| 102 | 2.30 (3H, s), 2.42 (2H, s), 3H under DMSO peak, 2.69 (1H, s), 2.83 (2H, s), 3.17 (3H, s), 3.60 (1H, bm), 3.92 (3H, s), 4.26 (2H, d, J = 5.1 Hz), 4.43 (2H, s), 5.28 (2H, s), 7.27-7.33 (2H, m), 7.44 (1H, s), 8.03 (1H, t, J = 5.0 Hz), 8.17 (2H, d, J = 13.6 Hz), 8.29 (1H, s) |
| 103 | 2.30 (6H, d, J = 3.8 Hz), 2.57 (2H, t, J = 5.9 Hz), 2.68 (2H, t, J = 6.0 Hz), 3.18 (3H, s), 3.46 (2H, s), 3.92 (3H, s), 4.27 (2H, d, J = 5.0 Hz), 4.46 (2H, s), 5.28 (2H, s), 6.64 (1H, dd, J = 9.7, 2.6 Hz), 6.90 (1H, dd, J = 9.5, 2.6 Hz), 7.26-7.33 (2H, m), 8.07 (2H, d, J = 12.6 Hz), 8.15 (1H, s) |
| 104 | 2.30 (3H, s), 2.33 (3H, s), 2.62 (2H, t, J = 6.0 Hz), 2.77 (2H, t, J = 6.0 Hz), 3.18 (3H, s), 3.47 (2H, s), 3.92 (3H, s), 4.26 (2H, d, J = 5.0 Hz), 4.44 (2H, s), 5.36 (2H, s), 6.94 (1H, d, J = 7.8 Hz), 7.06 (1H, d, J = 7.9 Hz), 7.25-7.34 (2H, m), 8.05 (1H, t, J = 5.1 Hz), 8.10 (1H, s), 8.15 (1H, s) |
| 105 | 2.29 (3H, s), 2.39 (3H, s), 3.01 (2H, t, J = 12.2 Hz), 3.16 (3H, s), 3.58 (2H, s), 3.92 (3H, s), 4.26 (2H, d, J = 5.0 Hz), 4.43 (2H, s), 5.33 (2H, s), 7.21-7.35 (4H, m), 7.52 (1H, s), 8.04 (1H, t, J = 5.1 Hz), 8.14 (1H, s), 8.19 (1H, s) |
| 106 | 2.29 (3H, s), 2.39 (3H, s), 3.01 (2H, t, J = 12.2 Hz), 3.17 (3H, s), 3.57 (2H, s), 3.92 (3H, s), 4.26 (2H, d, J = 5.0 Hz), 4.43 (2H, s), 5.32 (2H, s), 7.11 (1H, s), 7.22 (1H, d, J = 8.1 Hz), 7.25-7.34 (2H, m), 7.60 (1H, d, J = 8.1 Hz), 8.04 (1H, t, J = 5.1 Hz), 8.15 (1H, s), 8.18 (1H, s) |

TABLE 11-continued

¹H NMR data of examples (solvent d6 DMSO unless otherwise indicated)

| Example Number | Chemical shift |
|---|---|
| 107 | 2.30 (3H, s), 2.38 (4H, s), 2.81 (2H, t, J = 5.9 Hz), 3.17 (3H, s), 3.48 (2H, s), 3.92 (3H, s), 4.26 (2H, d, J = 5.0 Hz), 4.43 (2H, s), 5.28 (2H, s), 6.96 (1H, d, J = 7.9 Hz), 7.05 (1H, t, J = 7.7 Hz), 7.26-7.34 (2H, m), 8.04 (1H, t, J = 5.1 Hz), 8.11 (1H, s), 8.15 (1H, s) |
| 108 | (D2O) 2.27 (3H, s), 2.99 (3H, s), 3.23 (3H, s), 3.57-3.69 (1H, m), 3.76 (2H, m), 3.93 (3H, s), 4.07-4.21 (1H, m), 4.38 (2H, d, J = 8.7 Hz), 4.40-4.53 (5H, m), 5.27 (2H, s), 7.10 (1H, d, J = 8.9 Hz), 7.19 (2H, d, J = 5.3 Hz), 7.25 (2H, dd, J = 4.5, 2.3 Hz), 7.85-7.92 (1H, m), 7.97 (1H, s) |
| 109 | 2.30 (3H, s), 2.34 (3H, s), 2.65-2.76 (4H, m), 3.18 (3H, s), 3.53 (2H, s), 3.92 (3H, s), 4.26 (2H, d, J = 5.0 Hz), 4.45 (2H, s), 5.58 (2H, s), 7.23-7.36 (2H, m), 8.09 (1H, t, J = 5.0 Hz), 8.15 (1H, s), 8.22 (1H, s) |
| 110 | 2.30 (3H, s), 2.98-3.02 (2H, m), 3.18 (3H, s), 3.75 (2H, s), 3.92 (5H, d, J = 4.8 Hz), 4.26 (2H, d, J = 5.0 Hz), 4.43 (2H, s), 5.19 (2H, s), 6.93 (1H, d, J = 8.1 Hz), 7.06 (1H, dd, J = 8.2, 2.2 Hz), 7.10 (1H, d, J = 2.3 Hz), 7.26-7.34 (2H, m), 8.03 (1H, t, J = 5.1 Hz), 8.14 (1H, s), 8.16 (1H, s) |
| 114 | (d6 DMSO at 90° C.) 2.30 (6H, d, J = 12.1 Hz), 2.57 (2H, t, J = 5.9 Hz), 2.73 (2H, t, J = 6.0 Hz), 3.16 (3H, s), 3.45 (2H, s), 3.92 (3H, s), 4.25 (2H, d, J = 4.9 Hz), 4.42 (2H, s), 5.27 (2H, s), 6.89 (1H, d, J = 7.9 Hz), 7.03 (1H, t, J = 7.7 Hz), 7.22-7.37 (2H, m), 8.04 (1H, t, J = 5.1 Hz), 8.13 (2H, d, J = 17.6 Hz) |
| 115 | 2.29 (3H, s), 2.77-2.84 (4H, m), 2.94 (2H, td, J = 15.6, 4.3 Hz), 3.16 (3H, s), 3.74 (2H, s), 3.92 (3H, s), 4.25 (2H, d, J = 5.0 Hz), 4.42 (2H, s), 5.27 (2H, s), 6.22 (1H, tt, J = 55.7, 4.3, 4.2 Hz), 7.25-7.33 (2H, m), 7.41-7.43 (1H, m), 8.02 (1H, t, J = 5.1 Hz), 8.14 (1H, s), 8.16 (1H, s), 8.27-8.29 (1H, m) |
| 116 | 2.30 (3H, s), 2.35 (3H, s), 2.56 (2H, t, J = 5.8 Hz), 2.79 (2H, t, J = 5.9 Hz), 3.17 (3H, s), 3.43 (2H, s), 3.92 (3H, s), 4.27 (2H, d, J = 5.1 Hz), 4.44 (2H, s), 5.23 (2H, s), 6.86 (2H, d, J = 11.4 Hz), 7.27-7.34 (2H, m), 8.03 (1H, t, J = 5.1 Hz), 8.15 (2H, s) |
| 117 | 1.35 (6H, d, J = 6.6 Hz), 2.30 (3H, d, J = 0.9 Hz), 2.99-3.05 (1H, m), 3.16 (3H, s), 3.20-3.30 (2H, m), 3.64-3.69 (2H, m), 3.92 (3H, s), 4.23-4.28 (2H, m), 4.37-4.43 (4H, m), 5.34 (2H, s), 7.24-7.34 (2H, m), 7.59 (1H, d, J = 2.1 Hz), 8.04 (1H, t, J = 5.1 Hz), 8.17 (1H, s), 8.23 (1H, s), 8.43 (1H, d, J = 2.1 Hz), 10.63 (1H, br. s) |
| 118 | 2.27-2.32 (6H, m), 2.54 (2H, t, J = 6.0 Hz), 2.79 (2H, t, J = 6.0 Hz), 3.16 (3H, s), 3.39 (2H, s), 3.92 (3H, s), 4.25 (2H, d, J = 5.0 Hz), 4.42 (2H, s), 5.25 (2H, s), 6.94-6.99 (2H, m), 7.25-7.33 (2H, m), 8.04 (1H, t, J = 5.0 Hz), 8.09 (1H, s), 8.13-8.15 (1H, m) |
| 119 | 2.26-2.32 (3H, m), 2.56 (2H, t, J = 5.8 Hz), 2.77 (2H, t, J = 5.9 Hz), 3.17 (3H, s), 3.43 (2H, s), 3.92 (3H, s), 4.25 (2H, d, J = 5.0 Hz), 4.43 (2H, s), 5.19 (2H, s), 6.93 (1H, s), 6.97-7.01 (1H, m), 7.04-7.10 (1H, m), 7.24-7.33 (2H, m), 8.02 (1H, t, J = 5.1 Hz), 8.11 (1H, s), 8.14-8.15 (1H, m) |
| 120 | 1.44-1.54 (1H, m), 1.71-1.83 (2H, m), 2.22-2.32 (4H, m), 2.33-2.40 (1H, m), 2.42-2.48 (1H, m), 2.67-2.75 (1H, m), 2.86-3.00 (2H, m), 3.04-3.12 (1H, m), 3.16 (3H, s), 3.19-3.28 (1H, m), 3.92 (3H, s), 4.25 (2H, d, J = 5.1 Hz), 4.43 (2H, s), 5.21 (2H, s), 6.95-7.02 (2H, m), 7.07 (1H, d, J = 7.8 Hz), 7.23-7.34 (2H, m), 8.02 (1H, t, J = 5.1 Hz), 8.11 (1H, s), 8.14 (1H, s) |
| 121 | 2.23-2.27 (3H, m), 2.29 (3H, s), 2.39-2.47 (4H, m), 2.78-2.84 (4H, m), 3.17 (3H, s), 3.92 (3H, s), 4.25 (2H, d, J = 5.1 Hz), 4.43 (2H, s), 5.20 (2H, s), 6.97 (1H, dd, J = 7.6, 1.9 Hz), 7.00 (1H, d, J = 1.8 Hz), 7.08 (1H, d, J = 7.6 Hz), 7.25-7.33 (2H, m), 8.02 (1H, t, J = 5.1 Hz), 8.12 (1H, s), 8.15 (1H, d, J = 0.9 Hz) |
| 122 | 0.93 (6H, s), 2.29 (3H, s), 2.47-2.54 (4H, m), 2.73-2.83 (4H, m), 2.83-2.92 (1H, m), 3.17 (3H, s), 3.92 (3H, s), 4.25 (2H, d, J = 5.1 Hz), 4.43 (2H, s), 5.19 (2H, s), 6.93-7.02 (2H, m), 7.08 (1H, d, J = 7.8 Hz), 7.25-7.34 (2H, m), 8.02 (1H, t, J = 5.0 Hz), 8.13 (1H, s), 8.15 (1H, s) |
| 123 | 1.21 (3H, d, J = 6.5 Hz), 1.25 (3H, dd, J = 6.4, 2.4 Hz), 1.39-1.49 (2H, m), 2.31 (3H, dd, J = 4.8, 0.8 Hz), 2.32-2.44 (2H, m), 3.17 (3H, d, J = 0.9 Hz), 3.27-3.34 (1H, m), 3.93 (3H, s), 4.27 (2H, d, J = 4.0 Hz), 4.43 (2H, d, J = 13.1 Hz), 5.31-5.44 (4H, m), 7.24-7.36 (4H, m), 7.44-7.50 (1H, m), 8.05 (1H, q, J = 5.4 Hz), 8.19 (1H, dd, J = 6.4, 1.0 Hz), 8.23 (1H, d, J = 4.0 Hz), 9.80 (0.5H, d, J = 9.1 Hz), 10.56 (0.5H, d, J = 8.6 Hz) |
| 124 | 1.37 (3H, s), 1.72 (3H, s), 2.29 (3H, s), 2.83 (3H, d, J = 5.0 Hz), 3.16 (3H, s), 3.92 (3H, s), 4.26 (2H, d, J = 5.0 Hz), 4.43 (2H, s), 4.47 (1H, dd, J = 14.3, 8.2 Hz), 4.61 (1H, dd, J = 14.3, 5.5 Hz), 5.31 (2H, s), 7.19 (1H, dd, J = 7.9, 1.5 Hz), 7.25-7.35 (3H, m), 7.38 (1H, d, J = 7.9 Hz), 8.05 (1H, t, J = 5.1 Hz), 8.17 (1H, d, J = 1.0 Hz), 8.21 (1H, s), 11.19 (1H, s) |
| 125 | 2.28 (3H, s), 2.36 (3H, s), 2.80 (2H, t, J = 5.6 Hz), 3.53 (2H, s), 3.93 (3H, s), 4.04 (2H, t, J = 5.6 Hz), 4.23 (2H, d, J = 4.7 Hz), 5.30 (2H, s), 5.99 (1H, s), 7.26-7.35 (2H, m), 8.09 (1H, s), 8.26 (1H, s), 8.39 (1H, t, J = 4.8 Hz) |

TABLE 11-continued

¹H NMR data of examples (solvent d6 DMSO unless otherwise indicated)

| Example Number | Chemical shift |
|---|---|
| 126 | 0.80-0.92 (4H, m), 2.28 (3H, s), 2.29 (3H, s), 2.40 (2H, s), 3.17 (3H, s), 3.53 (2H, s), 3.92 (3H, s), 4.25 (2H, d, J = 5.0 Hz), 4.42 (2H, s), 5.17 (2H, s), 6.67 (1H, d, J = 8.1 Hz), 6.92 (1H, d, J = 1.8 Hz), 6.97 (1H, dd, J = 8.2, 1.9 Hz), 7.24-7.34 (2H, m), 8.02 (1H, t, J = 5.1 Hz), 8.10 (1H, s), 8.14 (1H, s) |
| 127 | 0.77-0.83 (2H, m), 0.85-0.91 (2H, m), 2.29 (3H, s), 2.75 (2H, s), 3.16 (3H, s), 3.85-3.95 (5H, m), 4.25 (2H, d, J = 5.0 Hz), 4.42 (2H, s), 5.17 (2H, s), 6.69 (1H, d, J = 8.1 Hz), 6.91 (1H, s), 6.98 (1H, d, J = 8.1 Hz), 7.24-7.34 (2H, m), 8.01 (1H, t, J = 5.1 Hz), 8.10 (1H, s), 8.15 (1H, s) |
| 128 | 1.31 (6H, s), 2.30 (3H, s), 2.62 (3H, t, J = 5.8 Hz), 2.91 (2H, t, J = 5.8 Hz), 3.17 (3H, s), 3.92 (3H, s), 4.26 (2H, d, J = 5.0 Hz), 4.44 (2H, s), 5.21 (2H, s), 6.89 (1H, dd, J = 7.6, 1.7 Hz), 6.98 (1H, d, J = 7.8 Hz), 7.20 (1H, d, J = 1.7 Hz), 7.23-7.35 (2H, m), 8.03 (1H, t, J = 5.0 Hz), 8.14 (2H, d, J = 13.4 Hz) |
| 129 | 1.28 (6H, s), 2.29 (3H, s), 2.31 (3H, s), 2.71 (4H, s), 3.16 (3H, s), 3.91 (3H, s), 4.25 (2H, d, J = 5.0 Hz), 4.44 (2H, s), 5.22 (2H, s), 6.85-6.94 (1H, m), 6.99 (1H, d, J = 7.8 Hz), 7.22-7.34 (3H, m), 8.02 (1H, t, J = 5.1 Hz), 8.13 (1H, s), 8.14 (1H, d, J = 1.0 Hz) |
| 130 | 1.17 (6H, s), 2.29 (3H, s), 2.67 (2H, s), 3.17 (3H, s), 3.80 (2H, s), 3.92 (3H, s), 4.22-4.29 (2H, m), 4.43 (2H, s), 5.17 (2H, s), 6.84-6.89 (1H, m), 6.99-7.05 (1H, m), 7.24-7.33 (3H, m), 8.02 (1H, t, J = 5.1 Hz), 8.10-8.17 (2H, m), NH not observed. |
| 131 | 2.26-2.30 (3H, m), 2.36 (3H, s), 2.60 (2H, t, J = 5.9 Hz), 2.81 (2H, t, J = 5.9 Hz), 3.49 (2H, s), 3.93 (3H, s), 4.22-4.26 (2H, m), 5.43 (2H, s), 7.04 (1H, d, J = 7.8 Hz), 7.27-7.35 (2H, m), 7.56 (1H, d, J = 7.9 Hz), 8.10 (1H, d, J = 1.0 Hz), 8.33 (1H, d, J = 1.0 Hz), 8.41 (1H, t, J = 4.8 Hz) |
| 132 | 1.34 (6H, t, J = 6.8 Hz), 2.30 (3H, s), 3.08-3.15 (1H, m), 3.16 (3H, s), 3.32-3.45 (2H, m), 3.59-3.66 (1H, m), 3.68-3.74 (1H, m), 3.92 (3H, s), 4.26 (2H, d, J = 4.6 Hz), 4.35-4.47 (4H, m), 5.38 (2H, s), 7.24-7.35 (2H, m), 7.61 (1H, s), 8.06 (1H, t, J = 5.1 Hz), 8.19 (1H, s), 8.25 (1H, s), 8.54 (1H, d, J = 2.0 Hz), 10.97 (1H, s) |
| 133 | 2.30 (s, 3H), 2.74 (t, 2H, J = 5.8 Hz), 3.17 (s, 3H), 3.85 (t, 2H, J = 5.8 Hz), 3.92 (s, 3H), 4.26 (d, 2H, 5.0 Hz), 4.44 (s, 2H), 4.64 (s, 2H), 5.21 (s, 2H), 6.90-6.95 (m, 1H), 7.05 (dd, 1H, J = 7.8, 1.9 Hz), 7.11 (d, 1H, J = 7.8 Hz), 7.25-7.34 (m, 2H), 8.03 (t, 1H, 5.0 Hz), 8.13 (s, 1H), 8.16 (s, 1H) |
| 134 | 1.20 (6H, s), 2.22-2.35 (8H, m), 3.17 (3H, s), 3.40 (2H, s), 3.92 (3H, s), 4.25 (2H, d, J = 5.0 Hz), 4.43 (2H, s), 5.18 (2H, s), 6.89 (1H, d, J = 1.9 Hz), 7.02 (1H, dd, J = 8.0, 1.9 Hz), 7.25-7.34 (3H, m), 8.02 (1H, t, J = 5.1 Hz), 8.14 (2H, d, J = 8.5 Hz) |
| 135 | 2.29 (3H, d, J = 0.8 Hz), 2.93 (2H, t, J = 6.7 Hz), 3.00 (3H, s), 3.17 (3H, s), 3.51 (2H, t, J = 6.7 Hz), 3.92 (3H, s), 4.26 (2H, d, J = 5.1 Hz), 4.44 (2H, s), 5.32 (2H, s), 7.12 (1H, d, J = 1.7 Hz), 7.17 (1H, dd, J = 1.7, 8.0 Hz), 7.25-7.34 (2H, m), 7.82 (1H, d, J = 7.9 Hz), 8.04 (1H, t, J = 5.1 Hz), 8.15 (1H, d, J = 1.0 Hz), 8.19 (1H, s) |
| 136 | 2.27 (3H, s), 2.35 (3H, s), 2.80 (2H, t, J = 5.6 Hz), 3.52 (2H, s), 3.92 (3H, s), 4.04 (2H, t, J = 5.6 Hz), 4.24 (2H, d, J = 4.8 Hz), 5.26 (2H, s), 5.97 (1H, s), 7.09-7.39 (3H, m), 8.09 (1H, d, J = 0.9 Hz), 8.22 (1H, s), 8.37 (1H, t, J = 4.9 Hz) |
| 137 | 2.26 (3H, s), 2.35 (3H, s), 2.59 (2H, t, J = 5.9 Hz), 2.81 (2H, t, J = 5.9 Hz), 3.51 (2H, s), 3.92 (3H, s), 4.24 (2H, d, J = 4.8 Hz), 5.38 (2H, s), 7.11-7.34 (3H, m), 7.46 (1H, d, J = 2.1 Hz), 8.06-8.10 (1H, m), 8.22-8.26 (1H, m), 8.32 (1H, d, J = 2.2 Hz), 8.35 (1H, t, J = 4.9 Hz) |
| 138 | 2.29 (3H, s), 2.92 (3H, s), 3.07 (1H, d, J = 17.9 Hz), 3.27 (1H, d, J = 17.8 Hz), 3.44 (1H, d, J = 9.9 Hz), 3.70 (1H, s), 3.93 (3H, s), 4.25 (1H, d, J = 4.9 Hz), 4.32 (1H, dd, J = 15.9, 8.2 Hz), 4.51 (1H, d, J = 15.5 Hz), 5.51 (2H, s), 7.17 (1H, d, J = 8.0 Hz), 7.28-7.35 (2H, m), 7.68 (1H, d, J = 8.0 Hz), 8.13 (1H, s), 8.42 (1H, s), 8.46 (1H, s) |
| 147 | 1.36 (6H, d, J = 6.5 Hz), 2.34 (3H, s), 3.29 (3H, s), 3.70 (1H, d, J = 6.9 Hz), 3.94 (3H, s), 4.35 (2H, d, J = 5.3 Hz), 4.47 (2H, s), 4.54 (2H, d, J = 14.0 Hz), 4.72 (2H, d, J = 14.5 Hz), 5.28 (2H, s), 7.20-7.35 (4H, m), 7.39 (1H, d, J = 7.8 Hz), 7.62 (1H, s), 7.65 (1H, t, J = 6.0 Hz), 8.11 (1H, s), 11.34 (1H, s) |
| 148 | 2.33 (6H, d, J = 10.0 Hz), 2.61 (2H, d, J = 6.2 Hz), 2.79 (2H, t, J = 5.8 Hz), 3.24 (3H, s), 3.48 (2H, s), 3.91 (3H, s), 4.28 (2H, d, J = 5.8 Hz), 4.41 (2H, s), 5.14 (2H, s), 6.94 (1H, s), 7.00 (1H, d, J = 7.9 Hz), 7.09 (1H, d, J = 7.9 Hz), 7.29 (2H, d, J = 8.2 Hz), 7.63 (1H, s), 7.86 (1H, t, J = 5.8 Hz), 8.22 (1H, s) |
| 149 | 0.80 (2H, dt, J = 5.2, 2.9 Hz), 0.86 (2H, dt, J = 8.1, 3.0 Hz), 1.94 (1H, ddd, J = 13.0, 8.3, 4.9 Hz), 2.32 (6H, d, J = 4.2 Hz), 2.57 (2H, t, J = 6.0 Hz), 2.78 (2H, t, J = 5.9 Hz), 3.45 (2H, s), 3.91 (3H, s), 4.30 (2H, d, J = 5.9 Hz), 5.20 (2H, s), 6.91 (1H, s), 6.97 (1H, d, J = 8.1 Hz), 7.09 (1H, d, J = 7.9 Hz), 7.29 (2H, d, J = 7.9 Hz), 7.56 (1H, s), 7.62 (1H, t, J = 6.0 Hz), 8.22 (1H, s) |
| 150 | 0.96 (4H, d, J = 7.8 Hz), 1.37 (6H, d, J = 6.5 Hz), 2.02 (1H, p, J = 6.7 Hz), 2.34 (3H, s), 3.69 (1H, s), 3.94 (3H, s), 4.33-4.37 (2H, m), 4.54 (2H, d, J = 12.5 Hz), 4.72 (2H, d, J = 14.8 Hz), 5.38 (2H, s), 7.24-7.32 (4H, m), 7.40 (1H, d, J = 7.9 Hz), 7.66 (1H, s), 7.84 (1H, s), 8.11 (1H, s), 11.60 (1H, s) |

TABLE 11-continued

¹H NMR data of examples (solvent d6 DMSO unless otherwise indicated)

| Example Number | Chemical shift |
|---|---|
| 151 | 2.23 (3H, s), 2.31 (3H, s), 2.33 (3H, s), 2.56 (2H, t, J = 5.9 Hz), 2.78 (2H, t, J = 5.9 Hz), 3.44 (2H, s), 3.91 (3H, s), 4.27 (2H, d, J = 5.8 Hz), 5.09 (2H, s), 6.86 (1H, s), 6.91-6.95 (1H, m), 7.09 (1H, d, J = 7.8 Hz), 7.29 (2H, d, J = 7.8 Hz), 7.59 (1H, s), 7.78 (1H, t, J = 5.8 Hz), 8.23 (1H, s) |
| 152 | 2.29 (3H, s), 2.30 (3H, s), 2.55 (2H, t, J = 6.0 Hz), 2.77 (2H, t, J = 6.0 Hz), 3.43 (2H, s), 3.90 (3H, s), 4.32 (2H, d, J = 5.3 Hz), 5.54 (2H, s), 7.01 (1H, s), 7.03-7.12 (2H, m), 7.24-7.33 (2H, m), 8.18 (1H, s), 8.51 (1H, t, J = 5.5 Hz), 8.55 (1H, s) |
| 153 | 1.33 (6H, dd, J = 6.5, 2.2 Hz), 2.30 (3H, s), 3.60-3.71 (1H, m), 3.91 (3H, s), 4.33 (2H, d, J = 4.8 Hz), 4.51 (2H, dd, J = 14.3, 8.3 Hz), 4.70 (2H, dd, J = 14.5, 6.7 Hz), 5.68 (2H, s), 7.25-7.34 (3H, m), 7.35-7.42 (2H, m), 8.20 (1H, s), 8.53 (1H, t, J = 5.5 Hz), 8.62 (1H, s), 11.44 (1H, s) |
| 155 | 2.30 (3H, s), 2.55 (2H, t, J = 5.9 Hz), 2.76 (2H, t, J = 5.9 Hz), 3.17 (3H, s), 3.42 (2H, s), 4.39 (2H, d, J = 5.3 Hz), 4.43 (2H, s), 5.19 (2H, s), 6.92 (1H, s), 6.98 (1H, dd, J = 7.8, 1.8 Hz), 7.03-7.28 (2H, m), 7.49 (1H, dd, J = 8.7, 1.4 Hz), 7.80 (1H, t, J = 8.2 Hz), 8.08 (1H, s), 8.18 (1H, t, J = 5.3 Hz), 9.10 (1H, s) |
| 156 | 2.30 (3H, s), 2.55 (2H, t, J = 5.9 Hz), 2.76 (2H, t, J = 5.9 Hz), 3.15 (3H, s), 3.42 (2H, s), 3.95 (3H, s), 4.28 (2H, d, J = 5.0 Hz), 4.43 (2H, s), 5.19 (2H, s), 6.93 (1H, s), 6.99 (1H, dd, J = 7.9, 1.8 Hz), 7.06 (1H, d, J = 7.8 Hz), 7.19 (1H, t, J = 53.0 Hz), 7.31 (1H, d, J = 8.9 Hz), 7.54 (1H, d, J = 8.8 Hz), 8.06 (1H, t, J = 5.0 Hz), 8.12 (1H, s), 8.94 (1H, s) |
| 157 | 2.06 (3H, t, J = 19.2 Hz), 2.30 (3H, s), 2.54 (2H, t, J = 5.9 Hz), 2.76 (2H, t, J = 5.9 Hz), 3.16 (3H, s), 3.41 (2H, s), 4.41-4.45 (4H, m), 5.19 (2H, s), 6.90-6.93 (1H, m), 6.96-7.00 (1H, m), 7.05 (1H, d, J = 7.0 Hz), 7.17 (1H, t, J = 51.9 Hz), 7.55 (1H, d, J = 8.4 Hz), 7.73 (1H, d, J = 8.1 Hz), 8.09 (1H, s), 8.17 (1H, dd, J = 5.3 Hz), 9.14 (1H, s) |
| 158 | 2.24 (3H, s), 2.38-2.47 (4H, m), 2.77-2.84 (4H, m), 3.17 (3H, s), 3.93 (3H, s), 4.31 (2H, d, J = 5.4 Hz), 4.43 (2H, s), 5.19 (2H, s), 6.95 (1H, dd, J = 7.5, 1.9 Hz), 6.98 (1H, d, J = 1.8 Hz), 7.07 (1H, d, J = 7.6 Hz), 7.32 (1H, dd, J = 8.8 Hz), 7.42 (1H, dd, J = 8.9, 1.4 Hz), 8.09 (1H, s), 8.12 (1H, t, J = 5.3 Hz), 9.11 (1H, d, J = 0.9 Hz) |
| 159 | 1.11 (2H, s), 2.29 (3H, s), 2.35 (3H, s), 2.62 (2H, t, J = 5.9 Hz), 2.78 (2H, t, J = 6.0 Hz), 3.08 (1H, s), 3.48 (2H, s), 3.93 (3H, s), 4.29 (2H, d, J = 4.8 Hz), 5.02 (2H, s), 6.40 (1H, dd, J = 7.1, 1.9 Hz), 6.59 (1H, s), 6.66 (1H, d, J = 1.9 Hz), 6.96 (1H, s), 6.98-7.11 (2H, m), 7.19-7.35 (2H, m), 7.81 (1H, d, J = 7.1 Hz), 8.12 (1H, s), 8.74 (1H, t, J = 4.8 Hz) |
| 160 | 2.26 (3H, s), 2.31 (3H, s), 2.56 (2H, t, J = 6.0 Hz), 2.77 (2H, t, J = 6.0 Hz), 3.43 (2H, s), 3.92 (3H, s), 4.28 (2H, d, J = 4.7 Hz), 5.04 (2H, s), 6.41 (1H, d, J = 9.6 Hz), 6.96 (1H, s), 7.00-7.09 (2H, m), 7.23-7.34 (2H, m), 7.74 (1H, dd, J = 9.6, 2.6 Hz), 8.12 (1H, s), 8.28 (1H, d, J = 2.6 Hz), 8.38 (1H, t, J = 4.9 Hz) |
| 161 | 2.25 (3H, s), 2.30 (3H, s), 2.54 (2H, t, J = 5.9 Hz), 2.75 (2H, t, J = 6.0 Hz), 3.41 (2H, s), 3.92 (5H, s), 4.34 (2H, d, J = 4.7 Hz), 6.91 (1H, s), 6.95-7.05 (2H, m), 7.23-7.34 (2H, m), 7.85 (1H, t, J = 2.2 Hz), 8.12 (1H, s), 8.57 (1H, d, J = 2.1 Hz), 8.66 (1H, d, J = 2.0 Hz), 8.77 (1H, t, J = 4.9 Hz) |
| 162 | (Chloroform-d) 2.43 (3H, d, J = 0.8 Hz), 2.99 (1H, dd, J = 17.4, 6.2 Hz), 3.35 (3H, s), 3.36 (3H, s), 3.46-3.56 (1H, m), 3.61 (1H, dt, J = 11.7, 6.1 Hz), 3.64-3.75 (1H, m), 3.93 (3H, s), 4.36-4.41 (2H, m), 4.44-4.57 (2H, m), 4.55 (2H, s), 5.17 (2H, s), 6.90 (1H, s), 6.99 (1H, t, J = 8.7 Hz), 7.13 (2H, dd, J = 8.8, 1.7 Hz), 7.21 (1H, d, J = 7.9 Hz), 7.84 (1H, d, J = 13.6 Hz), 8.27-8.34 (1H, m) |
| RC1 | 2.28 (3H, s), 3.17 (3H, s), 3.91 (3H, s), 4.26 (2H, d, J = 5.0 Hz), 4.45 (2H, s), 5.51 (2H, s), 7.23-7.34 (2H, m), 7.60-7.68 (1H, m), 7.81 (1H, d, J = 5.7 Hz), 7.92-8.00 (2H, m), 8.04 (1H, t, J = 5.0 Hz), 8.15 (1H, d, J = 1.0 Hz), 8.24 (1H, s), 8.50 (1H, d, J = 5.7 Hz), 9.30 (1H, s) |
| RC2 | 2.64 (3H, s), 3.19 (3H, s), 3.93 (3H, s), 4.23 (2H, d, J = 4.8 Hz), 4.44 (2H, s), 5.46 (2H, s), 7.33-7.43 (3H, m), 7.56 (1H, dd, J = 8.7, 1.5 Hz), 7.76 (1H, d, J = 1.2 Hz), 7.88 (1H, d, J = 8.6 Hz), 8.18-8.23 (3H, m), 9.75 (1H, s) |
| RC3 | 3.19 (3H, s), 3.93 (3H, s), 4.24 (2H, d, J = 5.4 Hz), 4.44 (2H, s), 5.50 (2H, s), 7.29-7.44 (2H, m), 7.53 (1H, dd, J = 8.3, 4.2 Hz), 7.61 (1H, dd, J = 8.7, 2.0 Hz), 7.82 (1H, d, J = 1.9 Hz), 8.00 (1H, d, J = 8.7 Hz), 8.18 (1H, t, J = 5.3 Hz), 8.21 (1H, s), 8.35 (1H, dd, J = 8.4, 1.8 Hz), 8.89 (1H, dd, J = 4.2, 1.7 Hz), 9.74 (1H, s) |
| RC5 | 1.89-1.92 (4H, m), 3.17 (3H, s), 3.43-3.46 (4H, m), 3.92 (3H, s), 4.22 (2H, d, J = 4.4 Hz), 4.42 (2H, s), 5.10 (2H, s), 7.29-7.35 (2H, m), 7.92 (1H, J = 0.8 Hz), 8.04 (1H, t, J = 5.0 Hz), 8.09 (1H, s), 8.34 (2H, s), 8.45 (1H, d, J = 0.9 Hz) |
| RC6 | 1.89-1.92 (4H, m), 2.28 (3H, s), 3.17 (3H, s), 3.45 (4H, t, J = 6.6 Hz), 3.92 (3H, s), 4.24 (2H, d, J = 4.6 Hz), 4.42 (2H, s), 5.11 (2H, s), 7.25-7.32 (2H, m), 8.00 (1H, t, J = 5.0 Hz), 8.09 (1H, s), 8.13 (1H, s), 8.34 (2H, s) |

TABLE 11-continued $^1$H NMR data of examples (solvent d6 DMSO unless otherwise indicated)

| Example Number | Chemical shift |
|---|---|
| RC7 | 1.89-1.92 (4H, m), 3.17 (3H, s), 3.43-3.46 (4H, m), 3.93 (3H, s), 4.25 (2H, d, J = 4.8 Hz), 4.42 (2H, s), 5.10 (2H, s), 7.28 (1H, t, J = 54.1 Hz), 7.31-7.38 (2H, m), 8.08 (1H, s), 8.09 (1H, t, J = 5.1 Hz), 8.33 (2H, s), 8.89 (1H, t, J = 1.4 Hz) |

Some of the specific examples in Table 11 were isolated in the form of their pharmaceutically acceptable salts, typically HCl salt. Thus, $^1$H NMR data was collected for some of these specific examples when in the form of a pharmaceutically acceptable salt. Where $^1$H NMR data has been collected on a HCl salt of one of the specific examples, an extra proton may have been detected. Those skilled in the art would readily be able to identify this extra proton. Those skilled in the art would also readily know how to convert from a salt form to a free base (and vice versa).

Biological Methods

The ability of the compounds of formula (I) to inhibit plasma kallikrein may be determined using the following biological assay:

Determination of the $IC_{50}$ for Plasma Kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human plasma kallikrein (Protogen) was incubated at 25° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

Data acquired from this assay are shown in Table 12 using the following scale:

| Category | $IC_{50}$ (nM) |
|---|---|
| A | <10 |
| B | 10-30 |
| C | 30-100 |
| D | 100-1000 |

Selected compounds were further screened for inhibitory activity against the related enzyme KLK1. The ability of the compounds of formula (I) to inhibit KLK1 may be determined using the following biological assay:

Determination of the $IC_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human KLK1 (Callbiochem) was incubated at 25° C. with the fluorogenic substrate H-DVal-Leu-Arg-AFC and various concentrations of the test compound. Residual enzyme activity (initial rate of reaction) was determined by measuring the change in optical absorbance at 410 nm and the $IC_{50}$ value for the test compound was determined.

Data acquired from this assay are shown in Table 12.

Selected compounds were further screened for inhibitory activity against the related enzyme FXIa. The ability of the compounds of formula (I) to inhibit FXIa may be determined using the following biological assay:

Determination of the % Inhibition for FXIa

FXIa inhibitory activity in vitro was determined using standard published methods (see e.g. Johansen et al., Int. J. Tiss. Reac. 1986, 8, 185; Shori et al., Biochem. Pharmacol., 1992, 43, 1209; Sturzebecher et al., Biol. Chem. Hoppe-Seyler, 1992, 373, 1025). Human FXIa (Enzyme Research Laboratories) was incubated at 25° C. with the fluorogenic substrate Z-Gly-Pro-Arg-AFC and 40 µM of the test compound (or alternatively at various concentrations of the test compound in order to determine $IC_{50}$). Residual enzyme activity (initial rate of reaction) was determined by measuring the change in optical absorbance at 410 nm and the IC50 value for the test compound was determined.

Data acquired from this assay are shown in Table 12.

TABLE 12

Enzyme inhibition data

| Example Number | $IC_{50}$ (human PKal) | $IC_{50}$ (human KLK1) nM | $IC_{50}$ (human FXIa) nM |
|---|---|---|---|
| 1 | A | >40000 | >40000 |
| 2 | A | >40000 | >40000 |
| 3 | A | >40000 | >40000 |
| 4 | A | >40000 | 1030 |
| 6 | A | >40000 | >40000 |
| 7 | A | >40000 | >40000 |
| 8 | B | >40000 | >40000 |
| 9 | C | >40000 | >40000 |
| 11 | A | >40000 | 18900 |
| 12 | A | >40000 | >40000 |
| 13 | A | >40000 | >40000 |
| 14 | A | >40000 | 28100 |
| 15 | A | >40000 | >40000 |
| 16 | A | >40000 | >40000 |
| 17 | A | >40000 | >40000 |
| 18 | A | >40000 | >40000 |
| 19 | A | >40000 | >40000 |
| 20 | B | >40000 | >40000 |
| 21 | A | >40000 | 36800 |
| 22 | A | >40000 | >40000 |
| 23 | A | >40000 | >40000 |
| 24 | A | >40000 | 23800 |
| 25 | A | >40000 | >40000 |
| 26 | A | >40000 | >40000 |
| 27 | A | >40000 | 33900 |
| 29 | A | >40000 | >40000 |
| 30 | A | >40000 | 39600 |
| 31 | A | >40000 | 34600 |
| 32 | A | >40000 | 19600 |
| 33 | A | | |
| 34 | A | >40000 | >40000 |
| 35 | C | >40000 | >40000 |
| 36 | A | >4000 | >4000 |
| 37 | A | >40000 | >40000 |
| 38 | A | >40000 | >40000 |
| 40 | B | >40000 | >40000 |
| 41 | A | >40000 | >40000 |
| 42 | A | >40000 | >40000 |
| 43 | A | >40000 | 31800 |

TABLE 12-continued

Enzyme inhibition data

| Example Number | IC$_{50}$ (human PKal) | IC$_{50}$ (human KLK1) nM | IC$_{50}$ (human FXIa) nM |
|---|---|---|---|
| 44 | A | >40000 | >40000 |
| 45 | A | >40000 | >40000 |
| 46 | A | >40000 | >40000 |
| 47 | C | >40000 | >40000 |
| 48 | C | >40000 | >40000 |
| 49 | B | >40000 | >40000 |
| 50 | A | >40000 | >40000 |
| 51 | A | >40000 | >40000 |
| 52 | A | >40000 | >40000 |
| 53 | C | >4000 | >4000 |
| 54 | A | >4000 | >4000 |
| 55 | A | >40000 | >40000 |
| 56 | A | >40000 | 16300 |
| 57 | A | >40000 | 28800 |
| 58 | A | >40000 | 17000 |
| 59 | A | >40000 | >40000 |
| 60 | A | >40000 | >40000 |
| 61 | C | >40000 | >40000 |
| 64 | C | >40000 | >40000 |
| 68 | B | >40000 | >40000 |
| 70 | B | >40000 | >40000 |
| 73 | C | >40000 | 11300 |
| 82 | A | >40000 | 18200 |
| 102 | A | >40000 | 34200 |
| 103 | C | >40000 | >40000 |
| 104 | C | >40000 | >40000 |
| 105 | A | >40000 | 30000 |
| 106 | A | >40000 | 23100 |
| 107 | A | >40000 | >40000 |
| 108 | D | >40000 | >40000 |
| 109 | D | >40000 | >40000 |
| 110 | D | >40000 | >40000 |
| 114 | B | >40000 | >40000 |
| 115 | B | >4000 | >4000 |
| 116 | A | >4000 | >4000 |
| 117 | B | >40000 | >40000 |
| 118 | A | >40000 | 9900 |
| 119 | A | | |
| 120 | A | >40000 | >40000 |
| 121 | A | >40000 | >40000 |
| 122 | A | >40000 | >40000 |
| 123 | C | >40000 | >40000 |
| 124 | C | >40000 | >40000 |
| 125 | A | >40000 | >40000 |
| 126 | A | >40000 | >40000 |
| 127 | A | >40000 | >40000 |
| 128 | C | | |
| 129 | B | | |
| 130 | B | | |
| 131 | B | | |
| 132 | B | | |
| 133 | D | >40000 | >40000 |
| 134 | B | >40000 | >40000 |
| 135 | B | >40000 | 16296 |
| 136 | A | >40000 | >40000 |
| 137 | A | >40000 | 21890 |
| 138 | B | >40000 | >40000 |
| 147 | B | >40000 | >40000 |
| 148 | B | >40000 | >40000 |
| 149 | B | >40000 | >40000 |
| 150 | B | >40000 | >40000 |
| 151 | B | >40000 | >40000 |
| 152 | A | >40000 | >40000 |
| 153 | A | >40000 | >40000 |
| 155 | D | >40000 | >40000 |
| 156 | A | >40000 | >40000 |
| 157 | D | >40000 | >40000 |
| 158 | A | >40000 | >40000 |
| 159 | D | >40000 | >40000 |
| 160 | A | >40000 | >40000 |
| 161 | A | >40000 | >40000 |
| RC1 | D | | |
| RC2 | A | >40000 | 218 |
| RC3 | A | >40000 | 1920 |
| RC4 | A | >40000 | 127 |
| RC5 | A | >40000 | 970 |
| RC6 | A | >40000 | 1840 |
| RC7 | A | >40000 | 559 |

Selected compounds were further screened for solubility in Fasted State Simulated Intestinal Fluid (FaSSIF). The solubility after 24 hrs in FaSSIF of the compounds of formula (I) may be determined using the following test method:

Approximately 1 mg of test compound is accurately weighed into a 2 mL vial. Volumes of the FaSSIF solution (pre-heated to 37° C.) were added to a vial to give a nominal concentration of 1 mg/mL (as free base). The FaSSIF solution was prepared on the day of use. The samples were vortexed before being placed in a Titramax 1000 shaker for 24 hrs at 37° C. and approximately 500 rpm. The samples were transferred to eppendorf tubes and centrifuged at 15,000 g (r.c.f.) for 10 min at 37° C. and analysed for concentration of test compound by LCMS.

Data acquired from this assay are shown in Table 13.

TABLE 13

Solubility

| Example Number | FASSIF Solubility 24 hrs, mg/mL |
|---|---|
| 1 | 0.93 |
| 2 | 0.71 |
| 4 | >1 |
| 11 | 0.73 |
| 13 | 0.86 |
| 15 | >1 |
| 22 | 0.76 |
| 23 | 0.87 |
| 24 | 0.73 |
| 25 | 1.00 |
| 26 | >1 |
| 27 | 0.96 |
| 30 | 0.92 |
| 34 | >1 |
| 35 | 0.51 |
| 36 | 0.88 |
| 37 | >1 |
| 38 | 0.74 |
| 40 | >1 |
| 41 | >1 |
| 42 | 0.87 |
| 43 | 0.80 |
| 44 | >1 |
| 45 | 0.84 |
| 46 | >1 |
| 50 | 0.72 |
| 51 | 0.77 |
| 54 | 0.82 |
| 55 | >1 |
| 117 | 0.90 |
| 118 | 0.93 |
| 119 | 0.96 |
| 122 | 0.73 |
| 125 | 0.65 |
| 126 | 0.88 |
| 127 | 0.81 |
| 132 | 0.56 |
| 133 | 0.05 |
| 136 | 0.73 |
| 137 | 0.81 |
| 138 | >1 |

TABLE 13-continued

Solubility

| Example Number | FASSIF Solubility 24 hrs, mg/mL |
|---|---|
| 147 | >1 |
| 148 | >1 |
| 149 | 0.91 |
| 151 | 0.75 |
| 152 | 1.00 |
| 153 | 0.95 |
| 156 | >1 |
| 160 | 0.82 |
| 161 | >1 |
| RC1 | 0.04 |
| RC2 | 0.02 |
| RC3 | 0.02 |
| RC4 | 0.17 |
| RC5 | 0.02 |
| RC6 | 0.10 |
| RC7 | 0.01 |

Pharmacokinetics

Pharmacokinetic studies of the compounds in Table 14 were performed to assess the pharmacokinetics following a single oral dose in male Sprague-Dawley rats. Two rats were given a single po dose of 5 mL/kg of a nominal 1 mg/mL (5 mg/kg) composition of test compound in 10% DMSO/10% cremophor/80% SWFI vehicle. Following dosing, blood samples were collected over a period of 24 hours. Sample times were 5, 15 and 30 minutes then 1, 2, 4, 6, 8 and 12 hours. Following collection, blood samples were centrifuged and the plasma fraction analysed for concentration of test compound by LCMS. Oral exposure data acquired from these studies are shown below:

TABLE 14

Oral exposure data

| Example Number | Dose po (mg/kg) | Cmax (ng/mL) |
|---|---|---|
| 1 | 6.1 | 88 |
| 2 | 6.8 | 134 |
| 13 | 5 | 88 |
| 15 | 5.1 | 78 |
| 23 | 4.9 | 20 |
| 24 | 5.1 | 24 |
| 37 | 5.0 | 38 |
| 38 | 6.1 | 51 |
| 46 | 5.6 | 34 |
| 54 | 5.0 | 154 |
| 55 | 5 | 136 |
| 126 | 6.3 | 63 |
| 127 | 5.2 | 9 |

X-Ray Crystal Data

Figure 2:
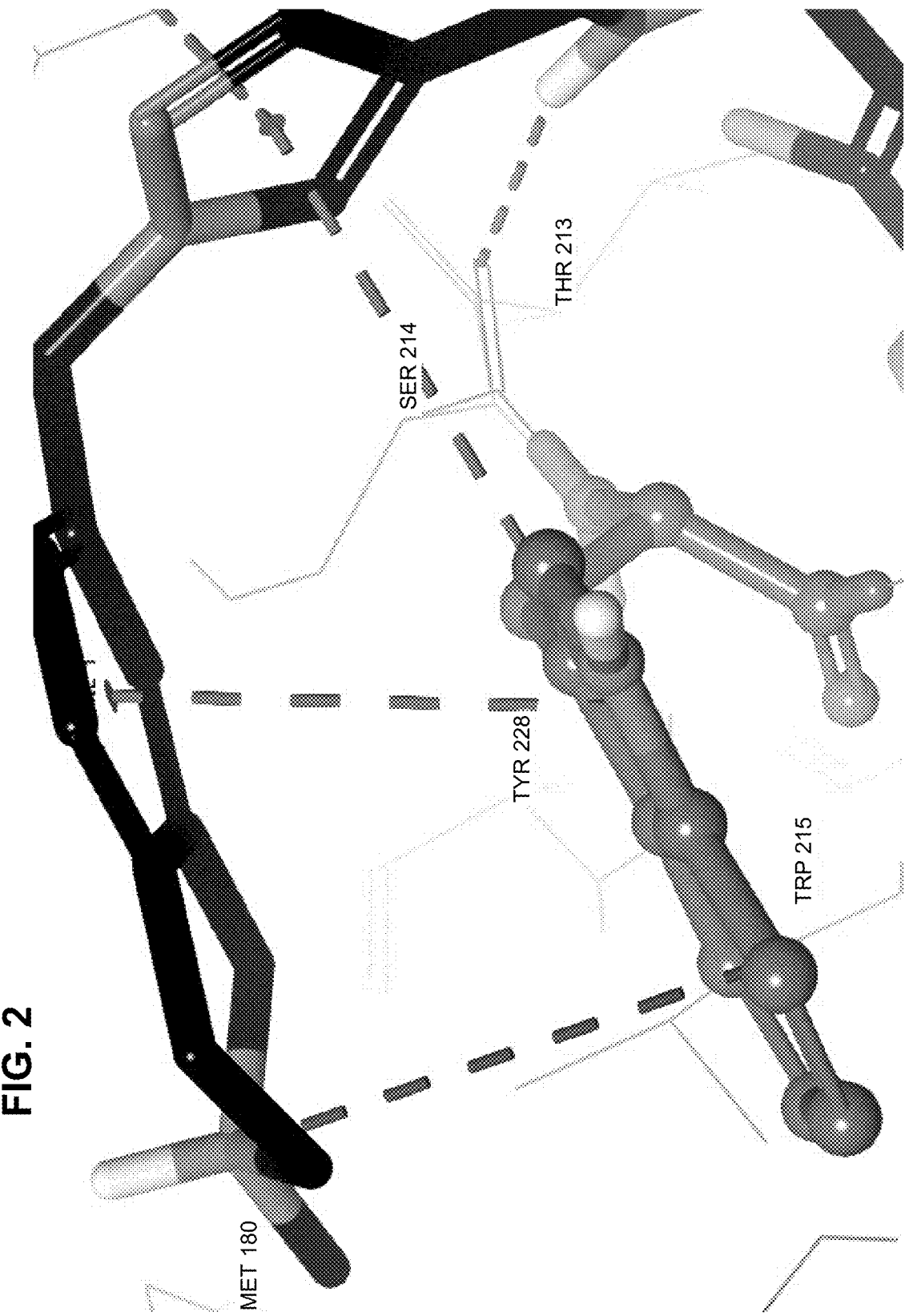
FIG. 2 is a diagram showing key interactions of Example 1 with human plasma kallikrein.
Figure 3:
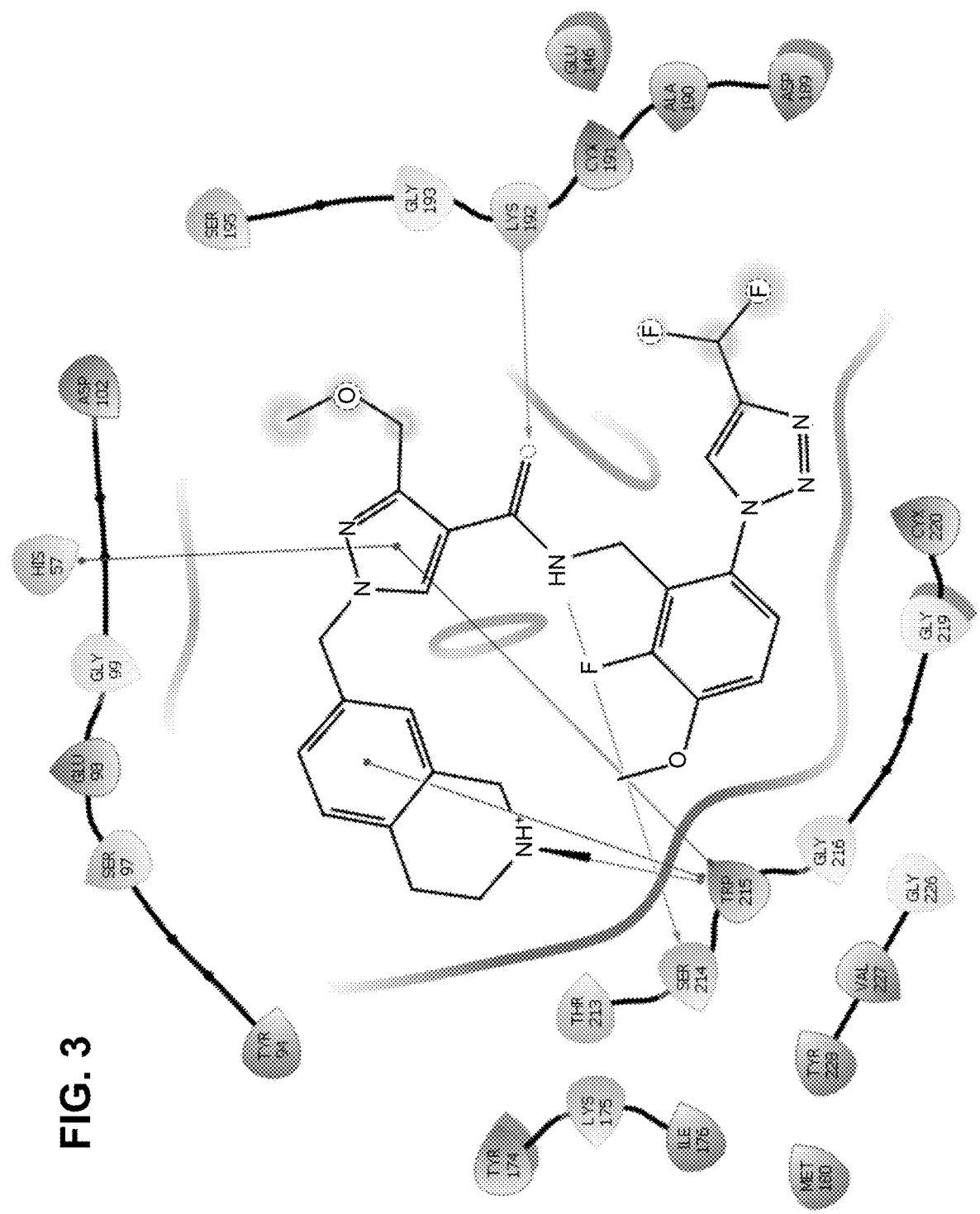
FIG. 3 is a diagram showing key interactions of Example 1 with human plasma kallikrein.
Figure 4:
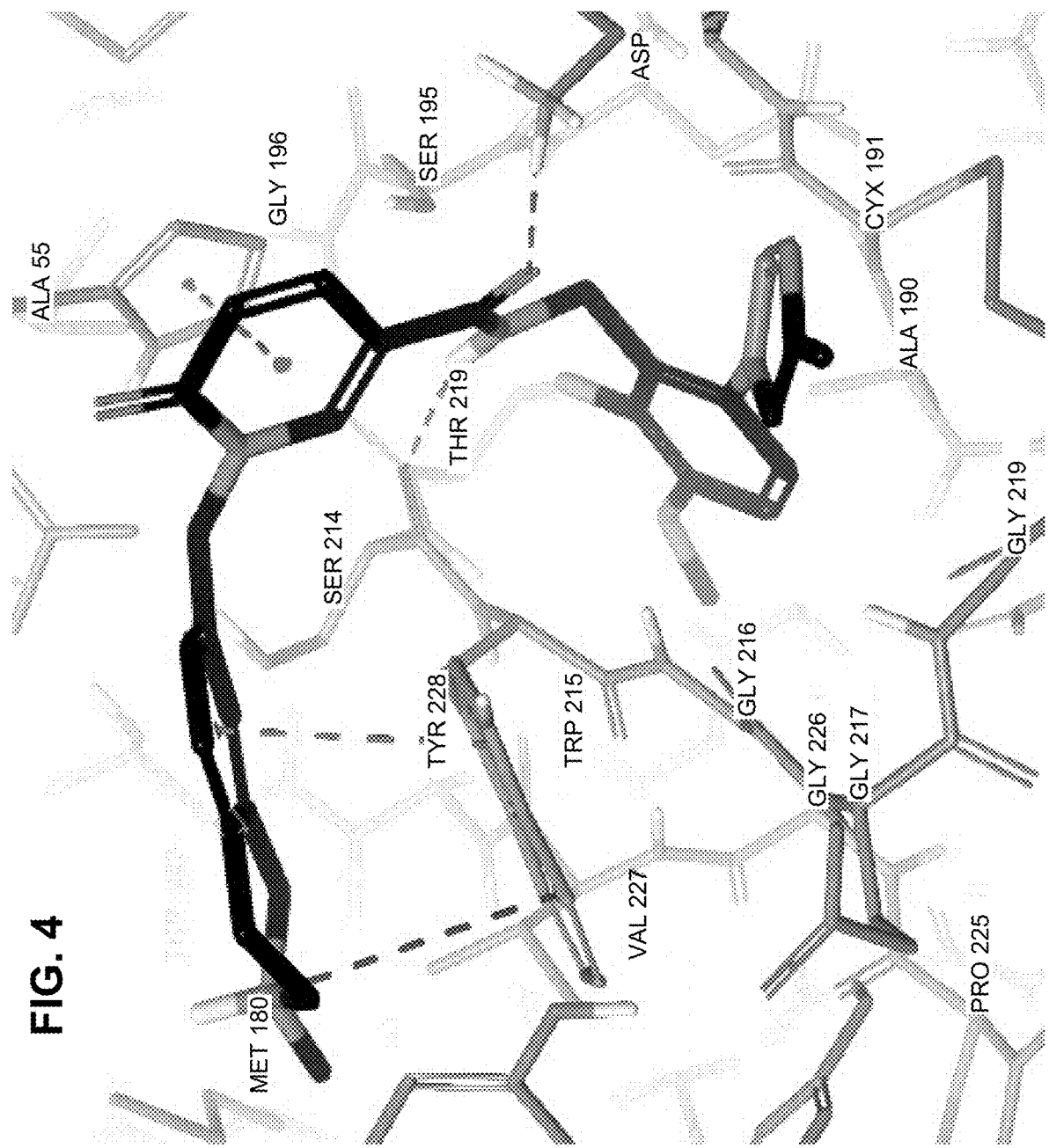
FIG. 4 is a diagram showing key interactions of Example 160 with human plasma kallikrein.
Figure 5:
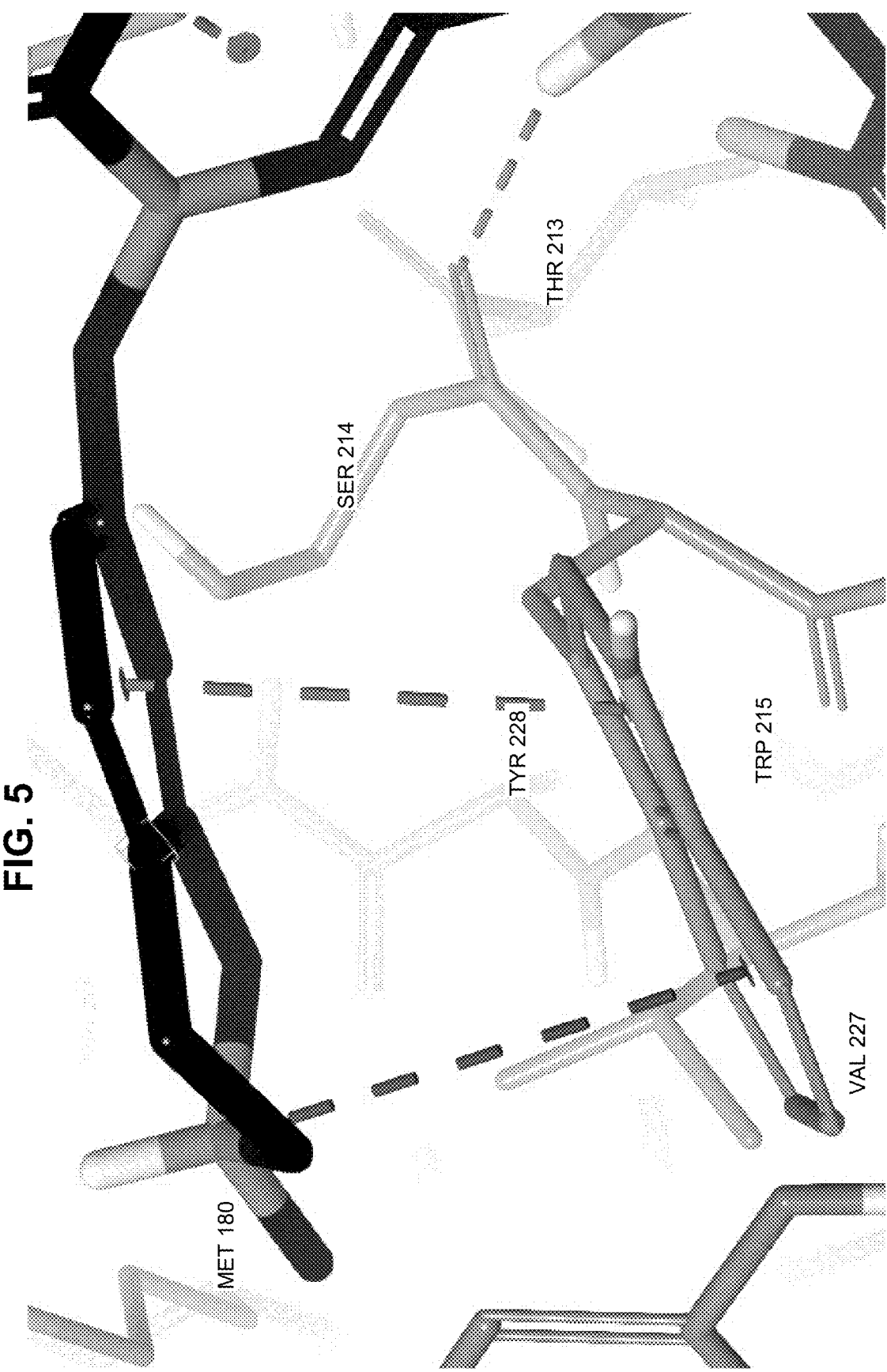
FIG. 5 is a diagram showing key interactions of Example 160 with human plasma kallikrein.
Figure 6:
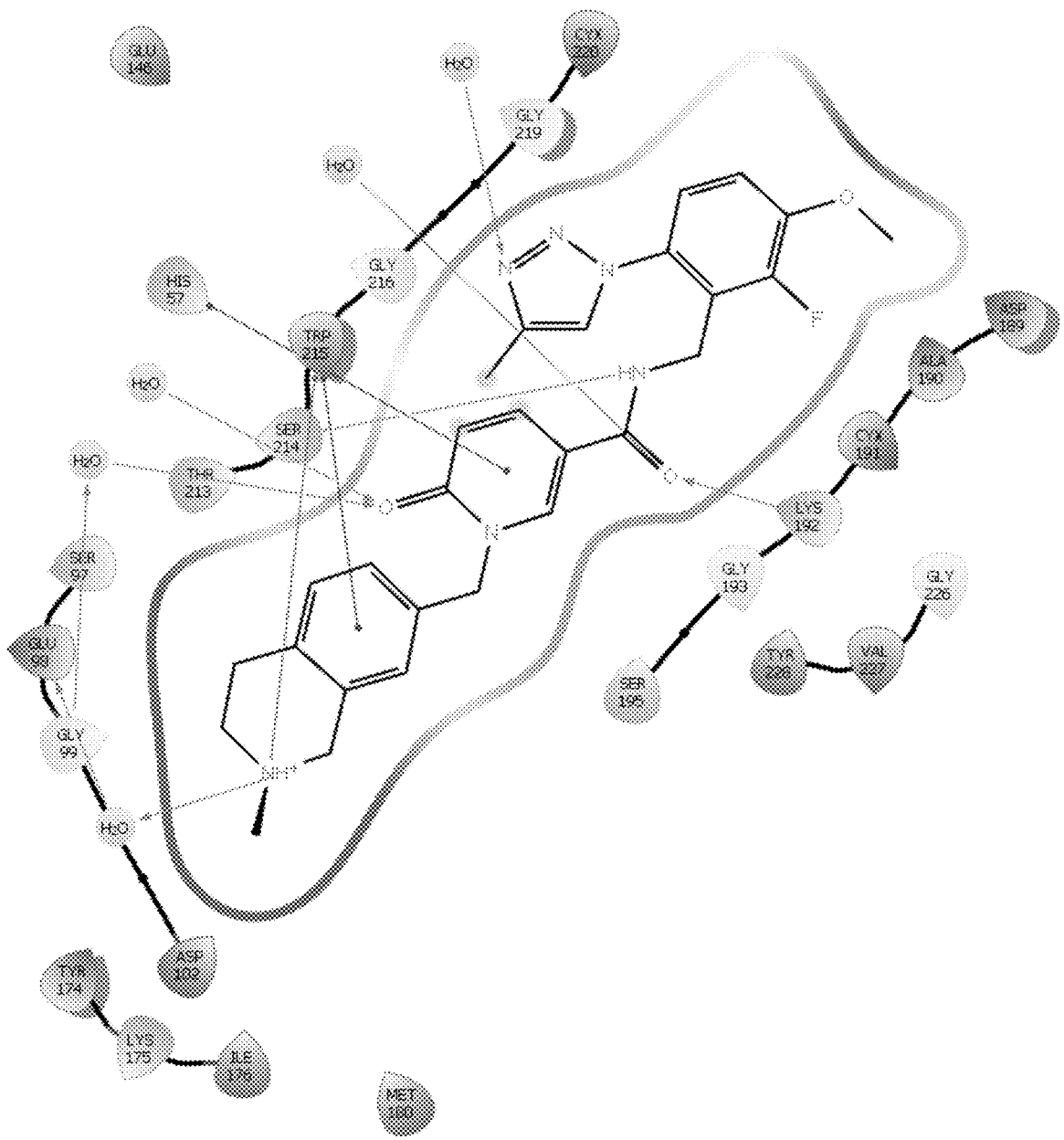
FIG. 6 is a diagram showing key interactions of Example 160 with human plasma kallikrein.
Figure 7:
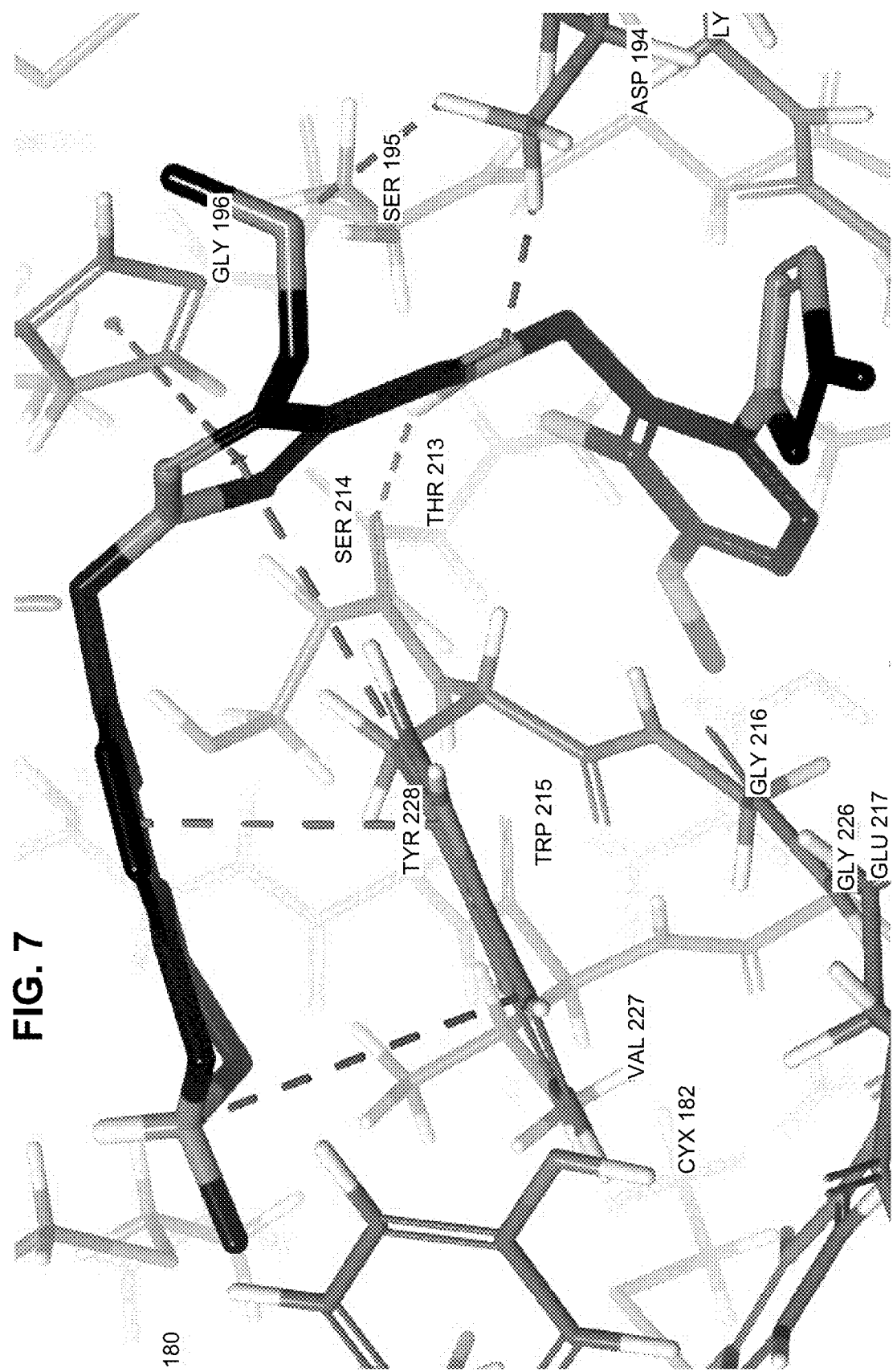
FIG. 7 is a diagram showing key interactions of Example 36 with human plasma kallikrein.
Figure 8:
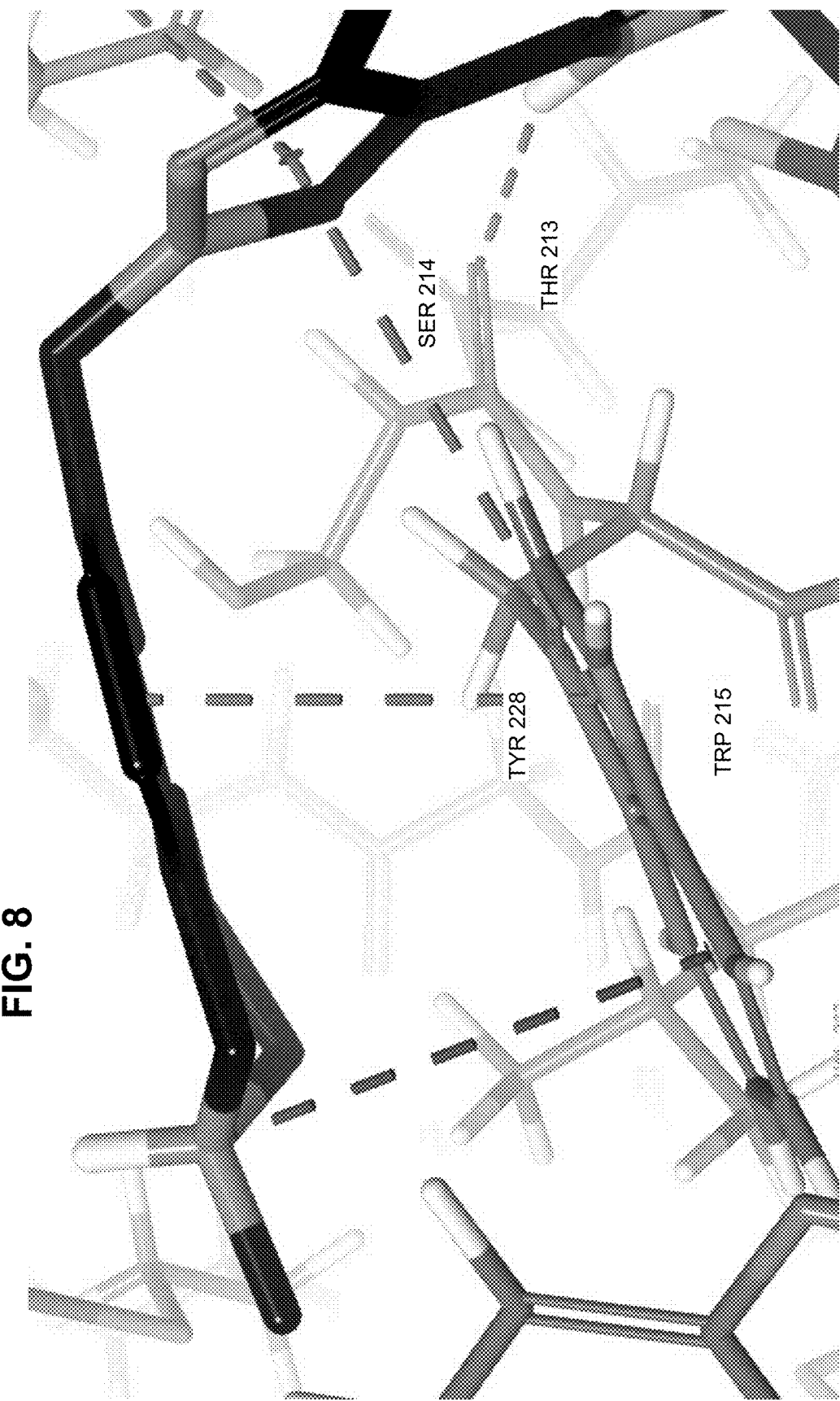
FIG. 8 is a diagram showing key interactions of Example 36 with human plasma kallikrein.
Figure 9:
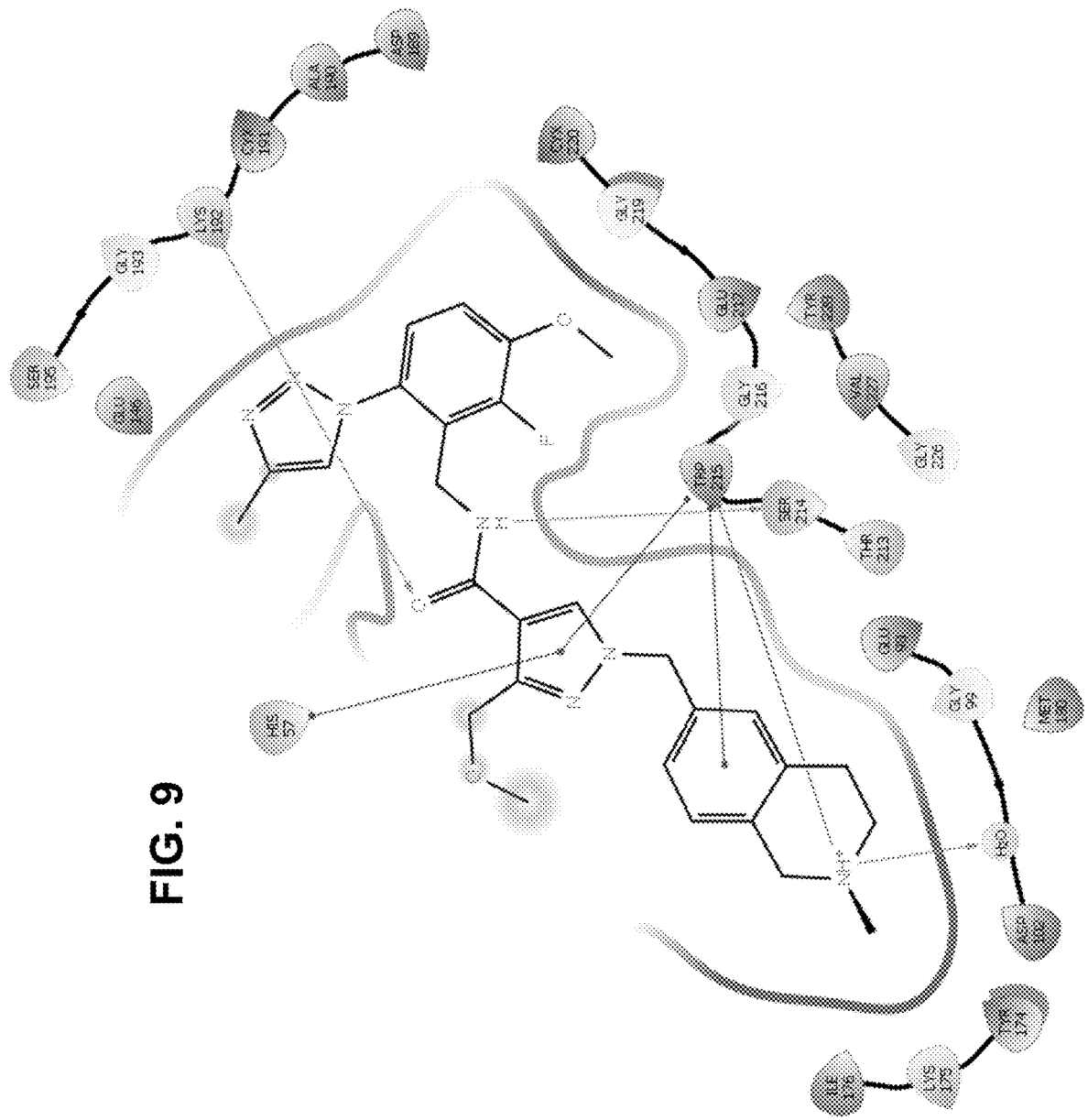
FIG. 9 is a diagram showing key interactions of Example 36 with human plasma kallikrein.
Figure 10:
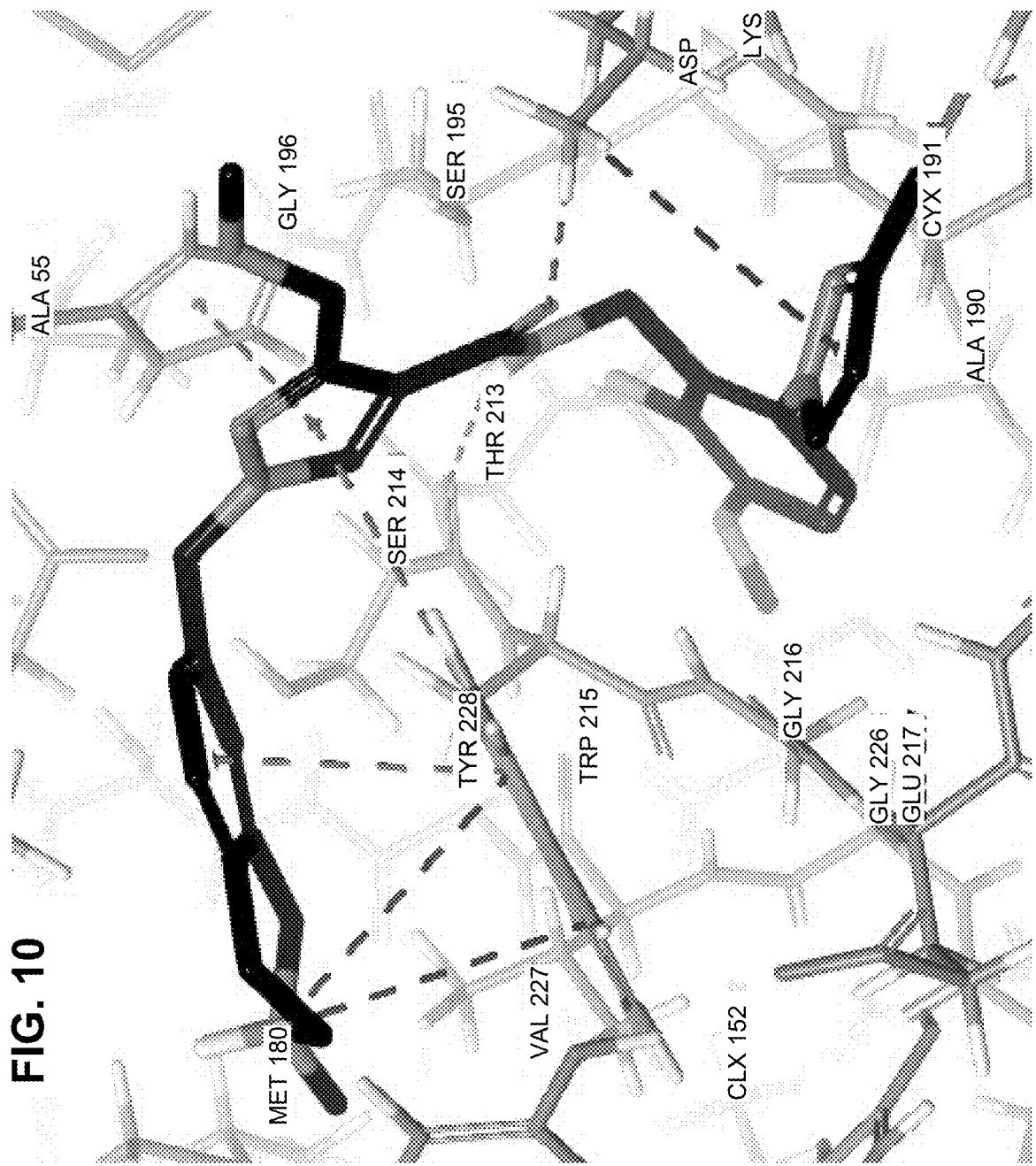
FIG. 10 is a diagram showing key interactions of Example 11 with human plasma kallikrein.
Figure 11:
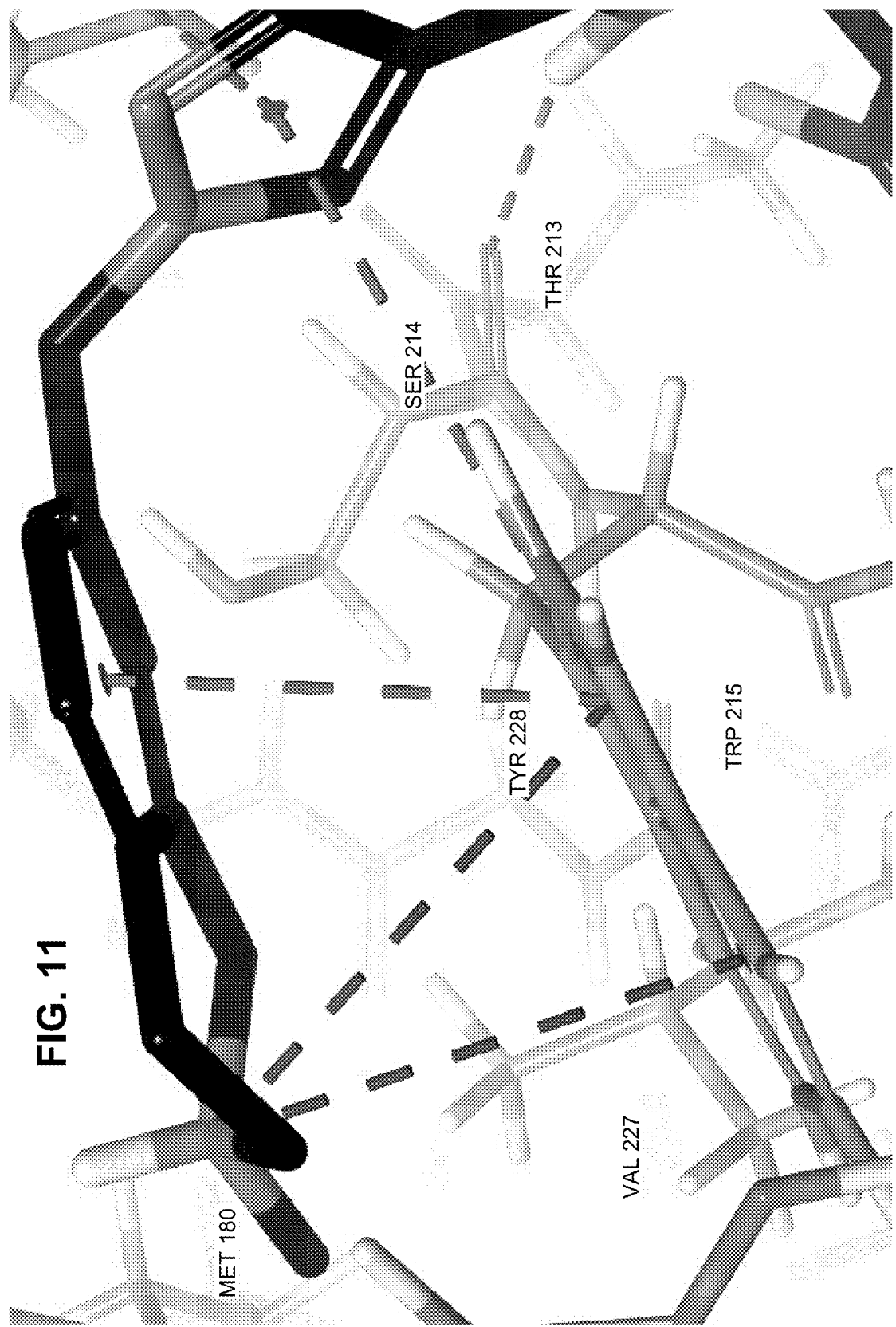
FIG. 11 is a diagram showing key interactions of Example 11 with human plasma kallikrein.
Figure 12:
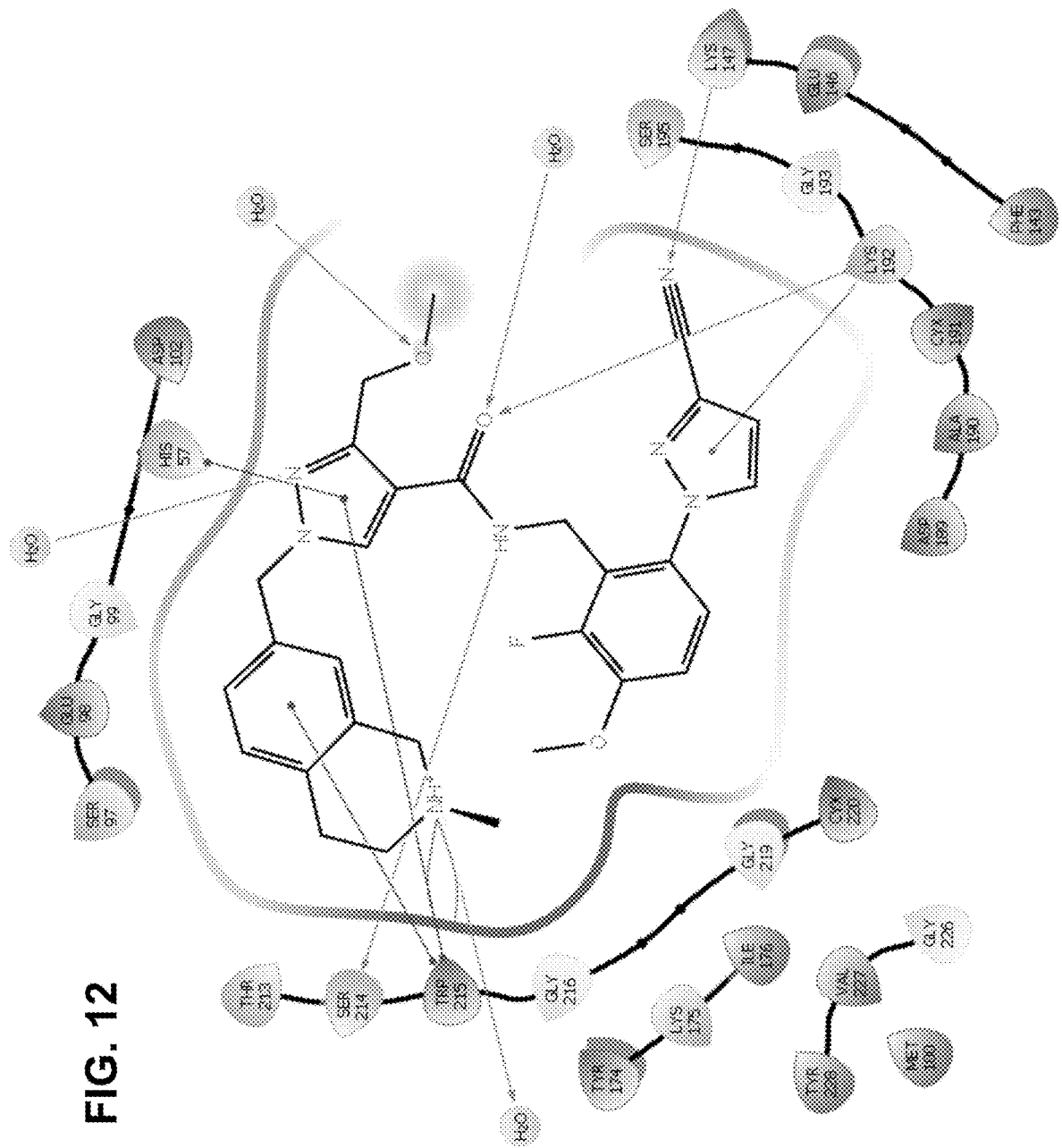
FIG. 12 is a diagram showing key interactions of Example 11 with human plasma kallikrein.
Figure 13:
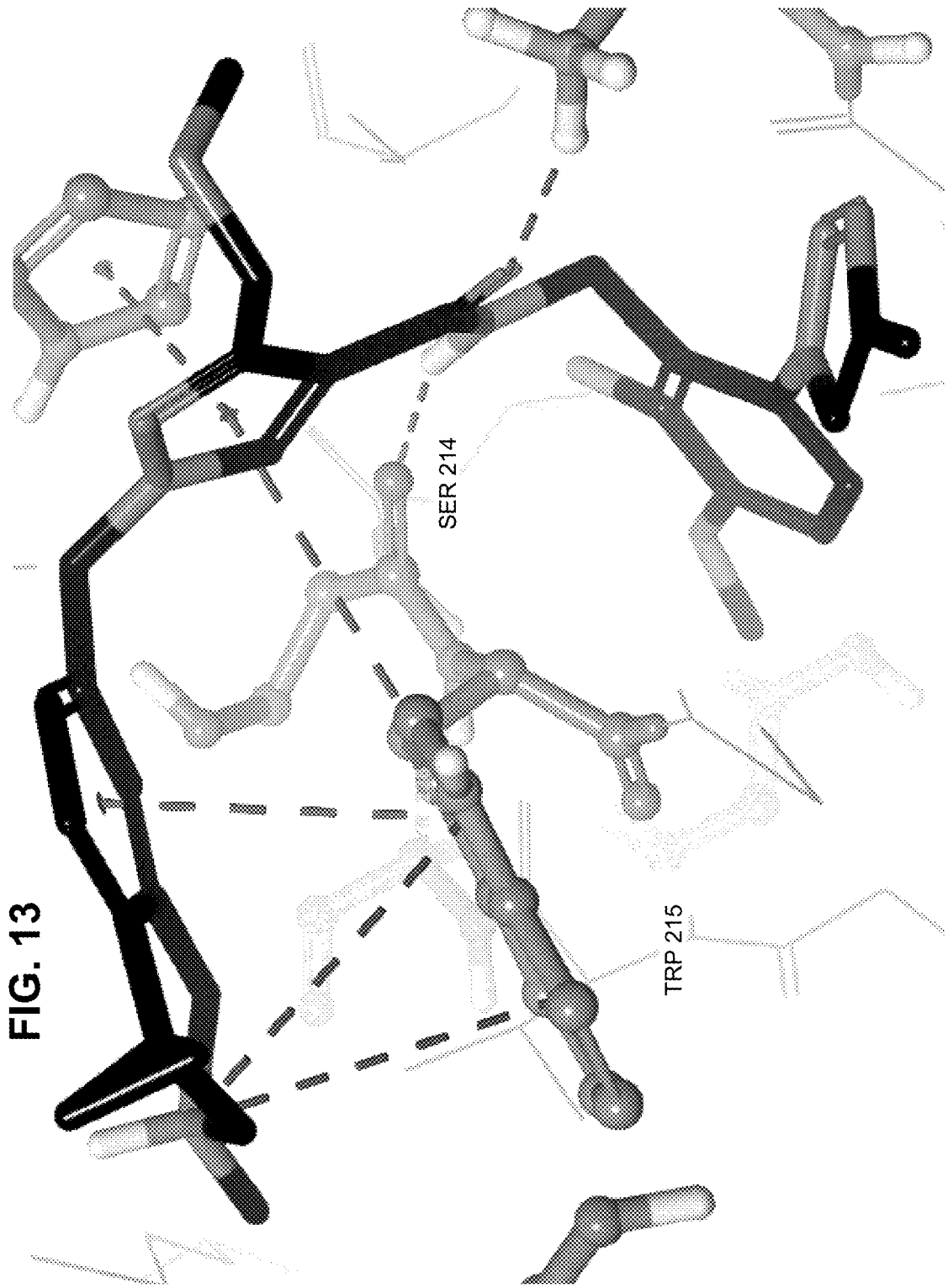
FIG. 13 is a diagram showing key interactions of Example 126 with human plasma kallikrein.
Figure 14:
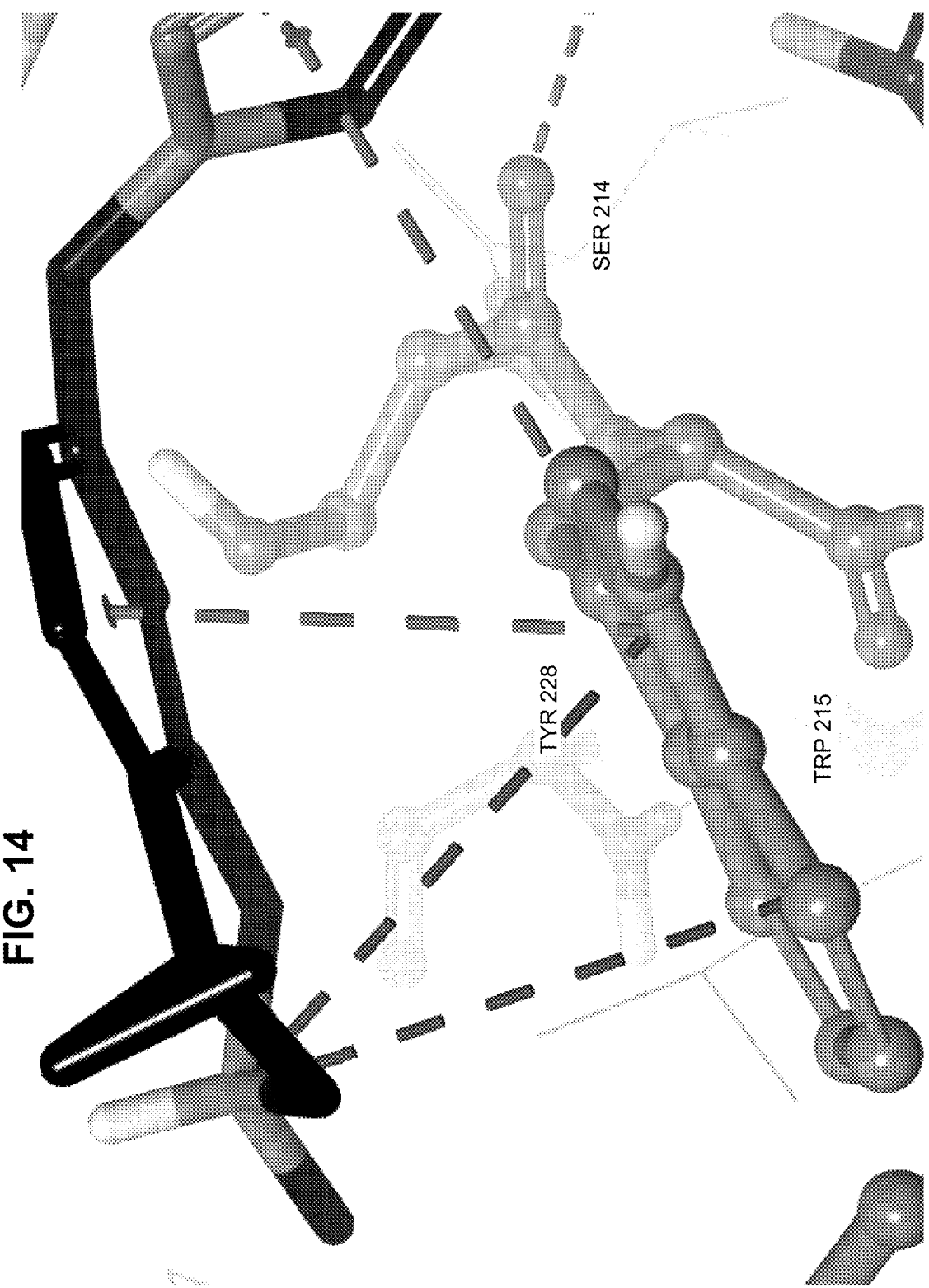
FIG. 14 is a diagram showing key interactions of Example 126 with human plasma kallikrein.
Figure 15:
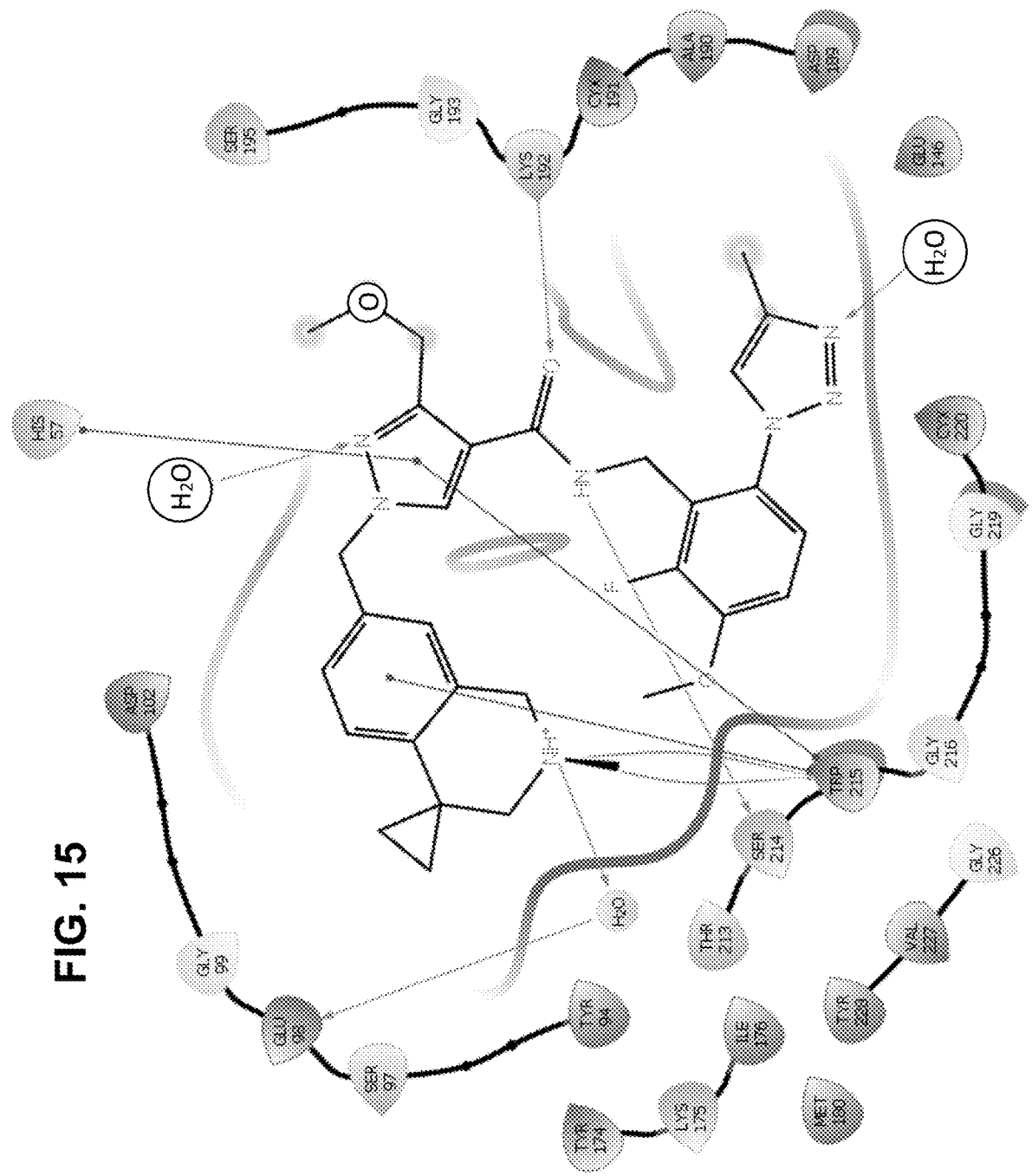
FIG. 15 is a diagram showing key interactions of Example 126 with human plasma kallikrein.
Figure 16:
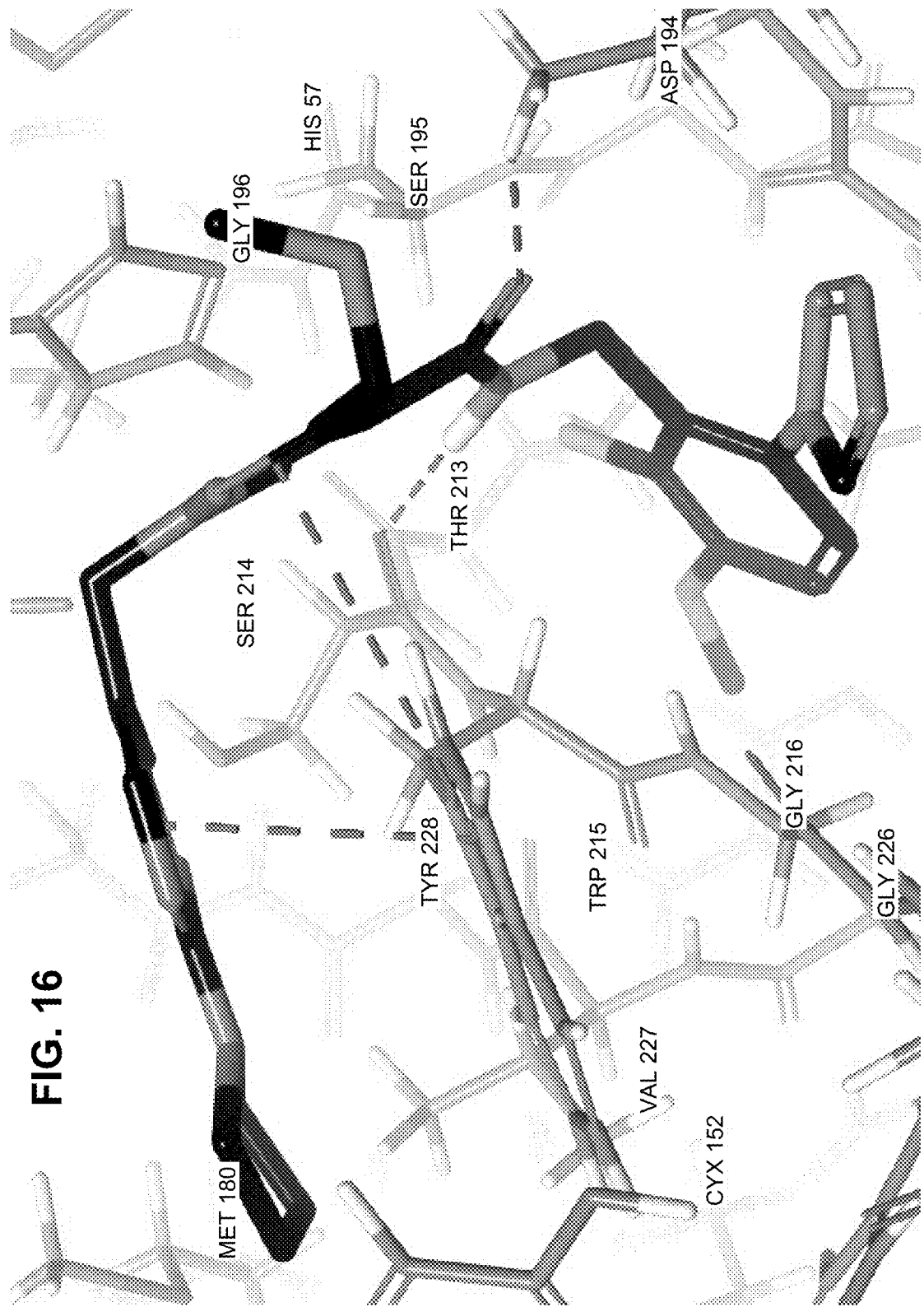
FIG. 16 is a diagram showing key interactions of RC4 with human plasma kallikrein.
Figure 17:
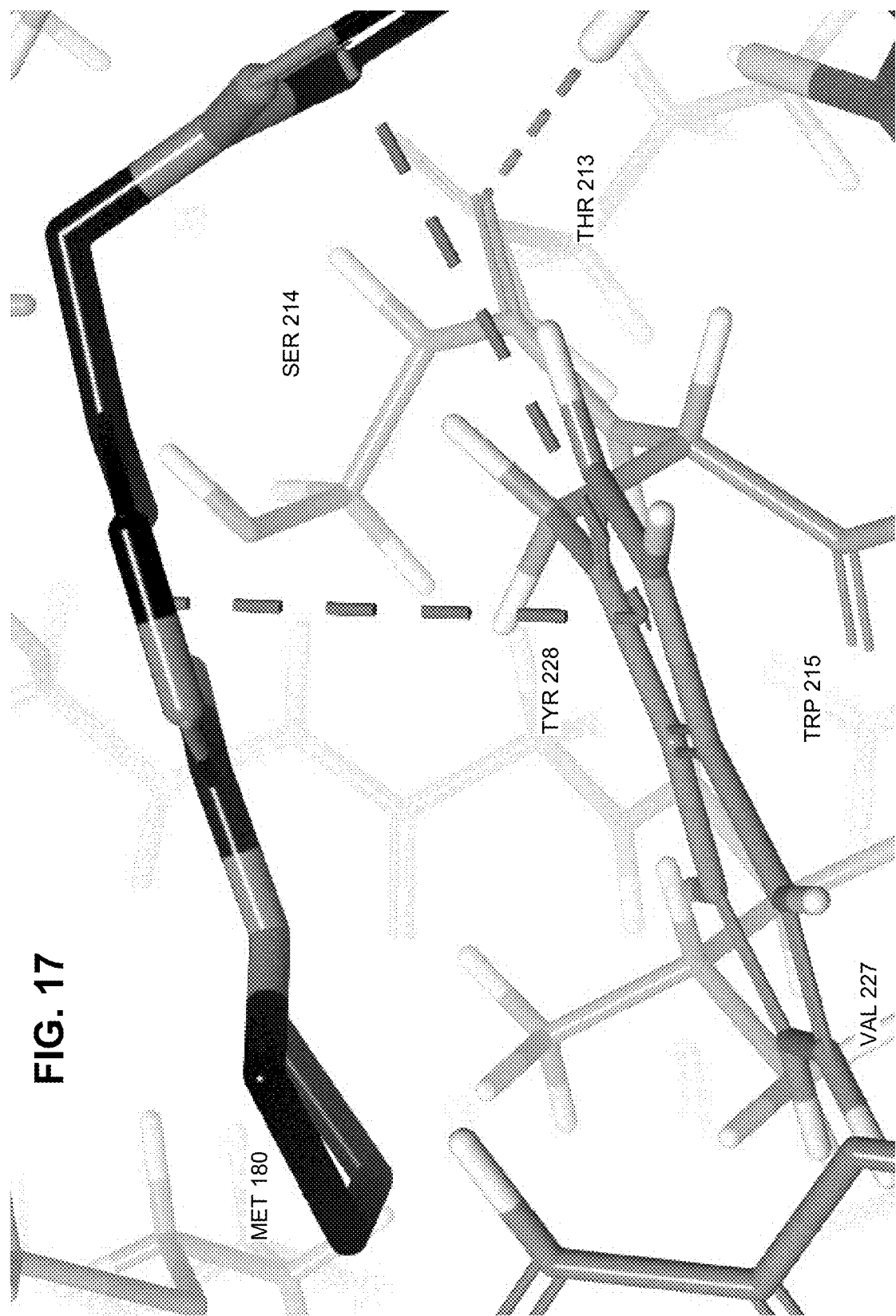
FIG. 17 is a diagram showing key interactions of RC4 with human plasma kallikrein.
Figure 18:
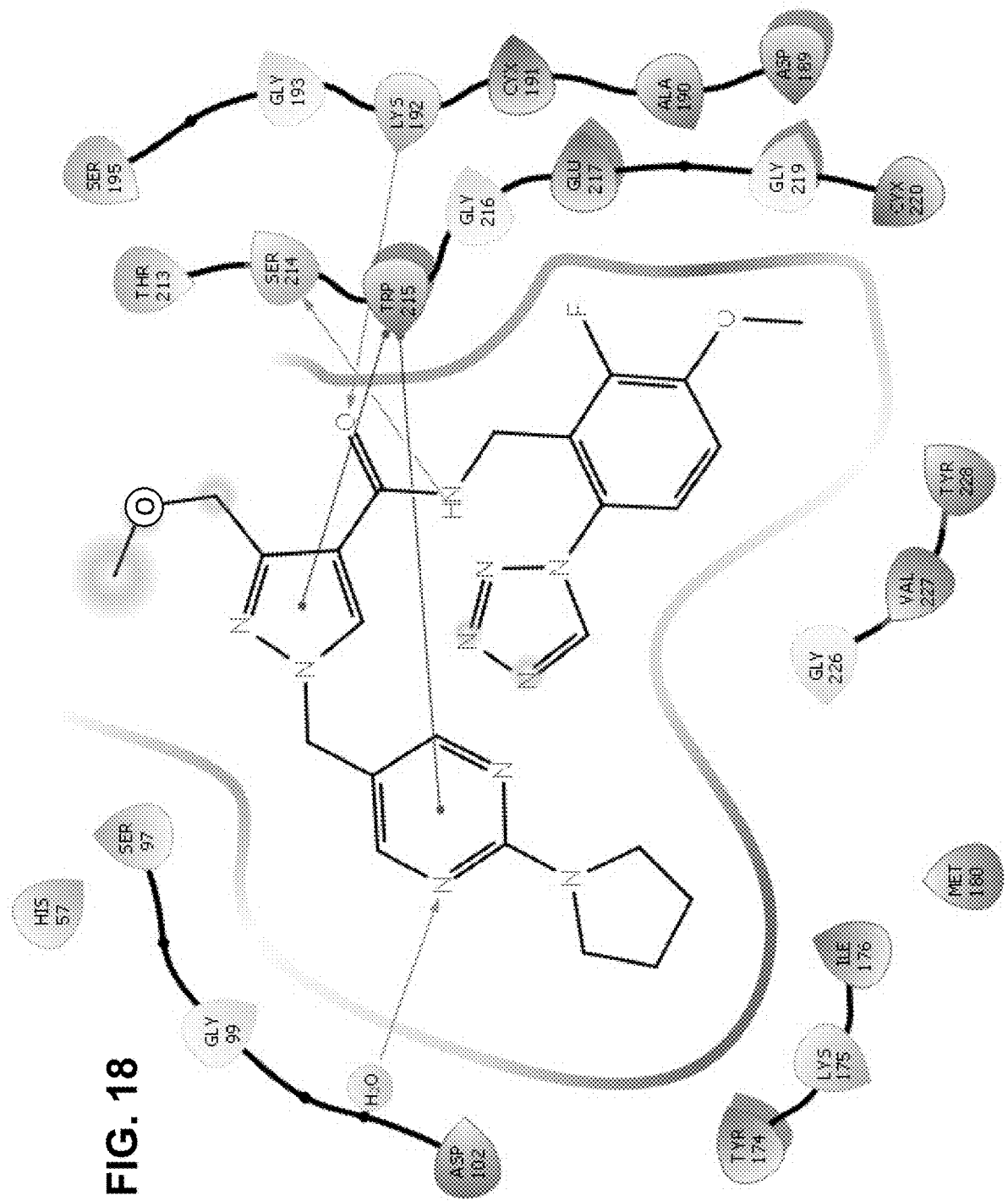
FIG. 18 is a diagram showing key interactions of RC4 with human plasma kallikrein.
Figure 19:
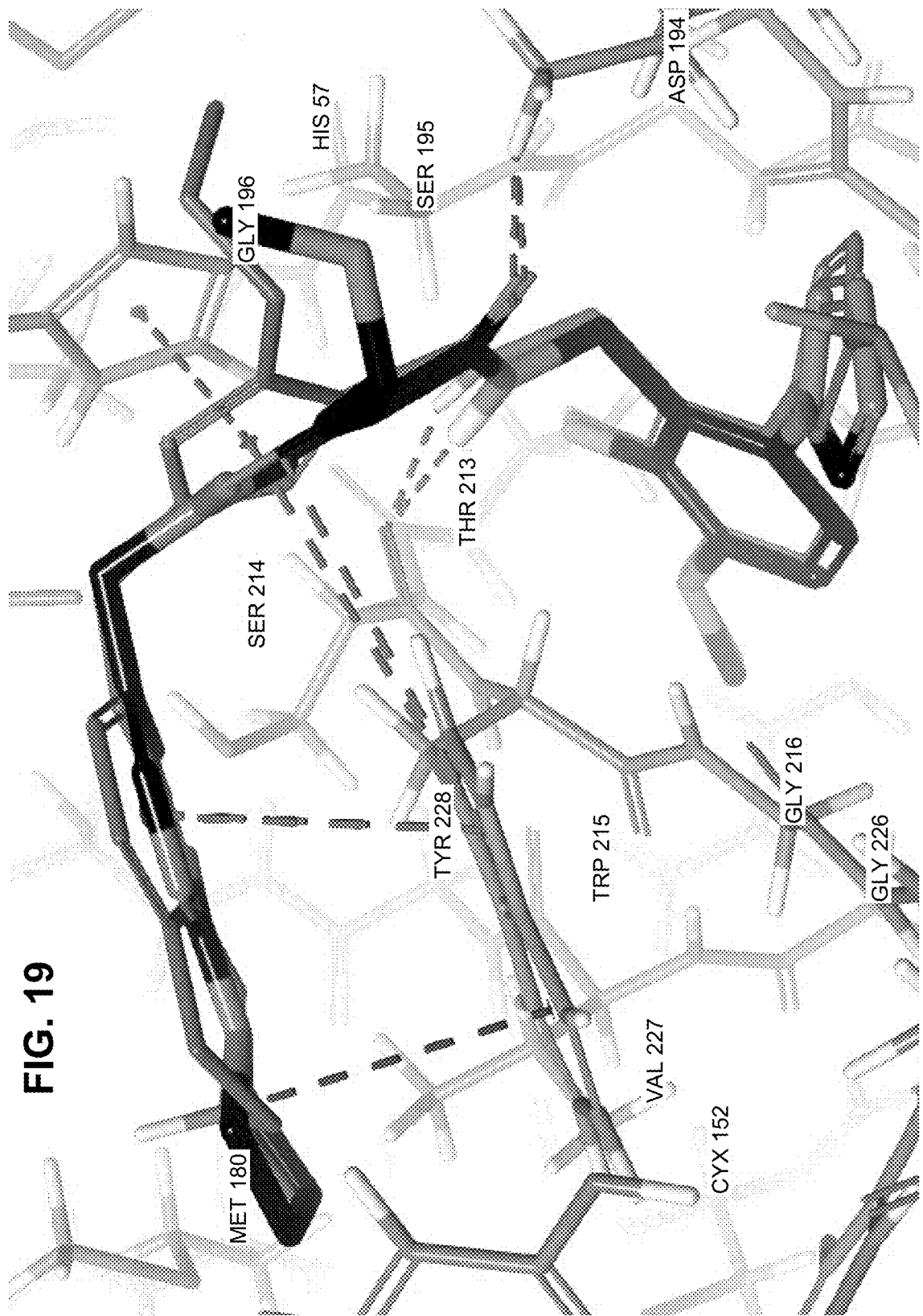
FIG. 19 is a diagram showing an overlay of the interactions of RC4 with Example 1 with plasma kallikrein.
Figure 20:
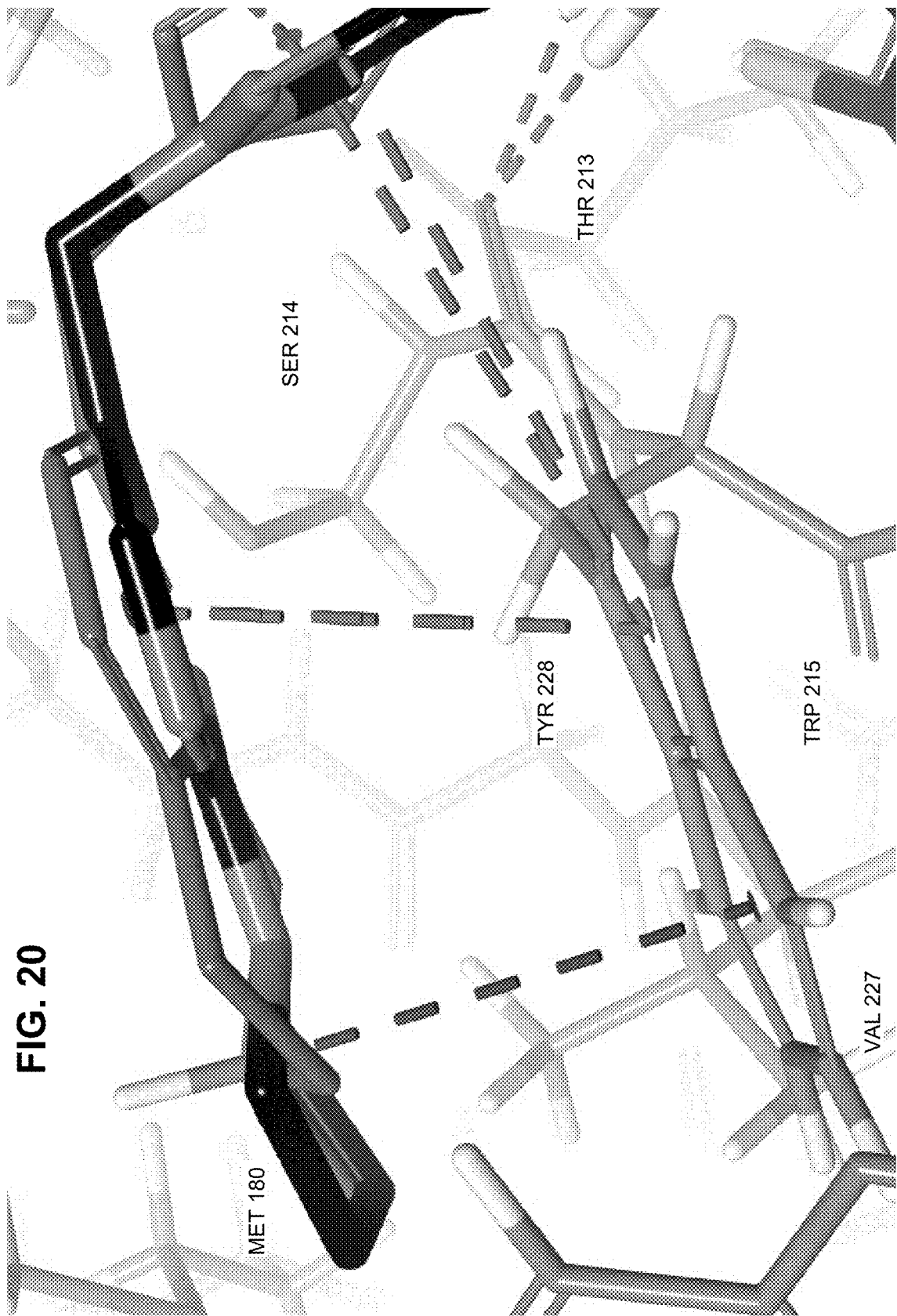
FIG. 20 is a diagram showing an overlay of the interactions of RC4 with Example 1 with plasma kallikrein.

Crystal structures were solved with molecular replacement using the structure of human plasma kallikrein bound to benzamidine (PDB code 2ANW) (Tang, Journal of Biological Chemistry, Vol. 280, no. 49, pp. 41077-41089, Dec. 9, 2005). The residues are numbered using the canonical chymotrypsin numbering system. FIGS. 1 to 20 were constructed using Maestro (Schrodinger).

FIGS. 1 to 20 show that compounds of the invention can make a series of key interactions with plasma kallikrein. In particular, compounds of the invention can make a cation Pi interaction between Trp215 and the heteroatom on A". Moreover, upon binding to plasma kallikrein, compounds of the invention can cause a shift in Trp215 to maximise the favourability of the cation Pi interaction. RC4 does not make this cation Pi interaction with Trp215. Without wishing to be bound by theory, the inventors consider that this cation Pi interaction contributes to the effects of the invention, which are inter alia, providing compounds with high potency and selectivity for inhibiting plasma kallikrein, and high solubility.

What is claimed is:

1. A compound that is:
N-({6-[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-7-yl)methyl]pyrazole-4-carboxamide;

N-{[2-fluoro-3-methoxy-6-(3-methyl-1,2,4-triazol-1-yl)phenyl]methyl}-3-(methoxymethyl)-1-[(2-methyl-3,4-dihydro-1H-isoquinolin-7-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-7-yl)methyl]pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-7-yl)methyl]pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-7-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-carboxamide;

1-[(2-ethyl-3,4-dihydro-1H-isoquinolin-7-yl)methyl]-N-({2-fluoro-3-methoxy-6-[3-(trifluoromethyl)-1,2,4-triazol-1-yl]phenyl}methyl)-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-7-yl)methyl]-3-(methoxymethyl)pyrazole-4-carboxamide;

N-{[6-(3-cyanopyrazol-1-yl)-2-fluoro-3-methoxyphenyl]methyl}-1-[(2-ethyl-3,4-dihydro-1H-isoquinolin-7-yl)methyl]-3-(methoxymethyl)pyrazole-4-arboxamide;

N-{[6-(4-cyanopyrazol-1-yl)-2-fluoro-3-methoxyphenyl]methyl}-1-[(2-isopropyl-3,4-dihydro-1H-isoquinolin-7-yl)methyl]-3-(methoxymethyl)pyrazole-4-arboxamide;

N-({6[4-(difluoromethyl)-1,2,3-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-3-(methoxymethyl)-1-[(2-methyl-3,4-dihydro-1H-isoquinolin-6-yl)methyl]pyrazole-4-carboxamide;

N-{[2-fluoro-3-methoxy-6-(4-methyl-1,2,3-triazol-1-yl)phenyl]methyl}-1-[(2-isopropyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-{[2-fluoro-3-methoxy-6-(4-methyl-1,2,3-triazol-1-yl)phenyl]methyl}-3-(methoxymethyl)pyrazole-4-carboxamide;

N-({6-[3-(difluoromethyl)-1,2,4-triazol-1-yl]-2-fluoro-3-methoxyphenyl}methyl)-3-(methoxymethyl)-1-[(2-methyl-3,4-dihydro-1H-isoquinolin-6-yl)methyl]pyrazole-4-carboxamide;

N-({2-fluoro-3-methoxy-6-[3-(trifluoromethyl)-1,2,4-triazol-1-yl]phenyl}methyl)-3-(methoxymethyl)-1-[(2-methyl-3,4-dihydro-1H-isoquinolin-6-yl)methyl]pyrazole-4-carboxamide;

N-{[6-(3-cyanopyrazol-1-yl)-2-fluoro-3-methoxyphenyl]methyl}-3-(methoxymethyl)-1-[(2-methyl-3,4-dihydro-1H-isoquinolin-6-yl)methyl]pyrazole-4-carboxamide;

N-({6-[3-(difluoromethyl)-1,2,4-triazol-1-yl]-2-fluoro-3-methoxyphenyl}methyl)-1-[(2-isopropyl-3,4-dihydro-1H-isoquinolin-6-yl)methyl]-3-(methoxymethyl)pyrazole-4-carboxamide;

N-({2-fluoro-3-methoxy-6-[3-(trifluoromethyl)-1,2,4-triazol-1-yl]phenyl}methyl)-1-[(2-isopropyl-3,4-dihydro-1H-isoquinolin-6-yl)methyl]-3-(methoxymethyl)pyrazole-4-carboxamide;

N-{[6-(3-cyanopyrazol-1-yl)-2-fluoro-3-methoxyphenyl]methyl}-1-[(2-isopropyl-3,4-dihydro-1H-isoquinolin-6-yl)methyl]-3-(methoxymethyl)pyrazole-4-carboxamide;

N-({6-[3-(difluoromethyl)-1,2,4-triazol-1-yl]-2-fluoro-3-methoxyphenyl}methyl)-1-[(2-ethyl-3,4-dihydro-1H-isoquinolin-6-yl)methyl]-3-(methoxymethyl)pyrazole-4-carboxamide;

1-[(2-ethyl-3,4-dihydro-1H-isoquinolin-6-yl)methyl]-N-({2-fluoro-3-methoxy-6-[3-(trifluoromethyl)-1,2,4-triazol-1-yl]phenyl}methl]-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-[(2-methyl-1,3-dihydroisoindol-5-yl)methyl]pyrazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-3-(methoxymethyl)pyrazol e-4-carboxamide;

1-[(6-fluoro-2-methyl-3,4-dihydro-1H-isoquinolin-7-yl)methyl]-N-{[2-fluoro-3-methoxy-6-[4-methyl-1,2,3-triazol-1-yl]phenyl]methyl}-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{[2-($^{2}H_3$)methyl-3,4-dihydro-1H-isoquinolin-7-yl]methyl}pyrazole-4-carboxamide;

N-{[2-fluoro-3-methoxy-6-(4-methyl-1,2,3-triazol-1-yl)phenyl]methyl}-1-[(3-isopropyl-1,2,4,5-tetrahydro-3-benzazepin-7-yl)methyl]-3-(methoxymethyl)pyrazole-4-carboxamide;

N-{[2-fluoro-3-methoxy-6-(4-methyl-1,2,3-triazol-1-yl)phenyl]methyl}-3-(methoxymethyl)-1-{2'-methyl-1',3'-dihydrospiro[cyclopropane-1,4'-isoquinoline]-7'-ylmethyl}pyrazole-4-carboxamide;

1-{2',3'-dihydro-1'H-spiro[cyclopropane-1,4'-isoquinoline]-7'-ylmethyl}-N-{[2-fluoro-3-methoxy-6-(4-methyl-1,2,3-triazol-1-yl)phenyl]methyl}-3-(methoxymethyl)pyrazole-4-carboxamide;

3-(difluoromethyl)-N-{[2-fluoro-3-methoxy-6-(4-methyl-1,2,3-triazol-1-yl)phenyl]methyl}-1-({5-methyl-4H,6H,7H-pyrazolo[1,5-a]pyrazin-2-yl}methyl)pyrazole-4-carboxamide;

3-(difluoromethyl)-N-{[2-fluoro-3-methoxy-6-(4-methyl-1,2,3-triazol-1-yl)phenyl]methyl}-1-(7-methyl-6,8-dihydro-5H-1,7-naphthyridin-3-yl}methyl)pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-1,2,3-triazole-4-carboxamide;

N-{[2-fluoro-3-methoxy-6-(4-methyl-1,2,3-triazol-1-yl)phenyl]methyl}-1-[(2-isopropyl-1,3-dihydroisoindol-5-yl)methyl]-1,2,3-triazole-4-carboxamide;

N-({2-chloro-6-[3-(difluoromethyl)-1,2,4-triazol-1-yl]-3-methoxyphenyl} methyl)-3-(methoxymethyl)-1-[(2-methyl-3,4-dihydro-1H-isoquinolin-7-yl)methyl]pyrazole-4-carboxamide;

N-{[2-fluoro-3-methoxy-6-(4-methyl-1,2,3-triazol-1-yl)phenyl]methyl}-1-[(2-methyl-3,4-dihydro-1H-isoquinolin-7-yl)methyl]-6-oxopyridine-3-carboxamide; or N-{[2-fluoro-3-methoxy-6-(4-methyl-1,2,3-triazol-1-yl)phenyl]methyl}-5-[(2-methyl-3,4-dihydro-1H-isoquinolin-7-yl)methyl]pyridine-3-carboxamide;

or a pharmaceutically acceptable salt or solvate thereof.

2. A compound of formula (I),

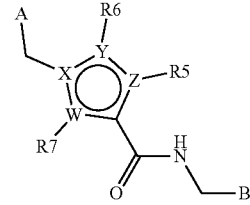

Formula (I)

wherein:
W, X, Y and Z are independently selected from C, C(R16)-C, C(R16)=C, C=N, O or N, such that the ring containing W, X, Y and Z forms pyrazolyl, imidazolyl, 1,2,3-triazolyl, pyridinyl, or 1,3-oxazolyl;

R5, R6, and R7 are independently absent or independently selected from H, alkyl, cycloalkyl, alkoxy, halo, OH, CN, CF$_3$, aryl, heteroaryl$^a$, N-linked pyrrolidinyl, N-linked piperidinyl, N-linked morpholinyl, N-linked piperazinyl, —NR13R14, —COOR13, —CONR13R14, or —NR13COR14;

R16 is independently selected from H, alkyl, cycloalkyl, alkoxy, halo, OH, CN, CF$_3$, aryl, heteroaryl$^a$, N-linked pyrrolidinyl, N-linked piperidinyl, N-linked morpholinyl, N-linked piperazinyl, —NR13R14, —COOR13, —CONR13R14, or —NR13COR14; or W, X, Y and Z are independently selected from C, C(R16)-C, C(R16)=C, C=N or N, and one of R5, R6, R7 or R16 is oxo such that the ring containing W, X, Y and Z is 2 pyridonyl or 4-pyridonyl;

wherein the others of R5, R6, R7 and R16 are independently absent or independently selected from H, alkyl, cycloalkyl, alkoxy, halo, OH, CN, CF$_3$, aryl heteroaryl$^a$, N-linked pyrrolidinyl, N-linked piperidinyl, N-linked morpholinyl, N-linked piperazinyl, —NR13R14, —COOR13, —CONR13R14, or —NR13COR14;

B is of Formula (II) comprising aromatic rings B' and B" that are linked by a bond:

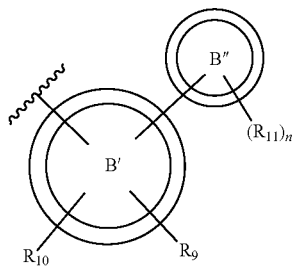

Formula (II)

B' is phenyl or pyridyl;
B" is pyrrolyl, pyrazolyl, triazolyl, or tetrazolyl;
n is 0, 1, or 2;
$R_9$ and $R_{10}$ are independently selected from H, alkyl, cycloalkyl, alkoxy, halo, OH, CN, or $CF_3$,
each $R_{11}$ is independently selected from alkyl, cycloalkyl, alkoxy, halo, OH, —COOR13, —CONR13NR14, CN, or $CF_3$;
A is a heterocyclic ring of Formula (III) comprising an aromatic ring (A') fused to a non-aromatic ring (A"):

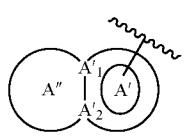

Formula (III)

A'1 and A'2 are independently C or N;
A' is heteroaryl or phenyl, wherein phenyl is optionally substituted with 1, 2, or 3 substituents independently selected from alkyl, alkoxy, OH, $OCF_3$, halo, CN, or $CF_3$, and wherein heteroaryl is optionally substituted as stated below;
A" is heterocycloalkyl;
optionally wherein a carbon ring atom on A" is substituted with an alkylene or a heteroalkylene such that the carbon ring atom on A" together with the alkylene or the heteroalkylene forms a cycloalkyl or heterocycloalkyl$^a$ that is spiro to ring A"; and/or optionally wherein two ring atoms on A" are linked by an alkylene or heteroalkylene to form a non-aromatic ring containing 5, 6, or 7 ring members;
alkyl is a linear saturated hydrocarbon having up to 10 carbon atoms ($C_1$-$C_{10}$) or a branched saturated hydrocarbon of between 3 and 10 carbon atoms ($C_3$-$C_{10}$); alkyl is optionally substituted with 1 or 2 substituents independently selected from ($C_1$-$C_6$)alkoxy, OH, —NR13R14, —COOR13, —CONR13R14, CN, $CF_3$, halo;
alkyl$^b$ is a linear saturated hydrocarbon having up to 10 carbon atoms ($C_1$-$C_{10}$) or a branched saturated hydrocarbon of between 3 and 10 carbon atoms ($C_3$-$C_{10}$); alkyl$^b$ is optionally substituted with 1 or 2 substituents independently selected from ($C_1$-$C_6$)alkoxy, OH, CN, $CF_3$, or halo;
alkylene is a bivalent linear saturated hydrocarbon having 1 to 5 carbon atoms ($C_1$-$C_5$); alkylene is optionally substituted with 1 or 2 substituents independently selected from alkyl, ($C_1$-$C_6$)alkoxy, OH, CN, $CF_3$, or halo;
aryl is phenyl, biphenyl or naphthyl; aryl is optionally substituted with 1, 2 or 3 substituents independently selected from alkyl, alkoxy, methylenedioxy, ethylenedioxy, OH, halo, CN, heteroaryl$^a$, —(CH$_2$)$_{0-3}$—O-heteroaryl$^a$, aryl$^b$, —O-aryl$^b$, —(CH$_2$)$_{1-3}$-aryl$^b$, —(CH$_2$)$_{1-3}$-heteroaryl$^a$, —COOR13, —CONR13R14, —(CH$_2$)$_{0-3}$—NR13R14, $OCF_3$ and $CF_3$;
aryl$^b$ is phenyl, biphenyl or naphthyl; aryl$^b$ is optionally substituted with 1, 2 or 3 substituents independently selected from alkyl$^b$, alkoxy, OH, halo, CN, or $CF_3$;
heteroalkylene is a bivalent linear saturated hydrocarbon having 2 to 5 carbon atoms ($C_2$-$C_5$), wherein at least one of the 2 to 5 carbon atoms is replaced with NR8, S, or O;
heteroalkylene is optionally substituted with 1 or 2 substituents independently selected from alkyl ($C_1$-$C_6$) alkoxy, OH, CN, $CF_3$, or halo;
cycloalkyl is a monocyclic saturated hydrocarbon ring of between 3 and 6 carbon atoms ($C_3$-$C_6$); cycloalkyl is optionally substituted with 1 or 2 substituents independently selected from alkyl, ($C_1$-$C_6$)alkoxy, OH, CN, $CF_3$, or halo;
alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy is optionally substituted with 1 or 2 substituents independently selected from OH, CN $CF_3$, or fluoro;
halo is F, Cl, Br, or I;
heteroaryl is a 5- or 6-membered carbon-containing aromatic ring containing one, two or three ring members that are selected from N, NR8, S, or O; heteroaryl is optionally substituted with 1, 2 or 3 substituents independently selected from alkyl, alkoxy, OH, $OCF_3$, halo, CN, or $CF_3$;
heteroaryl$^a$ is a 5, 6, 9 or 10 membered mono- or bi-cyclic aromatic ring, containing, where possible, 1, 2, 3 or 4 ring members independently selected from N, NR12, S or O; heteroaryl$^a$ is optionally substituted with 1, 2 or 3 substituents independently selected from alkyl, alkoxy, OH, $OCF_3$, halo, CN, aryl$^b$, —(CH$_2$)$_{0-3}$—NR13R14, heteroaryl$^b$, —COOR13, —CONR13R14 or $CF_3$;
heteroaryl$^b$ is a 5, 6, 9 or 10 membered mono- or bi-cyclic aromatic ring, containing, where possible, 1, 2 or 3 ring members independently selected from N, NR12, S or O; wherein heteroaryl$^b$ is optionally substituted with 1, 2 or 3 substituents independently selected from alkyl$^b$, alkoxy, OH, halo, CN, aryl$^b$, —(CH$_2$)$_{1-3}$-aryl$^b$, or $CF_3$;
heterocycloalkyl is a non-aromatic carbon-containing monocyclic ring containing 5, 6, or 7 ring members, wherein one or two ring members are independently selected from N, NR8, S, SO, $SO_2$, or O; wherein heterocycloalkyl is optionally substituted with 1, 2, or 3 substituents independently selected from alkyl, alkoxy, OH, $OCF_3$, halo, oxo or CN;
heterocycloalkyl$^a$ is a non-aromatic carbon-containing monocyclic ring containing 3, 4, 5, or 6, ring members, wherein at least one ring member is independently selected from NR8, S, SO, $SO_2$, or O; heterocycloalkyl$^a$ is optionally substituted with 1 or 2 substituents independently selected from alkyl (C1-C6)alkoxy, OH, CN, $CF_3$, or halo;
R8 is independently selected from H, alkyl, cycloalkyl, or heterocycloalkyl$^b$; heterocycloalkyl$^b$ is a non-aromatic carbon-containing monocyclic ring containing 3, 4, 5, or 6, ring members, wherein at least one ring member is independently selected from N, NR12, S, or O; heterocycloalkyl$^b$ is optionally substituted with 1 or 2 substituents independently selected from alkyl, (C$_1$-C$_6$) alkoxy, OH, CN, CF$_3$, or halo;

R12 is independently selected from H, alkyl$^b$ or cycloalkyl;

R13 and R14 are independently selected from H, alkyl$^b$, aryl$^b$ or heteroaryl$^b$ or R13 and R14 together with the nitrogen atom to which they are attached form a carbon-containing 4-, 5-, 6- or 7-membered heterocyclic ring, optionally containing an additional heteroatom selected from N, NR12, S, SO, SO$_2$, or O, which is optionally saturated or unsaturated with 1 or 2 double bonds and which is optionally mono- or di-substituted with substituents selected from oxo, alkyl$^b$, alkoxy, OH, halo or CF$_3$;

or a tautomer, stereoisomer, deuterated isotope, or pharmaceutically acceptable salt and/or solvate thereof.

3. The compound of formula (I) according to claim 2, or a tautomer, stereoisomer, a deuterated isotope, or a pharmaceutically acceptable salt and/or solvate thereof,
wherein W, X, Y and Z are independently selected from C, C(R16)-C, C(R16)=C, C=N or N, such that the ring containing W, X, Y and Z is pyrazolyl, imidazolyl, 1,2,3-triazolyl, or pyridinyl W, X, Y and Z are independently selected from C, C(R16)-C, C(R16)=C, C=N or N, and one of R5, R6, R7 or R16 is oxo such that the ring containing W, X, Y and Z is 2 pyridonyl or 4-pyridonyl;

wherein the others of R5, R6, R7 and R 16 are independently absent or independently selected from H, alkyl, cycloalkyl, alkoxy, halo, OH, CN, CF$_3$, aryl, heteroaryl$^a$, N-linked pyrrolidinyl, N-linked piperidinyl, N-linked morpholinyl, N-linked piperazinyl, —NR13R14, —COOR13, —CONR13R14, or —NR13COR14.

4. The compound of formula (I) according to claim 2, or a tautomer, stereoisomer, a deuterated isotope, or a pharmaceutically acceptable salt and/or solvate thereof,
wherein W, X, Y and Z are, independently, selected from C, C(R16)-C, C(R16)=C, C=N or N, such that the ring containing W, X, Y and Z is pyrazolyl, imidazolyl, 1,2,3-triazolyl, or pyridinyl;

R5, R6, and R7 are independently absent or independently selected from H, alkyl, cycloalkyl, alkoxy, halo, OH, CN, or CF$_3$;

R16 is independently selected from H, alkyl, cycloalkyl, alkoxy, halo, OH, CN, or CF$_3$; or W, X, Y and Z are independently selected from C, C(R16)-C, C(R16)=C, C=N or N, and one of R5, R6, R7 or R16 is oxo such that the ring containing W, X, Y and Z is 2 pyridonyl or 4-pyridonyl;

wherein the others of R5, R6, R7 and R16 are independently absent or independently selected from H, alkyl, cycloalkyl, alkoxy, halo, OH, CN, or CF$_3$.

5. The compound of formula (I) according to claim 2, or a tautomer, stereoisomer, a deuterated isotope, or a pharmaceutically acceptable salt and/or solvate thereof, wherein W, X, Y and Z are independently selected from C, C(R16)-C, C(R16)=C, C=N or N, such that the ring containing W, X, Y and Z is pyrazolyl, imidazolyl, 1,2,3-triazolyl, or pyridinyl.

6. The compound of formula (I) according to claim 2, or a tautomer, stereoisomer, a deuterated isotope, or a pharmaceutically acceptable salt and/or solvate thereof, wherein W, X, Y and Z are independently selected from C or N, such that the ring containing W, X, Y and Z is pyrazolyl, imidazolyl, or 1,2,3-triazolyl.

7. The compound of formula (I) according to claim 2, or a tautomer, stereoisomer, a deuterated isotope, or a pharmaceutically acceptable salt and/or solvate thereof, wherein W, X, Y and Z are independently selected from C or N, such that the ring containing W, X, Y and Z is pyrazolyl.

8. The compound of formula (I) according to claim 2, or a tautomer, stereoisomer, a deuterated isotope, or a pharmaceutically acceptable salt and/or solvate thereof, wherein at least one of R5, R6, or R7 is present and is not H.

9. The compound of formula (I) according to claim 2, or a tautomer, stereoisomer, a deuterated isotope, or a pharmaceutically acceptable salt and/or solvate thereof, wherein R7 is H.

10. The compound of formula (I) according to claim 2, or a tautomer, stereoisomer, a deuterated isotope, or a pharmaceutically acceptable salt and/or solvate thereof, wherein one of R5 or R6 is absent and one of R5 or R6 is alkyl substituted with alkoxy, which is optionally substituted.

11. The compound of formula (I) according to claim 10, or a tautomer, stereoisomer, a deuterated isotope, or a pharmaceutically acceptable salt and/or solvate thereof, wherein one of R5 or R6 is absent and one of R5 or R6 is —CH$_2$OMe.

12. The compound of formula (I) according to claim 2, or a tautomer, stereoisomer, a deuterated isotope, or a pharmaceutically acceptable salt and/or solvate thereof, wherein B' is phenyl, which is optionally substituted.

13. The compound of formula (I) according to claim 2, or a tautomer, stereoisomer, a deuterated isotope, or a pharmaceutically acceptable salt and/or solvate thereof, wherein R$_9$ is halo and R$_{10}$ is alkoxy.

14. The compound of formula (I) according to claim 13, or a tautomer, stereoisomer, a deuterated isotope, or a pharmaceutically acceptable salt and/or solvate thereof, wherein R$_9$ is F and R$_{10}$ is —OMe.

15. The compound of formula (I) according to claim 2, or a tautomer, stereoisomer, a deuterated isotope, or a pharmaceutically acceptable salt and/or solvate thereof, wherein B" is pyrrolyl, pyrazolyl, or triazolyl.

16. The compound of formula (I) according to claim 15, or a tautomer, stereoisomer, a deuterated isotope, or a pharmaceutically acceptable salt and/or solvate thereof, wherein B" is pyrazolyl or triazolyl.

17. The compound of formula (I) according to claim 16, or a tautomer, stereoisomer, a deuterated isotope, or a pharmaceutically acceptable salt and/or solvate thereof, wherein B" is pyrazolyl, which is optionally substituted.

18. The compound of formula (I) according to claim 16, or a tautomer, stereoisomer, a deuterated isotope, or a pharmaceutically acceptable salt and/or solvate thereof, wherein B" is 1,2,3-triazolyl, which is optionally substituted.

19. The compound of formula (I) according to claim 16, or a tautomer, stereoisomer, a deuterated isotope, or a pharmaceutically acceptable salt and/or solvate thereof, wherein B" is 1,2,4-triazolyl, which is optionally substituted.

20. The compound of formula (I) according to claim 2, or a tautomer, stereoisomer, a deuterated isotope, or a pharmaceutically acceptable salt and/or solvate thereof, wherein n is 1, and R11 is selected from alkyl, cyclopropyl, CN, or CF$_3$.

21. The compound of formula (I) according to claim 2, or a tautomer, stereoisomer, a deuterated isotope, or a pharmaceutically acceptable salt and/or solvate thereof, wherein A' is phenyl, which is optionally substituted.

22. The compound of formula (I) according to claim 2, or a tautomer, stereoisomer, a deuterated isotope, or a pharmaceutically acceptable salt and/or solvate thereof, wherein A' is heteroaryl, which is optionally substituted.

23. The compound of formula (I) according to claim 22, or a tautomer, stereoisomer, a deuterated isotope, or a pharmaceutically acceptable salt and/or solvate thereof, wherein A' is a 5-membered heteroaryl, which is optionally substituted.

24. The compound of formula (I) according to claim 23 or a tautomer, stereoisomer, a deuterated isotope, or a pharmaceutically acceptable salt and/or solvate thereof, wherein A' is selected from pyrrolyl or imidazolyl, which is optionally substituted.

25. The compound of formula (I) according to claim 22, or a tautomer, stereoisomer, a deuterated isotope, or a pharmaceutically acceptable salt and/or solvate thereof, wherein A' is a 6-membered heteroaryl, which is optionally substituted.

26. The compound of formula (I) according to claim 25, or a tautomer, stereoisomer, a deuterated isotope, or a pharmaceutically acceptable salt and/or solvate thereof, wherein A' is pyridinyl, which is optionally substituted.

27. The compound of formula (I) according to claim 2, or a tautomer, stereoisomer, a deuterated isotope, or a pharmaceutically acceptable salt and/or solvate thereof, wherein A" is a non-aromatic carbon-containing monocyclic ring containing 5 ring members, wherein one or two ring members are independently selected from N, NR8, S, or O, which is optionally substituted.

28. The compound of formula (I) according to claim 27, or a tautomer, stereoisomer, a deuterated isotope, or a pharmaceutically acceptable salt and/or solvate thereof, wherein A" is pyrrolidinyl, which is optionally substituted.

29. The compound of formula (I) according to claim 2, or a tautomer, stereoisomer, a deuterated isotope, or a pharmaceutically acceptable salt and/or solvate thereof, wherein A" is a non-aromatic carbon-containing monocyclic ring containing 6 ring members, wherein one or two ring members are independently selected from N, NR8, S, or O, which is optionally substituted.

30. The compound of formula (I) according to claim 29, or a tautomer, stereoisomer, a deuterated isotope, or a pharmaceutically acceptable salt and/or solvate thereof, wherein A" is piperidinyl, which is optionally substituted.

31. The compound of formula (I) according to claim 2, or a tautomer, stereoisomer, a deuterated isotope, or a pharmaceutically acceptable salt and/or solvate thereof, wherein A" is a non-aromatic carbon-containing monocyclic ring containing 7 ring members, wherein one or two ring members are independently selected from N, NR8, S, or O, which is optionally substituted.

32. The compound of formula (I) according to claim 31, or a tautomer, stereoisomer, a deuterated isotope, or a pharmaceutically acceptable salt and/or solvate thereof, wherein A" is azepanyl, which is optionally substituted.

33. The compound of formula (I) according to claim 2, or a tautomer, stereoisomer, a deuterated isotope, or a pharmaceutically acceptable salt and/or solvate thereof, wherein a carbon ring atom on A" is substituted with an alkylene such that the carbon ring atom on A" together with the alkylene forms a cycloalkyl that is spiro to ring A", which is optionally substituted.

34. The compound of formula (I) according to claim 2, or a tautomer, stereoisomer, a deuterated isotope, or a pharmaceutically acceptable salt and/or solvate thereof, wherein a carbon ring atom on A" is substituted with an alkylene such that the carbon ring atom on A" together with the alkylene forms a cyclopropane that is spiro to ring A", which is optionally substituted.

35. The compound of formula (I) according to claim 2, or a tautomer, stereoisomer, a deuterated isotope, or a pharmaceutically acceptable salt and/or solvate thereof, wherein two ring atoms on A" are linked by an alkylene or heteroalkylene to form a non-aromatic ring containing 5, 6, or 7 ring members.

36. The compound according to claim 2 that is a free base.

37. The compound according to claim 2 that is a pharmaceutically acceptable salt.

38. The compound according to claim 2 that is a pharmaceutically acceptable solvate.

39. The compound according to claim 2 that is a pharmaceutically acceptable solvate of a salt.

40. A pharmaceutical composition comprising:
  (i) the compound of claim 2, or a pharmaceutically acceptable salt thereof, pharmaceutically acceptable solvate thereof, or a pharmaceutically acceptable solvate of a salt thereof; and
  (ii) a pharmaceutically acceptable carrier, diluent or excipient.

41. The compound of formula (I) of claim 2, wherein the stereoisomer is an enantiomer or diastereoisomer, or a racemic or scalemic mixture thereof.

42. The compound of formula (I) according to claim 2, or a tautomer, a stereoisomer, a deuterated isotope, or a pharmaceutically acceptable salt and/or solvate thereof, wherein the ring containing W, X, Y and Z is imidazolyl.

43. The compound of formula (I) according to claim 2, or a tautomer, a stereoisomer, a deuterated isotope, or a pharmaceutically acceptable salt and/or solvate thereof, wherein the ring containing W, X, Y and Z is 1,2,3-triazolyl.

44. The compound of formula (I) according to claim 2, or a tautomer, a stereoisomer, a deuterated isotope, or a pharmaceutically acceptable salt and/or solvate thereof, wherein the ring containing W, X, Y and Z is 2- or 4-pyridonyl.

45. The compound of formula (I) according to claim 2, or a tautomer, a stereoisomer, a deuterated isotope, or a pharmaceutically acceptable salt and/or solvate thereof, wherein the ring containing W, X, Y and Z is pyridinyl.

46. The compound of formula (I) according to claim 2, or a tautomer, a stereoisomer, a deuterated isotope, or a pharmaceutically acceptable salt and/or solvate thereof, wherein the ring containing W, X, Y and Z is 1,3-oxazolyl.

* * * * *